United States Patent
Vlahov et al.

(10) Patent No.: US 12,178,892 B2
(45) Date of Patent: Dec. 31, 2024

(54) COMPOUNDS FOR POSITRON EMISSION TOMOGRAPHY

(71) Applicants: Endocyte, Inc., West Lafayette, IN (US); Purdue Research Foundation, West Lafayette, IN (US)

(72) Inventors: Iontcho R Vlahov, West Lafayette, IN (US); Christopher P Leamon, West Lafayette, IN (US); Philip S. Low, West Lafayette, IN (US); Garth L Parham, Largo, FL (US); Qingshou Chen, West Lafayette, IN (US)

(73) Assignees: Purdue Research Foundation, West Lafayette, IN (US); Endocyte, Inc., West Lafayette, IN (US)

( * ) Notice: Subject to any disclaimer, the term of this patent is extended or adjusted under 35 U.S.C. 154(b) by 213 days.

(21) Appl. No.: 17/488,810

(22) Filed: Sep. 29, 2021

(65) Prior Publication Data

US 2022/0125958 A1    Apr. 28, 2022

Related U.S. Application Data

(63) Continuation of application No. 16/157,024, filed on Oct. 10, 2018, now abandoned, which is a continuation of application No. 15/035,936, filed as application No. PCT/US2014/065467 on Nov. 13, 2014, now abandoned.

(60) Provisional application No. 61/904,400, filed on Nov. 14, 2013, provisional application No. 61/904,387, filed on Nov. 14, 2013, provisional application No. 61/909,822, filed on Nov. 27, 2013.

(51) Int. Cl.
A61K 51/04    (2006.01)

(52) U.S. Cl.
CPC .......... *A61K 51/0497* (2013.01); *A61K 51/04* (2013.01); *A61K 51/0459* (2013.01); *A61K 51/0482* (2013.01)

(58) Field of Classification Search
CPC .... A61K 51/00; A61K 51/04; A61K 51/0497; A61K 51/0459; A61K 51/0482; A61P 13/08; A61P 35/00; G01N 33/52; G01N 33/60; G01N 2800/00
USPC ........ 424/1.11, 1.65, 1.69, 9.1, 9.2, 9.3, 9.4; 534/7, 10–14
See application file for complete search history.

(56) References Cited

U.S. PATENT DOCUMENTS

| | | |
|---|---|---|
| 4,691,024 A | 9/1987 | Shirahata et al. |
| 4,713,249 A | 12/1987 | Schroder |
| 5,103,018 A | 4/1992 | Motomichi et al. |
| 5,266,333 A | 11/1993 | Cady et al. |
| 5,417,982 A | 5/1995 | Modi |
| 5,418,982 A | 5/1995 | Kishi |
| 5,627,165 A | 5/1997 | Glazier |
| 5,795,877 A | 8/1998 | Jackson et al. |
| 5,863,536 A | 1/1999 | Jackson et al. |
| 5,866,679 A | 2/1999 | DeFeo-Jones et al. |
| 5,902,817 A | 5/1999 | Jackson et al. |
| 5,948,750 A | 9/1999 | Garsky et al. |
| 5,962,237 A | 10/1999 | Ts'o et al. |
| 5,962,521 A | 10/1999 | Jackson et al. |
| 5,968,915 A | 10/1999 | Jackson et al. |
| 5,998,362 A | 12/1999 | Feng et al. |
| 6,054,444 A | 4/2000 | Jackson et al. |
| 6,127,333 A | 10/2000 | Brady et al. |
| 6,174,858 B1 | 1/2001 | Brady et al. |
| 6,177,404 B1 | 1/2001 | DeFeo-Jones et al. |
| 6,232,287 B1 | 5/2001 | Ruoslahti et al. |
| 6,368,598 B1 | 4/2002 | Anthony |
| 6,391,305 B1 | 5/2002 | Feng et al. |
| 6,428,785 B1 | 8/2002 | Gokcen |
| 6,479,470 B1 | 11/2002 | Kozikowski et al. |
| 6,528,499 B1 | 3/2003 | Kozikowski et al. |
| 6,692,724 B1 | 2/2004 | Yang et al. |
| 6,875,886 B2 | 4/2005 | Frangioni |
| 6,946,133 B1 | 9/2005 | Schlom et al. |
| 7,008,765 B1 | 3/2006 | Bussemakers et al. |
| 7,128,893 B2 | 10/2006 | Leamon et al. |
| 7,129,254 B2 | 10/2006 | Berger et al. |
| 7,147,837 B2 | 12/2006 | Lauffer et al. |

(Continued)

FOREIGN PATENT DOCUMENTS

| | | |
|---|---|---|
| AU | 2008289108 B2 | 9/2014 |
| AU | 2014348601 | 5/2016 |

(Continued)

OTHER PUBLICATIONS

"New Zealand Application Serial No. 758917, Subsequent Examiners Report mailed Feb. 9, 2022", 1 pg.

(Continued)

*Primary Examiner* — Michael G. Hartley
*Assistant Examiner* — Kaila A Craig
(74) *Attorney, Agent, or Firm* — Barnes & Thornburg LLP

(57) ABSTRACT

Described herein are compounds, compositions, and methods for diagnosing and/or monitoring pathogenic disease using positron emission tomography. Also described are conjugates of the formula B-L-P, wherein B is a radical of a targeting agent selected from vitamin receptor binding ligands (such as folate), PSMA binding ligands, or PSMA inhibitors; L is a divalent linker comprising aspartic acid, lysine, or arginine, and P is a radical of an imaging agent or radiotherapy agent, such as a radionuclide or radionuclide containing group, or a radical of a compound capable of binding a radionuclide, such as a metal chelating group.

2 Claims, 4 Drawing Sheets

(56) References Cited

U.S. PATENT DOCUMENTS

| | | |
|---|---|---|
| 7,192,586 B2 | 3/2007 | Bander |
| 7,226,577 B2 | 6/2007 | Cappelletti et al. |
| 7,232,805 B2 | 6/2007 | Weinshenker et al. |
| 7,361,338 B2 | 4/2008 | Jakobovits et al. |
| 7,381,745 B2 | 6/2008 | Kozikowski et al. |
| 7,399,460 B2 | 7/2008 | Wedeking et al. |
| 7,408,079 B2 | 8/2008 | Pomper et al. |
| 7,485,299 B2 | 2/2009 | Afar et al. |
| 7,514,078 B2 | 4/2009 | Bander et al. |
| 7,517,903 B2 | 4/2009 | Chen et al. |
| 7,534,580 B2 | 5/2009 | Reeves et al. |
| 7,601,332 B2 | 10/2009 | Vlahov et al. |
| 7,635,682 B2 | 12/2009 | Denmeade et al. |
| 7,638,122 B2 | 12/2009 | Yu et al. |
| 7,659,395 B2 | 2/2010 | Pajouhesh et al. |
| 7,662,795 B2 | 2/2010 | Rodriguez et al. |
| 7,696,185 B2 | 4/2010 | Berkman |
| 7,713,944 B2 | 5/2010 | Kinberger et al. |
| 7,740,847 B2 | 6/2010 | Allan et al. |
| 7,767,202 B2 | 8/2010 | Pardoll et al. |
| 7,767,803 B2 | 8/2010 | Diener et al. |
| 7,794,929 B2 | 9/2010 | Baylin et al. |
| 7,862,798 B2 | 1/2011 | Leamon et al. |
| 7,872,235 B2 | 1/2011 | Rousso et al. |
| 7,875,586 B2 | 1/2011 | Kovbasnjuk et al. |
| 7,879,981 B2 | 2/2011 | Obata |
| 7,910,594 B2 | 3/2011 | Vlahov et al. |
| RE42,275 E | 4/2011 | Berkman |
| 7,990,533 B2 | 8/2011 | Maier et al. |
| 8,000,773 B2 | 8/2011 | Rousso et al. |
| 8,101,369 B2 | 1/2012 | Nam et al. |
| 8,101,713 B2 | 1/2012 | Cuello et al. |
| 8,105,568 B2 | 1/2012 | Vlahov et al. |
| 8,153,595 B2 | 4/2012 | Chen |
| 8,211,401 B2 | 7/2012 | Babich et al. |
| 8,211,402 B2 | 7/2012 | Babich et al. |
| 8,211,473 B2 | 7/2012 | Troiano et al. |
| 8,211,635 B2 | 7/2012 | Barton |
| 8,227,634 B2 | 7/2012 | Pomper et al. |
| 8,236,330 B2 | 8/2012 | Zale et al. |
| 8,246,968 B2 | 8/2012 | Zale et al. |
| 8,258,111 B2 | 9/2012 | Shen et al. |
| 8,273,363 B2 | 9/2012 | Zale et al. |
| 8,313,128 B2 | 11/2012 | Belyea et al. |
| 8,313,728 B2 | 11/2012 | Leamon et al. |
| 8,388,977 B2 | 3/2013 | Low et al. |
| 8,404,817 B2 | 3/2013 | Sherman et al. |
| 8,414,898 B2 | 4/2013 | Afar et al. |
| 8,445,851 B2 | 5/2013 | Rousso et al. |
| 8,450,290 B2 | 5/2013 | Worm et al. |
| 8,465,725 B2 | 6/2013 | Babich et al. |
| 8,487,128 B2 | 7/2013 | Weissbach et al. |
| 8,487,129 B2 | 7/2013 | Babich et al. |
| 8,507,434 B2 | 8/2013 | Popel et al. |
| 8,557,772 B2 | 10/2013 | Popel et al. |
| 8,562,945 B2 | 10/2013 | Babich et al. |
| 8,603,499 B2 | 12/2013 | Zale et al. |
| 8,603,500 B2 | 12/2013 | Zale et al. |
| 8,603,501 B2 | 12/2013 | Zale et al. |
| 8,606,349 B2 | 12/2013 | Rousso et al. |
| 8,644,910 B2 | 2/2014 | Rousso et al. |
| 8,685,891 B2 | 4/2014 | Muraca |
| 8,703,918 B2 | 4/2014 | Colombatti et al. |
| 8,709,483 B2 | 4/2014 | Farokhzad et al. |
| 8,772,226 B2 | 7/2014 | Denmeade et al. |
| 8,772,459 B2 | 7/2014 | Ho et al. |
| 8,778,305 B2 | 7/2014 | Pomper et al. |
| 8,802,153 B2 | 8/2014 | Cheng et al. |
| 8,816,095 B2 | 8/2014 | Brown et al. |
| 8,834,842 B2 | 9/2014 | Leamon et al. |
| 8,840,865 B2 | 9/2014 | Babich et al. |
| 8,852,630 B2 | 10/2014 | Spiegel et al. |
| 8,859,509 B2 | 10/2014 | Spiegel et al. |
| 8,865,126 B2 | 10/2014 | Leamon et al. |
| 8,865,875 B2 | 10/2014 | Liu et al. |
| 8,877,970 B2 | 11/2014 | Zimmerman et al. |
| 8,901,294 B2 | 12/2014 | Kim et al. |
| 8,907,058 B2 * | 12/2014 | Low .................. A61P 25/28 530/330 |
| 8,916,161 B2 | 12/2014 | Buckley |
| 8,916,167 B2 | 12/2014 | Low et al. |
| 8,926,944 B2 | 1/2015 | Babich et al. |
| 8,926,945 B2 | 1/2015 | Port et al. |
| 8,940,871 B2 | 1/2015 | Wu et al. |
| 8,946,388 B2 | 2/2015 | Sahin et al. |
| 8,962,799 B2 | 2/2015 | Babich et al. |
| 8,986,655 B2 | 3/2015 | Weiss et al. |
| 8,987,319 B2 | 3/2015 | Miller |
| 9,044,468 B2 | 6/2015 | Pomper et al. |
| 9,056,841 B2 | 6/2015 | Pomper et al. |
| 9,193,763 B2 | 11/2015 | Low et al. |
| 9,226,981 B2 | 1/2016 | Pomper et al. |
| 9,242,012 B2 | 1/2016 | Ma et al. |
| 9,278,067 B2 | 3/2016 | Boulikas |
| 9,295,727 B2 | 3/2016 | Zale et al. |
| 9,309,193 B2 | 4/2016 | Babich et al. |
| 9,629,918 B2 | 4/2017 | Low et al. |
| 9,636,413 B2 | 5/2017 | Vlahov et al. |
| 9,687,572 B2 | 6/2017 | Babich et al. |
| 9,782,493 B2 | 10/2017 | Vlahov et al. |
| 9,801,956 B2 | 10/2017 | Kularatne et al. |
| 9,808,538 B2 | 11/2017 | Kularatne et al. |
| 9,951,324 B2 | 4/2018 | Low et al. |
| 9,968,691 B2 | 5/2018 | Kularatne et al. |
| 10,046,054 B2 | 8/2018 | Low et al. |
| 10,188,759 B2 | 1/2019 | Vlahov |
| 10,308,606 B2 | 6/2019 | Kularatne et al. |
| 10,363,388 B2 | 7/2019 | Fonseca et al. |
| 10,398,791 B2 | 9/2019 | Eder et al. |
| 10,406,240 B2 | 9/2019 | Low et al. |
| 10,456,482 B2 | 10/2019 | Kularatne et al. |
| 10,471,160 B2 | 11/2019 | Eder et al. |
| 10,485,878 B2 | 11/2019 | Low et al. |
| 10,517,956 B2 | 12/2019 | Low et al. |
| 10,517,957 B2 | 12/2019 | Low et al. |
| 10,557,128 B2 | 2/2020 | Low et al. |
| 10,624,969 B2 | 4/2020 | Low et al. |
| 10,624,970 B2 | 4/2020 | Low et al. |
| 10,624,971 B2 | 4/2020 | Low et al. |
| 10,646,581 B2 | 5/2020 | Low et al. |
| 10,688,200 B2 | 6/2020 | Kung et al. |
| 10,828,282 B2 | 11/2020 | Low et al. |
| 10,898,596 B2 | 1/2021 | Vlahov |
| 10,912,840 B2 | 2/2021 | Vlahov et al. |
| 11,045,564 B2 | 6/2021 | Eder et al. |
| 11,083,710 B2 | 8/2021 | Low et al. |
| 11,155,800 B2 | 10/2021 | Low et al. |
| 11,298,341 B2 | 4/2022 | Low et al. |
| 11,318,121 B2 | 5/2022 | Low et al. |
| 11,369,590 B2 | 6/2022 | Low et al. |
| 11,504,357 B2 | 11/2022 | Low et al. |
| 11,717,514 B2 | 8/2023 | Low et al. |
| 11,931,430 B2 | 3/2024 | Eder |
| 11,951,190 B2 | 4/2024 | Eder |
| 2001/0031252 A1 | 10/2001 | Low et al. |
| 2002/0001782 A1 | 1/2002 | Watanabe et al. |
| 2002/0055121 A1 | 5/2002 | Vielkind |
| 2002/0103136 A1 | 8/2002 | Feng |
| 2002/0115596 A1 | 8/2002 | Garsky et al. |
| 2002/0132983 A1 | 9/2002 | Junghans |
| 2003/0035804 A1 | 2/2003 | Anthony |
| 2003/0086900 A1 | 5/2003 | Low et al. |
| 2003/0133927 A1 | 7/2003 | DeFeo-Jones et al. |
| 2003/0138432 A1 | 7/2003 | Glazier |
| 2003/0207808 A1 | 11/2003 | Savitzky et al. |
| 2003/0215456 A1 | 11/2003 | Yao et al. |
| 2003/0220241 A1 | 11/2003 | DeFeo-Jones et al. |
| 2003/0232760 A1 | 12/2003 | Garsky et al. |
| 2004/0001846 A1 | 1/2004 | Israeli et al. |
| 2004/0002478 A1 | 1/2004 | Kozikowski et al. |
| 2004/0018203 A1 | 1/2004 | Pastan et al. |
| 2004/0029778 A1 | 2/2004 | Isaacs |
| 2004/0033195 A1 | 2/2004 | Leamon et al. |
| 2004/0052727 A1 | 3/2004 | Dalton et al. |

(56) References Cited

U.S. PATENT DOCUMENTS

| | | |
|---|---|---|
| 2004/0054190 A1 | 3/2004 | Pomper et al. |
| 2004/0058857 A1 | 3/2004 | Yao |
| 2004/0092890 A1 | 5/2004 | Ash |
| 2004/0110723 A1 | 6/2004 | Frangioni |
| 2004/0146516 A1 | 7/2004 | Roben et al. |
| 2004/0213791 A1 | 10/2004 | Bander et al. |
| 2004/0229845 A1 | 11/2004 | Frangioni |
| 2004/0242582 A1 | 12/2004 | Green et al. |
| 2005/0002942 A1 | 1/2005 | Vlahov et al. |
| 2005/0107325 A1 | 5/2005 | Manoharan et al. |
| 2005/0119166 A1 | 6/2005 | Brady et al. |
| 2005/0158780 A1 | 7/2005 | Lupold et al. |
| 2005/0234247 A1 | 10/2005 | Klar et al. |
| 2005/0239138 A1 | 10/2005 | Hess et al. |
| 2005/0239739 A1 | 10/2005 | Matulic-Adamic et al. |
| 2005/0245486 A1 | 11/2005 | Frangioni |
| 2005/0255042 A1 | 11/2005 | Lam et al. |
| 2006/0024317 A1 | 2/2006 | Boyd et al. |
| 2006/0052312 A1 | 3/2006 | Erhardt et al. |
| 2006/0062793 A1 | 3/2006 | Webb et al. |
| 2006/0105975 A1 | 5/2006 | Pendergrast et al. |
| 2006/0106047 A1 | 5/2006 | Jiang et al. |
| 2006/0140871 A1 | 6/2006 | Sillerud |
| 2006/0148718 A1 | 7/2006 | Brady et al. |
| 2006/0155021 A1 | 7/2006 | Lenges et al. |
| 2006/0155146 A1 | 7/2006 | Lenges et al. |
| 2007/0010014 A1 | 1/2007 | Wood et al. |
| 2007/0020177 A1 | 1/2007 | McGill et al. |
| 2007/0020327 A1 | 1/2007 | Fikes et al. |
| 2007/0031326 A1 | 2/2007 | Shirvan et al. |
| 2007/0031438 A1 | 2/2007 | Junghans |
| 2007/0041901 A1 | 2/2007 | Diener et al. |
| 2007/0117153 A1 | 5/2007 | Bieniarz et al. |
| 2007/0128670 A1 | 6/2007 | Klatzmann et al. |
| 2007/0134332 A1 | 6/2007 | Turnell et al. |
| 2007/0142296 A1 | 6/2007 | McBride et al. |
| 2007/0148662 A1 | 6/2007 | Israeli et al. |
| 2007/0160617 A1 | 7/2007 | Ma et al. |
| 2007/0172422 A1 | 7/2007 | Glazier |
| 2007/0179100 A1 | 8/2007 | Manoharan |
| 2007/0219165 A1 | 9/2007 | Berkman |
| 2007/0225213 A1 | 9/2007 | Kosak |
| 2007/0244055 A1 | 10/2007 | Brady et al. |
| 2007/0254316 A1 | 11/2007 | Rodriguez et al. |
| 2007/0254317 A1 | 11/2007 | Busseret-Michel et al. |
| 2008/0008649 A1 | 1/2008 | Cappelletti et al. |
| 2008/0008719 A1 | 1/2008 | Bowdish et al. |
| 2008/0089842 A1 | 4/2008 | Pagel et al. |
| 2008/0089869 A1 | 4/2008 | Denmeade et al. |
| 2008/0114153 A1 | 5/2008 | Steeves et al. |
| 2008/0175789 A1 | 7/2008 | Frangioni |
| 2008/0176821 A1 | 7/2008 | Kozikowski et al. |
| 2008/0193381 A1 | 8/2008 | Babich et al. |
| 2008/0214436 A1 | 9/2008 | Yu et al. |
| 2008/0248052 A1 | 10/2008 | Vlahov et al. |
| 2008/0269105 A1 | 10/2008 | Taft et al. |
| 2008/0311037 A1 | 12/2008 | Heston et al. |
| 2009/0117042 A1 | 5/2009 | Pomper et al. |
| 2009/0123467 A1 | 5/2009 | Bedi et al. |
| 2009/0180951 A1 | 7/2009 | Zimmerman et al. |
| 2009/0214636 A1 | 8/2009 | Low et al. |
| 2009/0247614 A1 | 10/2009 | Manoharan et al. |
| 2009/0258002 A1 | 10/2009 | Barrett et al. |
| 2009/0274625 A1 | 11/2009 | Denmeade et al. |
| 2010/0048490 A1 | 2/2010 | Vlahov et al. |
| 2010/0055735 A1 | 3/2010 | Low et al. |
| 2010/0092496 A1 | 4/2010 | Boyd et al. |
| 2010/0178246 A1 | 7/2010 | Babich et al. |
| 2010/0183509 A1 | 7/2010 | Babich et al. |
| 2010/0183517 A1 | 7/2010 | Berkman |
| 2010/0209343 A1 | 8/2010 | Bander et al. |
| 2010/0234450 A1 | 9/2010 | Schultz et al. |
| 2010/0240701 A1 | 9/2010 | Vlahov et al. |
| 2010/0324008 A1 | 12/2010 | Low et al. |
| 2011/0008253 A1 | 1/2011 | Babich et al. |
| 2011/0027180 A1 | 2/2011 | Magnani |
| 2011/0027274 A1 | 2/2011 | Cheng et al. |
| 2011/0064657 A1 | 3/2011 | Pomper et al. |
| 2011/0142760 A1 | 6/2011 | Pomper et al. |
| 2011/0172254 A1 | 7/2011 | Leamon et al. |
| 2011/0176998 A1 | 7/2011 | Pomper et al. |
| 2011/0200677 A1 | 8/2011 | Chandran et al. |
| 2011/0256157 A1 | 10/2011 | Howard et al. |
| 2011/0288152 A1 | 11/2011 | Low et al. |
| 2012/0009121 A1 | 1/2012 | Pomper et al. |
| 2012/0276162 A1 | 11/2012 | Zale et al. |
| 2012/0322741 A1 | 12/2012 | Low et al. |
| 2013/0034494 A1 | 2/2013 | Babich et al. |
| 2013/0172406 A1 | 7/2013 | Zale et al. |
| 2013/0315821 A1* | 11/2013 | D'Souza ............ A61K 51/0402 424/1.53 |
| 2013/0336888 A1 | 12/2013 | Babich et al. |
| 2014/0073763 A1 | 3/2014 | Low et al. |
| 2014/0107316 A1 | 4/2014 | Vlahov et al. |
| 2014/0140925 A1 | 5/2014 | Leamon et al. |
| 2014/0154702 A1 | 6/2014 | Parker et al. |
| 2014/0187501 A1 | 7/2014 | Bilodeau et al. |
| 2014/0228541 A1* | 8/2014 | D'Souza ................ C07K 7/06 548/546 |
| 2014/0314864 A1 | 10/2014 | Cheng et al. |
| 2015/0023875 A1 | 1/2015 | Farokhzad et al. |
| 2015/0079001 A1 | 3/2015 | Pomper et al. |
| 2015/0104387 A1 | 4/2015 | Pomper et al. |
| 2015/0110715 A1 | 4/2015 | Eder et al. |
| 2015/0110814 A1 | 4/2015 | Olson et al. |
| 2015/0246144 A1 | 9/2015 | Pomper et al. |
| 2015/0297735 A1 | 10/2015 | Vlahov et al. |
| 2015/0315196 A1 | 11/2015 | Howard |
| 2015/0366968 A1 | 12/2015 | Basilion |
| 2016/0045626 A1* | 2/2016 | McBride ............. C07D 403/12 424/1.69 |
| 2016/0067341 A1 | 3/2016 | Low et al. |
| 2016/0074526 A1 | 3/2016 | Bilodeau et al. |
| 2016/0114060 A1 | 4/2016 | Pomper et al. |
| 2016/0151508 A1 | 6/2016 | Low et al. |
| 2016/0208021 A1 | 7/2016 | Chang et al. |
| 2016/0220694 A1 | 8/2016 | Vlahov et al. |
| 2016/0228587 A1 | 8/2016 | Eder et al. |
| 2016/0256579 A1 | 9/2016 | Shalom |
| 2016/0287731 A1 | 10/2016 | Vlahov et al. |
| 2016/0361376 A1 | 12/2016 | Vlahov et al. |
| 2016/0361432 A1 | 12/2016 | Vlahov et al. |
| 2016/0361433 A1 | 12/2016 | Vlahov et al. |
| 2017/0226141 A1 | 8/2017 | Slusher et al. |
| 2017/0258923 A1 | 9/2017 | Low et al. |
| 2018/0207298 A1 | 7/2018 | Berkman et al. |
| 2018/0243431 A1 | 8/2018 | Low et al. |
| 2018/0256737 A1 | 9/2018 | Vlahov et al. |
| 2018/0271988 A1 | 9/2018 | Low et al. |
| 2018/0271989 A1 | 9/2018 | Low et al. |
| 2018/0271990 A1 | 9/2018 | Low et al. |
| 2018/0289827 A1 | 10/2018 | Low et al. |
| 2018/0289828 A1 | 10/2018 | Low et al. |
| 2018/0289829 A1 | 10/2018 | Low et al. |
| 2018/0303950 A1 | 10/2018 | Low et al. |
| 2018/0339071 A1 | 11/2018 | Jeong et al. |
| 2018/0346008 A1 | 12/2018 | Nahum et al. |
| 2019/0177345 A1 | 6/2019 | Larsen |
| 2019/0314515 A1 | 10/2019 | Vlahov et al. |
| 2019/0389951 A1 | 12/2019 | Murphy et al. |
| 2020/0155695 A1 | 5/2020 | Low et al. |
| 2020/0155696 A1 | 5/2020 | Low et al. |
| 2020/0188523 A1 | 6/2020 | Low et al. |
| 2020/0261592 A1 | 8/2020 | Low et al. |
| 2020/0297701 A1 | 9/2020 | Low et al. |
| 2021/0077468 A1 | 3/2021 | Low et al. |
| 2021/0154311 A1 | 5/2021 | Vlahov et al. |
| 2021/0154312 A1 | 5/2021 | Vlahov et al. |
| 2021/0161911 A1 | 6/2021 | Armour |
| 2021/0177996 A1 | 6/2021 | Eder et al. |
| 2021/0283279 A1 | 9/2021 | Eder et al. |
| 2021/0322388 A1 | 10/2021 | Low et al. |
| 2021/0323985 A1 | 10/2021 | Leamon et al. |
| 2021/0338641 A1 | 11/2021 | Low et al. |

(56) References Cited

U.S. PATENT DOCUMENTS

| | | |
|---|---|---|
| 2022/0096445 A1 | 3/2022 | Low et al. |
| 2022/0098564 A1 | 3/2022 | Low et al. |
| 2022/0125957 A1 | 4/2022 | Armour et al. |
| 2022/0220085 A1 | 7/2022 | Vlahov et al. |
| 2022/0265841 A1 | 8/2022 | Vlahov et al. |
| 2023/0000836 A1 | 1/2023 | Low et al. |
| 2023/0098279 A1 | 3/2023 | Leamon et al. |
| 2023/0346752 A1 | 11/2023 | Low et al. |

FOREIGN PATENT DOCUMENTS

| | | | |
|---|---|---|---|
| AU | 2014348601 A1 | 5/2016 | |
| CA | 2606138 A1 | 10/2005 | |
| CA | 2696627 C | 9/2016 | |
| CN | 1662263 A | 8/2005 | |
| CN | 101863924 A | 10/2010 | |
| CN | 102014956 A | 4/2011 | |
| CN | 103951668 A | 7/2014 | |
| CN | 104873982 A | 9/2015 | |
| CN | 109134602 A | 1/2019 | |
| CN | 111801121 A | 10/2020 | |
| DE | 202014008232 U1 | 3/2015 | |
| EP | 0116208 B1 | 3/1988 | |
| EP | 1177200 B1 | 6/2005 | |
| EP | 1472541 B1 | 9/2009 | |
| EP | 2136788 B1 | 10/2011 | |
| EP | 2373621 A2 | 10/2011 | |
| EP | 1999136 B1 | 10/2012 | |
| EP | 2436376 B1 | 7/2014 | |
| EP | 2759535 A1 | 7/2014 | |
| EP | 2240171 B1 | 8/2014 | |
| EP | 2170075 B1 | 12/2014 | |
| EP | 2823826 A2 | 1/2015 | |
| EP | 2097111 B1 | 7/2015 | |
| EP | 2938364 A1 | 11/2015 | |
| EP | 2993171 A1 | 3/2016 | |
| EP | 2706057 B1 | 4/2016 | |
| EP | 2389361 B1 | 8/2016 | |
| EP | 2318366 B1 | 5/2017 | |
| EP | 2408755 B1 | 5/2017 | |
| EP | 2644192 B1 | 5/2017 | |
| EP | 2644594 B1 | 8/2017 | |
| EP | 2648766 B1 | 4/2018 | |
| EP | 2942065 B1 | 6/2018 | |
| EP | 2921482 B1 | 9/2018 | |
| EP | 2187965 B1 | 10/2019 | |
| EP | 2958596 B1 | 12/2019 | |
| EP | 3388086 B1 | 10/2020 | |
| EP | 3038996 B1 | 6/2022 | |
| IL | 203998 A | 8/2015 | |
| JP | 2002506204 A | 2/2002 | |
| JP | 2004536034 A | 12/2004 | |
| JP | 2005274569 A | 10/2005 | |
| JP | 2006501149 A | 1/2006 | |
| JP | 2006514961 A | 5/2006 | |
| JP | 2006518712 A | 8/2006 | |
| JP | 2007521803 A | 8/2007 | |
| JP | 2009519209 | 5/2009 | |
| JP | 2009519209 A | 5/2009 | |
| JP | 2010515732 A | 5/2010 | |
| JP | 2010518112 A | 5/2010 | |
| JP | 2010532754 A | 10/2010 | |
| JP | 2010536790 A | 12/2010 | |
| JP | 2011132258 A | 7/2011 | |
| JP | 2012511023 A | 5/2012 | |
| JP | 2014221779 A | 11/2014 | |
| JP | 5902237 B2 | 4/2016 | |
| JP | 2016153410 A | 8/2016 | |
| JP | 2016535013 A | 11/2016 | |
| JP | 2017530109 A | 10/2017 | |
| JP | 2018058847 A | 4/2018 | |
| JP | 2018150350 A | 9/2018 | |
| JP | 6596479 B2 | 10/2019 | |
| JP | 6625690 B2 | 12/2019 | |
| JP | 2020073472 A | 5/2020 | |
| JP | 2020530007 A | 10/2020 | |
| KR | 20030031905 | 4/2003 | |
| KR | 20030031905 A | 4/2003 | |
| PH | 12016500656 B1 | 6/2016 | |
| RU | 2004136995 A | 7/2005 | |
| RU | 2404193 C2 | 11/2010 | |
| WO | 1988001622 A1 | 3/1988 | |
| WO | 1991007418 A1 | 5/1991 | |
| WO | 1995033766 A1 | 12/1995 | |
| WO | 1999045374 A2 | 9/1999 | |
| WO | 2000064911 A1 | 11/2000 | |
| WO | 2000066091 A1 | 11/2000 | |
| WO | 2001091807 A2 | 12/2001 | |
| WO | 2002043773 A2 | 6/2002 | |
| WO | 2002062398 A2 | 8/2002 | |
| WO | 2002098885 A1 | 12/2002 | |
| WO | 2003000201 A2 | 1/2003 | |
| WO | 2003060523 A1 | 7/2003 | |
| WO | 2003092742 A1 | 11/2003 | |
| WO | 2003097105 A1 | 11/2003 | |
| WO | 2003097647 A1 | 11/2003 | |
| WO | 2004010957 A2 | 2/2004 | |
| WO | 2004069159 A2 | 8/2004 | |
| WO | 2004069285 A1 | 8/2004 | |
| WO | 2005082023 A2 | 9/2005 | |
| WO | 2005112919 A2 | 12/2005 | |
| WO | 2006012527 A1 | 2/2006 | |
| WO | 2006093991 A1 | 9/2006 | |
| WO | 2006096754 A2 | 9/2006 | |
| WO | 2006104911 A2 | 10/2006 | |
| WO | 2006136564 A1 | 12/2006 | |
| WO | 2007006041 A2 | 1/2007 | |
| WO | 2007022493 A2 | 2/2007 | |
| WO | 2007022494 A2 | 2/2007 | |
| WO | 2007042504 A2 | 4/2007 | |
| WO | 2007106869 A1 | 9/2007 | |
| WO | 2008057437 A2 | 5/2008 | |
| WO | 2008058192 A2 | 5/2008 | |
| WO | 2008088648 A2 | 7/2008 | |
| WO | 2008098112 A2 | 8/2008 | |
| WO | 2008101231 A2 | 8/2008 | |
| WO | 2008121949 A1 | 10/2008 | |
| WO | 2009002529 A2 | 12/2008 | |
| WO | 2009002993 A1 | 12/2008 | |
| WO | 2009026177 A1 | 2/2009 | |
| WO | 2009070302 A1 | 6/2009 | |
| WO | 2009079024 A1 | 6/2009 | |
| WO | 2009082606 A2 | 7/2009 | |
| WO | 2009089383 A2 | 7/2009 | |
| WO | 2010014933 A2 | 2/2010 | |
| WO | 2010065899 A2 | 6/2010 | |
| WO | 2010065902 A2 | 6/2010 | |
| WO | 2010065906 A2 | 6/2010 | |
| WO | 2010108125 A2 | 9/2010 | |
| WO | 2011014821 A1 | 2/2011 | |
| WO | 2011017249 A1 | 2/2011 | |
| WO | 2011106639 A1 | 9/2011 | |
| WO | 2011108125 A2 | 9/2011 | |
| WO | 2012078534 A1 | 6/2012 | |
| WO | 2012166923 A2 | 12/2012 | |
| WO | 2012174136 A1 | 12/2012 | |
| WO | 2013022797 A1 | 2/2013 | |
| WO | 2013028664 A1 | 2/2013 | |
| WO | 2013130776 A1 | 9/2013 | |
| WO | 2014062697 A2 | 4/2014 | |
| WO | 2014078484 A1 | 5/2014 | |
| WO | 2014106208 A1 | 7/2014 | |
| WO | 2014127365 A1 | 8/2014 | |
| WO | 2014134543 A1 | 9/2014 | |
| WO | 2015027205 A1 | 2/2015 | |
| WO | 2015055318 A1 | 4/2015 | |
| WO | 2015057250 A1 | 4/2015 | |
| WO | 2015171792 A1 | 11/2015 | |
| WO | 2016030329 A1 | 3/2016 | |
| WO | 2016040179 A1 | 3/2016 | |
| WO | 2017116994 A1 | 7/2017 | |
| WO | 2018031507 A1 | 2/2018 | |
| WO | 2018108287 A1 | 6/2018 | |
| WO | 2018187791 A1 | 10/2018 | |

(56) References Cited

FOREIGN PATENT DOCUMENTS

| WO | 2018191376 A2 | 10/2018 |
|---|---|---|
| WO | 2019115684 A1 | 6/2019 |
| WO | 2019165200 A1 | 8/2019 |
| WO | 2019204335 A1 | 10/2019 |
| WO | 2020061293 A1 | 3/2020 |

OTHER PUBLICATIONS

"Korean Application Serial No. 10-2016-7015740, Notice of Preliminary Rejection mailed Nov. 19, 2020", (w/ English translation), 12 pgs.
"Australian Application Serial No. 2021200067, First Examination Report mailed Feb. 16, 2022", 4 pgs.
Nedrow-Byers, et al., "PSMA-Targeted SPECT Agents: Mode of Binding Effect on In Vitro Performance," 2013, The Prostate, 73(4) pp. 355-362.
Nedrow-Byers, et al., "A Phosphoramidate-Based Prostate-Specific Membrane Antigen-Targeted SPECT Agent," 2012, The Prostate, 72(8) pp. 904-912.
Oehr et al., "Imaging of prostate cancer," 2007, Current Opinion in Oncology, 19 pp. 259-264.
O'Keefe, et al., "Comparative Analysis of Prostate-Specific Membrane Antigen (PSMA) Versus a Prostate-Specific Membrane Antigen-Like Gene," 2004, The Prostate, 58(2) pp. 200-210.
Olsnes, S., et al., "Immunotoxins—Entry into Cells and Mechanisms of Action," 1989, Immunology Today, 10(9) pp. 291-295.
Omlin, et al., "Androgen- und Östrogen-biosynthesehemmer beim kastrationsresistenten Prostatakarzinom," 2012, Urologe, 51 pp. 8-14.
Omlin, et al., "Inhibitors of Androgen and Estrogen Biosynthesis in Castration-Resistant Prostate Cancer," English translation, 2012, Urologe, 51(1) pp. 8-14.
Osborne, et al., "A Prospective Pilot Study of 89Zr-J591/Prostate Specific Membrane Antigen Positron Emission Tomography in Men with Localized Prostate Cancer Undergoing Radical Prostatectomy," 2014, The Journal of Urology, 19195) pp. 1439-1445.
Oyama, et al., "11C-Acetate PET Imaging of Prostate Cancer," 2002, Journal of Nuclear Medicine, 43(2) pp. 181-186.
Oyama, et al., "11C-Acetate PET Imaging of Prostate Cancer: Detection of Recurrent Disease at PSA Relapse," 2003, Journal of Nuclear Medicine, 44(4) pp. 549-555.
Oyama, et al., "PET Imaging in Prostate Cancer," 2006, Hinyokika Kiyo, 52(6) pp. 503-505.
Paranjpe, P., et al., "Tumor-targeted bioconjugate based delivery of camptothecin: design, synthesis and in vitro evaluation," 2004, ScienceDirect Journal of Controlled Release, 100(2) pp. 275-292.
Parker, et al., "Design, production, and characterization of a single-chain variable fragment (ScFv) derived from the prostate specific membrane antigen (PSMA) monoclonal antibody J591," 2013, Protein Expression and Purification, 89 (2) pp. 136-145.
Pathak, T., et al., "Enzymic Protecting Group Techniques in Organic Synthesis," 2000, Stereoselective Biocatalysis pp. 775-797.
Pavlicek, et al., "Glutamate Carboxypeptidase II: An Overview of Structural Studies and Their Importance for Structure-Based Drug Design and Deciphering the Reaction Mechanism of the Enzyme," 2012, Current Medicinal Chemistry, 19(9) pp. 1300-1309.
Pavlicek, et al., "Structural characterization of P1'-diversified urea-based inhibitors of glutamate carboxypeptidase II," 2014, Bioorganic & Medicinal Chemistry Letters, 24(10) pp. 2340-2345.
PCT International Search Report for PCT/US2011/026238, completed Apr. 27, 2011.
PCT International Search Report and Written Opinion for International Patent Application No. PCT/US2020/033584, mailed Aug. 14, 2020 (12 pages).
PCT International Search Report for PCT/US2008/073375, completed Oct. 26, 2008.
PCT International Search Report for PCT/US2009/061049, completed Mar. 15, 2010.
PCT International Search Report for PCT/US2009/061067, completed May 28, 2010.
PCT International Search Report for PCT/US2013/070007, completed Mar. 5, 2014.
PCT International Search Report for PCT/US2014/065467, dated Apr. 15, 2015.
PCT International Search Report for PCT/US2016/012653, dated Mar. 11, 2016.
PCT International Search Report for PCT/US2021/018447, completed May 6, 2021.
PCT Search Report and Written Opinion prepared for PCT/US2019/027720, completed May 30, 2019.
PCT Search Report and Written Opinion prepared for PCT/US2019/051903, completed Oct. 25, 2019.
PCT Search Report and Written Opinion prepared for PCT/US2019/052161, completed Dec. 18, 2019.
Peltier, H., et al., "The Total Synthesis of Tubulysin D,"2006, Journal of the American Chemical Society, 128(50) pp. 16018-16019.
Perner, et al., "Prostate-specific membrane antigen expression as a predictor of prostate cancer progression," 2007, Human Pathology, 38(5) pp. 696-701.
Pillarsetty, et al., "2-18F-Fluoropropionic Acid as a PET Imaging Agent for Prostate Cancer," 2009, Journal of Nuclear Medicine, 50(10) pp. 1709-1714.
Pinto, et al., "Imaging in Prostate Cancer Staging: Present Role and Future Perspectives," 2012, Urology International, 88 pp. 125-136.
Pomper, M., et al., "11C-MCG: synthesis, uptake selectivity, and primate PET of a probe for glutamate carboxypeptidase II (NAALADase)," 2002, Molecular Imaging, 1(2) pp. 96-101.
Ponde, et al., "18F-Fluoroacetate: A Potential Acetate Analog for Prostate Tumor Imaging—In Vivo Evaluation of 18F-Fluoroacetate Versus 11C-Acetate," 2007, Journal of Nuclear Medicine, 48(3) pp. 420-428.
Poulsen, et al., "[18F] fluoromethylcholine (FCH) positron emission tomography/computed tomography (PET/CT) for lymph node staging of prostate cancer: a prospective study of 210 patients," 2012, BJU International, 110(11) pp. 1666-1671.
Poulsen, et al., "[18F]-fluorocholine positron-emission/computed tomography for lymph node staging of patients with prostate cancer: preliminary results of a prospective study," 2010, BJU International, 106(5) pp. 639-644.
Pratesi et al., "Design and solid phase synthesis of new DOTA conjugated (+)-biotin dimers planned to develop molecular weight-tuned avidin oligomers," Accepted Manuscript for Org Biomol Chem, pp. 1-15 (2013).
Preusser, et al., "Castration-Resistant Prostate Cancer," English translation, 2012, Urologe, 51(1) pp. 27-31.
Preusser, et al., "Kastrationsresistentes Prostatakarzinom," 2012, Urologe, 51 pp. 27-31.
Pubchem, Compound summary for: CID 58099954, Aug. 19, 2012.
Radioisotopes in Medicine, from http://www.word-nuclear.org/information-library/non-power-nuclear applications/radioisotopes-research/radioisotopes-in-medicine.aspx, Dec. 28, 2016, pp. 1-20.
Rahbar, K. et al., "Delayed response after repeated 177Lu-PSMA-617 radioligand therapy in patients with metatstatic castration resistant prostate cancer," European Journal of Nuclear Medicine and Molecular Imaging, 2017, 45(2) pp. 243-246.
Rais, et al., "Bioanalytical method for evaluating the pharmacokinetics of the GCP-II inhibitor 2-phosphonomethylpentanedioicacid (2-PMPA)," 2014, Journal of Pharmaceutical and Biomedical Analysis, 88(25) pp. 162-169.
Rajasekaran, et al., "A Novel Cytoplasmic Tail MXXXL Motif Mediates the Internalization of Prostate-specific Membrane Antigen," 2003, Molecular Biology of the Cell, 14(12) pp. 4835-4845.
Ranasinghe, M., et al., "A Facile Synthesis of Unsymmetrical Thiolsulfonates via Sulfonylation of Mercaptans," 1988, Synthetic Communications, 18(3) pp. 227-232.
Reddy, J., et al., "PSMA-specific anti-tumor activity of the targeted-tubulysin conjugate, EC1169," American Association for Cancer Research Annual Meeting (Apr. 8, 2013) Poster.
Reske, S., et al., "Imaging Prostate Cancer with 11C-Choline PET/CT," 2006, Journal of Nuclear Medicine, 47(8) pp. 1249-1254.

(56) References Cited

OTHER PUBLICATIONS

Reske, "Nuclear Imaging of Prostate Cancer," English translation, 2007, Urologe, 46(11) pp. 1485-1499.
Reske, et al., "[11C]choline PET/CT imaging in occult local relapse of prostate cancer after radical prostatectomy," 2008, European Journal of Nuclear Medicine and Molecular Imaging, 35 pp. 9-17.
Reske, et al., "[11C]Choline uptake with PET/CT for the initial diagnosis of prostate cancer: relation to PSA levels, tumour stage and anti-androgenic therapy," 2008, European Journal of Nuclear Medicine and Molecular Imaging, 35(9) pp. 1740-1741.
Uprimny, et al., "68Ga-PSMA ligand PET versus 18F-NaF PET: evaluation of response to 223Ra therapy in a prostate cancer patient," 2015, European Journal of Nuclear Medicine and Molecular Imaging, 42(2) pp. 362-363.
Vallabhajosula, et al., "Radioimmunotherapy of Prostate Cancer in Human Xenografts Using Monoclonal Antibodies Specific to Prostate Specific Membrane Antigen (PSMA): Studies in Nude Mice," 2004, The Prostate, 58(2) pp. 145-155.
Vavere, et al., "1-11C-Acetate as a PET Radiopharmaceutical for Imaging Fatty Acid Synthase Expression in Prostate Cancer," 2008, Journal of Nuclear Medicine, 49(2) pp. 327-334.
Vees, H., et al., "18F-choline and/or 11C-acetate positron emission tomography: detection of residual or progressive subclinical disease at very low prostate-specific antigen values ( <1 ng/ml) after radical prostatectomy," 2007, BJU International, 99(6) pp. 1415-1420.
Viola-Villegas, N., et al., "Targeting Gallium to Cancer Cells through the Folate Receptor," 2008, Drug Target Insights, 3 pp. 13-25.
Viola-Villegas, N., et al., "Targeting the Folate Receptor (FR): Imaging and Cytotoxicity of Rel Conjugates in FR-Overexpressing Cancer Cells," 2008, ChemMedChem, 3(9) pp. 1387-1394.
Violet, J., et al., "Long-Term Follow-up and Outcomes of Retreatment in an Expanded 50-Patient Single-Center Phase II Prospective Trial of 177Lu-PSMA-617 Theranostics in Metastatic Castration-Resistant Prostate Cancer," Journal of Nuclear Medicine, 2020, 61(6) pp. 857-865.
Vlahov, I., et al., "Design and regioselective synthesis of a new generation of targeted chemotherapeutics. Part 1: EC145, a folic acid conjugate of desacetylvinblastine monohydrazide," 2006, ScienceDirect, Bioorganic & Medical Chemistry Letters, 16(19) pp. 5093-5096.
Wang, et al., "Prostate-Specific Membrane Antigen Targeted Tubulysin Conjugates for Cancer Therapy," 246th ACS National Meeting and Exposition (Sep. 8, 2013) Poster.
Wang, et al., "Bioisosterism of urea-based GCPII inhibitors: Synthesis and structure-activity relationship studies," 2010, Bioorganic & Medicinal Chemistry Letters, 20(1) pp. 392-397.
Wang, et al., "Development of Targeted Near-Infrared Imaging Agents for Prostate Cancer," 2014, Molecular Cancer Therapeutics, 13(11) pp. 2595-2606.
Wang, Z., Single Low-Dose Injection of Evans Blue Modified PSMA-617 Radioligand Therapy Eliminates Prostate-Specific Membrane Antigen Positive Tumors, Bioconjugate Chemistry, 2018, 29, pp. 3213-3221.
Weineisen, et al., "Synthesis and preclinical evaluation of DOTAGA-conjugated PSMA ligands for functional imaging and endoradiotherapy of prostate cancer," 2014, EJNMMI Research, 4(63).
Weissbach, L., "Welche Inhalte sollte eine living guideline besetzen?," 2012, Urologe, 51 pp. 57-59.
Weissbach, L. "Which Components Should 'Living Guidelines' Contain?," English translation, 2012, Urologe, 51(1) pp. 57-59.
Whitaker, et al., "N-acetyl-L-aspartyl-L-glutamate peptidase-like 2 is overexpressed in cancer and promotes a pro-migratory and pro-metastatic phenotype," 2014, Oncogene, 33 pp. 5274-5287.
Wiberg, et al., "A comparison of some properties of C=O and C=S bonds," 2011, ARKIVOC, 5 pp. 45-56.
Wiehr, et al., "Pharmacokinetics and PET Imaging Properties of Two Recombinant Anti-PSMA Antibody Fragments in Comparison to their Parental Antibody," 2014, The Prostate, 74(7) pp. 743-755.
Wright, et al., "Expression of Prostate-Specific Membrane Antigen in Normal, Benign, and Malignant Prostate Tissues," 1995, Urologic Oncology, 1(1) pp. 18-28.
Wu, et al., "A mild deprotection procedure for tert-butyl esters and tert-butyl ethers using ZnBr2 in methylene chloride," 2000, Tetrahedron Letters, 41(16) pp. 2847-2849.
Wu, et al., "The molecular pruning of a phosphoramidate peptidomimetic inhibitor of prostate-specific membrane antigen," 2007, Bioorganic & Medicinal Chemistry, 15(23) pp. 7434-7443.
Yadav, M.P. et al., "177Lu-DKFZ-PSMA-617 therapy in metastatic castration resistant prostate cancer: safety, efficacy, and quality of life assessment," European Jouranl of Nuclear Medicine and Molecular Imaging, 2016, 44(1) pp. 81-91.
Yamaguchi, et al., "Prostate cancer: a comparative study of 11C-choline PET and MR imaging combined with proton MR spectroscopy," 2005, European Journal of Nuclear Medicine and Molecular Imaging, 32(7) pp. 742-748.
Yang, J., et al., "Characterization of the pH of Folate Receptor-Containing Endosomes and the Rate of Hydrolysis of Internalized Acid-Labile Folate-Drug Conjugates," 2007, Journal of Pharmacology and Experimental Therapeutics, 321(2) pp. 462-468.
Zaheer, et al., "New Agents and Techniques for Imaging Prostate Cancer," 2009, Journal of Nuclear Medicine, 50(9) pp. 1387-1390.
Zechmann, et al., "Radiation dosimetry and first therapy results with a 124I/131 I-labeled small molecule (MIP-1095) targeting PSMA for prostate cancer therapy," 2014, European Journal of Nuclear Medicine and Molecular Imaging, 41(7) pp. 1280-1292.
Zhang, et al., "A Remote Arene-Binding Site on Prostate Specific Membrane Antigen Revealed by Antibody-Recruiting Small Molecules," 2010, Journal of the American Chemical Society, 132(36) pp. 12711-12716.
Zhang, et al., "Prostate Specific Membrane Antigen (PSMA): A Novel Modulator of p38 for Proliferation, Migration, and Survival in Prostate Cancer Cells," 2013, The Prostate, 73(8) pp. 835-841.
Zhou J., et al., "NAAG Peptidase Inhibitors and Their Potential for Diagnosis and Therapy," 2005, Nature Reviews Drug Discovery, 4(12) pp. 1015-1026.
Zhou, J., "In vivo evaluation of medical device-associated inflammation using macrophage-specific position emission tomography (PET) imaging," 2013, Bioorganic and Medicinal Chemistry Letters, 23(7) pp. 2044-2047.
Zophel, K. and Kotzerke, J., "Is 11C-choline the most appropriate tracer for prostate cancer?" 2004, European Journal of Nuclear Medicine and Molecular Imaging, 31(5) pp. 756-759.
Fani, M. et al. In vivo imaging of folate receptor positive tumor xenografts using novel 68Ga-NODAGA-folate conjugates. Mol Pharm. May 7, 2012;9(5):1136-45.
Chopra, A., "68Ga-Labeled 2-[3-(1-carboxy-5-{7-[5-carboxy-5-(3-phenyl-2-{3-phenyl-2-[2-(4,7,10-tris-carboxymethyl-1,4,7,10-tetraazacyclododec-1-l)acetylamino]propionylamino}propionylamino)pentylcarbamoyl]heptanoylamino} pentyl)ureido]pe ntanedioic acid," 2010, Molecular Imaging and Contrast Agent Database (MICAD), pp. 2004-2013.
Chuu, et al., "Androgen suppresses proliferation of castrationresistant LNCaP 104-R2 prostate cancer cells through androgen receptor, Skp2, and c-Myc," 2011, Cancer Science, 102(11) pp. 2022-2028.
Cimitan, et al., "[18F]fluorocholine PET/CT imaging for the detection of recurrent prostate cancer at PSA relapse: experience in 100 consecutive patients," 2006, European Journal of Nuclear Medicine and Molecular Imaging, 33 pp. 1387-1398.
ClinicalTrials.gov, "PSMA-directed endoRadiotherapy of castration reSISTant Prostate Cancer (RESIST-PC). A Phase II clinical trial." Clinical Trial Results Website, Study Start Date Jul. 2017, Study Completetion Date Jan. 2020, 24 pages.
ClinicalTrials.gov, "99mTc-MIP-1404 for Imaging Prostate Cancer: Phase I Clinical Study to Assess the Image Quality of a Simplified Kit Formulation Compared to a Multi-step Preparation of 99mTc-MIP-1404," Identifier: NCT01654874, available online at: https://clinicaltrials.gov/ct2/show/NCT01654874.
ClinicalTrials.gov, "A Phase 1 Pilot Study of 99mTc-MIP-1404 SPECT/CT Imaging to Histology in Men With Prostate Cancer," Identifier: NCT01615406, available online at: https://clinicaltrials.gov/ct2/show/NCT01615406.

(56) References Cited

OTHER PUBLICATIONS

ClinicalTrials.gov, "A Phase 2 Study With MIP-1404 in Men With High-Risk PC Scheduled for RP and EPLND Compared to Histopathology," Identifier: NCT01667536, available online at: https://clinicaltrials.gov/ct2/show/NCT01667536?id=NCT01667536.
ClinicalTrials.gov, "Pilot Study of 99mTc-MIP-1404 SPECT/CT Imaging in Men With Prostate Cancer Undergoing Prostatectomy and/or Pelvic Lymph Node Dissection," Identifier: NCT01572701, available online at: https://clinicaltrials.gov/ct2/show/NCT01572701.
Colabufo, et al., "PB183, a sigma receptor ligand, as a potential PET probe for the imaging of prostate adenocarcinoma," 2008, Bioorganic & Medicinal Chemistry Letters, 18(6) pp. 1990-1993.
Cole, A., et al., "Cancer theranostics: the rise of targeted magnetic nanoparticles," 2011, Trends in Biotechnology, 29 (7) pp. 323-332.
Cunha, et al., "Tissue-specificity of prostate specific antigens: Comparative analysis of transcript levels in prostate and non-prostatic tissues," 2006, Cancer Letters, 236(2) pp. 229-238.
Dahl, et al., "Sarcosine induces increase in HER2/neu expression in androgen-dependent prostate cancer cells," 2011, Molecular Biology Reports, 38 pp. 4237-4243.
Davis, M., et al., "Crystal Structure of Prostate-Specific Membrane Antigen, A Tumor Marker and Peptidase," 2005, Proceedings of the National Academy of Sciences of the United States of America, 102(17) pp. 5981-5986.
De Santis, et al., "Role of Chemotherapy in Castration Resistant Prostate Cancer," 2012, English translation, Urologe, 51(1) pp. 39-43.
De Santis, et al., "Rolle der Chemotherapie beim kastrationsresistenten Prostatakarzinom," 2012, Urologe, 51 pp. 39-43.
Definition of ligand, Random House Kernerman Webster's College Dictionary, downloaded on Jan. 25, 2014 from http://www.thefreedictionary.com/ligand, 1 page.
Degrado, et al., "Synthesis and Evaluation of 18F-Labeled Choline Analogs as Oncologic PET Tracers," 2001, Journal of Nuclear Medicine, 42(12) pp. 1805-1814.
Degrado, et al., "Synthesis and Evaluation of 18F-labeled Choline as an Oncologic Tracer for Positron Emission Tomography: Initial Findings in Prostate Cancer," 2000, Cancer Research, 61(1) pp. 110-117.
Dimitrakopoulou-Strauss, et al., "PET Imaging of Prostate Cancer with 11C-Acetate," 2003, Nuclear Medicine, 44(4) pp. 556-558.
Divyya, et al., "GCPII modulates oxidative stress and prostate cancer susceptibility through changes in methylation of RASSF1, BNIP3, GSTP1 and Ec-SOD," 2013, Mol Biol Rep, 40 pp. 5541-5550.
DNA Interactive Agents, Chapter 6, pp. 386-485.
Drug Discovery General References pp. 98-184.
Drug Metabolism Chapters 7-8, pp. 486-592.
Dumas, et al., "Molecular Expression of PSMA mRNA and Protein in Primary Renal Tumors," 1999, International Journal of Cancer, 80(6) pp. 799-803.
Dusich, et al., "General Approach for the Preparation of Fluorescent PSMA/GCPII Inhibitors," 2006, Molecular Imaging. Abstract. Abstract ID: 470, Poster board space: 29. pp. 322-323.
Eder, et al., "Novel Preclinical and Radiopharmaceutical Aspects of [68Ga]Ga-PSMA-HBED-CC: A New PET Tracer for Imaging of Prostate Cancer," 2014, Pharmaceuticals, 7(7) pp. 779-796.
Eder, et al., "Pharmacokinetic Properties of Peptidic Radiopharmaceuticals: Reduced Uptake of (EH)3-Conjugates in Important Organs," 2013, Nuclear Medicine, 54(8) pp. 1-4.
Eder, et al., "Preclinical Evaluation of a Bispecific Low-Molecular HeterodimerTargeting Both PSMA and GRPR for Improved PET Imaging and Therapy of Prostate Cancer," 2014, The Prostate, 74(6) pp. 659-668.
Eder, et al., "PSMA as a target for radiolabelled small molecules," 2013, European Journal of Nuclear Medicine and Molecular Imaging, 40 pp. 819-823.
Eder, M., et al., "68Ga-complex Lipophilicity and the Targeting Property of a Urea-based PSMA Inhibitor for PET Imaging," 2012, Bioconjugate Chemistry, 23(4) pp. 688-697.
Eiber, et al., "68Ga-PSMA PET/MR with multimodality image analysis for primary prostate cancer," 2015, Abdom Imaging, 40(6) pp. 1769-1771.
Elsasser-Beile, et al., "A New Generation of Monoclonal and Recombinant Antibodies Against Cell-Adherent Prostate Specific Membrane Antigen for Diagnostic and Therapeutic Targeting of Prostate Cancer," 2006, The Prostate, 66(13) pp. 1359-1370.
Elsasser-Beile, et al., "PET Imaging of Prostate Cancer Xenografts with a Highly Specific Antibody against the Prostate-Specific Membrane Antigen," 2009, Journal of Nuclear Medicine, 50(4) pp. 606-611.
Elsasser-Beile, et al., "Targeted Therapies for Prostate Cancer Against the Prostate Specific Membrane Antigen," 2009, Current Drug Targets, 10(2) pp. 118-125.
El-Zaria, et al., "Preparation and evaluation of carborane-derived inhibitors of prostate specific membrane antigen (PSMA)," 2014, Dalton Transactions, 43 pp. 4950-4961.
Emmett, L. et al. Lutetium 177 PSMA radionuclide therapy for men with prostate cancer: a review of the current literature and discussion of practical aspects of therapy. J Med Radiat Sci. Mar. 2017;64(1):52-60. doi: 10.1002/jmrs.227.
Emonds, et al., "Do androgens control the uptake of 18F-FDG, 11C-choline and 11C-acetate in human prostate cancer cell lines?," 2011, European Journal of Nuclear Medicine and Molecular Imaging, 38(10) pp. 1842-1853.
Enzyme Inhibition, Chapter 5, pp. 286-385.
Enzymes, Chapter 4, pp. 186-285.
European Patent Application No. EP 14861854, by Endocyte, Inc. et al.; Partial Supplementary Search Report with Opinion dated May 19, 2017.
European Search Report in EP 18175078, completed Sep. 6, 2018.
European Search Report in EP 18175078.7 dated Sep. 14, 2018.
European Search Report in EP 18184296 dated Jan. 23, 2019.
European Search Report in EP 18184296 mailed Feb. 12, 2019.
European Search Report in EP 18203547 mailed Apr. 4, 2019.
European Search Report in EP 20180928.2, completed Dec. 7, 2020.
Evans, et al., "Noninvasive measurement of androgen receptor signaling with a positron-emitting radiopharmaceutical that targets prostate-specific membrane antigen," 2011, Proceedings of the National Academy of Sciences of the United States of America, 108(23) pp. 9578-9582.
Fair, et al., "Prostate-Specific Membrane Antigen," 1997, The Prostate, 32(2) pp. 140-148.
Fall, et al., "Prostate-Specific Antigen Levels as a Predictor of Lethal Prostate Cancer," 2007, Journal of the National Cancer Institute, 99(7) pp. 526-532.
Farokhzad, O., et al., "Nanoparticle-Aptamer Bioconjugates: A New Approach for Targeting Prostate Cancer Cells," 2004, Cancer Research, 64(21) pp. 7668-7672.
Fortmuller, et al., "Effective Targeting of Prostate Cancer by Lymphocytes Redirected by a PSMA x CD3 Bispecific Single-Chain Diabody," 2011, The Prostate, 71(6) pp. 588-596.
Fortuin, et al., "Value of PET/CT and MR Lymphography in Treatment of Prostate Cancer Patients With Lymph Node Metastases," 2012, International Journal of Radiation Oncology, Biology, Physics, 84(3) pp. 712-718.
Foss, C., et al. "Radiolabeled Small-molecule Ligands for Prostate-specific Membrane Antigen: In vivo Imaging in Experimental Models of Prostate Cancer," 2005, Clinical Cancer Research, 11(11) pp. 4022-4028.
Foss, et al., "GCPII Imaging and Cancer," 2012, Current Medicinal Chemistry, 19(9) pp. 1346-1359.
Foss, et al., "Synthesis and Validation of a Novel Small-Molecule Fluorescent Probe for PSMA Expression in Human Tumor Neovasculature," 2005, Abstract. Abstract ID: 362.
Franc, et al., "Detection and localization of carcinoma within the prostate using high resolution transrectal gamma imaging (TRGI) of monoclonal antibody directed at prostate specific membrane antigen

(56) References Cited

OTHER PUBLICATIONS (PSMA)—Proof of concept and initial imaging results," 2013, European Journal of Radiology, 82(11) pp. 1877-1884.
Frigerio, et al., "A single-chain fragment against prostate specific membrane antigen as a tool to build theranostic reagents for prostate cancer," 2013, European Journal of Cancer, 49(9) pp. 2223-2232.
Ghosh, et al., "Tumor Target Prostate Specific Membrane Antigen (PSMA) and its Regulation in Prostate Cancer," 2004, Journal of Cellular Biochemistry, 91(3) pp. 528-539.
Giovacchini, et al., "Predictive factors of [11C]choline PET/CT in patients with biochemical failure after radical prostatectomy," 2010, European Journal of Nuclear Medicine and Molecular Imaging, 37(2) pp. 301-309.
Gomez-Hens, A. and Aguilar-Caballos, M., "Long Wavelength Fluorophores: New Trends in Their Analytical Use," 2004, Trends in Analytical Chemistry, 23(2), pp. 127-136.
Goodman Jr., et al., "Interaction of prostate specific membrane antigen with clathrin and the adaptor protein complex-2," 2007, International Journal of Oncology, 31(5) pp. 1199-1203.
Graham, et al., "Radiofluorinated Derivatives of 2-(Phosphonomethyl)pentanedioic Acid as Inhibitors of Prostate Specific Membrane Antigen (PSMA) for the Imaging of Prostate Cancer," 2012.
Journal of Medicinal Chemistry, 55(22) pp. 9510-9520.
Grant, et al., "Prostate Specific Membrane Antigen (PSMA) Regulates Angiogenesis Independently of VEGF during Ocular Neovascularization," PLoS ONE 7(7): e41285.
Greene, T., and Wuts, P., "Protective Groups ion Organic Synthesis," 2d edition, John Wiley & Sons, Inc. New York (1991).
Gregor, et al., "Induction of autoantibodies to syngeneic prostate-specific membrane antigen by xenogeneic vaccination," 2005, International Journal of Cancer, 116(3) pp. 415-421.
Haberkorn, et al., "Mechanistic and high-throughput approaches for the design of molecular imaging probes and targeted therapeutics," 2014, Clinical and Translational Imaging, 2 pp. 33-41.
Haffner, et al., "Prostate-specific membrane antigen expression in the neovasculature of gastric and colorectal cancers," 2009, Human Pathology, 40(12) pp. 1754-1761.
Hain, et al., "Positron emission tomography for urological tumours," 2003, BJU International, 92(2) pp. 159-164.
Hamilou, Z. et al. Treatment of Castration-naive Metastatic Prostate Cancer. Eur Urol Focus. Dec. 2017;3(6):518-521. doi: 10.1016/j.euf.2018.02.004. Epub Feb. 27, 2018. PMID: 29500136.
Hara, et al., "11C-Choline and 2-Deoxy-2-[18F]Fluoro-D-Glucose in Tumor Imaging with Positron Emission Tomography," 2002, Molecular Imaging and Biology, 4(4) pp. 267-273.
Hara, et al., "Development of 18F-Fluoroethylcholine for Cancer Imaging with PET: Synthesis, Biochemistry, and Prostate Cancer Imaging," 2002, Journal of Nuclear Medicine, 43(2) pp. 187-199.
Hara, et al., "PET Imaging of Prostate Cancer Using Carbon-11-Choline," 1998, Journal of Nuclear Medicine, 39(6) pp. 990-995.
Harada, et al., "Preparation of Asymmetric Urea Derivatives that Target Prostate-Specific Membrane Antigen for SPECT Imaging," 2013, Journal of Medicinal Chemistry, 56(20) pp. 7890-7901.
Haseman, M., et al., "Capromab Pendetide Imaging of Prostate Cancer," 2009, Cancer Biotherapy and Radiopharmaceuticals, 15(2) pp. 131-140.
Heidenreich, A., "Immunotherapy For Metastatic Prostate Cancer—Do We Really Need This?," English translation (Abstract Only), 2012, Urologe, 51(1) pp. 32-38.
Heidenreich, A., "Immuntherapie beim metastasierten Prostatakarzinom—brauchen wir diese wirklich?," 2012, Urologe, 51 pp. 32-38.
Henne, W., et al., "Synthesis and activity of a folate peptide camptothecin prodrug," 2006, ScienceDirect, Bioorganic & Medical Chemistry Letters 16(20) pp. 5350-5355.
Henry, et al., "A Prostate-Specific Membrane Antigen-Targeted Monoclonal Antibody-Chemotherapeutic Conjugate Designed for the Treatment of Prostate Cancer," 2004, Cancer Research, 64(21) pp. 7995-8001.

Hillier, et al., "[131I] MIP-1466, a small molecule prostate-specific membrane antigen (PSMA) inhibitor for targeted radiotherapy of prostate cancer (PCa)," 2012, Journal of Nuclear Medicine, 53(1) pp. 170.
Hillier, et al., "123I-MIP-1072, a Small-Molecule Inhibitor of Prostate-Specific Membrane Antigen, Is Effective at Monitoring Tumor Response to Taxane Therapy," 2011, Journal of Nuclear Medicine, 52(7) pp. 1087-1093.
Hillier, et al., "99mTc-Labeled Small-Molecule Inhibitors of Prostate-Specific Membrane Antigen for Molecular Imaging of Prostate Cancer," 2013, Journal of Nuclear Medicine, 54(8) pp. 1369-1376.
Hillier, S., et al., "Preclinical Evaluation of Novel Glutamate-Urea-Lysine Analogues That Target Prostate-Specific Membrane Antigen as Molecular Imaging Pharmaceuticals for Prostate Cancer," 2009, Cancer Research, 69(17) pp. 6932-6940.
Hlouchova, et al., "Biochemical characterization of human glutamate carboxypeptidase III," 2007, Journal of Neurochemistry, 101(3) pp. 682-696.
Hlouchova, et al., "GCPII Variants, Paralogs and Orthologs," 2012, Current Medicinal Chemistry, 19(9) pp. 1316-1322.
Hlouchova, et al., "Structural insight into the evolutionary and pharmacologic homology of glutamate carboxypeptidases II and III," 2009, FEBS Journal, 276)16) pp. 4448-4462.
Ho, et al., "Molecular Imaging, Pharmacokinetics, and Dosimetry of 111In-AMBA in Human Prostate Tumor-Bearing Mice," 2011, Journal of Biomedicine and Biotechnology, Article ID 101497, 8 pages.
Hofman, M.S., et al., "[177Lu]Lu-PSMA-617 versus cabazitaxel in patients with metastatic castration-resistant prostate cancer (TheraP): a randomised, open-label, phase 2 trial," Published Online at The Lancet, Articles, Feb. 11, 2021, pp. 1-8.
Holland, et al., "89Zr-DFO-J591 for ImmunoPET of Prostate-Specific Membrane Antigen Expression In Vivo," 2010, Journal of Nuclear Medicine, 51(8) pp. 1293-1300.
Hong, et al., "Positron emission tomography imaging of prostate cancer," 2010, Amino Acids, 39(1) pp. 11-27.
Hospers, et al., "PET Imaging of Steroid Receptor Expression in Breast and Prostate Cancer," 2008, Current Pharmaceutical Design, 14(28) pp. 3020-3032.
Huang, et al., "Improving the Biodistribution of PSMA-Targeting Tracers With Highly Negatively Charged Linker," 2014, The Prostate, 74(7) pp. 702-713.
Huang, et al., "PSMA-Targeted Stably Linked 'Dendrimer-Glutamate Urea-Methotrexate' as a Prostate Cancer Therapeutic," 2014, Biomacromolecules, 15(3) pp. 915-923.
Humblet, et al., "High-affinity Near-infrared Fluorescent Small-molecule Contrast Agents for In Vivo Imaging of Prostate-specific Membrane Antigen," 2005, Molecular Imaging, 4(4) pp. 448-462.
Humblet, et al., "Multivalent Scaffolds for Affinity Maturation of Small Molecule Cell Surface Binders and Their Application to Prostate Tumor Targeting," 2009, Journal of Medicinal Chemistry, 52(2) pp. 544-550.
Humblet, V., et al., "An HPLC/mass spectrometry platform for the development of multimodality contrast agents and targeted therapeutics: prostate-specific membrane antigen small molecule derivatives," 2006, Contrast Media and Molecular Imaging, 1(5) pp. 196-211.
Husarik, et al., "Evaluation of [18F]-choline PET/CT for staging and restaging of prostate cancer," 2008, European Journal of Nuclear Medicine and Molecular Imaging, 35 pp. 253-263.
Hwang, et al., "Imaging Prostate Derived Tumors with PET and N-(3-[18F]Fluoropropyl)putrescine," 1990, Nuclear Medicine and Biology, 17(6) pp. 525-532.
Hwang, et al., "N-3-[18F]Fluoropropylputrescine as Potential PET Imaging Agent for Prostate and Prostate Derived Tumors," 1989, Journal of Nuclear Medicine, 30(7) pp. 1205-1210.
Igerc, et al., "The value of 18F-Choline PET/CT in patients with elevated PSA-level and negative prostate needle biopsy for localisation of prostate cancer," 2008, European Journal of Nuclear Medicine and Molecular Imaging, 35(5) pp. 976-983.
Ikotun, O.F., et al. Investigation of a Vitamin B12 Conjugate as a PET Imaging Probe. 2014, ChemMedChem, 9: 1244-1251.

(56) References Cited

OTHER PUBLICATIONS

Istard Posters, 2012, European Journal of Nuclear Medicine and Molecular Imaging, 39(2) pp. 304-353.
Jackson, et al., "Design, Synthesis, and Biological Activity of a Potent Inhibitor of the Neuropeptidase N-Acetylated α-Linked Acidic Dipeptidase," 1996, Journal of Medicinal Chemistry, 39(2) pp. 619-622.
Jackson, P. and Slusher, B., "Design of NAALADase Inhibitors: A Novel Neuroprotective Strategy," 2001, Current Medicinal Chemistry, 8(8) pp. 949-957.
Jadvar, et al., "Glucose Metabolism of Human Prostate Cancer Mouse Xenografts," 2005, Molecular Imaging, 4(2) pp. 91-97.
Jadvar, et al., "Imaging evaluation of prostate cancer with 18F-fluorodeoxyglucose PET/CT: utility and limitations," 2013, European Journal of Nuclear Medicine and Molecular Imaging, 40 (Suppl 1) pp. S5-S10.
Jadvar, et al., "Molecular imaging of prostate cancer with 18F-fluorodeoxyglucose PET," 2009, Nature Reviews Urology, 6(6) pp. 317-323.
Jadvar, et al., "Molecular Imaging of Prostate Cancer: PET Radiotracers," 2012, AJR, 199 pp. 278-291.
Jambor, et al., "Functional Imaging of Localized Prostate Cancer Aggressiveness Using 11C-Acetate PET/CT and 1H-MR Spectroscopy," 2010, Journal of Nuclear Medicine, 51(11) pp. 1676-1683.
James, S., "Urea Based Rhenium Tricarbonyl Dipeptide Compounds as Potential Radiopharmaceuticals for PSMA Imgaging," Poster. INOR 258, http://oasys2.confex.com/acs/7219nm/techprogram/P830271.html (2018) (1 page).
Jayaprakash, S., et al. "Design and Synthesis of a PSMA inhibitor-doxorubicin Conjugate for Targeted Prostate Cancer Therapy," 2006, ChemMedChem, 1(3) pp. 299-302.
Jemaa, et al., "A Comparison of the Biological Features of Prostate Cancer with (PSA+, PSMA+) Profile according to RKIP," 2013, BioMed Research International, 2013(12) Article ID 409179, 7 pages.
Jemaa, et al., "A novel regulation of PSMA and PSA expression by Q640X AR in 22Rv1 and LNCaP prostate cancer cells," 2013, Cell Biology International, 37(5) pp. 464-470.
Jemaa, et al., "Cellular distribution and heterogeneity of PSA and PSMA expression in normal, hyperplasia and human prostate cancer," 2013, La Tunisie Medicale, 91(7) pp. 458-463.
Jeong, et al., "Preparation of a Promising Angiogenesis PET Imaging Agent: 68Ga-Labeled c(RGDyK)-Isothiocyanatobenzyl-1,4,7-Triazacyclononane-1,4,7-Triacetic Acid and Feasibility Studies in Mice," 2008, The Journal of Nuclear Medicine, 49(5) pp. 830-836.
Kahn, et al., "111Indium-Capromab Pendetide in the Evaluation of Patients with Residual or Recurrent Prostate Cancer After Radical Prostatectomy," 1998, The Journal of Urology, 159(6) pp. 2041-2047.
Kairemo K. et al., Lu-177-PSMA treatment for metastatic prostate cancer-case examples of miracle responses, Urology Herald, 07.03. 2018, v. 6, No. 1, p. 65-75.
Kasperzyk, et al., "Prostate-Specific Membrane Antigen Protein Expression in Tumor Tissue and Risk of Lethal Prostate Cancer," Cancer Epidemiol Biomarkers Prev, 22(12) pp. 2354-2363.
Kasten, et al., "Targeting prostate cancer cells with PSMA inhibitor-guided gold nanoparticles," 2013, Bioorganic & Medicinal Chemistry Letters, 23(2) pp. 565-568.
Kaur, G., et al., "Biological evaluation of tubulysin A: a potential anticancer and antiangiogenic natural product," 2006, Biochemical Journal, 396(2) pp. 235-242.
Khreish, F. et al.225Ac-PSMA-617/1 77Lu-PSMA-617 tandem therapy of metastatic castration-resistant prostate cancer: pilot experience. European Journal of Nuclear Medicine and Molecular Imaging (2020) 47:721-728. https://doi.org/10.1007/s00259-019-04612-0.
Kim, et al., "Tribody: Robust Self-Assembled Trimeric Targeting Ligands with High Stability and Significantly Improved Target-Binding Strength," 2013, Biochemistry, 52(41) pp. 7283-7294.

Kinoshita, et al., "Expression of Prostate-Specific Membrane Antigen in Normal and Malignant Human Tissues," 2006, World Journal of Surgery, 30(4) pp. 628-636.
Klotz, L. "Cancer overdiagnosis and overtreatment," 2012, Current Opinion in Urology, 22(3) pp. 203-209.
Klusak, et al., "Reaction Mechanism of Glutamate Carboxypeptidase II Revealed by Mutagenesis, X-ray Crystallography, and Computational Methods," 2009, Biochemistry, 48(19) pp. 4126-4138.
Kosuri, et al., "Review of Salvage Therapy for Biochemically Recurrent Prostate Cancer: The Role of Imaging and Rationale for Systemic Salvage Targeted Anti-Prostate-SpecificMembrane Antigen Radioimmunotherapy," 2012, Advances in Urology, 2012(6) Article ID 921674, 8 pages.
Kothari, et al., "18F-labeled small molecule inhibitors of prostate specific membrane antigen (PSMA) for PET imaging of prostate cancer," 2012, Journal of Nuclear Medicine, 53(1) pp. 1721.
Kotzerke, et al., "PET for Prostate Cancer Imaging: Still a Quandary or the Ultimate Solution?," 2002, The Journal of Nuclear Medicine, 43(2) pp. 200-202.
Kovar, et al., "Pharmacokinetic and Biodistribution Assessment of a Near Infrared-Labeled PSMA-Specific Small Molecule in Tumor-Bearing Mice," 2014, Prostate Cancer, 2014 Article ID 104248, 10 pages.
Kozikowski, A., et al., "Design of Remarkably Simple, Yet Potent Urea-Based Inhibitors of Glutamate Carbozypeptidase II (NAALADase)," 2001, Journal of Medicinal Chemistry, 44(3) pp. 298-301.
Kozikowski, A., et al., "Synthesis of Urea-Based Inhibitors as Active Site Probes of Glutamate Carboxypeptidase II: Efficacy as Analgesic Agents," 2004, Journal of Medicinal Chemistry, 47(7) pp. 1729-1738.
Kratochwil, C et al. Targeted alpha-Therapy of Metastatic Castration-Resistant Prostate Cancer with 225Ac-PSMA-617: Swimmer-Plot Analysis Suggests Efficacy Regarding Duration of Tumor Control; J Nucl Med. 2018. vol. 59, No. 5, pp. 795-802, DOI: 10.2967/jnumed.117.203539, Jan. 11, 2018 (Jan. 11, 2018).
Kratochwil, C., et al., "[177Lu]Lutetium-labelled PSMA ligand-induced remission in a patient with metastatic prostate cancer," Eur J Nucl Med Mol Imaging, 2015, 42, 987-88.
Kratochwil, C., et al., "PSMA-Targeted Radionuclide Therapy of Metastatic Castration-Resistant Prostate Cancer with 177 Lu-Labeled PSMA-617," The Journal of Nuclear Medicine, Mar. 16, 2016, 57(8) pp. 1170-1176.
Kratochwil, et al. "225Ac-PSMA-617 for PSMA-Targeted a-Radiation Therapy of Metastatic Castration-Resistant Prostate Cancer." J Nucl Med 2016; 57:1941-1944. DOI: 10.2967/jnumed. 116.178673.
Krohn, et al., "[68Ga]PSMA-HBED uptake mimicking lymph node metastasis in coeliac ganglia: an important pitfall in clinical practice," 2015, European Journal of Nuclear Medicine and Molecular Imaging, 42(2) pp. 210-214.
Kularatne, S., et al., "Comparative Analysis of Folate Derived PET Imaging Agents with [18F]-2-Fluoro-2-deoxy-D-glucose Using Rodent Inflammatory Paw Model," 2013, Molecular Pharmaceutics, 10(8) pp. 3103-3111.
Kularatne, et al., "Design, Synthesis, and Preclinical Evaluation of Prostate-Specific Membrane Antigen Targeted 99mTc-Radioimaging Agents," 2009, Molecular Pharmaceutics, 6(3) pp. 790-800.
Kularatne, S., et al., "Prostate-specific membrane antigen targeted imaging and therapy of prostate cancer using a PSMA inhibitor as a homing ligand," 2009, Molecular Pharmaceutics, 6(3) pp. 780-789.
Kularatne, S., et al., "Synthesis and Biological Analysis of Prostate-Specific Membrane Antigen-Targeted Anticancer Prodrugs," 2010, Journal of Medicinal Chemistry, 53(21) pp. 7767-7777.
Kuru, et al., "MRI Navigated Stereotactic Prostate Biopsy," English Translation, 2012, Urologe, 51(1) pp. 50-56.
Kuru, et al., "MRT-navigierte stereotaktische Prostatabiopsie," 2012, Urologe, 51 pp. 50-56.
Kwee, et al., "18F-choline PET/CT imaging of RECIST measurable lesions in hormone refractory prostate cancer," 2009, Annals of Nuclear Medicine, 23 pp. 541-548.

(56) References Cited

OTHER PUBLICATIONS

Lambert, et al., "Molecular Evolution of the Transferrin Receptor/Glutamate Carboxypeptidase II Family," 2007, Journal of Molecular Evolution, 64(1) pp. 113-128.

Lange, P., "ProstaScint scan for staging prostate cancer," 2001, Urology, 57(3) pp. 402-406.

Lapi, et al., "Assessment of an 18F-Labeled Phosphoramidate Peptidomimetic as a New Prostate-Specific Membrane Antigen-Targeted Imaging Agent for Prostate Cancer," 2009, Journal of Nuclear Medicine, 50(12) pp. 2042-2048.

Larock, R., "Comprehensive Organic Transformations: A Guide to Functional Group Preparations," VCH Publishers, Inc. New York (1989).

Larson, S., et al., "Tumor Localization of 16β-18F-Fluoro-5α-Dihydrotestosterone Versus 18F-FDG in Patients with Progressive, Metastatic Prostate Cancer," 2004, Journal of Nuclear Medicine, 45(3) pp. 366-373.

Lau, J., "Bench to Bedside: Albumin Binders for Improved Cancer Radioligand Therapies," 2019, Bioconjugate Chemistry, 30, pp. 487-502.

Afshar-Oromieh, et al., "[68Ga]Gallium-labelled PSMA ligand as superior PET tracer for the diagnosis of prostate cancer: comparison with 18F-FECH," 2012, European Journal of Nuclear Medicine and Molecular Imaging, 39 pp. 1085-1086.

Afshar-Oromieh, et al., "Comparison of PET imaging with a 68Ga-labelled PSMA ligand and 18F-choline-based PET/CT for the diagnosis of recurrent prostate cancer," 2014, European Journal of Nuclear Medicine and Molecular Imaging, 41(1) pp. 11-20.

Afshar-Oromieh, et al., "Comparison of PET/CT and PET/MRI hybrid systems using a 68Ga-labelled PSMA ligand for the diagnosis of recurrent prostate cancer: initial experience," 2014, European Journal of Nuclear Medicine and Molecular Imaging, 41(5) pp. 887-897.

Afshar-Oromieh, et al., "PET imaging with a [68Ga]gallium-labelled PSMA ligand for the diagnosis of prostate cancer: biodistribution in humans and first evaluation of tumour lesions," 2013, European Journal of Nuclear Medicine and Molecular Imaging, 40 pp. 486-495.

Afshar-Oromieh, et al., "PET/MRI with a 68Ga-PSMA ligand for the detection of prostate cancer," 2013, European Journal of Nuclear Medicine and Molecular Imaging, 40(10) pp. 1629-1630.

Afshar-Oromieh, et al., "The diagnostic value of PET/CT imaging with the 68Ga-labelled PSMA ligand HBED-CC in the diagnosis of recurrent prostate cancer," 2015, European Journal of Nuclear Medicine and Molecular Imaging, 42 pp. 197-209.

Aggarwal, et al., "A Dimeric Peptide That Binds Selectively to Prostate-Specific Membrane Antigen and Inhibits its Enzymatic Activity," 2006, Cancer Research, 66(18) pp. 9171-9177.

Ahmadzadehfar, H. et al. "Early side effects and first results of radioligand therapy with (177)Lu-DKFZ-617 PSMA of castrate-resistant metastatic prostate cancer: a two-centre study." EJNMMI Res. Dec. 2015;5(1):114. doi: 10.1186/s13550-015-0114-2. Epub Jun. 20, 2015.

Ahmadzadehfar, H., et al., "Overall survival and response pattern of castration-resistant metastatic prostate cancer to multiple cycles of radioligand therapy using [177Lu] Lu-PSMA-617," European Journal of Nuclear Medicine and Molecular Imaging, 2017, 44(9) pp. 1448-1454.

Alt, et al., "High-Resolution Animal PET Imaging of Prostate Cancer Xenografts with Three Different 64Cu-Labeled Antibodies against Native Cell-Adherent PSMA," 2010, The Prostate, 70(13) pp. 1413-1421.

Ananias, et al., "Expression of the Gastrin-Releasing Peptide Receptor, the Prostate Stem Cell Antigen and the Prostate-Specific Membrane Antigen in Lymph Node and Bone Metastases of Prostate Cancer," 2009, The Prostate, 69(10) pp. 1101-1108.

Anderson, et al., "Substrate specificity of prostate-specific membrane antigen," 2007, Bioorganic & Medicinal Chemistry, 15(21) pp. 6678-6686.

Antunes, et al., "PGC and PSMA in prostate cancer diagnosis: tissue analysis from biopsy samples," 2013, International Brazilian Jurnal of Urology, 39(5) pp. 649-656.

Armor, et al., "A comparison of 2D and 3D regions within the same patient to derive organ and tissue kinetics," 2012, Journal of Nuclear Medicine, 53(1) pp. 13.

Bacich, et al., "Cloning, expression, genomic localization, and enzymatic activities of the mouse homolog of prostate-specific membrane antigen/NAALADase/folate hydrolase," 2001, Mammalian Genome, 12 pp. 117-123.

Baiz, et al., "Synthesis and Characterization of a Novel Prostate Cancer-Targeted Phosphatidylinositol-3-kinase Inhibitor Prodrug," 2012, Journal of Medicinal Chemistry, 55(18 pp. 8038-8046.

Banerjee, et al., "64Cu-Labeled Inhibitors of Prostate-Specific Membrane Antigen for PET Imaging of Prostate Cancer," 2014, Journal of Medicinal Chemistry, 57(6) pp. 2657-2669.

Banerjee, et al., "68Ga-Labeled Inhibitors of Prostate-Specific Membrane Antigen (PSMA) for Imaging Prostate Cancer," 2010, Journal of Medicinal Chemistry, 53(14) pp. 5333-5341.

Banerjee, et al., "A Modular Strategy to Prepare Multivalent Inhibitors of Prostate-Specific Membrane Antigen (PSMA)," 2011, Oncotarget, 2(12) pp. 1244-1253.

Banerjee, et al., "Effect of Chelators on the Pharmacokinetics of 99mTc-Labeled Imaging Agents for the Prostate- Specific Membrane Antigen (PSMA)," 2013, Journal of Medicinal Chemistry, 6(15)5 pp. 6108-6121.

Banerjee, S., et al., "Sequential SPECT and Optical Imaging of Experimental Models of Prostate Cancer with a Dual Modality Inhibitor of the Prostate-Specific Membrane Antigen," 2011, Angewandte Chemie International Edition, 50(39) pp. 9167-9170.

Banerjee, S., et al., "Synthesis and Evaluation of Technetium-99m- and Rhenium-Labeled Inhibitors of the Prostate-Specific Membrane Antigen (PSMA)," 2008, Journal of Medicinal Chemistry, 51(15) pp. 4504-4517.

Barinka, et al., "A high-resolution structure of ligand-free human glutamate carboxypeptidase II," 2007, Acta Crystallographica, 63(3) pp. 150-153.

Barinka, et al., "Interactions between Human Glutamate Carboxypeptidase II and Urea-Based Inhibitors: Structural Characterization," 2008, Journal of Medicinal Chemistry, 51 pp. 7737-7743.

Barinka, et al., "Structural Insight into the Pharmacophore Pocket of Human Glutamate Carboxypeptidase II," 2007, Journal of Medicinal Chemistry, 50(14) pp. 3267-3273.

Barrett, et al., "First-in-Man Evaluation of 2 High-Affinity PSMA-Avid Small Molecules for Imaging Prostate Cancer," 2013, Journal of Nuclear Medicine, 54(3) pp. 380-387.

Beheshti, et al., "Prostate Cancer: Role of SPECT and PET in Imaging Bone Metastases," 2009, Seminars in Nuclear Medicine, 39(6) pp. 396-407.

Belloli, et al., "Characterization of preclinical models of prostate cancer using PET-based molecular imaging," 2009, European Journal of Nuclear Medicine and Molecular Imaging, 36 pp. 1245-1255.

Benesova et al., "Linker Modification Strategies To Control the Prostate-Specific Membrane Antigen (PSMA)—Targeting and Pharmacokinetic Properties of DOTA-Conjugated PSMA Inhibitors," J Med Chem. 59(5):1761-75 (2016).

Benesova, M. et al. "Preclinical Evaluation of a Tailor-Made DOTA-Conjugated PSMA Inhibitor with Optimized Linker Moiety for Imaging and Endoradiotherapy of Prostate Cancer." J Nucl Med. Jun. 2015;56(6):914-20. doi: 10.2967/jnumed.114.147413. Epub Apr. 16, 2015.

Bennett, V. and Simmons, M., "Analysis of fluorescently labeled substance P analogs: binding, imaging and receptor activation," 2001, BMC Chemical Biology, 1:1. doi:10.1186/1472-6769-1-1.

Bostwick, et al., "Prostate Specific Membrane Antigen Expression in Prostatic Intraepithelial Neoplasia and Adenocarcinoma," 1998, Cancer, 82(11) pp. 2256-2261.

Bouchelouche, et al., "'Image and treat': an individualized approach to urological tumors," 2010, Current Opinion in Oncology, 22(3) pp. 274-280.

(56) References Cited

OTHER PUBLICATIONS

Bouchelouche, et al., "Imaging Prostate Cancer: An Update on Positron Emission Tomography and Magnetic Resonance Imaging," 2010, Current Urology Reports, 11 pp. 180-190.
Bouchelouche, et al., "PET/CT Imaging and Radioimmunotherapy of Prostate Cancer," 2011, Seminar in Nuclear Medicine, 41(1) pp. 29-44.
Bouchelouche, et al., "Prostate Specific Membrane Antigen—A Target for Imaging and Therapy with Radionuclides," 2010, Discovery Medicine, 9(44) pp. 55-61.
Bouchelouche, K., et al., "Positron emission tomography/computed tomography and radioimmunotherapy of prostate cancer," Current Opinion in Oncology, 21(5) pp. 469-474.
Brauer, A. et al., "177Lu-PSMA-617 radioligand therapy and outcome in patients with metastasized castration-resistant prostate cancer," European Journal of Nuclear Medicine and Molecular Imaging, 2017, 44(10) pp. 1663-1670.
Bzdega, et al., "The cloning and characterization of a second brain enzyme with NAAG peptidase activity," 2004, Journal of Neurochemistry, 89(3) pp. 627-635.
Ceci, et al., "11C-Choline PET/CT in patients with hormone-resistant prostate cancer showing biochemical relapse after radical prostatectomy," 2013, European Journal of Nuclear Medicine and Molecular Imaging, 40(2) pp. 149-155.
Chandran, et al., "Characterization of a targeted nanoparticle functionalized with a urea-based inhibitor of prostate-specific membrane antigen (PSMA)," 2008, Cancer Biology & Therapy, 7(6) pp. 974-982.
Chang, et al., "Five Different Anti-Prostate-specific Membrane Antigen (PSMA) Antibodies Confirm PSMA Expression in Tumor-associated Neovasculature," 1999, Cancer Research, 59(13) pp. 3192-3198.
Chang, et al., "The clinical role of prostate-specific membrane antigen (PSMA)," 2002, Urologic Oncology, 7(1) pp. 7-12.
Chatalic, K. et al. Towards Personalized Treatment of Prostate Cancer: PSMA I&T, a Promising Prostate-Specific Membrane Antigen-Targeted Theranostic Agent. Theranostics. 2016; 6(6): pp. 849-861.
Chen, et al., "2-(3-{1-Carboxy-5-[(6-[18F]Fluoro-Pyridine-3-Carbonyl)-Amino]-Pentyl}-Ureido)-Pentanedioic Acid, [18F]DCFPyL, a PSMA-Based PET Imaging Agent for Prostate Cancer," 2011, Clinical Cancer Research, 17(24) pp. 7645-7653.
Chen, et al., "A low molecular weight PSMA-based fluorescent imaging agent for cancer," 2009, Biochemical and Biophysical Research Communications, 390(3) pp. 624-629.
Chen, et al., "PSMA-Targeted Theranostic Nanoplex for Prostate Cancer Therapy," 2012, ACS Nano, 6(9) pp. 7752-7762.
Chen, et al., "Synthesis and Biological Evaluation of Low Molecular Weight Fluorescent Imaging Agents for the Prostate-Specific Membrane Antigen,"2012, Bioconjugate Chemisty, 23(12) pp. 2377-2385.
Chen, Y., et al., "Radiohalogenated Prostate-Specific Membrane Antigen (PSMA)-Based Ureas as Imaging Agents for Prostate Cancer," 2008, Journal of Medicinal Chemistry, 51(24), pp. 7933-7943.
Chopra, A., "68Ga-Labeled 2-{3-[5-(7-{1-benzyloxycarbonyl-5-[2-(4,7,10-triscarboxymethyl-1,4,7,10-tetraazacyclododec-1-1)acetylamino]pentylcarbamoyl}-heptanoylamino)-1-carboxypentyl]ureido}pentanedioic acid," 2010, Molecular Imaging and Contrast Agent Database (MICAD), pp. 2004-2013.
Leek, et al., "Prostate-specific membrane antigen: evidence for the existence of a second related human gene," 1995, British Journal of Cancer, 72 pp. 583-588.
Lees, et al., "Active surveillance in prostate cancer: patient selection and triggers for intervention," 2012, Current Opinion in Urology, 22(3) pp. 210-215.
Lesche, et al., "Preclinical evaluation of BAY 1075553, a novel 18F-labelled inhibitor of prostate-specific membrane antigen for PET imaging of prostate cancer," 2014, European Journal of Nuclear Medicine and Molecular Imaging, 41 pp. 89-101.

Liu, et al., "A targeted low molecular weight near-infrared fluorescent probe for prostate cancer," 2010, Bioorganic & Medicinal Chemistry Letters, 20(23) pp. 7124-7126.
Liu, et al., "C-11 Choline PET/CT Imaging for Differentiating Malignant From Benign Prostate Lesions," 2008, Clinical Nuclear Medicine, 33(10) pp. 671-676.
Liu, et al., "Constitutive and Antibody-induced Internalization of Prostate-specific Membrane Antigen," 1998, Cancer Research, 58(18) pp. 4055-4060.
Liu, et al., "Functional prostate-specific membrane antigen is enriched in exosomes from prostate cancer cells," 2014, International Journal of Oncology, 44(3) pp. 918-922.
Liu, et al., "Prolonged androgen deprivation leads to downregulation of androgen receptor and prostate-specific membrane antigen in prostate cancer cells," 2012, International Journal of Oncology, 41(6) pp. 2087-2092.
Liu, et al., "Pseudoirreversible Inhibition of Prostate-Specific Membrane Antigen by Phosphoramidate Peptidomimetics," 2008, Biochemistry, 47(48) pp. 12658-12660.
Liu, et al., "Targeting prostate cancer cells with a multivalent PSMA inhibitor-guided streptavidin conjugate," 2012, Bioorganic & Medicinal Chemistry Letters, 22(12) pp. 3931-3934.
Liu, M., et al., "Synthesis and Biological Evaluation of Diethylenetriamine Pentaacetic acid-Polyethylene Glycol Folate: A new Folate-Derived, 99mTc-Based Radiopharmaceutical," 2005, Bioconjugate Chemistry, 16(5) pp. 1126-1132.
Lord, et al., "18F-Fluorocholine integrated PET/MRI for the initial staging of prostate cancer," 2011, European Journal of Nuclear Medicine and Molecular Imaging, 38 pp. 2288.
Lu, G., et al., "Synthesis and SAR of 99mTc/Re-labeled small molecule prostate specific membrane antigen inhibitors with novel polar chelates," 2013, Bioorganic and Medicinal Chemistry Letters, 23(5) pp. 1557-1563.
Luboldt, et al., "Prostate Carcinoma: Diffusion-weighted Imaging as Potential Alternative to Conventional MR and 11C-Choline PET/CT for Detection of Bone Metastases," 2008, Radiology, 249(3) pp. 1017-1025.
Lupold, S., et al., "Identification and Characterization of Nuclease-stabilized RNA Molecules that Bind Human Prostate Cancer Cells via the Prostate-specific Membrane Antigen," 2002, Cancer Research, 62(14) pp. 4029-4033.
Lutje, et al., "Dual-Modality Image-Guided Surgery of Prostate Cancer with a Radiolabeled Fluorescent Anti-PSMA Monoclonal Antibody," 2014, Journal of Nuclear Medicine, 55(6) pp. 995-1001.
Lutje, et al., "Prospects in Radionuclide Imaging of Prostate Cancer," 2012, The Prostate, 72(11) pp. 1262-1272.
Lymperis et al., "Radiometal-Dependent Biological Profile of the Radiolabeled Gastrin-Releasing Peptide Receptor Antagonist SB3 in Cancer Theranostics: Metabolic and Biodistribution Patterns Defined by Neprilysin," Bioconjug Chem. 29(5):1774-84 (2018).
Majer, P. et al. Discovery of Orally Available Prodrugs of the Glutamate Carboxypeptidase II (GCPII) Inhibitor 2-Phosphonomethylpentanedioic Acid (2-PMPA). Journal of Medicinal Chemistry, 2016. 59 (6), pp. 2810-2819. DOI: 10.1021/acs.jmedchem.6b00062.
Majer, P., et al., "Synthesis and Biological Evaluation of Thiol-Based Inhibitors of Glutamate Carboxypeptidase II: Discovery of an Orally Active GCP II Inhibitor," 2003, Journal of Medicinal Chemistry, 46(10) pp. 1989-1996.
Malik, et al., "One pot radiofluorination of a new potential PSMA ligand [Al18F]NOTA-DUPA-Pep," 2012, Journal of Labelled Compounds and Radiopharmaceuticals, 55(9) pp. 320-325.
Malik, et al., "Radiosynthesis of a new PSMA targeting ligand ([18F]FPy-DUPA-Pep)," 2011, Applied Radiation and Isotopes, 69(7) pp. 1014-1018.
Mannweiler, et al., "Heterogeneity of Prostate-Specific Membrane Antigen (PSMA) Expression in Prostate Carcinoma with Distant Metastasis," 2009, Pathology and Oncology Research, 15(2) pp. 167-172.
Maresca, et al., "Influence of functionalized chelators on affinity and pharmacokinetics of 99mTc(CO)3-labeled small molecules targeting prostate specific membrane antigen (PSMA)," 2010, Journal of Nuclear Medicine, 51(2) pp. 250.

(56) References Cited

OTHER PUBLICATIONS

Maresca, K., et al., "A Series of Halogenated Heterodimeric Inhibitors of Prostate Specific Membrane Antigen (PSMA) as Radiolabeled Probes for Targeting Prostate Cancer," 2009, Journal of Medicinal Chemistry, 52(2) pp. 347-357.
Maresca, K., et al., "Molecular targeting of prostate cancer with small molecule inhibitors of prostate specific membrane antigen (PSMA)," 2007, Journal of Nuclear Medicine, 48 (Supplement 2 ).
Martin, P., et al., "A New Access to 2'-O-Alkylated Ribonucleosides and Properties of 2'-O-Alkylated Oligoribonucleotides," 1995, Helvetica Chimica Acta, 78(2) pp. 486-504 and Abstract.
Matthies, et al., "Imaging of prostate cancer metastases with 18F-fluoroacetate using PET/CT," 2004, European Journal of Nuclear Medicine and Molecular Imaging, 31 pp. 797.
Mcbride, et al., "Radiofluorination using aluminum-fluoride (Al18F)", 2013, EJNMMI Research, 3(36) pp. 1-11.
Mcnamara, J., et al., "Cell Type Specific Delivery of siRNAs with Aptamer-siRNA Chimeras," 2006, Nature Biotechnolgy, 24(8) pp. 1005-1015.
Mease, et al., "PET Imaging in Prostate Cancer: Focus on Prostate-Specific Membrane Antigen," 2013, Current Topics in Medicinal Chemistry, 13(8) pp. 951-962.
Mease, R., "General Approach for the Preparation of Fluorescent PSMA GCPII Inhibitors", Abstract ID: 470 Poster board space: 29, Molecular Imaging, vol. 5, No. 3, (Jul. 2006), 322-323.
Mease, R., et al., "N-[N-[(S)-1,3-Dicarboxypropyl]Carbamoyl]-4-[18F]Fluorobenzyl-LCysteine, [18F]DCFBC: A New Imaging Probe for Prostate Cancer," 2008, Clinical Cancer Research, 14(10) pp. 3036-3043.
Meighan, et al., "Recombinant Glutamate Carboxypeptidase II (Prostate Specific Membrane Antigen-PSMA)—Cellular Localization and Bioactivity Analyses," 2003, Journal of Protein Chemistry, 22(4) pp. 317-326.
Meinenhofer, et al., "Solid-Phase Synthesis with Attachment of Peptide to Resin through an Amino Acid Side Chain: [8-Lysine]-Vasopressin," 1971, Proceedings of the National Academy of Sciences of the United States of America, 68(5) pp. 1006-1009.
Meinhardt, et al., "Laparoscopic Sentinel Lymph Node Biopsy for Prostate Cancer: The Relevance of Locations Outside the Extended Dissection Area," 2011, Prostate Cancer, 2012 Article ID 751753, 4 pages.
Melby, E., et at., "Entry of Protein Toxins in Polarized Epithelial Cells," Cancer Research, 1993, 53(8) pp. 1755-1760.
Mertens, et al., "PET with 18F-labelled choline-based tracers for tumour imaging: a review of the literature," 2010, European Journal of Nuclear Medicine and Molecular Imaging, 37 pp. 2188-2193.
Mesters, J., et al., "Structure of Glutamate Carboxypeptidase II, a Drug Target in Neuronal Damage and Prostate Cancer," 2006, The EMBO Journal, 25(6) pp. 1375-1384.
Mhawech-Fauceglia, et al., "Prostate-specific membrane antigen (PSMA) protein expression in normal and neoplastic tissues and its sensitivity and specificity in prostate adenocarcinoma: an immunohistochemical study using mutiple tumour tissue microarray technique," 2007, Histopathology, 50(4) pp. 472-483.
Mier, W., et al., "Conjugation of DOTA Using Isolated Phenolic Active Esters: The Labeling and Biodistribution of Albumin as Blood Pool Marker," 2005, Bioconjugate Chemistry, 16(1) pp. 237-240.
Milowsky, et al., "Phase I Trial of Yttrium-90-Labeled Anti-Prostate-Specific Membrane Antigen Monoclonal Antibody J591 for Androgen-Independent Prostate Cancer," 2004, Journal of Clinical Oncology, 22(13) pp. 2522-2531.
Minner, et al., "High Level PSMA Expression Is Associated With Early PSA Recurrence in Surgically Treated Prostate Cancer," 2011, The Prostate, 71(3) pp. 281-288.
Mlcochova, et al., "Mapping of the active site of glutamate carboxypeptidase II by site-directed mutagenesis," 2007, FEBS Journal, 274 pp. 4731-4741.
Moltzahn, et al., "Die ossäre Metastasierung des Prostatakarzinoms," 2012, Urologe, 51 pp. 20-26.

Moltzhan, et al., "Bone Metastasis in Prostate Cancer," English translation, 2012, Urologe, 51(1) pp. 20-26.
Morris, et al., "11C-acetate PET imaging in prostate cancer," 2007, European Journal of Nuclear Medicine and Molecular Imaging, 34 pp. 181-184.
Muller, C., et al., "Synthesis and in Vitro/in Vivo Evaluation of Novel 99mTc(CO)3-Folates," 2006, Bioconjugate Chemistry, 17(3) pp. 797-806.
Murphy, et al., "Current Evaluation of the Tissue Localization and Diagnostic Utility of Prostate Specific Membrane Antigen," 1998, Cancer, 83(11) pp. 2259-2269.
Nan, F., et al., "Dual Function Glutamate-Related Ligands: Discovery of a Novel, Potent Inhibitor of Glutamate Carboxypeptidase II Possessing mGluR3 Agonist Activity," 2000, Journal of Medicinal Chemistry, 43(5) pp. 772-774.
Reske, et al., "Advancement of PET and PET/CT in Prostate Carcinoma," English translation, 2006, Urologe, 45(6) pp. 707-714.
Reske, et al., "Nuklearmedizinische Diagnostik beim Prostatakarzinom," 2007, Urologe, 46 pp. 1485-1499.
Reske, et al., "PET and PET/CT in Relapsing Prostate Carcinoma," English translation, 2006, Urologe, 45(10) pp. 1240-1250.
Reske, et al., "PET und PET/CT in der Rezidivdiagnostik des Prostatakarzinoms," 2006, Urologe, 45 pp. 1240-1250.
Reske, et al., "Weiterentwicklung der PET und des PET/CT beim Prostatakarzinom," 2006, Urologe, 45 pp. 707-714.
Rinnab, et al., "[11C]Choline PET/CT for Targeted Salvage Lymph Node Dissection in Patients with Biochemical Recurrence after Primary Curative Therapy for Prostate Cancer," 2008, Urology International, 81 pp. 191-197.
Rinnab, et al., "[11C]choline PET/CT in prostate cancer patients with biochemical recurrence after radical prostatectomy," 2009, World Journal of Urology, 27 pp. 619-625.
Rinnab, L., et al., "Evaluation of [11C]-choline positron-emission/computed tomography in patients with increasing prostate-specific antigen levels after primary treatment for prostate cancer," 2007, BJU International, 100(4), pp. 786-793.
Rioja, et al., "Role of positron emission tomography in urological oncology," BJU International, 106(11) pp. 1578-1593.
Ristau, et al., "The prostate-specific membrane antigen: Lessons and current clinical implications from 20 years of research," 2014, Urologic Oncology: Seminars and Original Investigations, 32(3) pp. 272-279.
Roethke, M., et al. "Potenziale der PET/MRT in der Diagnostik des Prostatakariznoms," 2013, Radiologe, 53(8) pp. 676-681.
Roethke, et al., "Hyrbid Positron Emission Tomography-Magnetic Resonance Imaging with Gallium 68 Prostate-specific Membrane Antigen Tracer: A Next Step for Imaging of Recurrent Prostate Cancer-Preliminary Results," 2013, European Urology, 64(5) pp. 862-864.
Rong, et al., "Molecular Modeling of the Interaction of Glutamate Carboxypeptidase II with Its Potent NAAG-Based Inhibitors," 2002, Journal of Medicinal Chemistry, 45(19) pp. 4140-4152.
Rosar, F. et al. Molecular imaging and biochemical response assessment after a single cycle of [225Ac]Ac-PSMA-617/[177Lu]LuPSMA-617 tandem therapy in mCRPC patients whohave progressed on [177Lu]Lu-PSMA-617 monotherapy. Theranostics. 2021; 11(9): 4050-4060. doi: 10.7150/thno.56211.
Rosenthal, S., et al., "Utility of Capromab Pendetide (ProstaScint) Imaging in the Management of Prostate Cancer," 2001, Techniques in Urology, 7(1) pp. 27-37.
Rossi et al., "N-Nmoc-L-glutamate, a new caged glutamate with high chemical stability and low pre-photolysis activity," J Biol Chem. 272(52):32933-9 (1997).
Roy, J., et al., "DUPA Conjugation of a Cytotoxic Indenoisoquinoline Topoisomerase I Inhibitor for Selective Prostate Cancer Cell Targeting," 2015, Journal of Medicinal Chemistry, 58(7) pp. 3094-3103.
Rybalov, et al., "Impact of total PSA, PSA doubling time and PSA velocity on detection rates of 11C-Choline positron emission tomography in recurrent prostate cancer," 2013, World Journal of Urology, 31(2) pp. 319-323.
Sacha, et al., "Expression of Glutamate Carboxypeptidase II in Human Brain," 2007, Neuroscience, 144(4) pp. 1361-1372.

(56) References Cited

OTHER PUBLICATIONS

Sartor, O. et al., "Lutetium-177-PSMA-617 for Metastatic Castration-Resistant Prostate Cancer," The New England Journal of Medicine, Jun. 23, 2021, pp. 1-13.

Sathekge, M., et al., "225Ac-PSMA-617 in chemotherapy-naïve patients with advanced prostate cancer: a pilot study," European Journal of Nuclear Medicine and Molecular Imaging, Springer Berlin Heidelberg, Sep. 19, 2018, 46(1) pp. 129-138.

Scattoni, et al., "Detection of Lymph-Node Metastases with Integrated [11C]Choline PET/CT in Patients with PSA Failure after Radical Retropubic Prostatectomy: Results Confirmed by Open Pelvic-Retroperitoneal Lymphadenectomy," 2007, European Urology, 52(2) pp. 423-429.

Schafer, et al., "A dimerized urea-based inhibitor of the prostate-specific membrane antigen for 68Ga-PET imaging of prostate cancer," 2012, EJNMMI Research, 2(1) pp. 23.

Scheffel, et al., "PET Imaging of GRP Receptor Expression in Prostate Cancer," 2004, The Journal of Nuclear Medicine, 45(8) pp. 1277-1278.

Scher, B., et al., "Value of 11C-choline PET and PET/CT in patients with suspected prostate cancer," 2007, European Journal of Nuclear Medicine and Molecular Imaging, 34 pp. 45-53.

Scher, et al., "PET/CT imaging of recurrent prostate cancer," 2008, European Journal of Nuclear Medicine and Molecular Imaging, 35 pp. 5-8.

Schulke, N., et al., "The homodimer of prostate-specific membrane antigen is a functional target for cancer therapy," 2003, Proceedings of the National Academy of Sciences of the United States of America, 100(22) pp. 12590-12595.

Schuster, D., et al., "Initial Experience with the Radiotracer Anti-1-Amino-3-18F-Fluorocyclobutane-1-Carboxylic Acid with PET/CT in Prostate Carcinoma," 2007, Journal of Nuclear Medicine, 48(1) pp. 56-63.

Shvarts, et al., "Positron Emission Tomography in Urologic Oncology," 2002, Cancer Control, 9(4) pp. 335-342.

Silver, et al., "Prostate-specific Membrane Antigen Expression in Normal and Malignant Human Tissues," 1997, Clinical Cancer Research, 3(1) pp. 81-85.

Silvola, J., et al., "Al18F-NOTA-Folate Accumulates in Atherosclerotic Plaques and Can be Detected by PET/CT", Poster presented Nov, 7, 2015 in Orlando, FL at the 2015 American Heart Association, Resuscitation Science Symposium (http://newsroom_heart.org/events/scientific-sessions-2015-newsroom- 2942760).

Simone, et al., "What's in a Label? Radioimmunotherapy for Metastatic Prostate Cancer," 2013, Clinical Cancer Research, 19(18) pp. 4908-4910.

Slusher, et al., "Immunocytochemical Localization of the N-Acetyl-Aspartyl-Glutamate (NAAG) Hydrolyzing Enzyme N-Acetylated α-Linked Acidic Dipeptidase (NAALADase)," 1992, The Journal of Comparative Neuorology, 315(2) pp. 217-229.

Slusher, et al., "Selective inhibition of NAALADase, which converts NAAG to glutamate, reduces ischemic brain injury," 1999, Nature Medicine, 5(12) pp. 1396-1402.

Soloviev, et al., "PET imaging with 11C-acetate in prostate cancer: a biochemical, radiochemical and clinical perspective," 2008, European Journal of Nuclear Medicine and Molecular Imaging, 35(5) pp. 942-949.

Spahn, et al., "How Should Hormone Therapy for Castration-Resistant Prostate Cancer be Continued?," English translation, 2012, Urologe, 51(1) pp. 15-19.

Spahn, et al., "Wie soll die Hormontherapie beim kastrationsresistenten Prostatakarzinom fortgeführt werden?," 2012, Urologe, 51 pp. 15-19.

Supplemental European Search Report, prepared for EP Application No. 19789294, mailed Nov. 26, 2021.

Sweat, et al., "Prostate-Specific Membrane Antigen Expression is Greatest in Prostate Adenocarcinoma and Lymph Node Metastases," 1998, Urology, 52(4) pp. 637-640.

Tang, et al., "Prostate targeting ligands based on N-acetylated α-linked acidic dipeptidase," 2003, Biochemical and Biophysical Research Communications, 307(1) pp. 8-14.

Tang, et al., "Updated Application of Prostate-Specific Membrane Antigen to the Diagnosis and Treatment of Prostate Cancer," 2008, National Journal of Andrology, 14(1) pp. 79-82.

Tasch, J., et al., "A Unique Folate Hydrolase, Prostate-Specific Membrane Antigen (PSMA): A Target for Immunotherapy?" 2001, Critical Reviews in Immunology, 21(1-3) pp. 249-261.

Taylor, et al., "Prostate Cancer Targeting Motifs: Expression of anb3, Neurotensin Receptor 1,Prostate Specific Membrane Antigen, and Prostate Stem Cell Antigen in Human Prostate Cancer Cell Lines and Xenografts," 2012, The Prostate, 72(5) pp. 523-532.

Tehrani, O., et al., "Tumor Imaging Using 1-(2'-deoxy-2'-18F-Fluoro-β-D-Arabinofuranosyl) Thymine and PET," 2007, Journal of Nuclear Medicine, 48(9) pp. 1436-1441.

Testa, et al., "Prostate Cancer: Sextant Localization with MR Imaging, MR Spectroscopy, and 11C-Choline PET/CT," 2007, Radiology, 244(3).

Thalmann, G., "Advanced Prostate Cancer," English translation, 2012, Urologe, 51(1) pp. 7.

Thalmann, G., "Fortgeschrittenes Prostatakarzinom," 2012, Urologe, 51 pp. 7.

The Chemistry of Oxygen and Sulfur, https://web.archive.org/web/20080625021202/http://chemed.chem.purdue.edu/genchem/topicreview/bp/ch10/group6.php#oxygen (date Jun. 25, 2008) accessed online on May 31, 2019, 21 pages (Year: 2008).

Truffert, J., et al., "Synthesis, Purification, and Characterization of Two Peptide-Oligonucleotide Conjugates as Potential Artificial Nucleases," 1996, Tetrahedron, 52(8) pp. 3005-3016.

Tykvart, et al., "Rational design of urea-based glutamate carboxypeptidase II (GCPII) inhibitors as versatile tools for specific drug targeting and delivery," 2014, Bioorganic & Medicinal Chemistry, 22(15) pp. 4099-4108.

Behr, S.C. et al. Phase I Study of CTT1057, an 18F-Labeled Imaging Agent with Phosphoramidate Core Targeting Prostate-Specific Membrane Antigen in Prostate Cancer. J Nucl Med 2019; 60:910-916.

Bellmunt, J. et al. Castration-resistant prostate cancer: new science and therapeutic prospects. Therapeutic advances in medical oncology. May 2010; 2(3):189-207.

Calais, J. et al. Prospective phase 2 trial of PSMA-targeted molecular Radiotherapy with 177Lu-PSMA-617 for metastatic castration-reSISTant Prostate Cancer (RESIST-PC): efficacy results of the UCLA cohort. J Nucl Med, 2021, 62:1440-1446.

Jivan, S. et al. P 140: Fully automated preparation of [18F]CTT1057, a new prostate cancer imaging agent, prepared using the ORA Neptis Perform Synthesizer®. 22nd International Symposium on Radiopharmaceutical Sciences, Poster: S297, J Label Compd Radiopharm, 2017: 60 (Suppl. 1): S111-S640.

Koseki, Y. et al. Drug release is determined by the chain length of fatty acid-conjugated anticancer agent as one component of nano-prodrug. Bulletin of the Chemical Society of Japan. May 2016; 89(5): 540-5.

Nedelcovych, M.T. et al. JHU-2545 selectively shields salivary glands and kidneys during PSMA-targeted radiotherapy. bioRxiv. Oct. 30, 2018:457085.

Rathke, H. et al. Repeated 177Lu-Labeled PSMA-617 Radioligand Therapy Using Treatment Activities of Up to 9.3 GBq. J Nucl Med, 2018, 59, 459-465.

Rich, J.N. Cancer stem cells in radiation resistance. Cancer research. Oct. 1, 2007; 67(19):8980-4.

Seifert, R. et al. Radioligand therapy using [177Lu]Lu-PSMA-617 in mCRPC: a pre-VISION single-center analysis. European Journal of Nuclear Medicine and Molecular Imaging (2020) 47:2106-2112.

Silverman, R., "The Organic Chemistry of Drug Design and Drug Action," Elsevier Academic Press, 2nd Edition, Jan. 12, 2004, Hardback ISBN: 9780126437324.

European Supplemental Search Report, prepared for EP Application No. 21757774, completed Jun. 5, 2024.

Drake, C.G. et al. Blocking the regulatory T cell molecule LAG-3 augments in vivo anti-tumor immunity in an autochthonous mode I of prostate cancer. Journal of Clinical Oncology, 2006 ASCO

(56) References Cited

OTHER PUBLICATIONS

Annual Meeting Proceedings (Post-Meeting Edition). vol. 24, No. 1SS (Jun. 20 Supplement), 2006: 2573.
Fay, A.P. et al. Blocking the PD-1/PD-LI axis in advanced prostate cancer: are we moving in the right direction? Ann Transl Med 2019;7(Suppl I):S7.

* cited by examiner

COMPOUNDS FOR POSITRON EMISSION TOMOGRAPHY

CROSS-REFERENCE TO RELATED APPLICATIONS

This application is a continuation of U.S. application Ser. No. 16/157,024, filed Oct. 10, 2018, which is a continuation of U.S. application Ser. No. 15/035,936, filed May 11, 2016, which is the national stage filing under 35 U.S.C. § 371 of International Application No. PCT/US2014/0650467, filed Nov. 13, 2014, which claims the benefit under 35 U.S.C. § 119(e) of U.S. Provisional Application Ser. No. 61/904,387, filed Nov. 14, 2013, 61/904,400, filed Nov. 14, 2013, and 61/909,822, filed Nov. 27, 2013, the disclosure of each of which is incorporated herein by reference in its entirety.

TECHNICAL FIELD

The invention described herein pertains to compounds, compositions, and methods for diagnosing and/or monitoring diseases and disease states using radionuclides. In particular, the invention described herein pertains to compounds, compositions, and methods for diagnosing and/or monitoring pathogenic disease states using radionuclides for positron emission tomography (PET).

BACKGROUND AND SUMMARY OF THE INVENTION

PET is a nuclear imaging methodology that detects pairs of gamma rays emitted indirectly by a positron-producing radionuclide. Because the two emitted gamma rays travel in exactly opposite directions, it is possible to locate their site of origin and thereby reconstruct a three-dimensional image of all positron emitters from a computer analysis of the origins of emitted gamma rays. Compared to other radio-imaging modalities, such as SPECT, PET reportedly shows higher sensitivity (about 2 orders of magnitude), better spatial resolution (about 5 mm), greater signal to noise, and superior tracer quantification in both preclinical and clinical applications. In addition, in contrast to the about 90 minutes required for body scans for a standard SPECT imaging, PET image acquisition may be routinely performed in about 20 minutes. Moreover, in vivo PET imaging generally requires only subnanomolar ($10^{-10}$ to $10^{-12}$) concentrations of radiotracer, which reportedly minimizes potential damage to other biological systems. Finally, PET allows for quantitative dynamic imaging, which may facilitate kinetic studies of target engagement through receptor occupancy. It has been discovered herein that PET agents may be targeted to predetermined tissues using vitamin receptors and/or prostate-specific membrane antigen (PSMA).

For example, vitamin receptors are overexpressed on certain pathogenic cells, including many cancer cell types, activated macrophages, and activated monocytes. In particular, folate receptors are overexpressed in many cancers. The folate receptor, a 38 KD GPI-anchored protein that binds the vitamin folic acid with high affinity (<1 nM), is overexpressed on many malignant tissues, including ovarian, breast, bronchial, and brain cancers. It is estimated that 95% of all ovarian carcinomas overexpress the folate receptor. In contrast, with the exception of kidney, choroid plexus, and placenta, normal tissues express low or nondetectable levels of the folate receptor. Most cells also use an unrelated reduced folate carrier to acquire the necessary folic acid.

Folate receptors are also overexpressed on activated macrophages, and activated monocytes. Further, it has also been reported that the folate receptor p, the nonepithelial isoform of the folate receptor, is expressed on activated, but not resting, synovial macrophages. Activated macrophages can participate in the immune response by nonspecifically engulfing and killing foreign pathogens within the macrophage, by displaying degraded peptides from foreign proteins on the macrophage cell surface where they can be recognized by other immune cells, and by secreting cytokines and other factors that modulate the function of T and B lymphocytes, resulting in further stimulation of immune responses. However, activated macrophages can also contribute to the pathophysiology of disease in some instances. For example, activated macrophages can contribute to atherosclerosis, rheumatoid arthritis, autoimmune disease states, and graft versus host disease, among other disease states.

Following receptor binding of vitamins to vitamin receptors, such as folic acid and analogs and derivatives of folic acid to folate receptors, rapid endocytosis delivers the vitamin into the cell, where it is unloaded in an endosomal compartment at lower pH. Importantly, covalent conjugation of small molecules, proteins, and even liposomes to vitamins and other vitamin receptor binding ligands does not block the ability of the ligand to bind to its receptor, and therefore, such ligand conjugates can readily be delivered to and can enter cells by receptor-mediated endocytosis. Accordingly, diagnostic, imaging, and therapeutic agents can be targeted to vitamin receptors, including the folate receptor, for delivery into vitamin receptor expressing cells.

The prostate is a male reproductive organ that functions to produce and store seminal fluid, which provides nutrients and fluids for the survival of sperm introduced into the vagina during reproduction. Like other tissues, the prostate gland may develop either malignant (cancerous) or benign (non-cancerous) tumors. Prostate cancer is reportedly one of the most common male cancers in western societies, and is the second leading form of malignancy among American men.

Prostate-specific membrane antigen (PSMA) is a biomarker that is overexpressed on prostate cancer. PSMA is over-expressed in the malignant prostate tissues when compared to other organs in the human body such as kidney, proximal small intestine, and salivary glands. PSMA is also expressed on the neovasculature within many non-prostate solid tumors, including lung, colon, breast, renal, liver and pancreatic carcinomas, but not on normal vasculature. However, PSMA is expressed minimally in brain. PSMA is a type II cell surface membrane-bound glycoprotein with ~110 kD molecular weight, including an intracellular segment (amino acids 1-18), a transmembrane domain (amino acids 19-43), and an extensive extracellular domain (amino acids 44-750). Though the functions of the intracellular segment and the transmembrane domains are currently reported to be insignificant, the extracellular domain is involved in several distinct activities. For example, PSMA plays a role in the central nervous system, where it metabolizes N-acetyl-aspartyl glutamate (NAAG) into glutamic and N-acetyl aspartic acid. PSMA also plays a role in the proximal small intestine where it removes γ-linked glutamate from poly-γ-glutamated folate and α-linked glutamate from peptides and small molecules.

Though the particular function of PSMA on prostate cancer cells remains unresolved, PSMA is known to undergo rapid internalization into the cell, similar to cell surface bound receptors like vitamin receptors. PSMA is internalized through clathrin-coated pits and subsequently can either recycle to the cell surface or go to lysosomes. Accordingly, diagnostic, imaging, and therapeutic agents can be targeted to PSMA for delivery into PSMA expressing cells, such as prostate cancer cells.

It has been discovered herein that the compounds and compositions described herein are useful for targeting and delivering radionuclides for diagnosing and/or monitoring various diseases and disease states caused by pathogenic cell populations. In addition, it has been discovered that the compounds and compositions described herein are also useful for targeting and delivering radionuclides for treating various diseases and disease states caused by pathogenic cell populations in radiotherapy.

In one illustrative and non-limiting embodiment of the invention described herein, compounds and compositions described herein are used for diagnosing and/or monitoring, or treating various diseases and disease states caused by pathogenic cell populations. In another illustrative embodiment, methods are described herein for administering compounds and compositions described herein for diagnosing and/or monitoring, or treating various diseases and disease states caused by pathogenic cell populations. In another embodiment, uses of compounds and compositions are described herein for manufacturing medicaments for diagnosing and/or monitoring, or treating various diseases and disease states caused by pathogenic cell populations. In another embodiment, kits are described herein for preparing and/or using compounds and compositions described herein for diagnosing and/or monitoring, or treating various diseases and disease states caused by pathogenic cell populations.

DETAILED DESCRIPTION

Figure 1A:
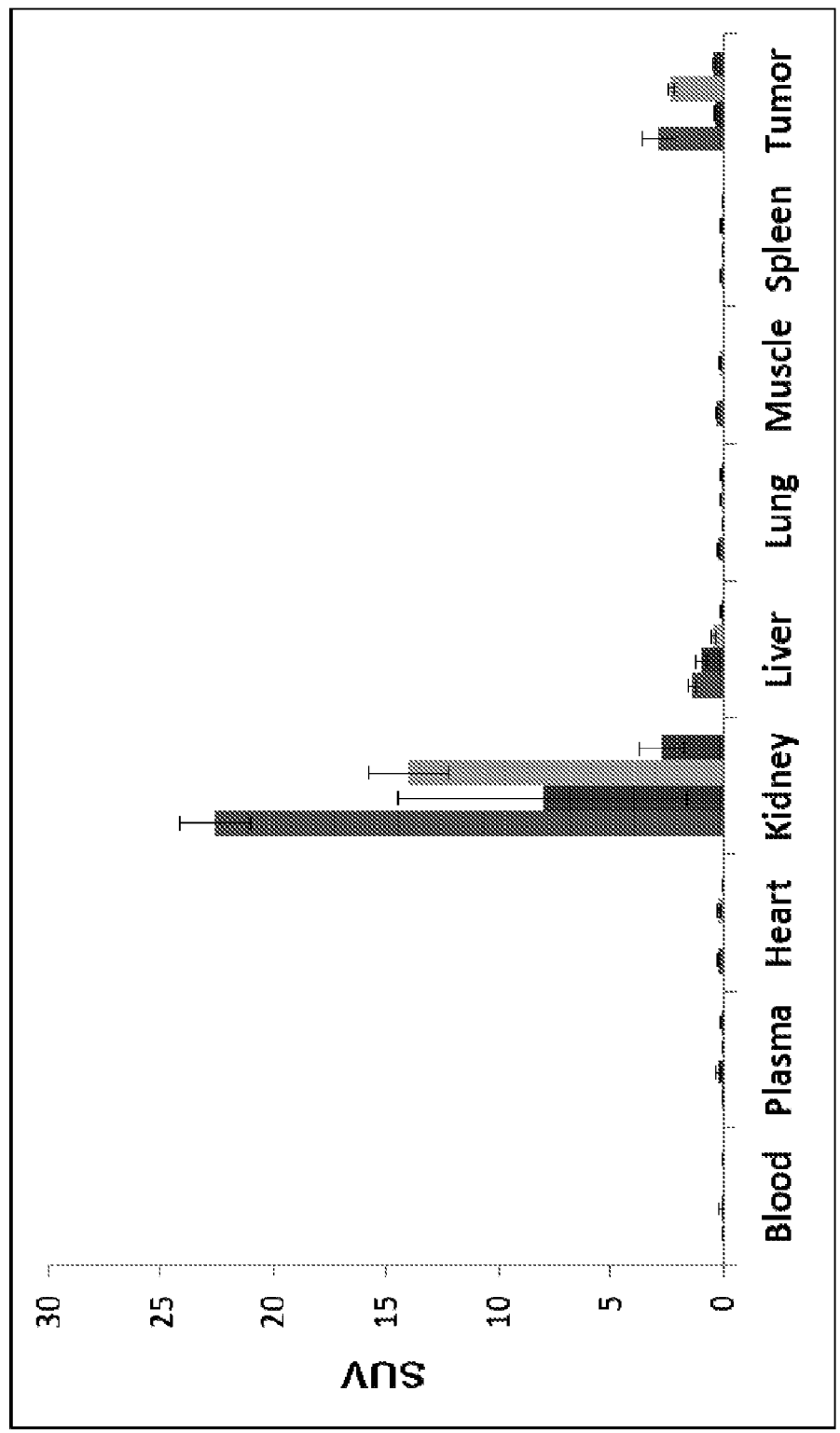
FIG. 1A shows a postmortem biodistribution study of $^{18}$F-AIF-QC07017 and $^{18}$F-AIF-QC07043 folate-NOTA-Al-$^{18}$F conjugates in various tissues at 90 minutes post injection in nude mice bearing KB tumor xenografts. For each tissue, the histogram is in groups of 4 from left to right: $^{18}$F-AIF-QC07017, $^{18}$F-AIF-QC07017+excess folic acid, $^{18}$F-AIF-QC07043, $^{18}$F-AIF-QC07043+excess folic acid.

In each of the foregoing and each of the following embodiments, it is to be understood that the formulae include and represent not only all pharmaceutically acceptable salts of the compounds, but also include any and all hydrates and/or solvates of the compound formulae. It is appreciated that certain functional groups, such as the hydroxy, amino, and like groups form complexes and/or coordination compounds with water and/or various solvents, in the various physical forms of the compounds. Accordingly, the formulae described herein are to be understood to include and represent those various hydrates and/or solvates. It is also to be understood that the non-hydrates and/or non-solvates of the compound formulae are described by such formula, as well as the hydrates and/or solvates of the compound formulae.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is appreciated that certain functional groups, such as the hydroxy, amino, and like groups form complexes and/or coordination compounds with water and/or various solvents, in the various physical forms of the compounds. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. In addition, it is to be understood that the compositions may be prepared from various co-crystals of the compounds described herein.

Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, (21$^{st}$ ed., 2005)).

In each of the foregoing and each of the following embodiments, it is also to be understood that the formulae include and represent each possible isomer, such as stereoisomers and geometric isomers, both individually and in any and all possible mixtures. In each of the foregoing and each of the following embodiments, it is also to be understood that the formulae include and represent any and all crystalline forms, partially crystalline forms, and non crystalline and/or amorphous forms of the compounds.

Illustrative embodiments of the invention are described by the following clauses:

A conjugate of the formula

B-L-P or a pharmaceutically acceptable salt thereof, wherein B is a radical of a targeting agent selected from vitamin receptor binding ligands, PSMA binding ligands, and PSMA inhibitors, L is a divalent linker, and P is a radical of an imaging agent or radiotherapy agent, such as a radionuclide or radionuclide containing group, or a precursor thereof, or a radical of a compound capable of binding a radionuclide or radionuclide containing group, such as a metal chelating group.

The conjugate of the preceding clause wherein the targeting agent is a radical of a folate receptor binding ligand.

The conjugate of any one of the preceding clauses wherein the targeting agent is a radical of a folic acid.

The conjugate of any one of the preceding clauses comprising folate-Asp.

The conjugate of any one of the preceding clauses comprising folate-Asp-Arg.

The conjugate of any one of the preceding clauses comprising folate-Arg.

The conjugate of any one of the preceding clauses wherein the linker comprises a polypeptide.

The conjugate of any one of the preceding clauses wherein the linker comprises a polypeptide comprising lysine, arginine, or aspartic acid, or a combination thereof.

The conjugate of any one of the preceding clauses wherein the linker comprises a lysine.

The conjugate of any one of the preceding clauses wherein the linker comprises Lys.

The conjugate of any one of the preceding clauses wherein the linker comprises Arg-Lys.

The conjugate of any one of the preceding clauses wherein the linker comprises Arg-Arg-Lys.

The conjugate of any one of the preceding clauses wherein the linker comprises Asp-Arg-Arg-Lys.

The conjugate of any one of the preceding clauses wherein the linker does not include a polyamine radical, such as a polyamine diradical of the formula NH—(CH$_2$)$_2$—NH.

The conjugate of any one of the preceding clauses wherein P comprises the formula

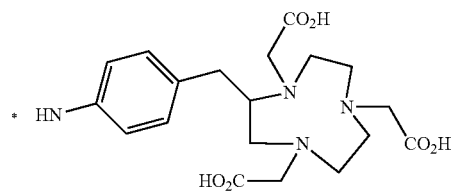 [SMILES: Nc1ccc(CC2CN(CC(=O)O)CCN(CC(=O)O)CCN2CC(=O)O)cc1]

or a derivative thereof comprising a chelated metal.

The conjugate of any one of the preceding clauses comprising the formula

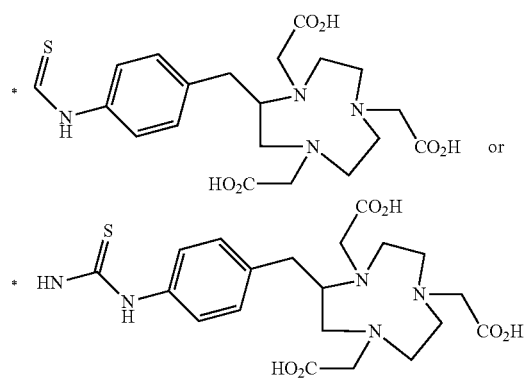

or a derivative thereof comprising a chelated metal.

The conjugate of any one of the preceding clauses comprising folate-PEG.

The conjugate of any one of the preceding clauses comprising folate-PEG$_2$.

The conjugate of any one of the preceding clauses comprising folate-PEG$_6$.

The conjugate of any one of the preceding clauses comprising folate-PEG$_{12}$.

The conjugate of any one of the preceding clauses wherein the linker comprises [(CH$_2$)$_2$O]$_n$, [(CH$_2$)$_2$O]$_n$—(CH$_2$)$_2$—C(O), [(CH$_2$)$_2$O]$_n$—(CH$_2$)$_2$—C(O)NH, [(CH$_2$)$_2$O]$_n$ —(CH$_2$)$_2$—C(O)NH—(CH$_2$)$_2$, [(CH$_2$)$_2$O]$_2$—(CH$_2$)$_n$—C(O)NH—(CH$_2$)$_2$NH, where n is an integer from 1 to about 12.

The conjugate of any one of the preceding clauses wherein the linker comprises [(CH$_2$)$_2$O]$_2$, [(CH$_2$)$_2$O]$_6$, or [(CH$_2$)$_2$O]$_{12}$.

The conjugate of any one of the preceding clauses wherein the linker comprises (CH$_2$)$_2$O—(CH$_2$)$_2$—C(O), [(CH$_2$)$_2$O]$_2$—(CH$_2$)$_2$—C(O), [(CH$_2$)$_2$O]$_6$—(CH$_2$)$_2$—C(O), or [(CH$_2$)$_2$O]$_{12}$—(CH$_2$)$_2$—C(O).

The conjugate of any one of the preceding clauses wherein the linker comprises (CH$_2$)$_2$O—(CH$_2$)$_2$—C(O)NH, [(CH$_2$)$_2$O]$_2$—(CH$_2$)$_2$—C(O)NH, [(CH$_2$)$_2$O]$_6$—(CH$_2$)$_2$—C(O)NH, or [(CH$_2$)$_2$O]$_{12}$—(CH$_2$)$_2$—C(O)NH.

The conjugate of any one of the preceding clauses wherein the linker comprises (CH$_2$)$_2$O—(CH$_2$)$_2$—C(O)NH—(CH$_2$)$_2$, [(CH$_2$)$_2$O]$_2$—(CH$_2$)$_2$—C(O)NH—(CH$_2$)$_2$, [(CH$_2$)$_2$O]$_6$—(CH$_2$)$_2$—C(O)NH—(CH$_2$)$_2$, or [(CH$_2$)$_2$O]$_{12}$—(CH$_2$)$_2$—C(O)NH—(CH$_2$)$_2$.

The conjugate of any one of the preceding clauses wherein the linker comprises (CH$_2$)$_2$O—(CH$_2$)$_2$—C(O)NH—(CH$_2$)$_2$NH, [(CH$_2$)$_2$O]$_2$—(CH$_2$)$_2$—C(O)NH—(CH$_2$)$_2$NH, [(CH$_2$)$_2$O]$_6$—(CH$_2$)$_2$—C(O)NH—(CH$_2$)$_2$NH, or [(CH$_2$)$_2$O]$_{12}$—(CH$_2$)$_2$—C(O)NH—(CH$_2$)$_2$NH.

The conjugate of any one of the preceding clauses wherein the linker comprises $NH[(CH_2)_2O]_n$, $NH[(CH_2)_2O]_n$—$(CH_2)_2$—$C(O)$, $NH[(CH_2)_2O]_n$—$(CH_2)_2$—$C(O)NH$, $NH[(CH_2)_2O]_n$—$(CH_2)_2$—$C(O)NH$—$(CH_2)_2$, $NH[(CH_2)_2O]_n$—$(CH_2)_2$—$C(O)NH$—$(CH_2)_2NH$, where n is an integer from 1 to about 12.

The conjugate of any one of the preceding clauses wherein the linker comprises $NH(CH_2)_2O$, $NH[(CH_2)_2O]_2$, $NH[(CH_2)_2O]_6$, $NH[(CH_2)_2O]_{12}$.

The conjugate of any one of the preceding clauses wherein the linker comprises $NH(CH_2)_2O$—$(CH_2)_2$—$C(O)$, $NH[(CH_2)_2O]_2$—$(CH_2)_2$—$C(O)$, $NH[(CH_2)_2O]_6$—$(CH_2)_2$—$C(O)$, or $NH[(CH_2)_2O]_{12}$—$(CH_2)_2$—$C(O)$.

The conjugate of any one of the preceding clauses wherein the linker comprises $NH(CH_2)_2O$—$(CH_2)_2$—$C(O)NH$, $NH[(CH_2)_2O]_2$—$(CH_2)_2$—$C(O)NH$, $NH[(CH_2)_2O]_6$—$(CH_2)_2$—$C(O)NH$, or $NH[(CH_2)_2O]_{12}$—$(CH_2)_2$—$C(O)NH$.

The conjugate of any one of the preceding clauses wherein the linker comprises $NH(CH_2)_2O$—$(CH_2)_2$—$C(O)NH$—$(CH_2)_2$, $NH[(CH_2)_2O]_2$—$(CH_2)_2$—$C(O)NH$—$(CH_2)_2$, $NH[(CH_2)_2O]_6$—$(CH_2)_2$—$C(O)NH$—$(CH_2)_2$, or $NH[(CH_2)_2O]_{12}$—$(CH_2)_2$—$C(O)NH$—$(CH_2)_2$.

The conjugate of any one of the preceding clauses wherein the linker comprises $NH(CH_2)_2O$—$(CH_2)_2$—$C(O)NH$—$(CH_2)_2NH$, $NH[(CH_2)_2O]_2$—$(CH_2)_2$—$C(O)NH$—$(CH_2)_2NH$, $NH[(CH_2)_2O]_6$—$(CH_2)_2$—$C(O)NH$—$(CH_2)_2NH$, or $NH[(CH_2)_2O]_{12}$—$(CH_2)_2$—$C(O)NH$—$(CH_2)_2NH$.

The conjugate of any one of the preceding clauses wherein the linker comprises $NH[(CH_2)_2O]_n$—$(CH_2)_2NH$, where n is an integer from 1 to about 12.

The conjugate of any one of the preceding clauses wherein the linker comprises $NH(CH_2)_2O$—$(CH_2)_2NH$, $NH[(CH_2)_2O]_2$—$(CH_2)_2NH$, $NH[(CH_2)_2O]_6$—$(CH_2)_2NH$, or $NH[(CH_2)_2O]_{12}$—$(CH_2)_2NH$.

The conjugate of any one of the preceding clauses wherein the linker comprises $NH[(CH_2)_2O]_n$—$(CH_2)_2NH$—$C(O)$—$(CH_2)_2$—$C(O)$, where n is an integer from 1 to about 12.

The conjugate of any one of the preceding clauses wherein the linker comprises $NH(CH_2)_2O$—$(CH_2)_2NH$—$C(O)$—$(CH_2)_2$—$C(O)$, $NH[(CH_2)_2O]_2$—$(CH_2)_2NH$—$C(O)$—$(CH_2)_2$—$C(O)$, $NH[(CH_2)_2O]_6$—$(CH_2)_2NH$—$C(O)$—$(CH_2)_2$—$C(O)$, or $NH[(CH_2)_2O]_{12}$—$(CH_2)_2NH$—$C(O)$—$(CH_2)_2$—$C(O)$.

The conjugate of any one of the preceding clauses comprising the formula

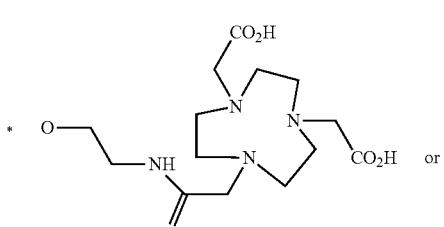

or

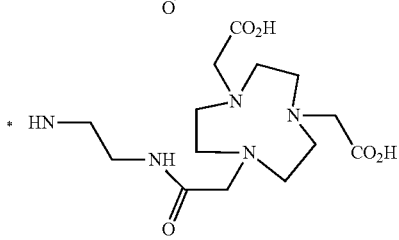

or a derivative thereof comprising a chelated metal.

The conjugate of any one of the preceding clauses where P comprises the formula

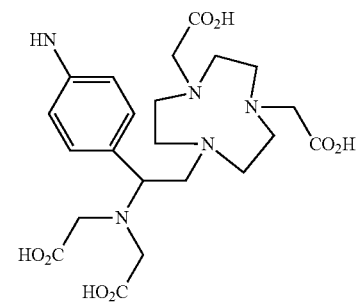

or a derivative thereof comprising a chelated metal.

The conjugate of any one of the preceding clauses comprising the formula

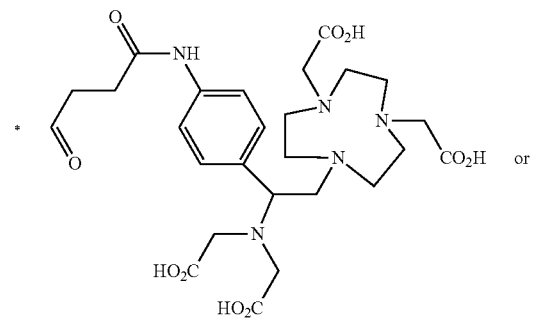

or

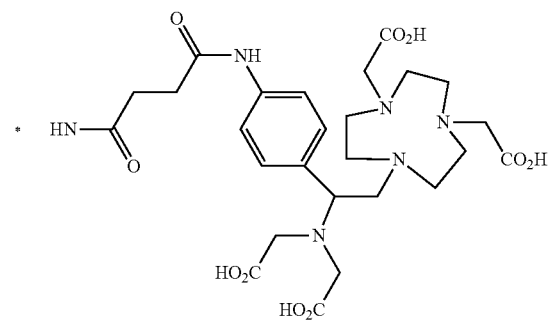

or a derivative thereof comprising a chelated metal.

The conjugate of any one of the preceding clauses wherein the targeting agent is a radical of a PSMA binding ligand or PSMA inhibitor.

The conjugate of any one of the preceding clauses wherein the targeting agent is a radical of a PSMA inhibitor.

The conjugate of any one of the preceding clauses comprising the formula

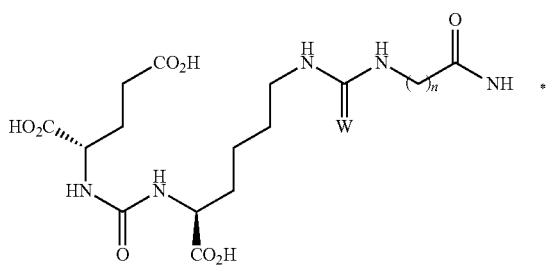

wherein n is an integer selected from 1, 2, 3, 4, 5, 6, 7, 8, 9, or 10; or

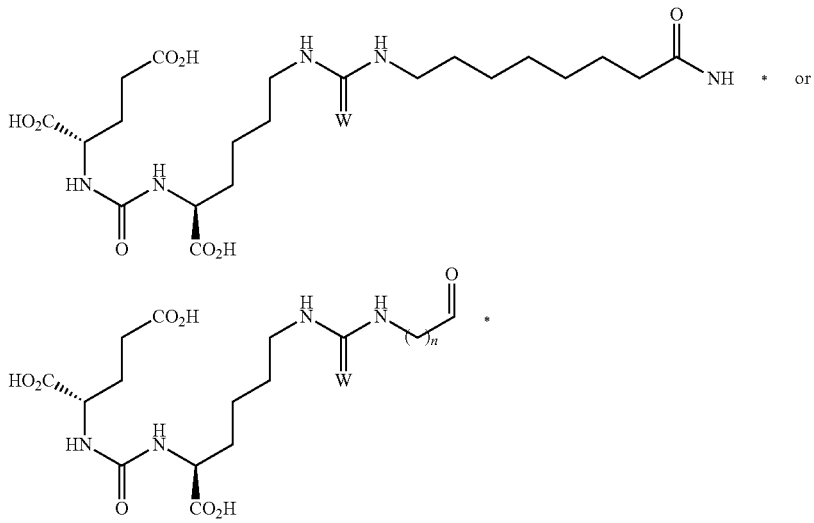

wherein n is an integer selected from 1, 2, 3, 4, 5, 6, 7, 8, 9, or 10; or

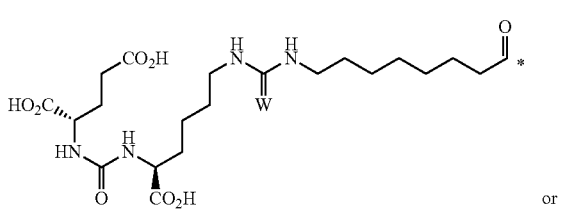

or

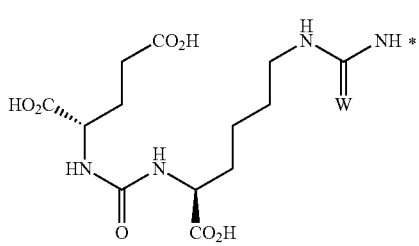

where W is O or S.

The conjugate of any one of the preceding clauses wherein the linker comprises a polypeptide.

The conjugate of any one of the preceding clauses wherein the linker comprises a polypeptide comprising phenylalanine, lysine, arginine, or aspartic acid, or a combination thereof.

The conjugate of any one of the preceding clauses wherein the linker comprises a lysine.

The conjugate of any one of the preceding clauses wherein the linker comprises Lys.

The conjugate of any one of the preceding clauses wherein the linker comprises Arg-Lys.

The conjugate of any one of the preceding clauses wherein the linker comprises Asp-Arg-Lys.

The conjugate of any one of the preceding clauses wherein the linker comprises Arg-Asp-Arg.

The conjugate of any one of the preceding clauses wherein the linker comprises Arg-Asp-Arg-Lys.

The conjugate of any one of the preceding clauses wherein the linker comprises Phe-Arg-Asp.

The conjugate of any one of the preceding clauses wherein the linker comprises Phe-Arg-Asp-Arg.

The conjugate of any one of the preceding clauses wherein the linker comprises Phe-Arg-Asp-Arg-Lys.

The conjugate of any one of the preceding clauses wherein the linker comprises Phe-Phe-Arg.

The conjugate of any one of the preceding clauses wherein the linker comprises Phe-Phe-Arg-Asp.

The conjugate of any one of the preceding clauses wherein the linker comprises Phe-Phe-Arg-Asp-Arg.

The conjugate of any one of the preceding clauses wherein the linker comprises Phe-Phe-Arg-Asp-Arg-Lys.

The conjugate of any one of the preceding clauses wherein the radical of the radionuclide or radionuclide containing group, or precursor thereof, or compound capable of binding a radionuclide or radionuclide containing group comprises a radical of NOTA.

The conjugate of any one of the preceding clauses wherein P comprises the formula

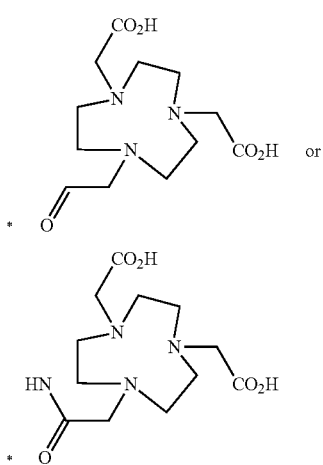

or a derivative thereof comprising a chelated metal.

The conjugate of any one of the preceding clauses comprising the formula

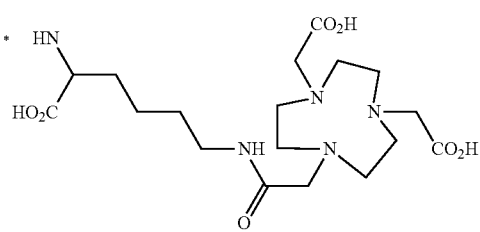 [SMILES: NC(CCCCNC(=O)CN1CCN(CC(=O)O)CCN(CC(=O)O)CC1)C(=O)O]

or a derivative thereof comprising a chelated metal.

The conjugate of any one of the preceding clauses comprising the formula

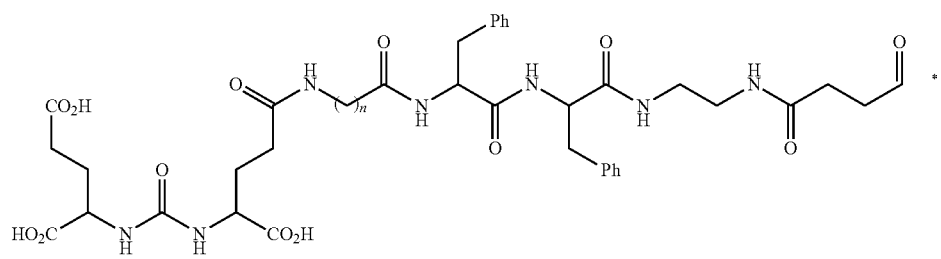

wherein n is an integer selected from 1, 2, 3, 4, 5, 6, 7, 8, 9, or 10.

The conjugate of any one of the preceding clauses comprising the formula

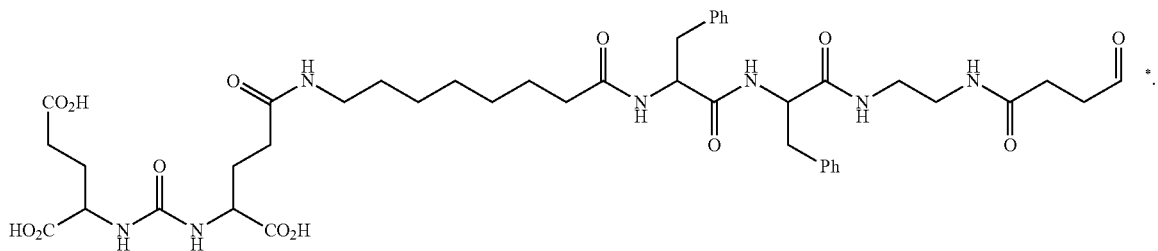 [SMILES: O=CCCC(=O)NCCNC(=O)C(Cc1ccccc1)NC(=O)C(Cc1ccccc1)NC(=O)CCCCCCCNC(=O)CCC(NC(=O)NC(CCC(=O)O)C(=O)O)C(=O)O]

The conjugate of any one of the preceding clauses wherein the linker comprises the formula

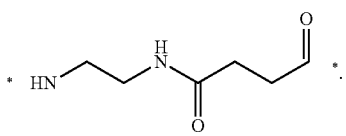

The conjugate of any one of the preceding clauses wherein the linker comprises the formula

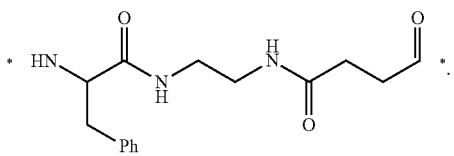 [SMILES: NC(Cc1ccccc1)C(=O)NCCNC(=O)CCC=O]

The conjugate of any one of the preceding clauses wherein the linker comprises the formula

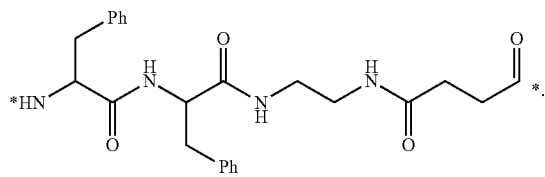

The conjugate of any one of the preceding clauses wherein one or more of the phenylalanines is L-phenylalanine.

The conjugate of any one of the preceding clauses comprising the formula

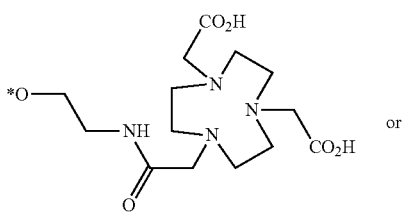

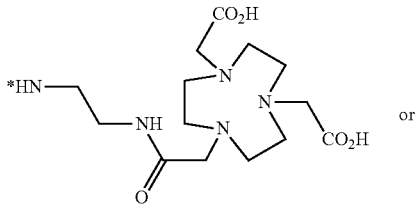

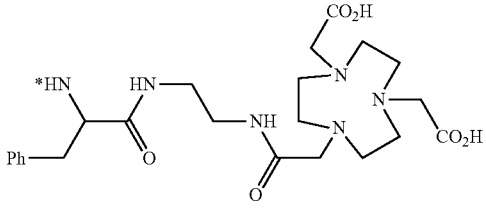

or a derivative thereof comprising a chelated metal.

The conjugate of any one of the preceding clauses where P comprises the formula

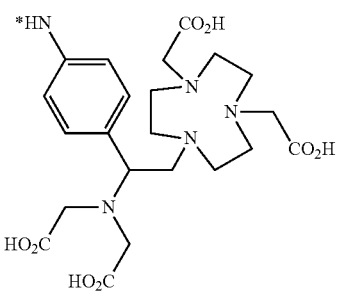

or a derivative thereof comprising a chelated metal.

The conjugate of any one of the preceding clauses comprising the formula

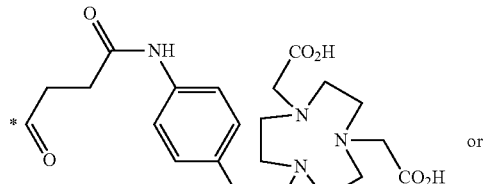

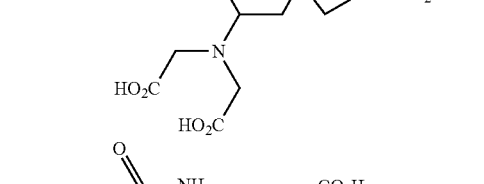

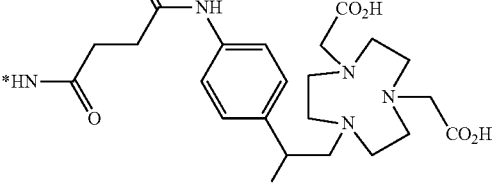

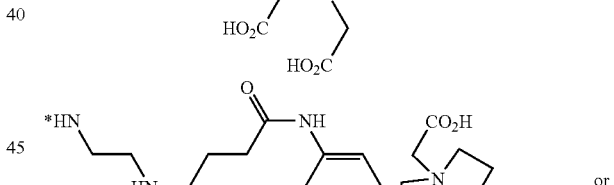

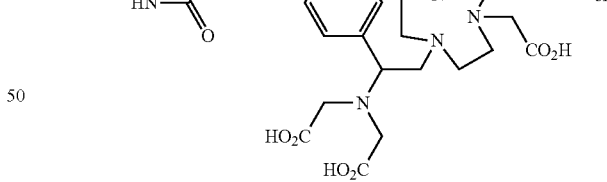

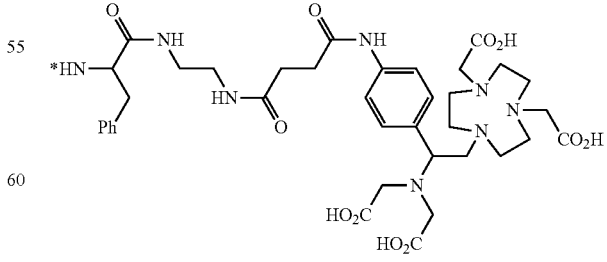

or a derivative thereof comprising a chelated metal.

The conjugate of any one of the preceding clauses wherein the radionuclide is a positron emitting radionuclide.

The conjugate of any one of the preceding clauses wherein the radionuclide is a metal ion.

The conjugate of any one of the preceding clauses wherein the radionuclide is a metal salt.

The conjugate of any one of the preceding clauses comprising an aluminum halide, such as an aluminum fluoride, aluminum chloride, aluminum bromide, or aluminum iodide.

The conjugate of any one of the preceding clauses comprising an aluminum fluoride.

The conjugate of any one of the preceding clauses comprising an aluminum $^{18}$F-fluoride.

The conjugate of any one of the preceding clauses comprising an aluminum iodide.

The conjugate of any one of the preceding clauses comprising an aluminum $^{125}$I-iodide.

The conjugate of any one of the preceding clauses comprising a gallium ion.

The conjugate of any one of the preceding clauses comprising a $^{66}$Ga ion.

The conjugate of any one of the preceding clauses comprising a $^{68}$Ga ion.

The conjugate of any one of the preceding clauses comprising a zirconium ion.

The conjugate of any one of the preceding clauses comprising a $^{89}$Zr ion.

The conjugate of any one of the preceding clauses comprising a copper ion.

The conjugate of any one of the preceding clauses comprising a $^{64}$Cu ion.

The conjugate of any one of the preceding clauses wherein the radionuclide is a radiotherapy agent, such as iodine, including $^{131}$I, lutetium, including $^{177}$Lu, yttrium, including $^{90}$Y, strontium, including $^{89}$Sr, samarium, including $^{153}$Sm, and the like, or a radiotherapy agent containing group.

The conjugate of any one of the preceding clauses comprising a lutetium ion, such as a $^{177}$Lu ion.

The conjugate of any one of the preceding clauses comprising a yttrium ion, such as a $^{90}$Y ion.

A conjugate of the formulae

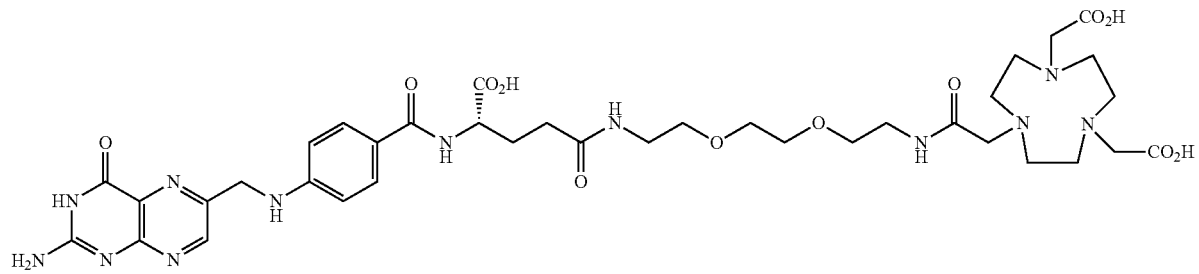

QC07017

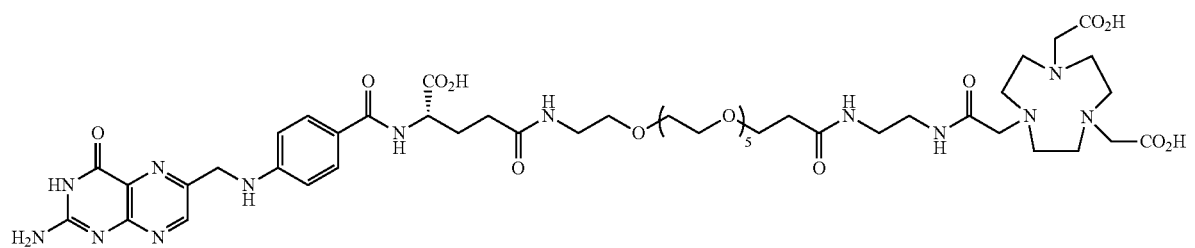

QC07029

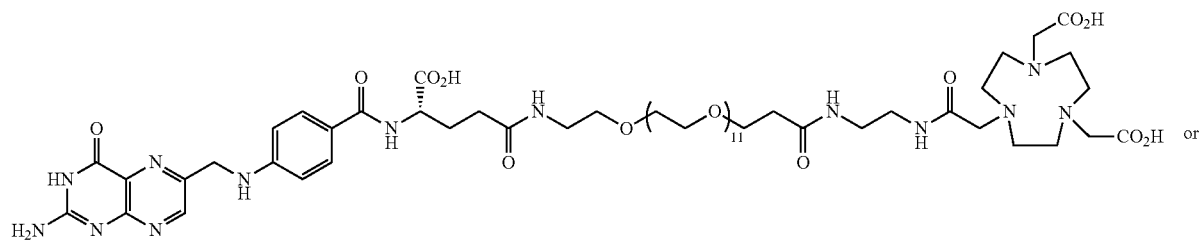

QC07043 or

-continued
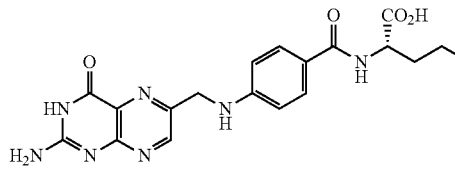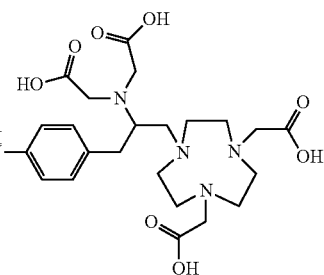
folate-C-NETA
or a pharmaceutically acceptable salt thereof.
15. A conjugate of the formulae
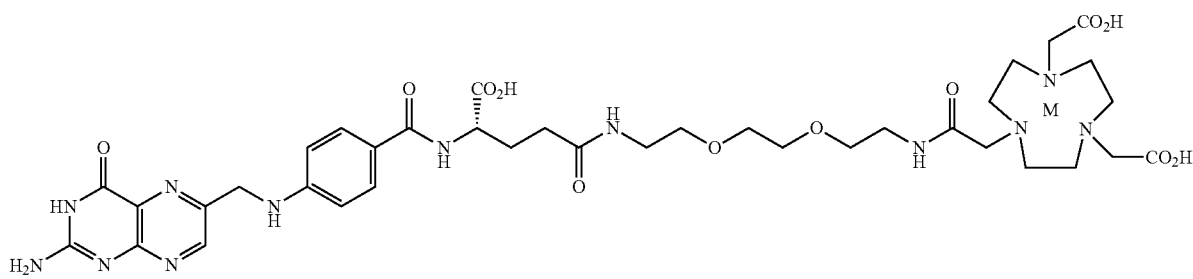
(QC07017)
folate-NOTA-Al$^{18}$F
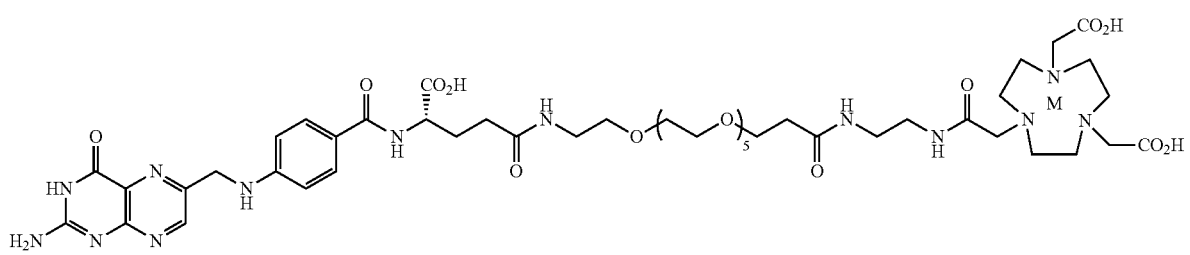
(QC07029)
FA-PEG$_6$-NOTA-Al-$^{18}$F conjugate
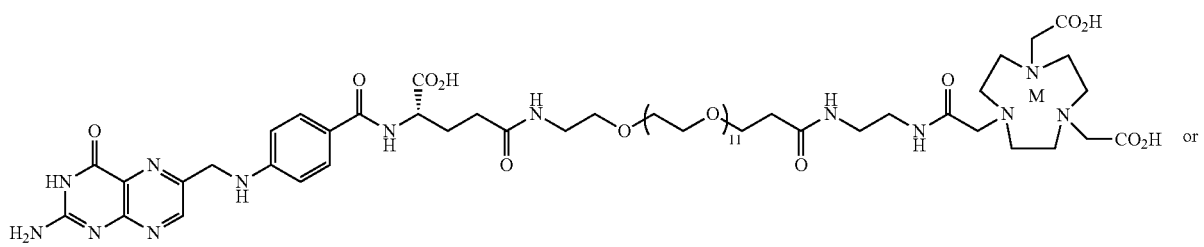
(QC07043)
or
M = Al-$^{18}$F or $^{68}$Ga
FA-PEG$_{12}$-NOTA-Al-$^{18}$F conjugate -continued
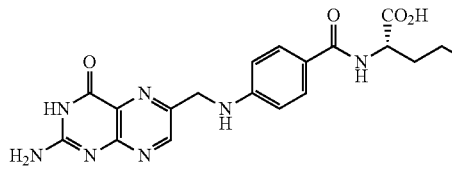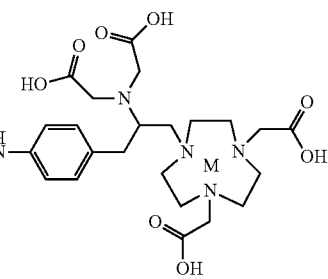
M = Al-$^{18}$F or $^{68}$Ga
folate-C-NETA-M
or a pharmaceutically acceptable salt thereof.
A conjugate of the formulae
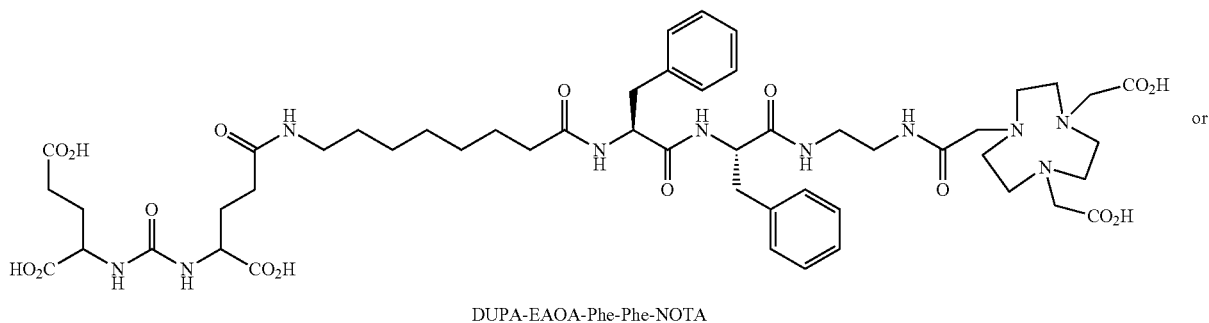
DUPA-EAOA-Phe-Phe-NOTA
or
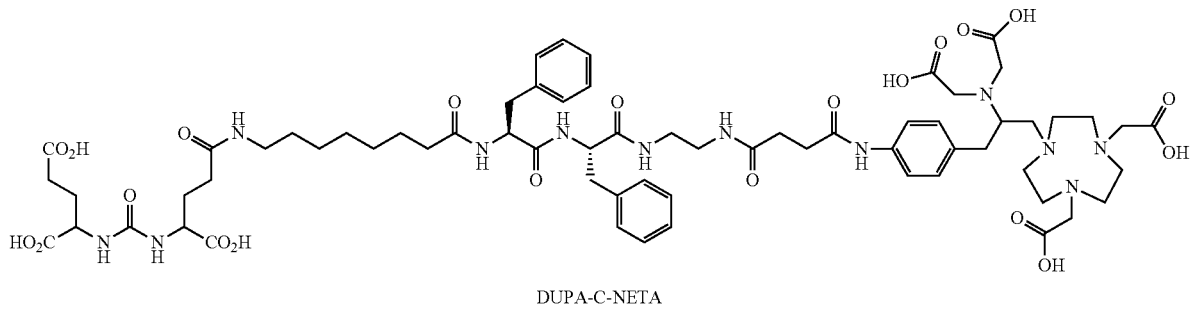
DUPA-C-NETA
or a pharmaceutically acceptable salt thereof.
50. A conjugate of the formulae
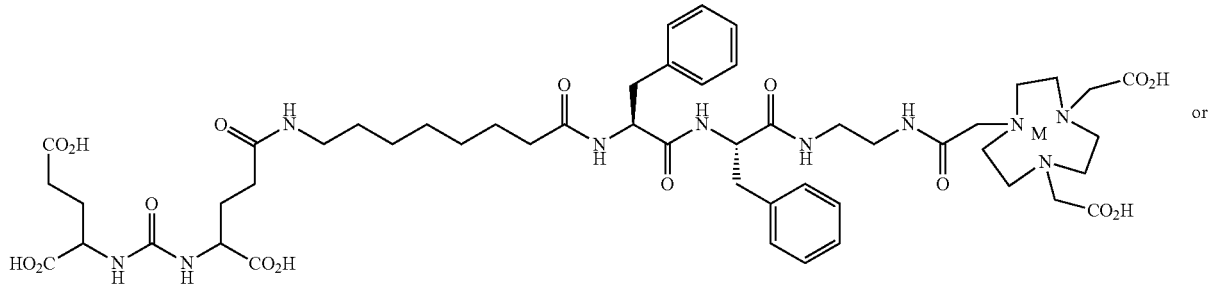
M = $^{68}$Ga, $^{64}$Cu or Al-$^{18}$F
DUPA-EAOA-Phe-Phe-NOTA-$^{64}$Cu/Al-$^{18}$F
or -continued

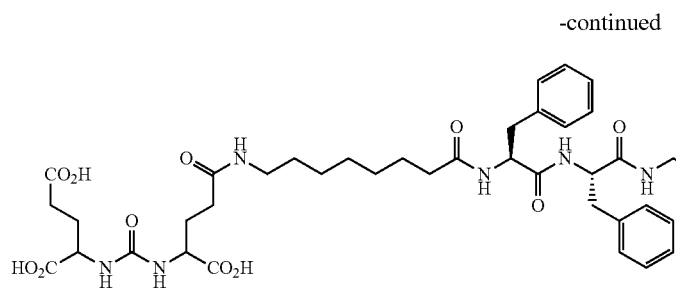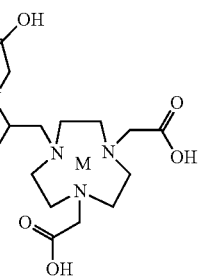

M = Al-$^{18}$F, $^{68}$Ga, $^{177}$Lu or $^{90}$Y
DUPA-C-NETA-M or a pharmaceutically acceptable salt thereof.

The conjugate of any one of the preceding clauses wherein P comprises the formula

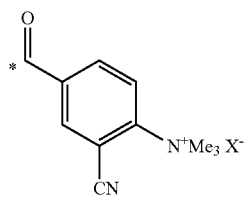

wherein X$^-$ is the conjugate base of an acid, such as trifluoromethanesulfonic acid.

The conjugate of any one of the preceding clauses comprising the formula

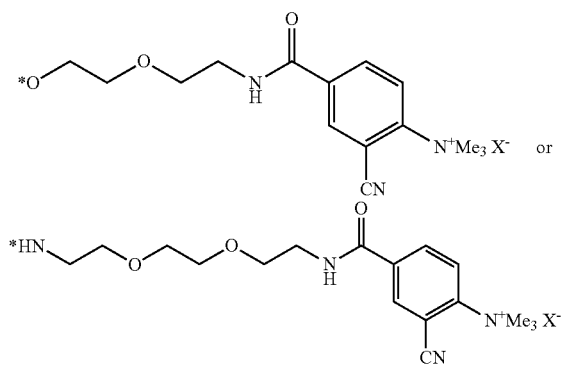

where X$^-$ is a conjugate base of an acid, such as trifluoromethanesulfonic acid.

The conjugate of any one of the preceding clauses wherein P comprises the formula

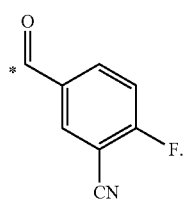

The conjugate of any one of the preceding clauses wherein P comprises the formula

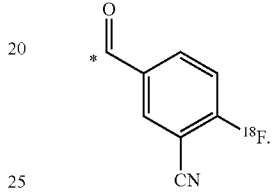

The conjugate of any one of the preceding clauses comprising the formula

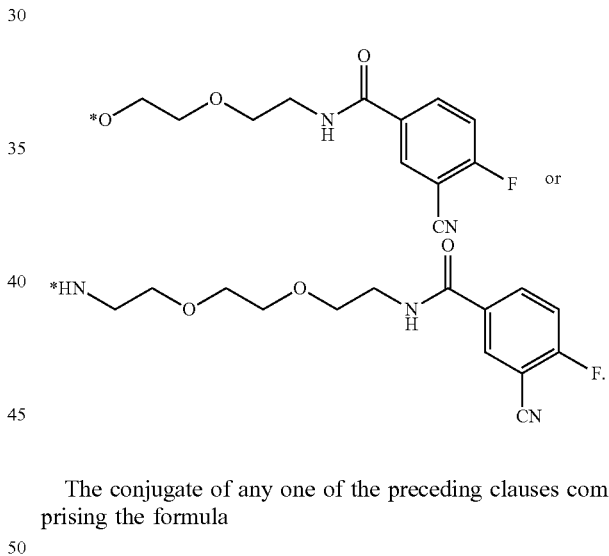

The conjugate of any one of the preceding clauses comprising the formula

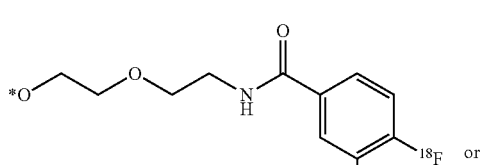

The conjugate of any one of the preceding clauses wherein P comprises the formula *NH—C(CH$_2$OH)$_3$.

The conjugate of any one of the preceding clauses comprising a boron fluoride.

The conjugate of any one of the preceding clauses comprising a boron $^{18}$F-fluoride.

A pharmaceutical composition comprising one or more of the conjugates of any one of the preceding clauses, in combination with one or more carriers, diluents, or excipients, or a combination thereof.

A unit dose or unit dosage form composition comprising a diagnostically effective amount of one or more of the conjugates of any one of the preceding clauses, optionally in combination with one or more carriers, diluents, or excipients, or a combination thereof for diagnosing and/or monitoring a pathogenic cell population, such as a cancer or inflammatory disease.

A unit dose or unit dosage form composition comprising a therapeutically effective amount of one or more of the conjugates of any one of the preceding clauses, optionally in combination with one or more carriers, diluents, or excipients, or a combination thereof for treating a pathogenic cell population, such as a cancer or inflammatory disease.

A composition for diagnosing and/or monitoring a disease or disease state caused at least in part by a pathogenic cell population, such as a cancer or inflammatory disease, in a host animal, the composition comprising a diagnostically effective amount of one or more of the conjugates of any one of the preceding clauses; or a pharmaceutical composition comprising a diagnostically effective amount of one or more of the conjugates of any one of the preceding clauses, optionally further comprising one or more carriers, diluents, or excipients, or a combination thereof.

A composition for treating a disease or disease state caused at least in part by a pathogenic cell population, such as a cancer or inflammatory disease, in a host animal, the composition comprising a therapeutically effective amount of one or more of the conjugates of any one of the preceding clauses; or a pharmaceutical composition comprising a therapeutically effective amount of one or more of the conjugates of any one of the preceding clauses, optionally further comprising one or more carriers, diluents, or excipients, or a combination thereof.

A method for diagnosing and/or monitoring a disease or disease state caused at least in part by a pathogenic cell population, such as a cancer or inflammatory disease, in a host animal, the method comprising the step of administering to the host animal a diagnostically effective amount of one or more of the conjugates of any one of the preceding clauses; or a pharmaceutical composition comprising a diagnostically effective amount of one or more of the conjugates of any one of the preceding clauses, optionally further comprising one or more carriers, diluents, or excipients, or a combination thereof.

A method for treating a disease or disease state caused at least in part by a pathogenic cell population, such as a cancer or inflammatory disease, in a host animal, the method comprising the step of administering to the host animal a therapeutically effective amount of one or more of the conjugates of any one of the preceding clauses; or a pharmaceutical composition comprising a therapeutically effective amount of one or more of the conjugates of any one of the preceding clauses, optionally further comprising one or more carriers, diluents, or excipients, or a combination thereof.

Use of one or more of the conjugates of any one of the preceding clauses; or a pharmaceutical composition comprising one or more of the conjugates of any one of the preceding clauses, optionally further comprising one or more carriers, diluents, or excipients, or a combination thereof, in the manufacture of a medicament for diagnosing and/or monitoring a disease or disease state caused at least in part by a pathogenic cell population, such as a cancer or inflammatory disease, in a host animal.

Use of one or more of the conjugates of any one of the preceding clauses; or a pharmaceutical composition comprising one or more of the conjugates of any one of the preceding clauses, optionally further comprising one or more carriers, diluents, or excipients, or a combination thereof, in the manufacture of a medicament for treating a disease or disease state caused at least in part by a pathogenic cell population, such as a cancer or inflammatory disease, in a host animal.

A kit comprising one or more of the conjugates of any one of the preceding clauses, or a pharmaceutical composition thereof, optionally further comprising one or more carriers, diluents, or excipients, or a combination thereof; an optional solvent; an optional reaction container, and a set of instructions for preparing one or more radionuclides and combining the one or more radionuclides with the one or more of the conjugates to prepare an imaging agent, diagnostic agent, or therapeutic agent.

A kit comprising one or more of the conjugates of any one of the preceding clauses, or a pharmaceutical composition thereof, optionally further comprising one or more carriers, diluents, or excipients, or a combination thereof; an optional solvent; an optional reaction container, and a set of instructions for preparing one or more radionuclides and combining the one or more radionuclides with the one or more of the conjugates to prepare an imaging agent, diagnostic agent, or therapeutic agent.

It is to be understood that in each instance where a compound or chemical formula includes an atom or locus that is marked with or includes a (*), the (*) indicates that the compound or chemical formula is a radical having an open valence at that atom or locus, and that atom or locus is the location for attachment of another radical.

In another illustrative embodiment, the conjugate, composition, unit dose, method, use, or kit of any other embodiment described herein comprises a compound of formula

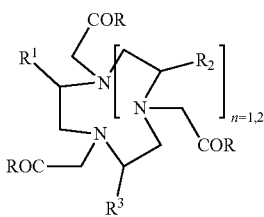

or a derivative thereof comprising a chelated metal; or a radical of the foregoing, where each R is in each instance independently selected to form a carboxylic acid or salt thereof, ester, or amide, and R$^1$, R$^2$, and R$^3$, are each independently selected from hydrogen, and alkyl, cycloalkyl, aryl, arylalkyl, heteroaryl, and heteroarylalkyl, each of which is optionally substituted.

In another illustrative embodiment, the conjugate, composition, unit dose, method, use, or kit of any other embodiment described herein comprises 1,4,7,10-tetraazacyclodo-decane-1,4,7,10-tetraacetic acid (DOTA) or a derivative thereof comprising a chelated metal; or a radical of the foregoing.

In another illustrative embodiment, the conjugate, composition, unit dose, method, use, or kit of any other embodiment described herein comprises a compound of formula

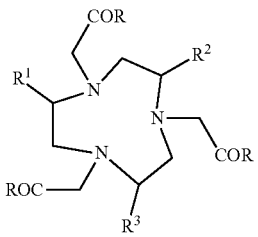

or a derivative thereof comprising a chelated metal; or a radical of the foregoing, where each R is in each instance independently selected to form a carboxylic acid or salt thereof, ester, or amide, and $R^1$, $R^2$, and $R^3$, are each independently selected from hydrogen, and alkyl, cycloalkyl, aryl, arylalkyl, heteroaryl, and heteroarylalkyl, each of which is optionally substituted, such as the following illustrative compounds:

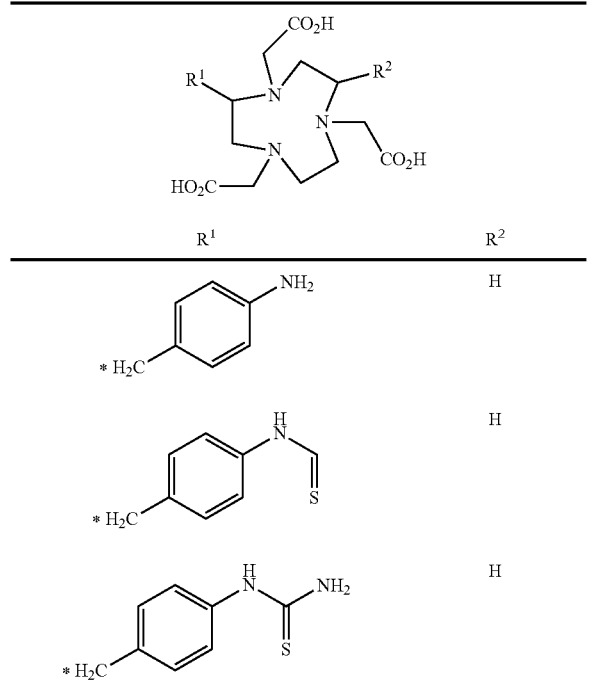

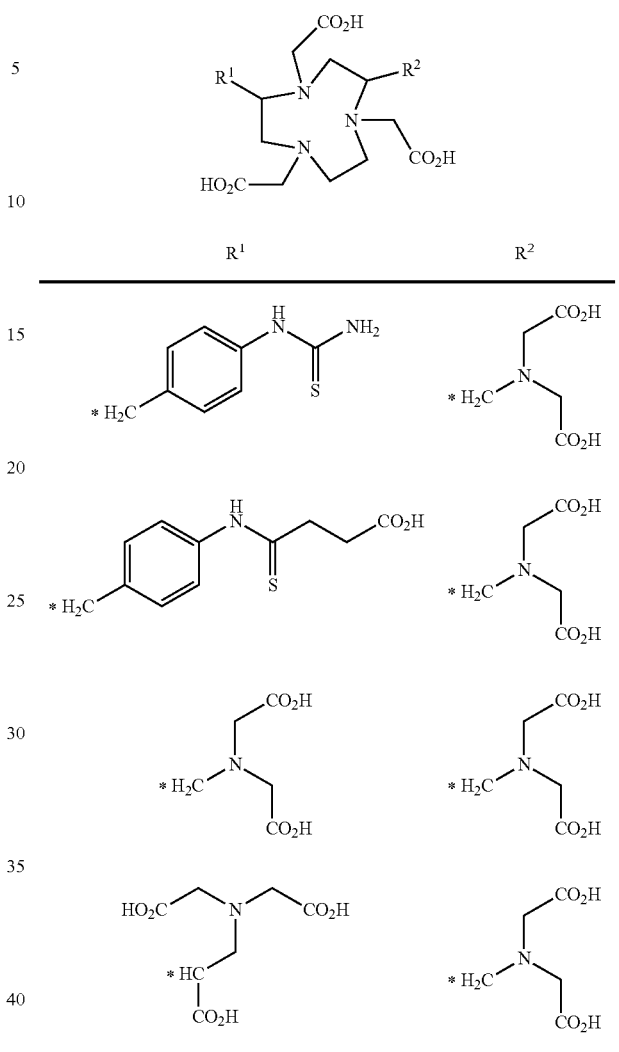

or caboxylic acid salt or a carboxamide derivative ($CONH_2$) thereof, or a radical of any of the foregoing; or a derivative thereof comprising a chelated metal.

In another illustrative embodiment, the conjugate, composition, unit dose, method, use, or kit of any other embodiment described herein comprises a compound of formula

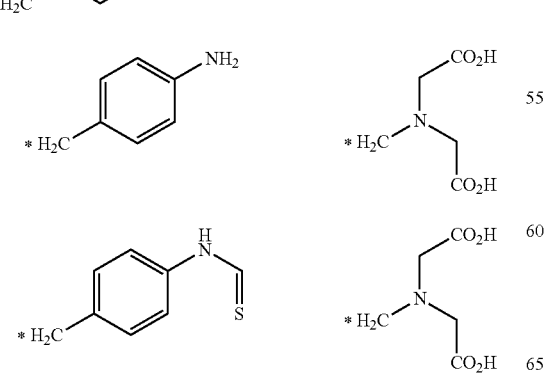

or a derivative thereof comprising a chelated metal; or a radical of the foregoing, where $R^4$ and $R^5$ are selected from hydrogen, and alkyl, cycloalkyl, aryl, arylalkyl, heteroaryl, and heteroarylalkyl, each of which is optionally substituted, such as the following illustrative compounds:

| $R^4$ | $R^5$ |
|---|---|
| 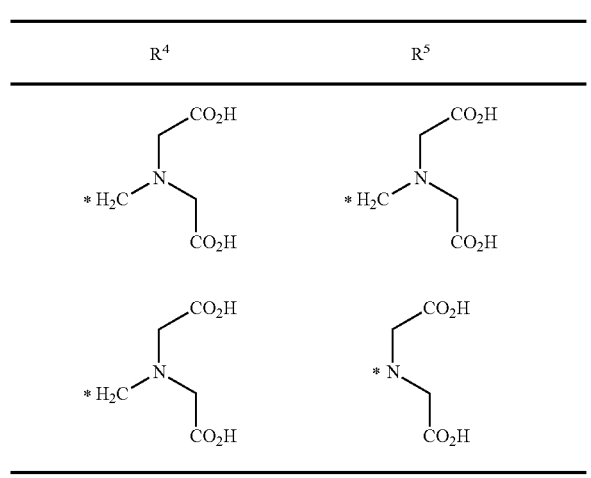 | | or a carboxylic acid salt or carboxamide derivative (CONH$_2$) thereof, or a radical of any of the foregoing; or a derivative thereof comprising a chelated metal.

In another illustrative embodiment, the conjugate, composition, unit dose, method, use, or kit of any other embodiment described herein comprises a compound of formula

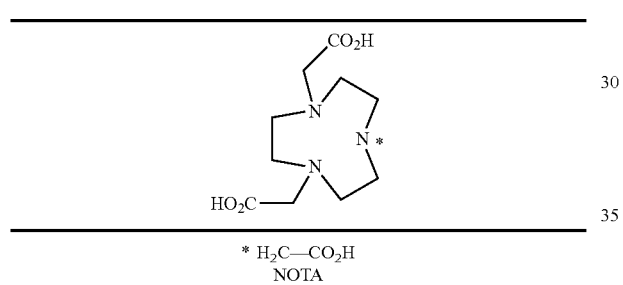
NOTA

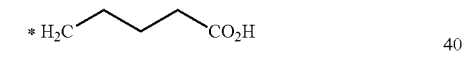
NODA-HA

NODA-MPN

NODA-MBA

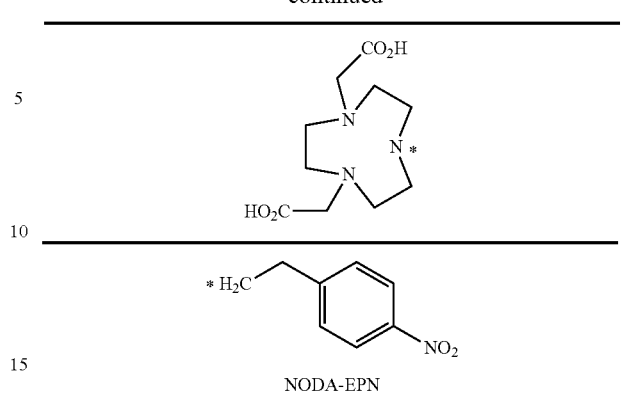

NODA-EPN

NODA-MPAA

NODA-EBA

NODA-BAEM

NODA-MPH

NODA-MPAED

NODA-MPAEM

-continued
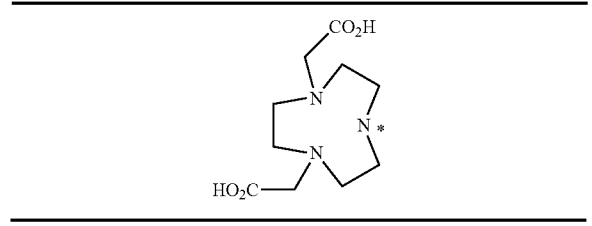
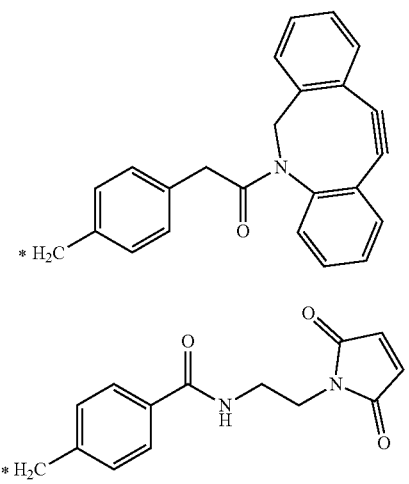
NODA-MBEM
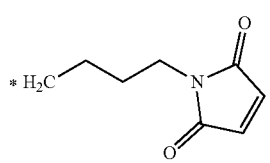
NODA-BM
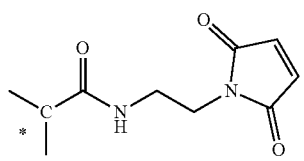
NODA-EA
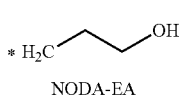
NODA-butyne
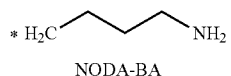
NODA-BA
-continued
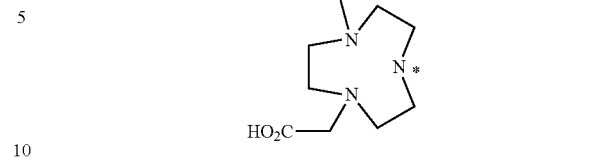
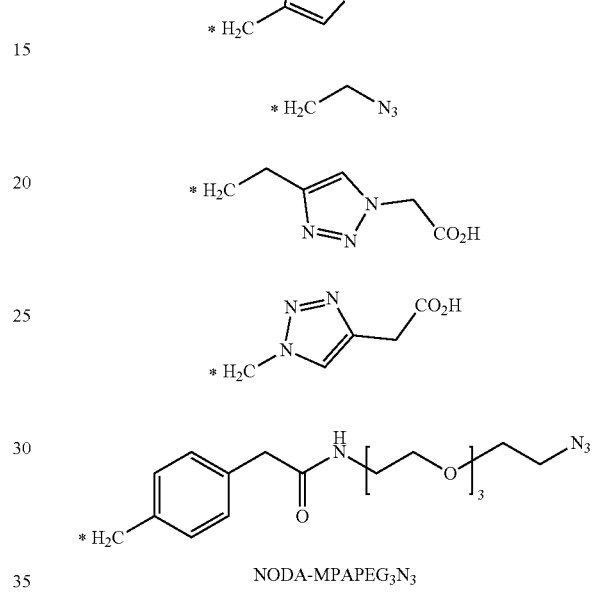
NODA-MPAPEG3N3
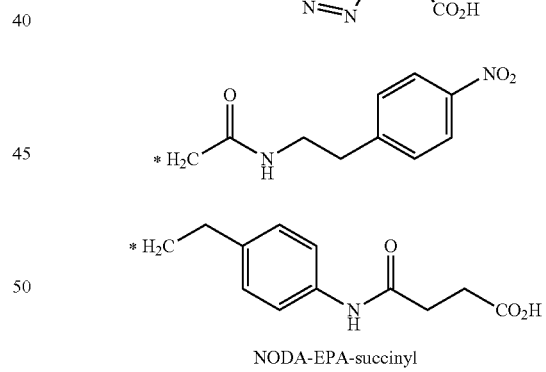
NODA-EPA-succinyl
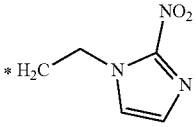
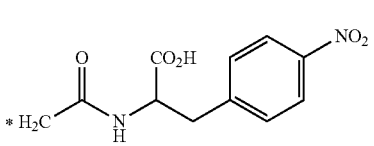 [SMILES: CC(=O)NC(Cc1ccc([N+](=O)[O-])cc1)C(=O)O]

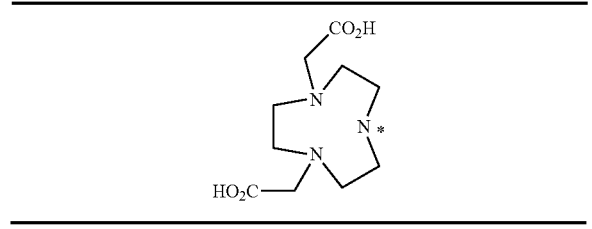

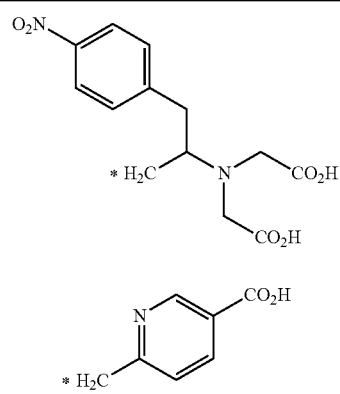

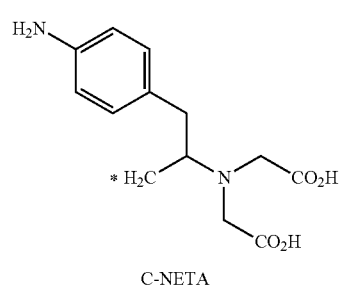 [SMILES: CC(Cc1ccc(N)cc1)N(CC(=O)O)CC(=O)O]

C-NETA

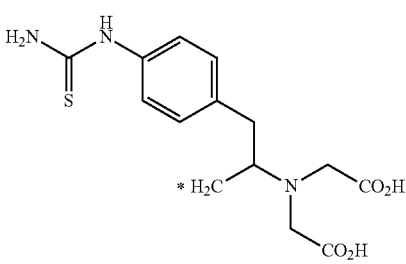 [SMILES: CC(Cc1ccc(NC(N)=S)cc1)N(CC(=O)O)CC(=O)O]

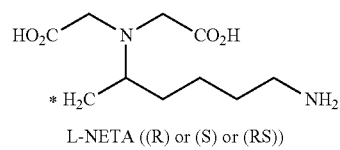 [SMILES: CC(CCCCN)N(CC(=O)O)CC(=O)O]

L-NETA ((R) or (S) or (RS))

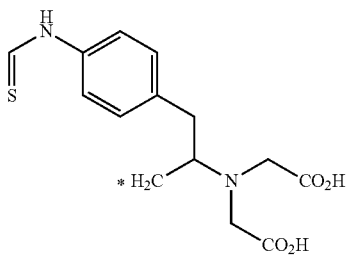 [SMILES: CC(Cc1ccc(NC=S)cc1)N(CC(=O)O)CC(=O)O]

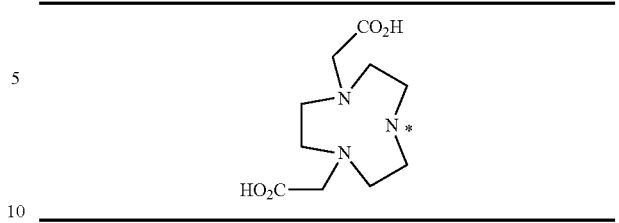

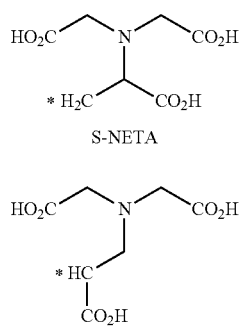

S-NETA

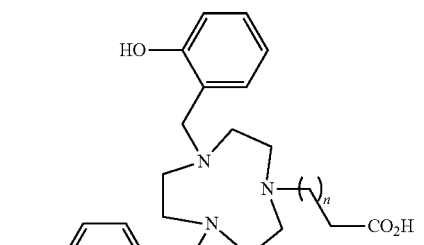

or a carboxylic acid salt or carboxamide derivative (CONH$_2$) thereof, or a radical of any of the foregoing; or a derivative thereof comprising a chelated metal.

In another illustrative embodiment, the conjugate, composition, unit dose, method, use, or kit of any other embodiment described herein comprises a compound selected from the formulae

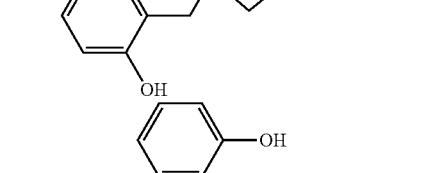

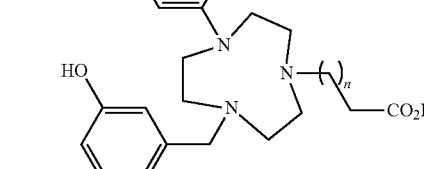

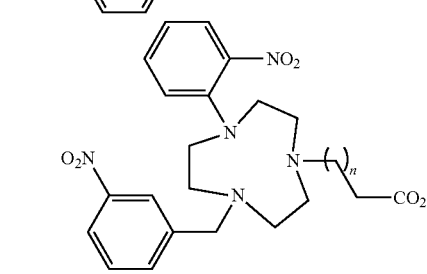

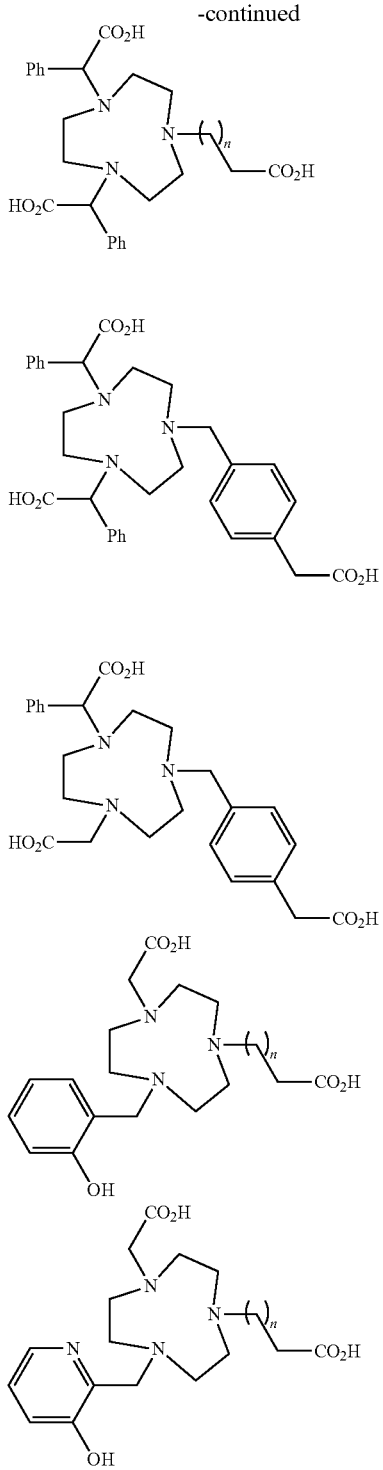

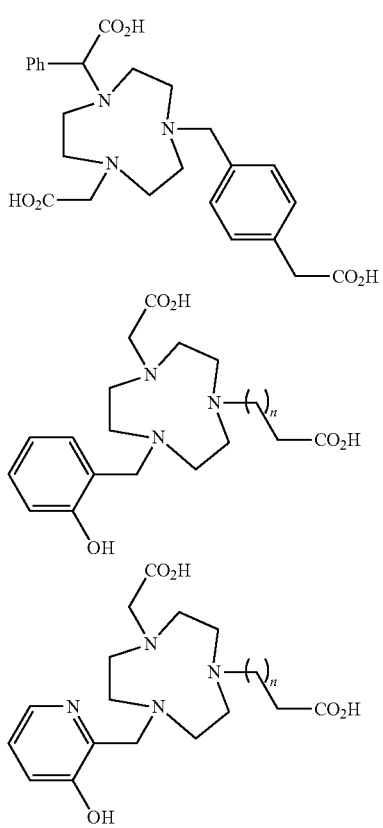

or a carboxylic acid salt or carboxamide derivative (CONH$_2$) thereof, or a radical of any of the foregoing, where n is an integer selected from 1, 2, 3, 4, 5, or 6; or a derivative thereof comprising a chelated metal.

As used herein the term "radical" generally refers to an open valence compound or chemical fragment that results after the removal of a hydrogen atom or a hydroxyl group from a carboxylic acid. For example, the following radicals may be formed from L-NETA

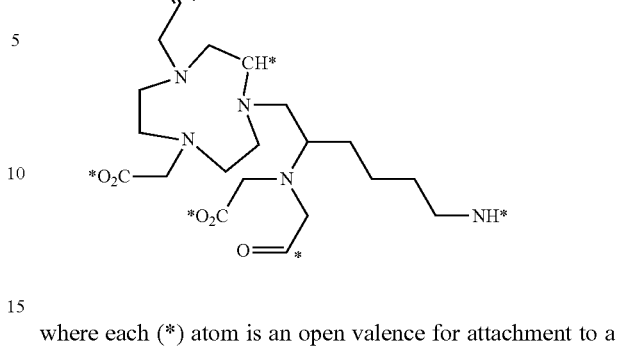

where each (*) atom is an open valence for attachment to a linker and/or targeting agent.

It is to be understood that the foregoing compounds and radicals thereof, may be further functionalized to attach reactive groups for the subsequent attachment of linkers and/or targeting groups. Illustratively, the following reactive intermediates are described herein

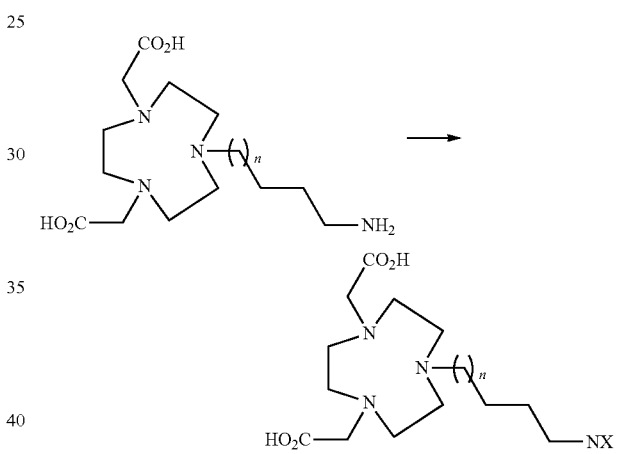

where n is 0 or 1, and NX is

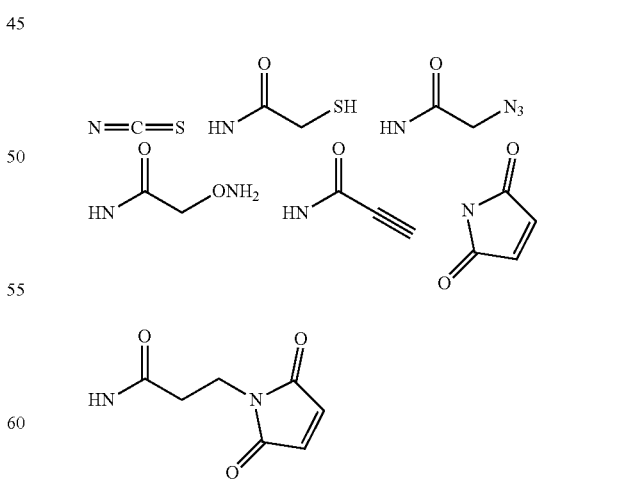

and the like.

It is to be understood that the following compounds, and metal chelates thereof, are not conjugates of the invention:

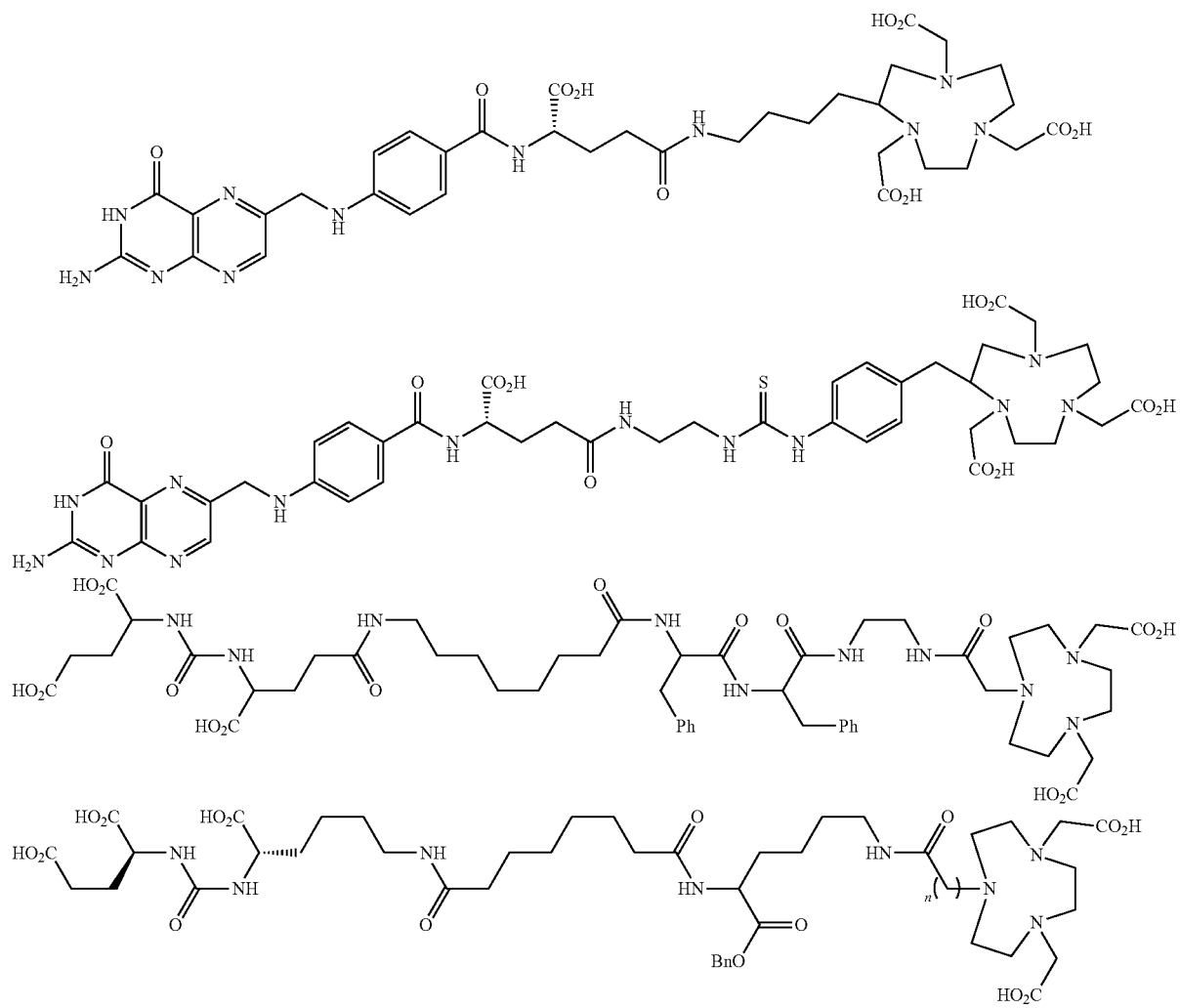

where n is 1 or 3.

The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "alkyl" includes a chain of carbon atoms, which is optionally branched. As used herein, the terms "alkenyl" and "alkynyl" each include a chain of carbon atoms, which is optionally branched, and include at least one double bond or triple bond, respectively. It is to be understood that alkynyl may also include one or more double bonds. It is to be further understood that in certain embodiments, alkyl is advantageously of limited length, including $C_1$-$C_{24}$, $C_1$-$C_{12}$, $C_1$-$C_8$, $C_1$-$C_6$, and $C_1$-$C_4$. Illustratively, such particularly limited length alkyl groups, including $C_1$-$C_8$, $C_1$-$C_6$, and $C_1$-$C_4$ may be referred to as lower alkyl. It is to be further understood that in certain embodiments alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. Illustratively, such particularly limited length alkenyl and/or alkynyl groups, including $C_2$-$C_8$, $C_2$-$C_6$, and $C_2$-$C_4$ may be referred to as lower alkenyl and/or alkynyl. It is appreciated herein that shorter alkyl, alkenyl, and/or alkynyl groups may add less lipophilicity to the compound and accordingly will have different pharmacokinetic behavior. In embodiments of the invention described herein, it is to be understood, in each case, that the recitation of alkyl refers to alkyl as defined herein, and optionally lower alkyl. In embodiments of the invention described herein, it is to be understood, in each case, that the recitation of alkenyl refers to alkenyl as defined herein, and optionally lower alkenyl. In embodiments of the invention described herein, it is to be understood, in each case, that the recitation of alkynyl refers to alkynyl as defined herein, and optionally lower alkynyl. Illustrative alkyl, alkenyl, and alkynyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like, and the corresponding groups containing one or more double and/or triple bonds, or a combination thereof.

As used herein, the term "alkylene" includes a divalent chain of carbon atoms, which is optionally branched. As used herein, the term "alkenylene" and "alkynylene" includes a divalent chain of carbon atoms, which is optionally branched, and includes at least one double bond or triple bond, respectively. It is to be understood that alkynylene may also include one or more double bonds. It is to be further understood that in certain embodiments, alkylene is advantageously of limited length, including $C_1$-$C_{24}$, $C_1$-$C_{12}$, $C_1$-$C_8$, $C_1$-$C_6$, and $C_1$-$C_4$. Illustratively, such particularly limited length alkylene groups, including $C_1$-$C_8$, $C_1$-$C_6$, and $C_1$-$C_4$ may be referred to as lower alkylene. It is to be further understood that in certain embodiments alkenylene and/or alkynylene may each be advantageously of limited length, including $C_2$-$C_{24}$, $C_2$-$C_{12}$, $C_2$-$C_8$, $C_2$-$C_6$, and $C_2$-$C_4$. Illustratively, such particularly limited length alkenylene and/or alkynylene groups, including $C_2$-$C_8$, $C_2$-$C_6$, and $C_2$-$C_4$ may be referred to as lower alkenylene and/or alkynylene. It is appreciated herein that shorter alkylene, alkenylene, and/or alkynylene groups may add less lipophilicity to the compound and accordingly will have different pharmacokinetic behavior. In embodiments of the invention described herein, it is to be understood, in each case, that the recitation of alkylene, alkenylene, and alkynylene refers to alkylene, alkenylene, and alkynylene as defined herein, and optionally lower alkylene, alkenylene, and alkynylene. Illustrative alkyl groups are, but not limited to, methylene, ethylene, n-propylene, isopropylene, n-butylene, isobutylene, sec-butylene, pentylene, 1,2-pentylene, 1,3-pentylene, hexylene, heptylene, octylene, and the like.

As used herein, the term "linker" includes is a chain of atoms that connects two or more functional parts of a molecule to form a conjugate. Illustratively, the chain of atoms is selected from C, N, O, S, Si, and P, or C, N, O, S, and P, or C, N, O, and S. The chain of atoms covalently connects different functional capabilities of the conjugate, such as targeting agents, drugs, diagnostic agents, imaging agents, and the like. The linker may have a wide variety of lengths, such as in the range from about 2 to about 100 atoms in the contiguous backbone. The atoms used in forming the linker may be combined in all chemically relevant ways, such as chains of carbon atoms forming alkylene, alkenylene, and alkynylene groups, and the like; chains of carbon and oxygen atoms forming ethers, polyoxyalkylene groups, or when combined with carbonyl groups forming esters and carbonates, and the like; chains of carbon and nitrogen atoms forming amines, imines, polyamines, hydrazines, hydrazones, or when combined with carbonyl groups forming amides, ureas, semicarbazides, carbazides, and the like; chains of carbon, nitrogen, and oxygen atoms forming alkoxyamines, alkoxylamines, or when combined with carbonyl groups forming urethanes, amino acids, acyloxylamines, hydroxamic acids, and the like; and many others. In addition, it is to be understood that the atoms forming the chain in each of the foregoing illustrative embodiments may be either saturated or unsaturated, thus forming single, double, or triple bonds, such that for example, alkanes, alkenes, alkynes, imines, and the like may be radicals that are included in the linker. In addition, it is to be understood that the atoms forming the linker may also be cyclized upon each other or be part of cyclic structure to form divalent cyclic structures that form the linker, including cyclo alkanes, cyclic ethers, cyclic amines, and other heterocycles, arylenes, heteroarylenes, and the like in the linker. In this latter arrangement, it is to be understood that the linker length may be defined by any pathway through the one or more cyclic structures. Illustratively, the linker length is defined by the shortest pathway through the each one of the cyclic structures. It is to be understood that the linkers may be optionally substituted at any one or more of the open valences along the chain of atoms, such as optional substituents on any of the carbon, nitrogen, silicon, or phosphorus atoms. It is also to be understood that the linker may connect the two or more functional parts of a molecule to form a conjugate at any open valence, and it is not necessary that any of the two or more functional parts of a molecule forming the conjugate are attached at any apparent end of the linker.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

As used herein, the terms "optionally substituted aryl" and "optionally substituted heteroaryl" include the replacement of hydrogen atoms with other functional groups on the aryl or heteroaryl that is optionally substituted. Such other functional groups, also referred to herein as aryl substituents, illustratively include, but are not limited to, amino, hydroxy, halo, thio, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxy, thio, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

Illustrative substituents include, but are not limited to, a radical —$(CH_2)_x Z^X$, where x is an integer from 0-6 and $Z^X$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, and nitro; or $Z^X$ is selected from —$CO_2R^4$ and —$CONR^5R^6$, where $R^4$, $R^5$, and $R^6$ are each independently selected in each occurrence from hydrogen, $C_1$-$C_6$ alkyl, aryl-$C_1$-$C_6$ alkyl, and heteroaryl-$C_1$-$C_6$ alkyl.

It is to be understood that in every instance disclosed herein, the recitation of a range of integers for any variable describes the recited range, every individual member in the range, and every possible subrange for that variable. For example, the recitation that n is an integer from 0 to 8, describes that range, the individual and selectable values of 0, 1, 2, 3, 4, 5, 6, 7, and 8, such as n is 0, or n is 1, or n is 2, etc. In addition, the recitation that n is an integer from 0 to 8 also describes each and every subrange, each of which may for the basis of a further embodiment, such as n is an integer from 1 to 8, from 1 to 7, from 1 to 6, from 2 to 8, from 2 to 7, from 1 to 3, from 2 to 4, etc.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is appreciated that certain functional groups, such as the hydroxy, amino, and like groups form complexes and/or coordination compounds with water and/or various solvents, in the various physical forms of the compounds. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein.

Illustratively, compositions may include one or more carriers, diluents, and/or excipients. The compounds described herein, or compositions containing them, may be formulated in a diagnostically or therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, ($21^{st}$ ed., 2005)).

The term "diagnostically effective amount" as used herein, refers to that amount of active compound or pharmaceutical agent that elicits the biological or medicinal response in a tissue system, animal or human that is being sought by a researcher, veterinarian, medical doctor or other clinician, which includes diagnosis and/or monitoring of the symptoms of the disease or disorder being treated. Illustrative diagnostically effective amounts of the conjugate to be administered to the host animal include about 1 pg/kg to about 10 mg/kg, 1 ng/kg to about 10 mg/kg, or from about 10 µg/kg to about 1 mg/kg, or from about 100 µg/kg to about 500 µg/kg.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill. Illustrative therapeutically effective amounts of the conjugate to be administered to the host animal include about 1 pg/kg to about 10 mg/kg, 1 ng/kg to about 10 mg/kg, or from about 10 μg/kg to about 1 mg/kg, or from about 100 μg/kg to about 500 μg/kg.

The term "administering" as used herein includes all means of introducing the compounds and compositions described herein to the host animal, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically-acceptable carriers, adjuvants, and/or vehicles.

The above described formula includes all stereoisomeric variations. For example, the amino acid may be selected from alanine, aspartic acid, asparagine, cysteine, glutamic acid, phenylalanine, histidine, isoleucine, lysine, leucine, methionine, proline, glutamine, arginine, serine, threonine, valine, tryptophan, tyrosine, and ornithine, and the like.

It is to be understood that in every instance disclosed herein, the recitation of a range of integers for any variable describes the recited range, every individual member in the range, and every possible subrange for that variable. For example, the recitation that n is an integer from 0 to 8, describes that range, the individual and selectable values of 0, 1, 2, 3, 4, 5, 6, 7, and 8, such as n is 0, or n is 1, or n is 2, etc. In addition, the recitation that n is an integer from 0 to 8 also describes each and every subrange, each of which may for the basis of a further embodiment, such as n is an integer from 1 to 8, from 1 to 7, from 1 to 6, from 2 to 8, from 2 to 7, from 1 to 3, from 2 to 4, etc.

In another embodiment, the linkers described herein include a polyether, such as the linkers of the following formulae:

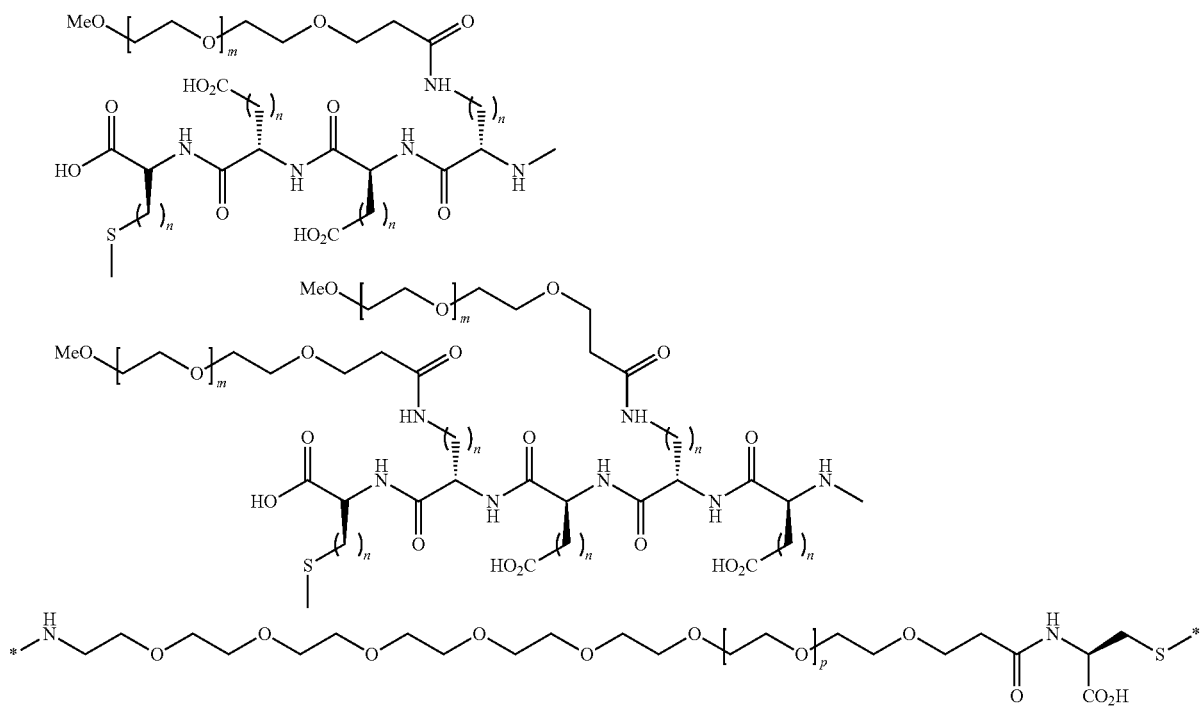

As used herein, the term "amino acid" refers generally to beta, gamma, and longer amino acids, such as amino acids of the formula:

where R is hydrogen, alkyl, acyl, or a suitable nitrogen protecting group, R' and R" are hydrogen or a substituent, each of which is independently selected in each occurrence, and q is an integer such as 1, 2, 3, 4, or 5. Illustratively, R' and/or R" independently correspond to, but are not limited to, hydrogen or the side chains present on naturally occurring amino acids, such as methyl, benzyl, hydroxymethyl, thiomethyl, carboxyl, carboxylmethyl, guanidinopropyl, and the like, and derivatives and protected derivatives thereof.

where m is an integer independently selected in each instance from 1 to about 8; p is an integer selected from 1 to about 10; and n is an integer independently selected in each instance from 1 to about 3. In one aspect, m is independently in each instance 1 to about 3. In another aspect, n is 1 in each instance. In another aspect, p is independently in each instance about 4 to about 6. Illustratively, the corresponding polypropylene polyethers corresponding to the foregoing are described herein and may be included in the conjugates as linkers. In addition, it is appreciated that mixed polyethylene and polypropylene polyethers may be included in the conjugates as linkers. Further, cyclic variations of the foregoing polyether compounds, such as those that include tetrahydrofuranyl, 1,3-dioxanes, 1,4-dioxanes, and the like are described herein.

In another embodiment, the linkers described herein include a plurality of hydroxyl functional groups, such as linkers that incorporate monosaccharides, oligosaccharides, polysaccharides, and the like. It is to be understood that the polyhydroxyl containing linkers comprise a plurality of —(CROH)— groups, where R is hydrogen or alkyl.

In another embodiment, the linkers include one or more of the following diradicals:

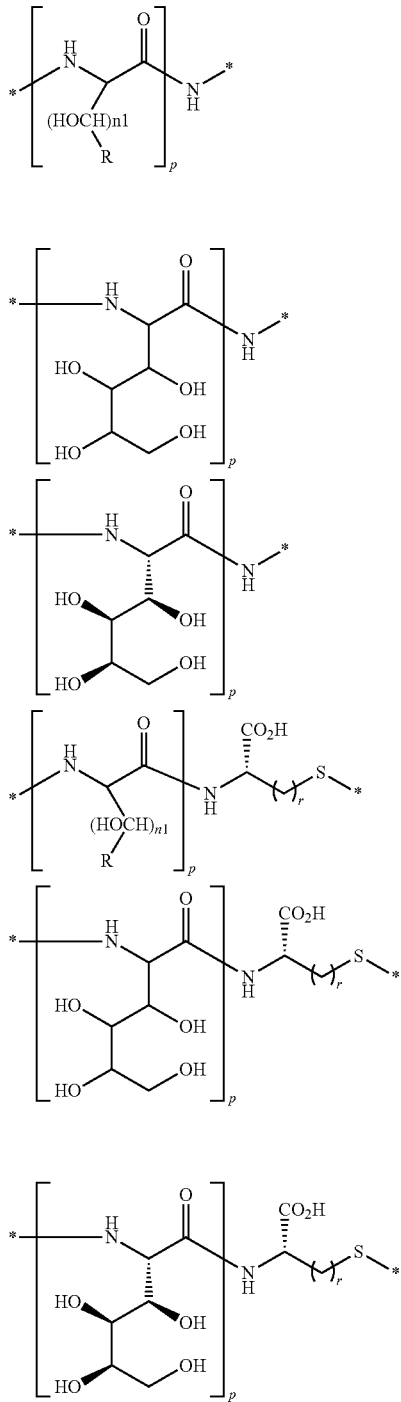

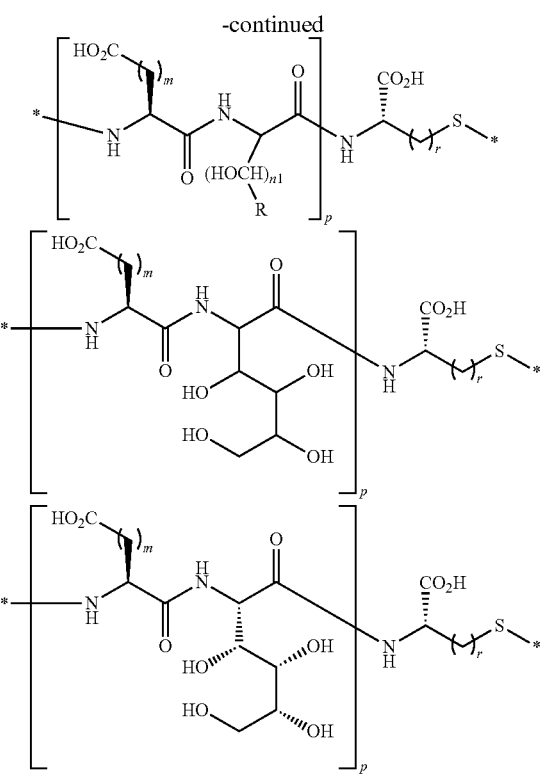

wherein R is H, alkyl, cycloalkyl, or arylalkyl; m is an integer from 1 to about 3; n1 is an integer from 1 to about 5, or n1 is an integer from 2 to about 5, p is an integer from 1 to about 5, and r is an integer selected from 1 to about 3. In one aspect, the integer n is 3 or 4. In another aspect, the integer p is 3 or 4. In another aspect, the integer r is 1.

In another embodiment, the linkers include one or more of the following diradicals:

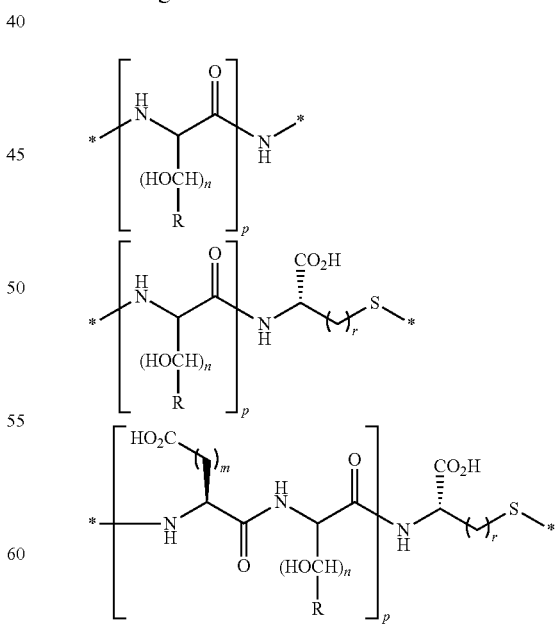

wherein R is H, alkyl, cycloalkyl, or arylalkyl; m is an integer from 1 to about 3; n is an integer from 1 to about 5, or from 2 to about 5, p is an integer from 1 to about 5, and r is an integer selected from 1 to about 3. In one aspect, the integer n is 3 or 4. In another aspect, the integer p is 3 or 4. In another aspect, the integer r is 1.
In another embodiment, the linker includes one or more of the following cyclic polyhydroxyl groups:
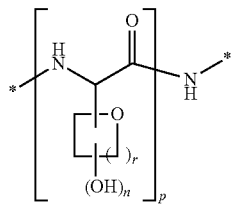
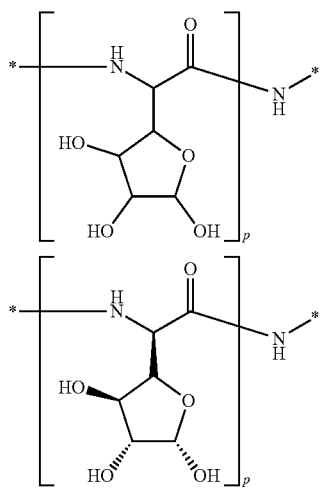
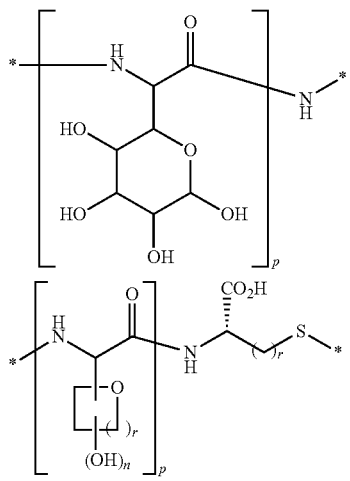
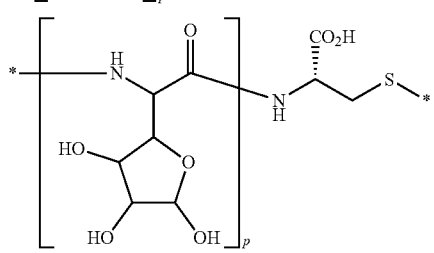
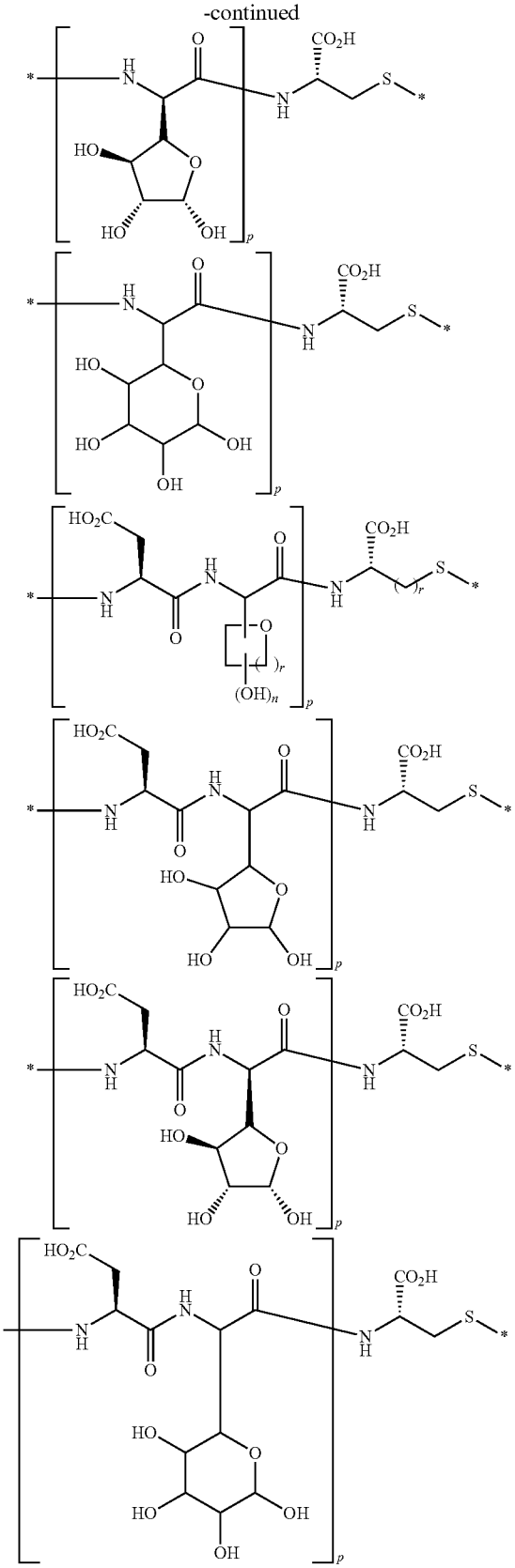
wherein n is an integer from 2 to about 5, p is an integer from 1 to about 5, and each r is an independently selected integer from 1 to about 4. In one aspect, the integer n is 3 or 4. In another aspect, the integer p is 3 or 4. In another aspect, each integer r is independently 2 or 3. It is understood that all stereochemical forms of such sections of the linkers are described herein. For example, in the above formula, the section may be derived from ribose, xylose, glucose, mannose, galactose, or other sugar and retain the stereochemical arrangements of pendant hydroxyl and alkyl groups present on those molecules. In addition, it is to be understood that in the foregoing formulae, various deoxy compounds are also described. Illustratively, compounds of the following formulae are described:

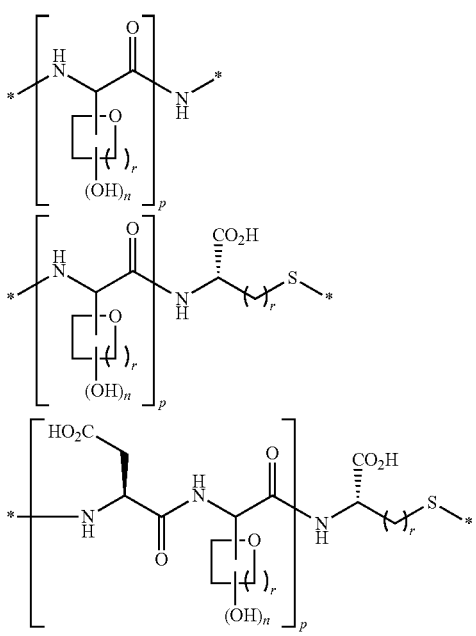

wherein n is equal to or less than r, such as when r is 2 or 3, n is 1 or 2, or 1, 2, or 3, respectively.

In another embodiment, the linker includes a polyhydroxyl compound of the following formula:

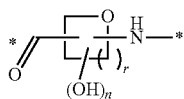

wherein n and r are each an integer selected from 1 to about 3. In one aspect, the linker includes one or more polyhydroxyl compounds of the following formulae:

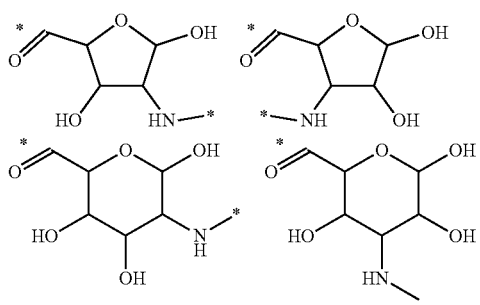

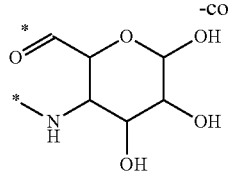

It is understood that all stereochemical forms of such sections of the linkers are described herein. For example, in the above formula, the section may be derived from ribose, xylose, glucose, mannose, galactose, or other sugar and retain the stereochemical arrangements of pendant hydroxyl and alkyl groups present on those molecules.

In another configuration, the linkers L described herein include polyhydroxyl groups that are spaced away from the backbone of the linker. In one embodiment, such carbohydrate groups or polyhydroxyl groups are connected to the back bone by a triazole group, forming triazole-linked linkers. Illustratively, such linkers include diradicals of the following formulae:

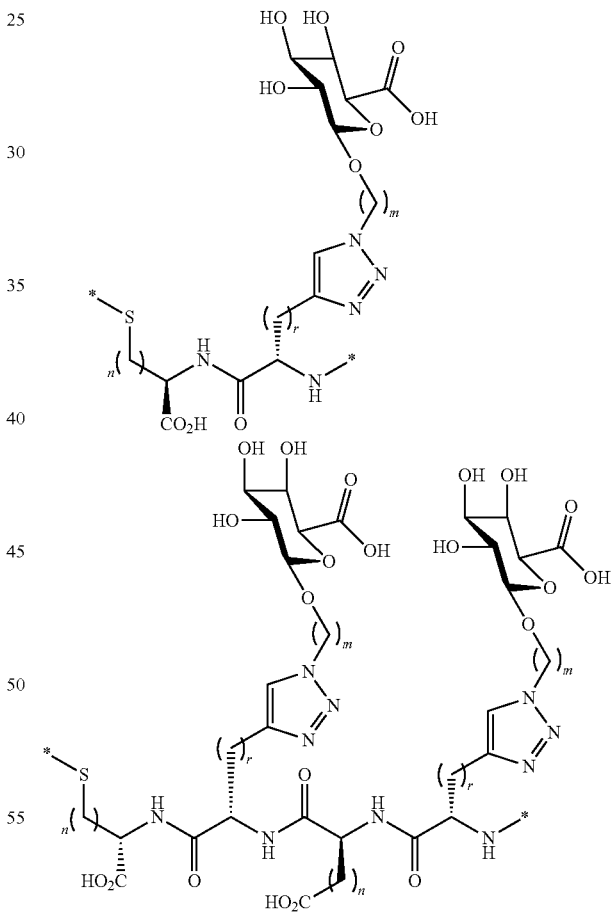

wherein n, m, and r are integers and are each independently selected in each instance from 1 to about 5. In one illustrative aspect, m is independently 2 or 3 in each instance. In another aspect, r is 1 in each instance. In another aspect, n is 1 in each instance. In one variation, the group connecting the polyhydroxyl group to the backbone of the linker is a different heteroaryl group, including but not limited to, pyrrole, pyrazole, 1,2,4-triazole, furan, oxazole, isoxazole, thienyl, thiazole, isothiazole, oxadiazole, and the like. Similarly, divalent 6-membered ring heteroaryl groups are described. Other variations of the foregoing illustrative linkers include oxyalkylene groups, such as the following formulae:

In another embodiment, such carbohydrate groups or polyhydroxyl groups are connected to the back bone by an amide group, forming amide-linked linkers. Illustratively, such linkers include diradicals of the following formulae:

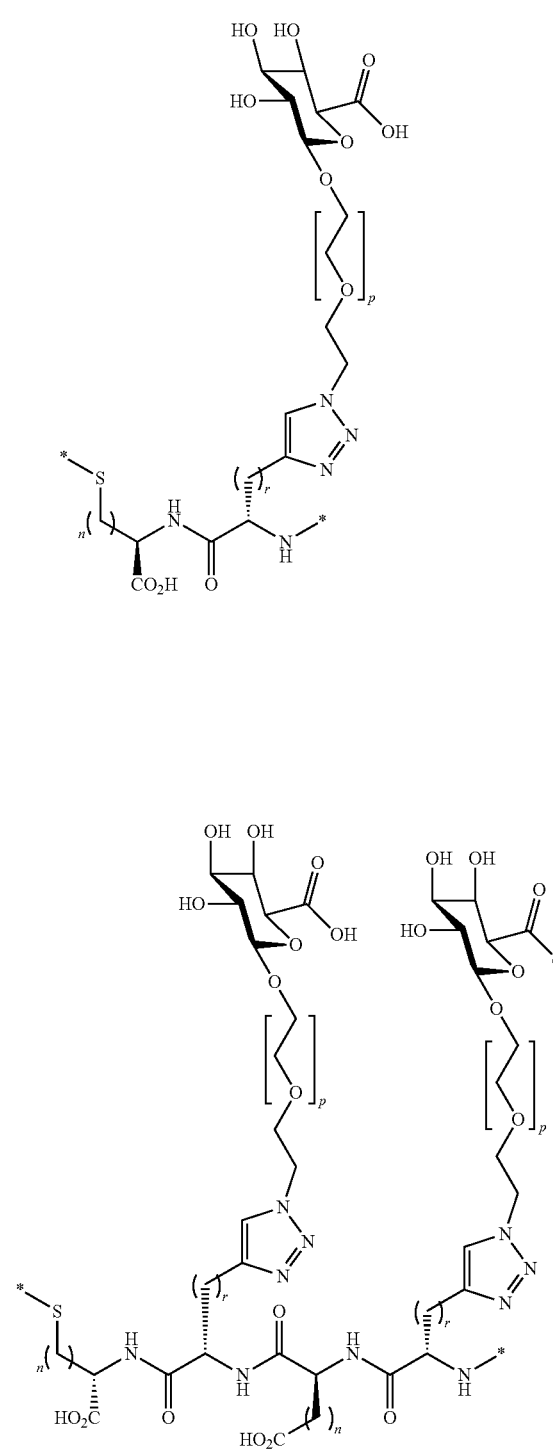

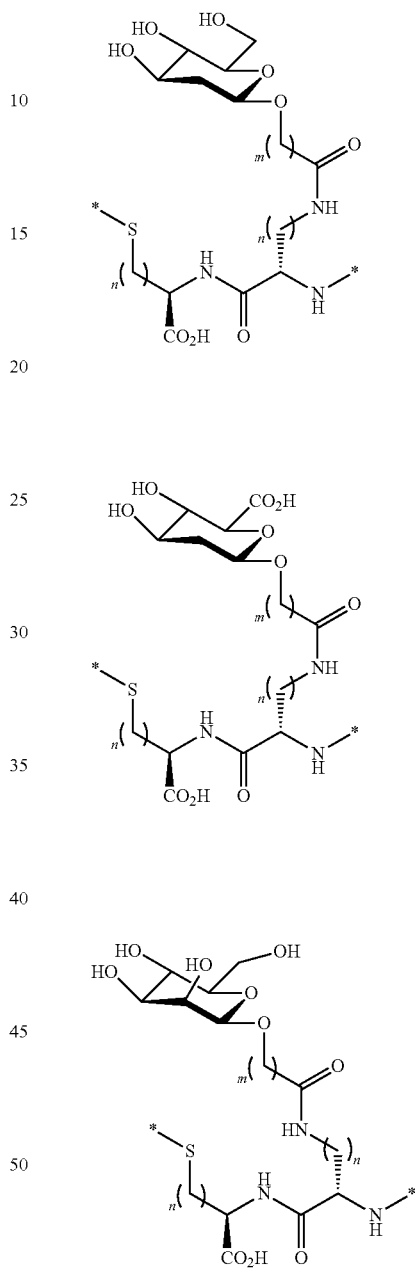

wherein n and r are integers and are each independently selected in each instance from 1 to about 5; and p is an integer selected from 1 to about 4.

wherein each n is an independently selected integer from 1 to about 3, and m is an independently selected integer from 1 to about 22. In one illustrative aspect, each n is independently 1 or 2. In another illustrative aspect, m is selected from about 6 to about 10, illustratively 8. In one variation, the group connecting the polyhydroxyl group to the backbone of the linker is a different functional group, including but not limited to, esters, ureas, carbamates, acylhydrazones, and the like. Similarly, cyclic variations are described. Other variations of the foregoing illustrative linkers include oxyalkylene groups, such as the following formulae:

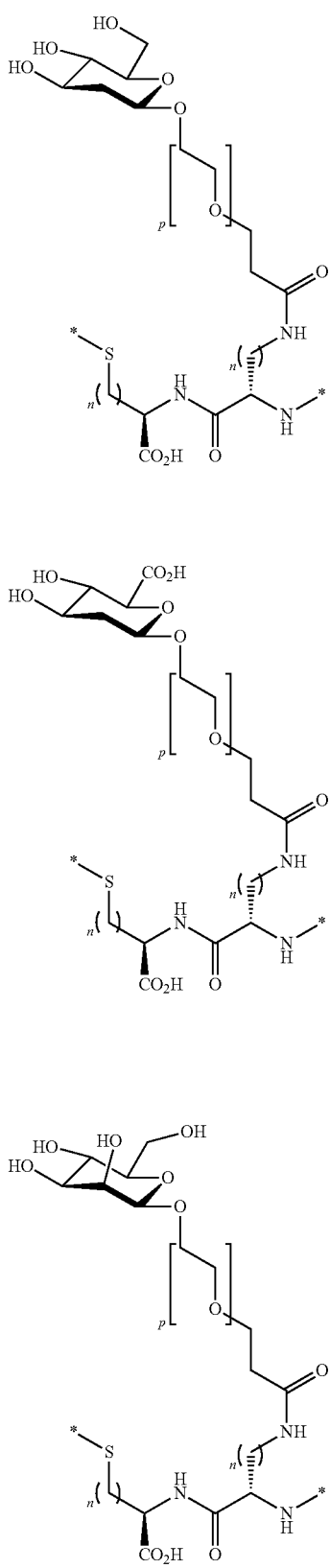
wherein n is in each instance an independently selected integer from 1 to about 5; and p is an integer selected from 1 to about 4.
In another embodiment, the linkers include one or more of the following diradicals:
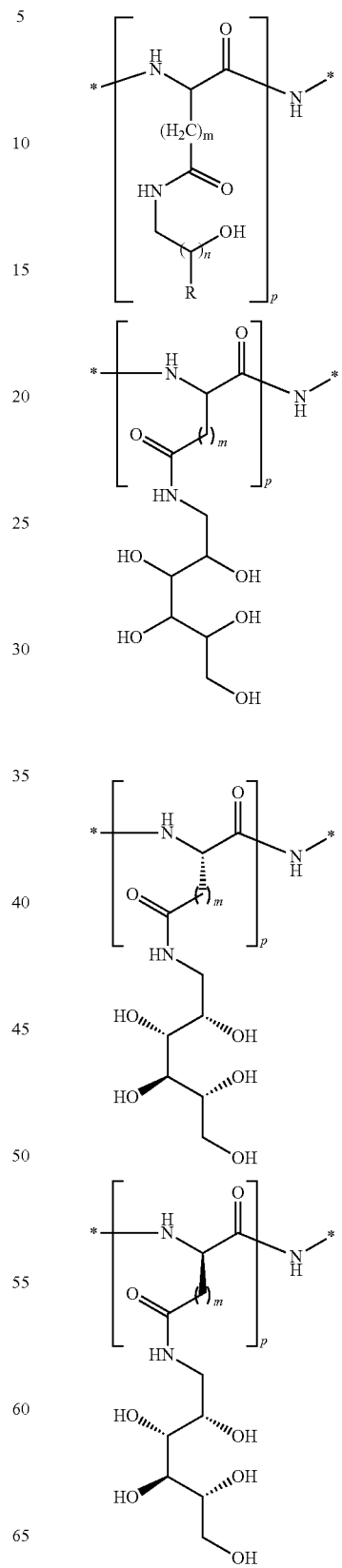

53
-continued
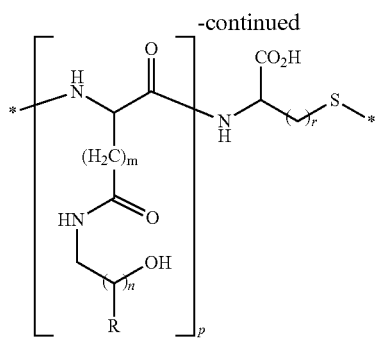
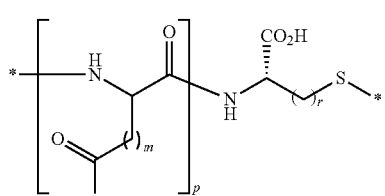
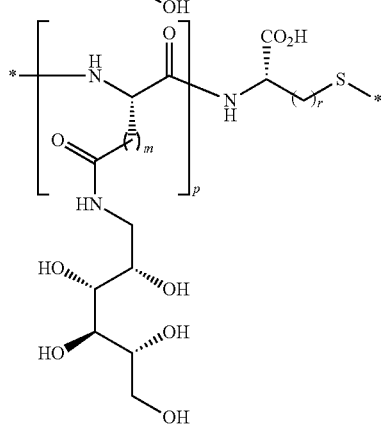
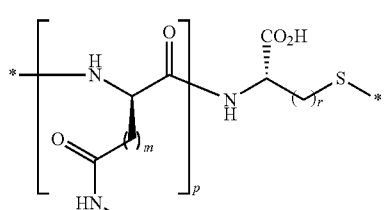
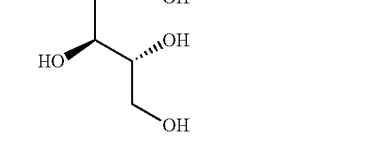
54
-continued
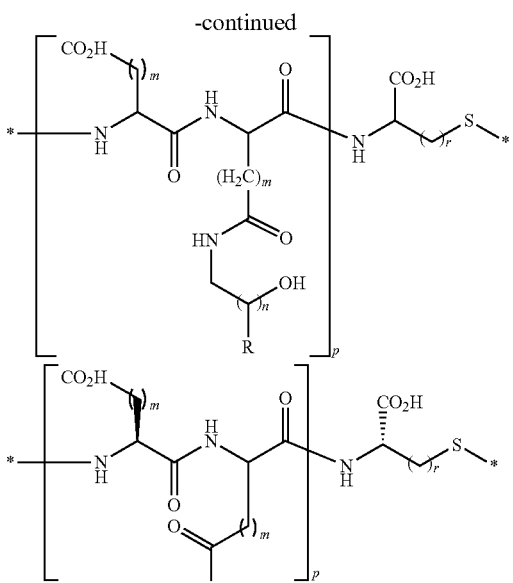
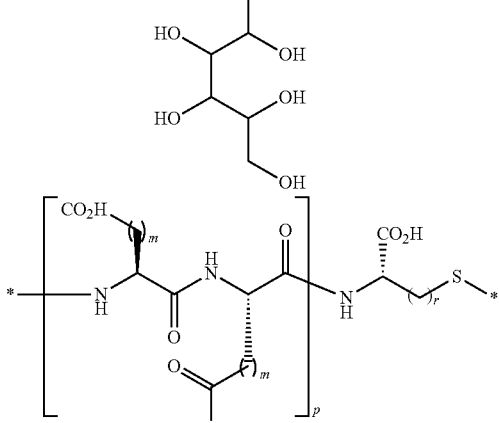
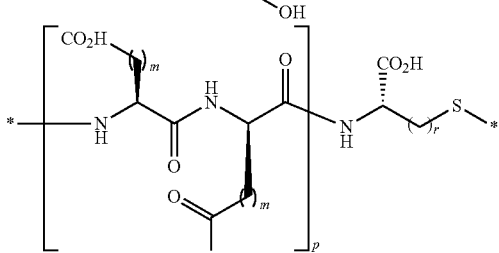

wherein R is H, alkyl, cycloalkyl, or arylalkyl; each m is an independently selected integer from 1 to about 3; each n is an independently selected integer from 1 to about 6, p is an integer from 1 to about 5, and r is an integer selected from 1 to about 3. In one variation, each n is independently 3 or 4. In another variation, the integer p is 3 or 4. In another variation, the integer r is 1.

In another embodiment, the linkers include one or more of the following diradicals:

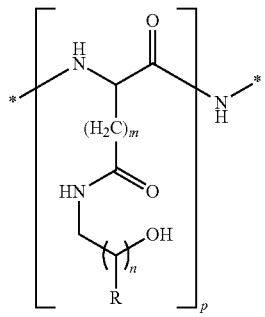

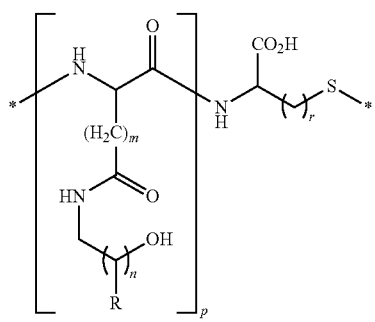

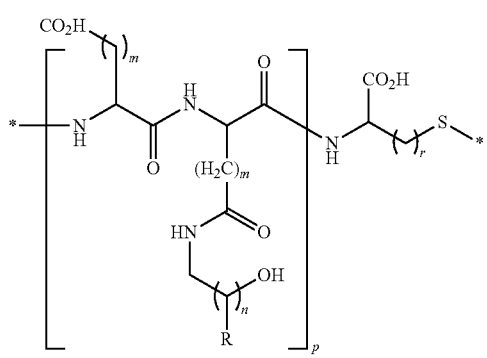

wherein R is H, alkyl, cycloalkyl, or arylalkyl; each m is an independently selected integer from 1 to about 3; each n is an independently selected integer from 2 to about 6, p is an integer from 1 to about 5, and r is an integer selected from 1 to about 3. In one variation, each n is independently 3 or 4. In another variation, the integer p is 3 or 4. In another variation, the integer r is 1.

In another embodiment, the linkers include one or more of the following diradicals:

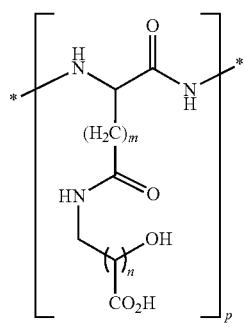

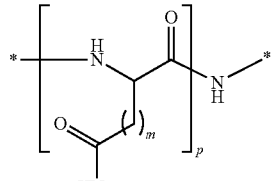

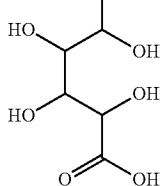

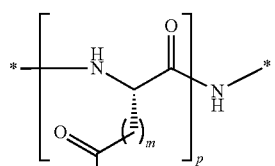

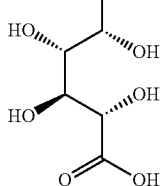

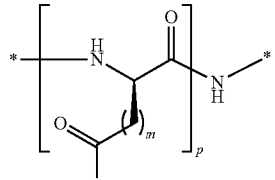

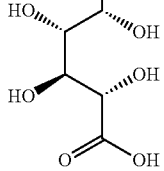

57
-continued
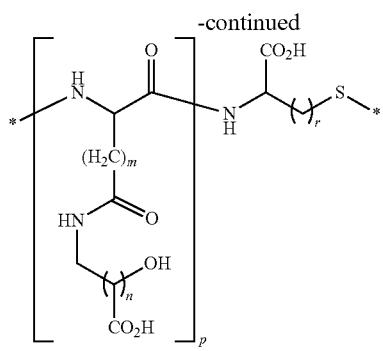
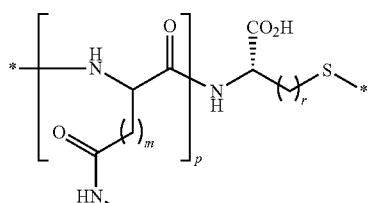
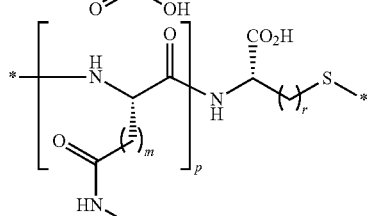
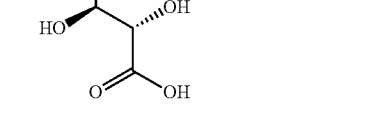
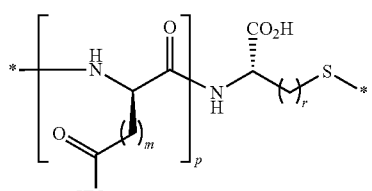
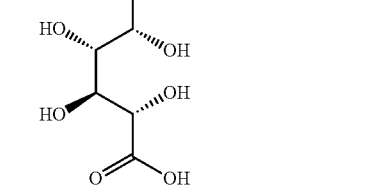
58
-continued
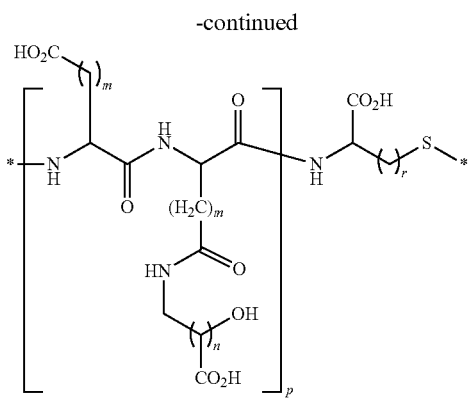
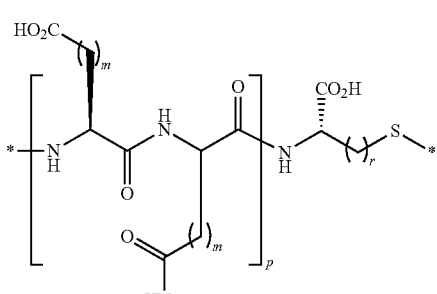
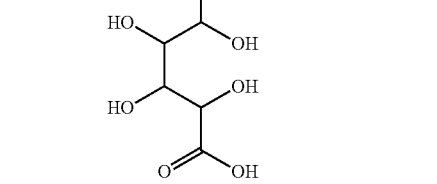
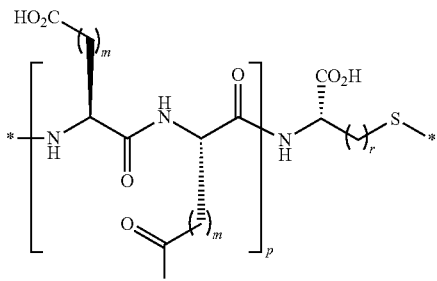
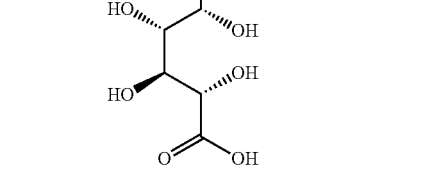

-continued

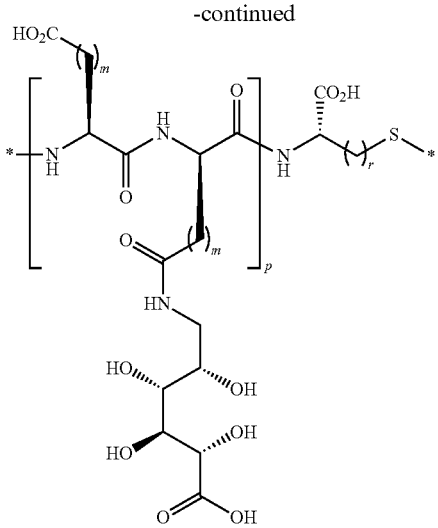

wherein each m is an independently selected integer from 1 to about 3; each n is an independently selected integer from 1 to about 6, p is an integer from 1 to about 5, and r is an integer selected from 1 to about 3. In one variation, each n is independently 3 or 4. In another variation, the integer p is 3 or 4. In another variation, the integer r is 1.

In another embodiment, the linkers include one or more of the following diradicals:

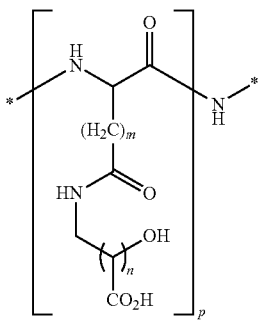

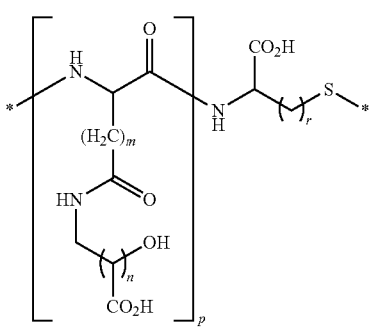

-continued

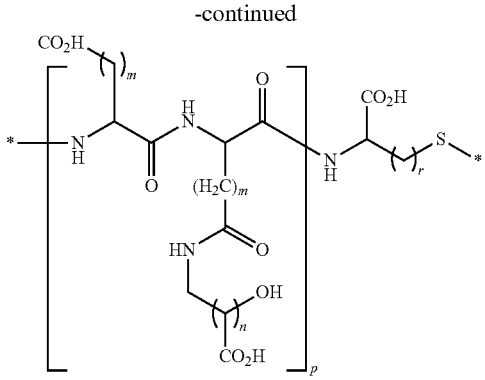

wherein each m is an independently selected integer from 1 to about 3; each n is an independently selected integer from 2 to about 6, p is an integer from 1 to about 5, and r is an integer selected from 1 to about 3. In one variation, each n is independently 3 or 4. In another variation, the integer p is 3 or 4. In another variation, the integer r is 1.

In another embodiment, the linkers include one or more of the following diradicals:

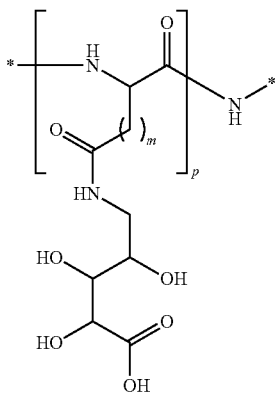

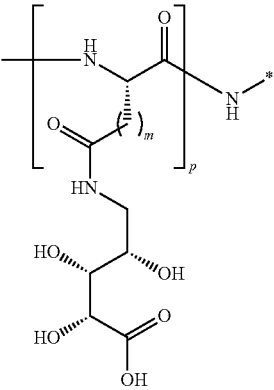

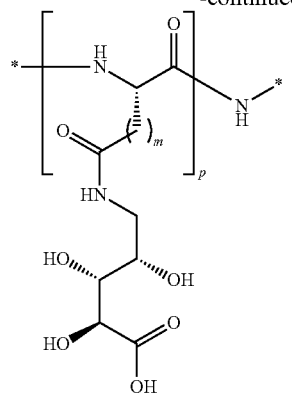
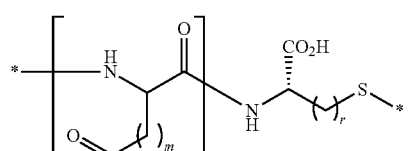
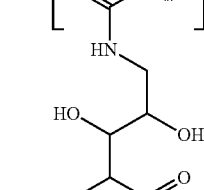
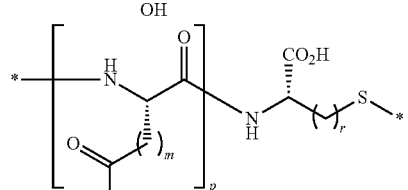
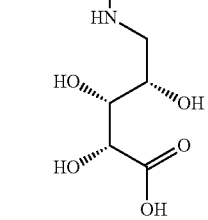
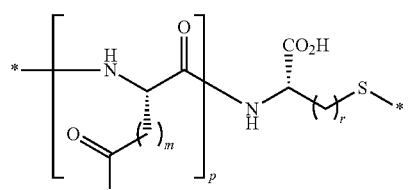
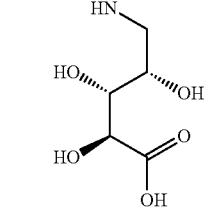
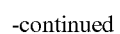
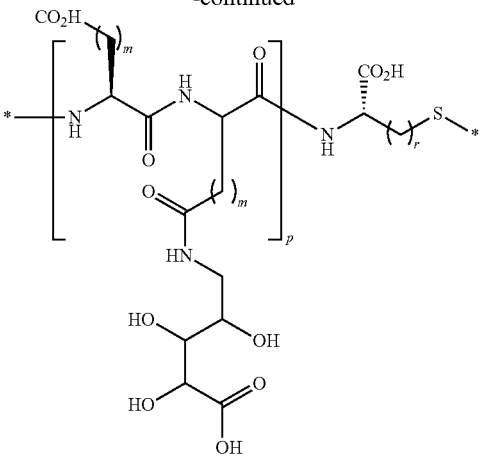
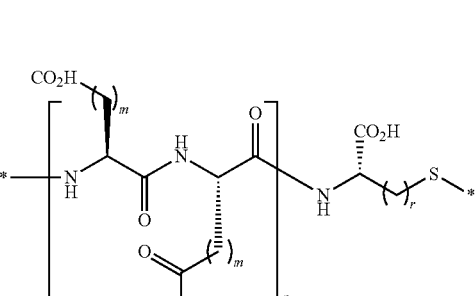
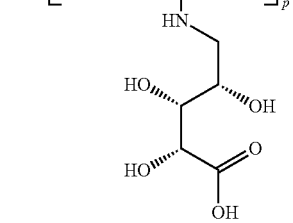
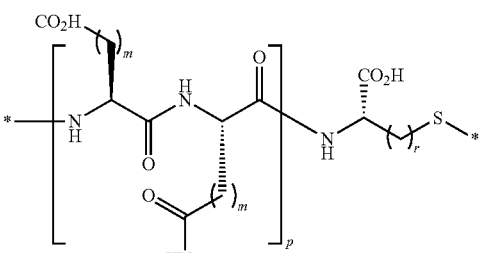
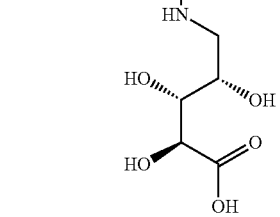
wherein each m is an independently selected integer from 1 to about 3, p is an integer from 1 to about 5, and r is an integer selected from 1 to about 3. In another variation, the integer p is 3 or 4. In another variation, the integer r is 1.
In another embodiment, the linker is a combination of backbone and branching side motifs such as is illustrated by the following formulae

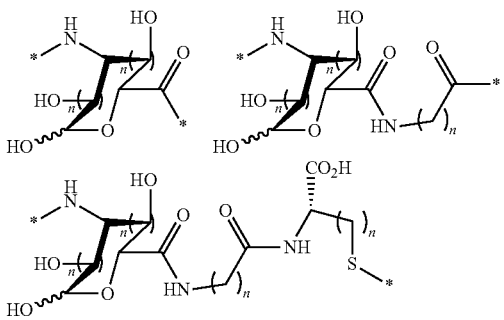

wherein n is an integer independently selected in each instance from 0 to about 3. The above formula are intended to represent 4, 5, 6, and even larger membered cyclic sugars. In addition, it is to be understood that the above formula may be modified to represent deoxy sugars, where one or more of the hydroxy groups present on the formulae are replaced by hydrogen, alkyl, or amino. In addition, it is to be understood that the corresponding carbonyl compounds are described by the above formulae, where one or more of the hydroxyl groups is oxidized to the corresponding carbonyl. In addition, in this illustrative embodiment, the pyranose includes both carboxyl and amino functional groups and (a) can be inserted into the backbone and (b) can provide synthetic handles for branching side chains in variations of this embodiment. Any of the pendant hydroxyl groups may be used to attach other chemical radicals, including additional sugars to prepare the corresponding oligosaccharides. Other variations of this embodiment are also described, including inserting the pyranose or other sugar into the backbone at a single carbon, i.e. a spiro arrangement, at a geminal pair of carbons, and like arrangements. For example, one or two ends of the linker, or the agent P, or the ligand B may be connected to the sugar to be inserted into the backbone in a 1,1; 1,2; 1,3; 1,4; 2,3, or other arrangement.

In another embodiment, the linkers include one or more amino groups of the following formulae:

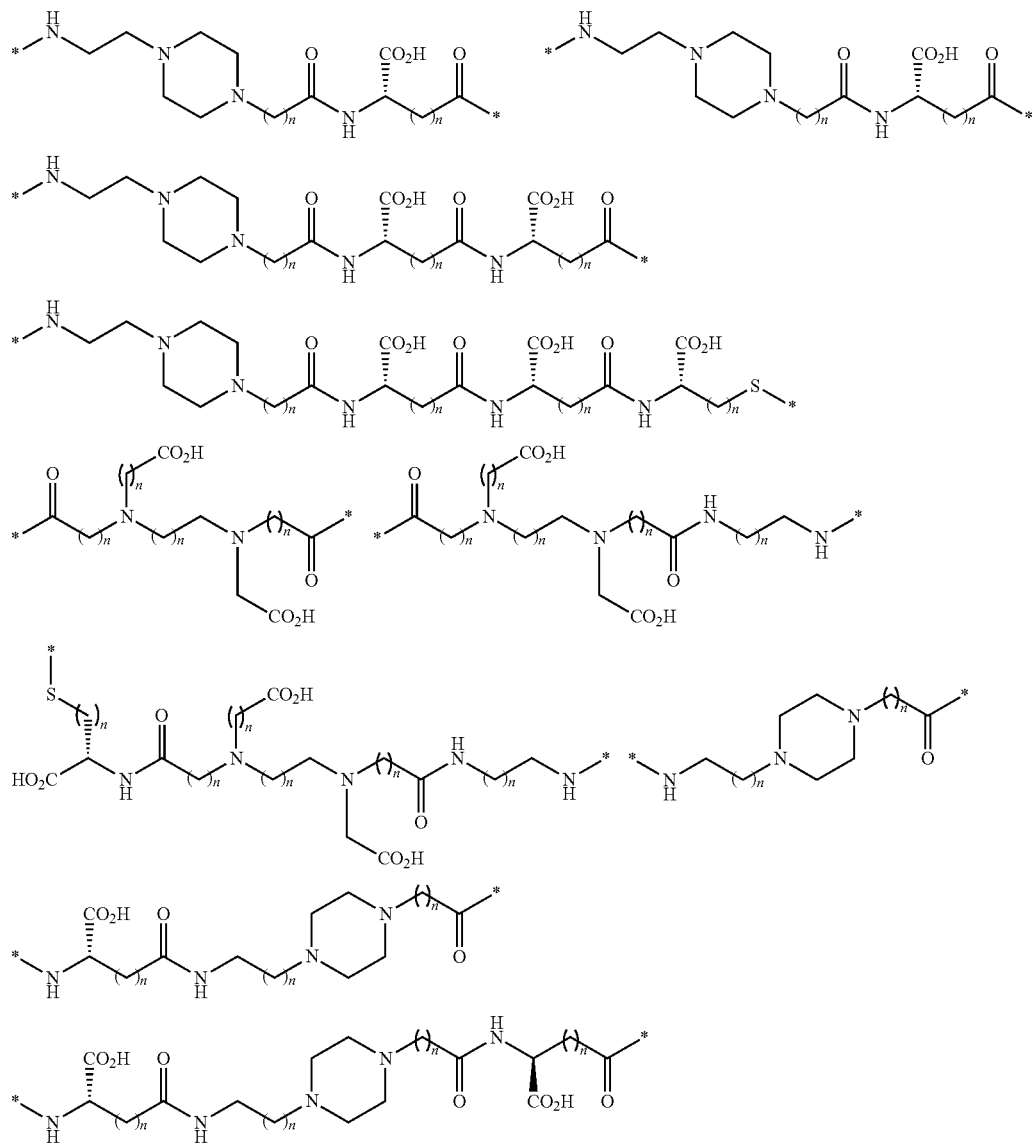

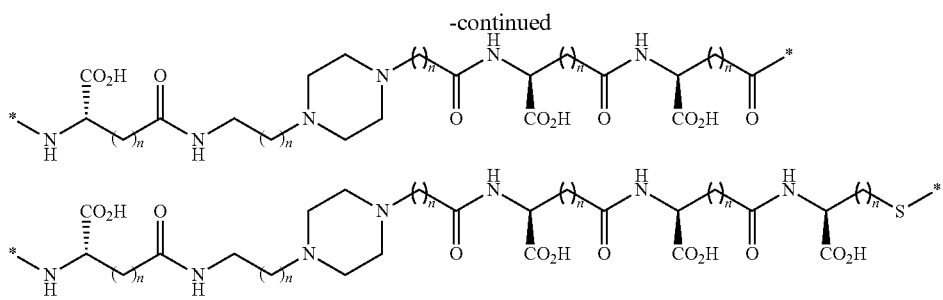

where each n is an integer independently selected in each instance from 1 to about 3. In one aspect, the each n is independently 1 or 2 in each instance. In another aspect, the integer n is 1 in each instance.

In another embodiment, the linker is a sulfuric acid ester, such as an alkyl ester of sulfuric acid. Illustratively, the linker is of the following formula:

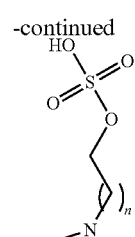

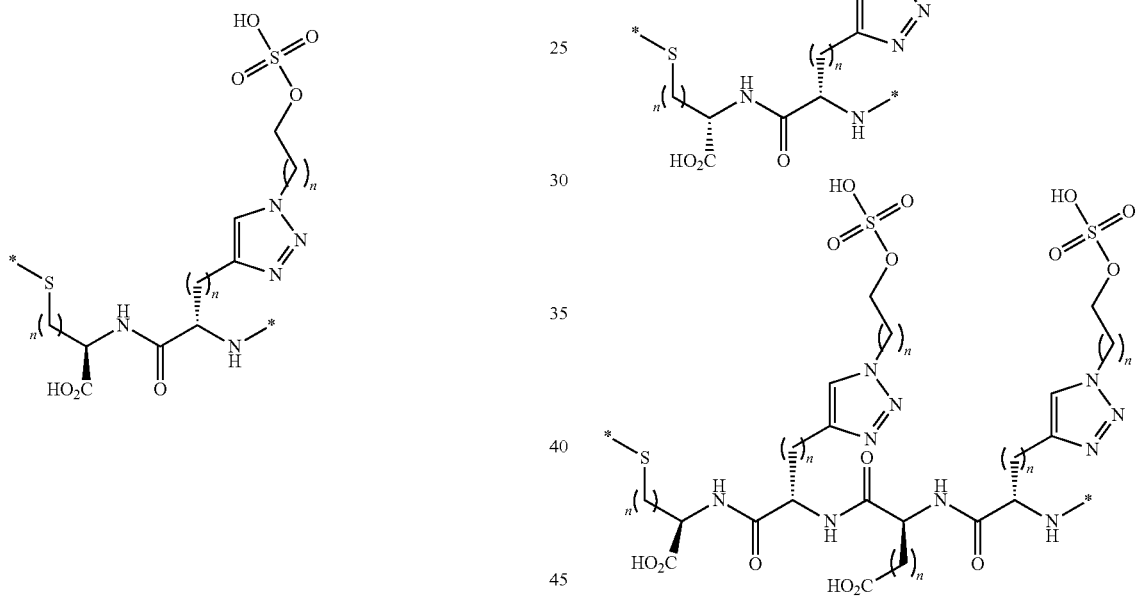

where each n is an integer independently selected in each instance from 1 to about 3. Illustratively, each n is independently 1 or 2 in each instance.

It is understood, that in such polyhydroxyl, polyamino, carboxylic acid, sulfuric acid, and like linkers that include free hydrogens bound to heteroatoms, one or more of those free hydrogen atoms may be protected with the appropriate hydroxyl, amino, or acid protecting group, respectively, or alternatively may be blocked as the corresponding pro-drugs, the latter of which are selected for the particular use, such as pro-drugs that release the parent drug under general or specific physiological conditions.

It is to be understood that in each of the foregoing illustrative examples, the stereochemical configurations shown herein are merely illustrative, and other stereochemical configurations are described. For example in one variation, the corresponding unnatural amino acid configurations may be included in the conjugated described herein as follows:

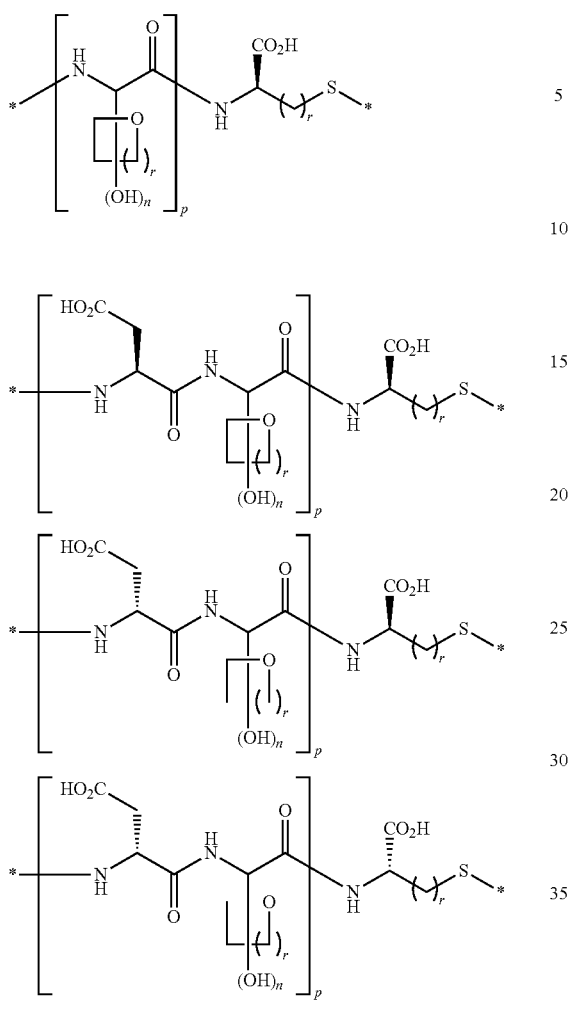

wherein each n is an independently selected integer from 2 to about 5, p is an integer from 1 to about 5, and r is an integer from 1 to about 4, as described above.

It is to be further understood that in the foregoing embodiments, open positions, such as (*) atoms are locations for attachment of the targeting agent B or the agent (P). In addition, it is to be understood that such attachment of either or both of B and A may be direct or through an intervening linker. Illustrative additional linkers are described in U.S. Pat. No. 7,601,332, the disclosure of which is incorporated herein by reference.

Illustrative bivalent radicals forming part of the linker.

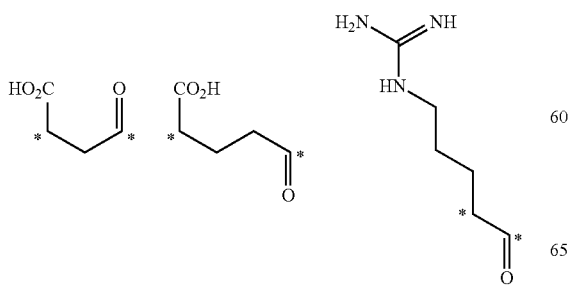

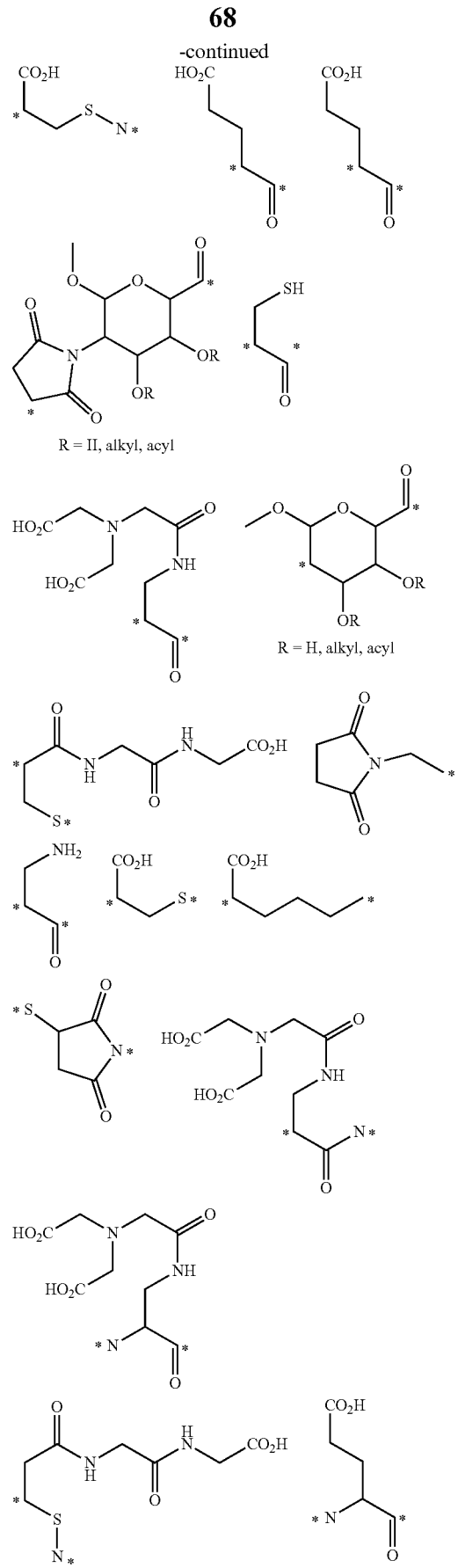

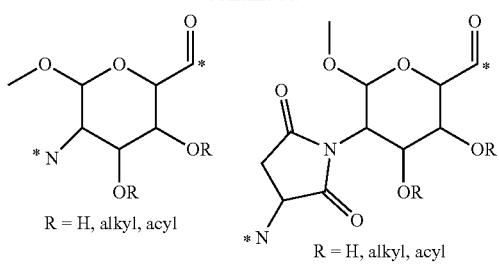
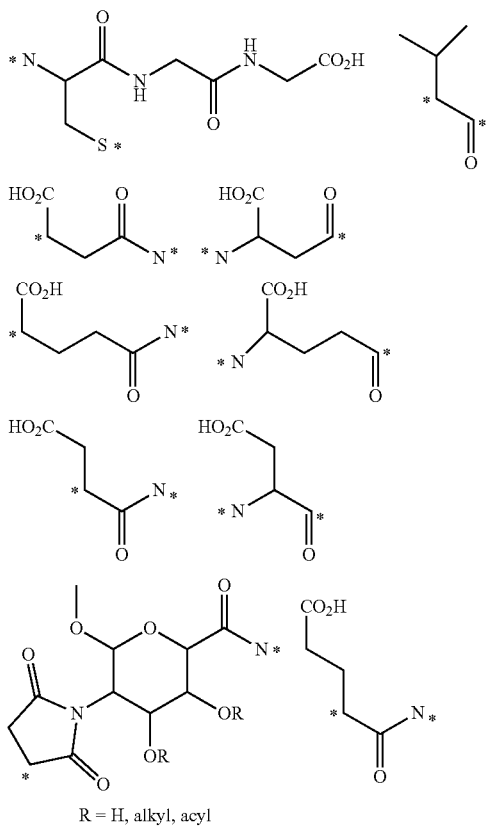
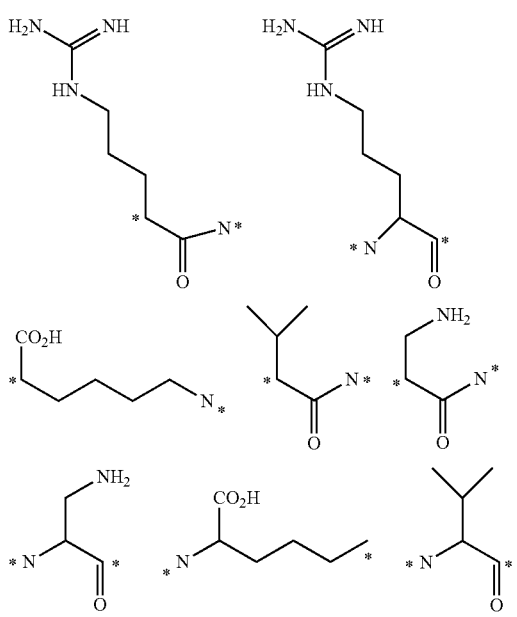

It is to be understood that the bivalent linkers may be combined in any chemically relevant way, either directly or via an intervening heteroatom to construct the linkers described herein.

In another embodiment, the polyvalent linkers described herein comprise a linker selected from the group consisting of carbonyl, thionocarbonyl, alkylene, cycloalkylene, alkylenecycloalkyl, alkylenecarbonyl, cycloalkylenecarbonyl, carbonylalkylcarbonyl, 1 alkylenesuccinimid-3-yl, 1 (carbonylalkyl)succinimid-3-yl, alkylenesulfoxyl, sulfonylalkyl, alkylenesulfoxylalkyl, alkylenesulfonylalkyl, carbonyltetrahydro-2H-pyranyl, carbonyltetrahydrofuranyl, 1-(carbonyltetrahydro-2H-pyranyl)succinimid-3-yl, and 1-(carbonyltetrahydrofuranyl)succinimid-3-yl.

In another embodiment, the compounds described herein comprise one or more amino acids.

The compounds described herein can be used for both human clinical medicine and veterinary applications. Thus, the host animal harboring the population of pathogenic cells and administered the compounds described herein can be human or, in the case of veterinary applications, can be a laboratory, agricultural, domestic, or wild animal. The present invention can be applied to host animals including, but not limited to, humans, laboratory animals such rodents (e.g., mice, rats, hamsters, etc.), rabbits, monkeys, chimpanzees, domestic animals such as dogs, cats, and rabbits, agricultural animals such as cows, horses, pigs, sheep, goats, and wild animals in captivity such as bears, pandas, lions, tigers, leopards, elephants, zebras, giraffes, gorillas, dolphins, and whales.

The compounds, compositions, methods, and uses described herein are useful for diagnosing and/or monitoring diseases caused at least in part by populations of pathogenic cells, which may cause a variety of pathologies in host animals. As used herein, the term "pathogenic cells" or "population of pathogenic cells" generally refers to cancer cells, infectious agents such as bacteria and viruses, bacteria- or virus-infected cells, inflammatory cells, activated macrophages capable of causing a disease state, and any other type of pathogenic cells that uniquely express, preferentially express, or overexpress binding sites for the targeting agents described herein.

Illustratively, the population of pathogenic cells can be a cancer cell population that is tumorigenic, including benign tumors and malignant tumors, or it can be non-tumorigenic. The cancer cell population can arise spontaneously or by such processes as mutations present in the germline of the host animal or somatic mutations, or it can be chemically-, virally-, or radiation-induced. The invention can be utilized to diagnose, monitor, and/or treat such cancers, including carcinomas, sarcomas, lymphomas, Hodgekin's disease, melanomas, mesotheliomas, Burkitt's lymphoma, nasopharyngeal carcinomas, leukemias, and myelomas. The cancer cell population can include, but is not limited to, oral, thyroid, endocrine, skin, gastric, esophageal, laryngeal, pancreatic, colon, bladder, bone, ovarian, cervical, uterine, breast, testicular, prostate, rectal, kidney, liver, and lung cancers.

Illustratively, the population of pathogenic cells can also be activated monocytes or macrophages associated with disease states such as fibromyalgia, rheumatoid arthritis, osteoarthritis, ulcerative colitis, Crohn's disease, psoriasis, osteomyelitis, multiple sclerosis, atherosclerosis, pulmonary fibrosis, sarcoidosis, systemic sclerosis, organ transplant rejection (GVHD), lupus erythematosus, Sjögren's syndrome, glomerulonephritis, inflammations of the skin, such as psoriasis, and the like, chronic inflammations, and inflammations due to injury, such as head or spinal cord injury, embolisms, and the like.

The conjugates described herein can be formed from, for example, a wide variety of vitamins or receptor-binding vitamin analogs/derivatives, linkers, and imaging and radiotherapy agents. The conjugates described herein are capable of selectively targeting a population of pathogenic cells in the host animal due to preferential expression of a receptor for the targeting agent, such as a vitamin, accessible for binding, on the pathogenic cells. Illustrative vitamin moieties that can be used as the targeting agent (B) include carnitine, inositol, lipoic acid, pyridoxal, ascorbic acid, niacin, pantothenic acid, folic acid, riboflavin, thiamine, biotin, vitamin $B_{12}$, and the lipid soluble vitamins A, D, E and K. These vitamins, and their receptor-binding analogs and derivatives, constitute an illustrative targeting entity that can be coupled with the imaging or radiotherapy agent by a bivalent linker (L) to form a targeting agent (B) imaging or radiotherapy agent conjugate as described herein. The term vitamin is understood to include vitamin analogs and/or derivatives, unless otherwise indicated. Illustratively, pteroic acid which is a derivative of folate, biotin analogs such as biocytin, biotin sulfoxide, oxybiotin and other biotin receptor-binding compounds, and the like, are considered to be vitamins, vitamin analogs, and vitamin derivatives. It should be appreciated that vitamin analogs or derivatives as described herein refer to vitamins that incorporates an heteroatom through which the vitamin analog or derivative is covalently bound to the bivalent linker (L).

Illustrative vitamin moieties include folic acid, biotin, riboflavin, thiamine, vitamin $B_{12}$, and receptor-binding analogs and derivatives of these vitamin molecules, and other related vitamin receptor binding molecules.

In one embodiment, the targeting group B is a folate, an analog of folate, or a derivative of folate. It is to be understood as used herein, that the term folate is used both individually and collectively to refer to folic acid itself, and/or to such analogs and derivatives of folic acid that are capable of binding to folate receptors.

Illustrative embodiments of vitamin analogs and/or derivatives include folate and analogs and derivatives of folate such as folinic acid, pteropolyglutamic acid, and folate receptor-binding pteridines such as tetrahydropterins, dihydrofolates, tetrahydrofolates, and their deaza and dideaza analogs. The terms "deaza" and "dideaza" analogs refer to the art-recognized analogs having a carbon atom substituted for one or two nitrogen atoms in the naturally occurring folic acid structure, or analog or derivative thereof. For example, the deaza analogs include the 1-deaza, 3-deaza, 5-deaza, 8-deaza, and 10-deaza analogs of folate, folinic acid, pteropolyglutamic acid, and folate receptor-binding pteridines such as tetrahydropterins, dihydrofolates, and tetrahydrofolates. The dideaza analogs include, for example, 1,5-dideaza, 5,10-dideaza, 8,10-dideaza, and 5,8-dideaza analogs of folate, folinic acid, pteropolyglutamic acid, and folate receptor-binding pteridines such as tetrahydropterins, dihydrofolates, and tetrahydrofolates. Other folates useful as complex forming ligands for this invention are the folate receptor-binding analogs aminopterin, amethopterin (also known as methotrexate), $N^{10}$-methylfolate, 2-deamino-hydroxyfolate, deaza analogs such as 1-deazamethopterin or 3-deazamethopterin, and 3',5'-dichloro-4-amino-4-deoxy-$N^{10}$-methylpteroylglutamic acid (dichloromethotrexate). The foregoing folic acid analogs and/or derivatives are conventionally termed "folates," reflecting their ability to bind with folate-receptors, and such ligands when conjugated with exogenous molecules are effective to enhance transmembrane transport, such as via folate-mediated endocytosis as described herein.

Additional analogs of folic acid that bind to folic acid receptors are described in US Patent Application Publication Serial Nos. 2005/0227985 and 2004/0242582, the disclosures of which are incorporated herein by reference. Illustratively, radicals of such folate analogs have the general formula:

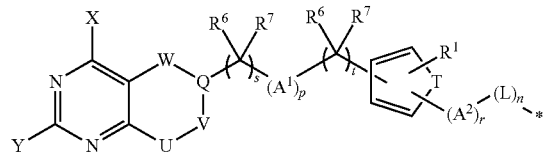

wherein
  X and Y are each-independently selected from the group consisting of halo, $R^2$, $OR^2$, $SR^3$, and $NR^4R^5$;
  U, V, and W represent divalent moieties each independently selected from the group consisting of $(R^{6a})C=$, $N=$, $(R^{6a})C(R^{7a})$, and $N(R^{4a})$;
  Q is selected from the group consisting of C and CH;
  T is selected from the group consisting of S, O, N, NH, and —C=C—;

$A^1$ and $A^2$ are each independently selected from the group consisting of oxygen, sulfur, C(Z), C(Z)O, OC(Z), $N(R^{4b})$, $C(Z)N(R^{4b})$, $N(R^{4b})C(Z)$, $OC(Z)N(R^{4b})$, $N(R^{4b})C(Z)O$, $N(R^{4b})C(Z)N(R^{5b})$, S(O), $S(O)_2$, $N(R^{4a})S(O)_2$, $C(R^{6b})(R^{7b})$, N(C≡CH), $N(CH_2C≡CH)$, $C_1$-$C_{12}$ alkylene, and $C_1$-$C_{12}$ alkyeneoxy, where Z is oxygen or sulfur;

$R^1$ is selected from the group consisting of hydrogen, halo, $C_1$-$C_{12}$ alkyl, and $C_1$-$C_{12}$ alkoxy; $R^2$, $R^3$, $R^{4a}$, $R^{4b}$, $R^5$, $R^{5b}$, $R^{6b}$, and $R^{7b}$ are each independently selected from the group consisting of hydrogen, halo, $C_1$-$C_{12}$ alkyl, $C_1$-$C_{12}$ alkoxy, $C_1$-$C_{12}$ alkanoyl, $C_1$-$C_{12}$ alkenyl, $C_1$-$C_{12}$ alkynyl, ($C_1$-$C_{12}$ alkoxy)carbonyl, and ($C_1$-$C_{12}$ alkylamino)carbonyl;

$R^6$ and $R^7$ are each independently selected from the group consisting of hydrogen, halo, $C_1$-$C_{12}$ alkyl, and $C_1$-$C_{12}$ alkoxy; or, $R^6$ and $R^7$ are taken together to form a carbonyl group; $R^6$ and $R^{7a}$ are each independently selected from the group consisting of hydrogen, halo, $C_1$-$C_{12}$ alkyl, and $C_1$-$C_{12}$ alkoxy; or $R^{6a}$ and $R^{7a}$ are taken together to form a carbonyl group;

L is one or more, such as 1, 2, 3, 4, 5, 6, 7, 8, 9, or 10, amino acids; and n, p, r, s and t are each independently either 0 or 1.

As used herein, it is to be understood that the term folate refers both individually to folic acid used in forming a conjugate, or alternatively to a folate analog or derivative thereof that is capable of binding to folate or folic acid receptors.

In another embodiment, the targeting group is a PSMA ligand or inhibitor, such as a derivative of pentanedioic acid of the formula:

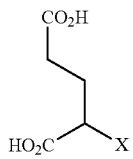

wherein X is $RP(O)(OH)CH_2$— (U.S. Pat. No. 5,968,915); $RP(O)(OH)N(R^1)$— (U.S. Pat. No. 5,863,536); RP(O)(OH)O— (U.S. Pat. No. 5,795,877); RN(OH)C(O)Y— or RC(O)NH(OH)Y, wherein Y is —$CR_1R_2$—, —$NR_3$— or —O— (U.S. Pat. No. 5,962,521); RS(O)Y, $RSO_2Y$, or RS(O)(NH)Y, wherein Y is —$CR_1R_2$—, —$NR_3$— or —O— (U.S. Pat. No. 5,902,817); and RS-alkyl, wherein R is for example hydrogen, alkyl, aryl, or arylalkyl, each of which may be optionally substituted (J. Med. Chem. 46:1989-1996 (2003)).

In each of the foregoing formulae, R, $R_1$, $R_2$, and $R_3$ are each independently selected from hydrogen, $C_1$-$C_9$ straight or branched chain alkyl, $C_2$-$C_9$ straight or branched chain alkenyl, $C_3$-$C_8$ cycloalkyl, $C_5$-$C_7$ cycloalkenyl, and aryl. In addition, in each case, each of R, $R_1$, $R_2$, and $R_3$ may be optionally substituted, such as with one or more groups selected from $C_3$-$C_8$ cycloalkyl, $C_5$-$C_7$ cycloalkenyl, halo, hydroxy, nitro, trifluoromethyl, $C_1$-$C_6$ straight or branched chain alkyl, $C_2$-$C_6$ straight or branched chain alkenyl, $C_1$-$C_4$ alkoxy, $C_2$-$C_4$ alkenyloxy, phenoxy, benzyloxy, amino, aryl. In one aspect, aryl is selected from 1-naphthyl, 2-naphthyl, 2-indolyl, 3-indolyl, 2-furyl, 3-furyl, 2-thienyl, 3-thienyl, 2-pyridyl, 3-pyridyl, 4-pyridyl, benzyl, and phenyl, and in each case aryl may be optionally substituted with one or more, illustratively with one to three, groups selected from halo, hydroxy, nitro, trifluoromethyl, $C_1$-$C_6$ straight or branched chain alkyl, $C_2$-$C_6$ straight or branched chain alkenyl, $C_1$-$C_4$ alkoxy, $C_2$-$C_4$ alkenyloxy, phenoxy, benzyloxy, and amino. In one variation of each of the above formulae, R is not hydrogen.

Illustrative PSMA ligands (U.S. Pat. No. 5,968,915) include 2-[[methylhydroxyphosphinyl]methyl]pentanedioic acid; 2-[[ethylhydroxyphosphinyl]methyl]pentanedioic acid; 2-[[propylhydroxyphosphinyl]methyl]pentanedioic acid; 2-[[butylhydroxyphosphinyl]methyl]pentanedioic acid; 2-[[cyclohexylhydroxyphosphinyl]methyl]pentanedioic acid; 2-[[phenylhydroxyphosphinyl]methyl]pentanedioic acid; 2-[[2-(tetrahydrofuranyl)hydroxyphosphinyl]methyl] pentanedioic acid; 2-[[(2-tetrahydropyranyl) hydroxyphosphinyl]methyl] pentanedioic acid; 2-[[((4-pyridyl)methyl)hydroxyphosphinyl]methyl] pentanedioic acid; 2-[[((2-pyridyl)methyl)hydroxyphosphinyl]methyl] pentanedioic acid; 2-[[(phenylmethyl)hydroxyphosphinyl] methyl] pentanedioic acid; 2-[[((2-phenylethyl)methyl)hydroxyphosphinyl]methyl] pentanedioic acid; 2-[[((3-phenylpropyl)methyl)hydroxyphosphinyl]methyl] pentanedioic acid; 2-[[((3-phenylbutyl)methyl)hydroxyphosphinyl] methyl] pentanedioic acid; 2-[[((2-phenylbutyl)methyl)hydroxyphosphinyl]methyl] pentanedioic acid; 2-[[(4-phenylbutyl)hydroxyphosphinyl]methyl]pentanedioic acid; and 2-[[(aminomethyl)hydroxyphosphinyl]methyl]pentanedioic acid.

Illustrative PSMA ligands (U.S. Pat. No. 5,863,536) include N-[methylhydroxyphosphinyl]glutamic acid; N-[ethylhydroxyphosphinyl]glutamic acid; N-[propylhydroxyphosphinyl]glutamic acid; N-[butylhydroxyphosphinyl]glutamic acid; N-[phenylhydroxyphosphinyl]glutamic acid; N-[(phenylmethyl)hydroxyphosphinyl]glutamic acid; N-[((2-phenylethyl)methyl)hydroxyphosphinyl]glutamic acid; and N-methyl-N-[phenylhydroxyphosphinyl]glutamic acid.

Illustrative PSMA ligands (U.S. Pat. No. 5,795,877) include 2-[[methylhydroxyphosphinyl]oxy]pentanedioic acid; 2-[[ethylhydroxyphosphinyl]oxy]pentanedioic acid; 2-[[propylhydroxyphosphinyl]oxy]pentanedioic acid; 2-[[butylhydroxyphosphinyl]oxy]pentanedioic acid; 2-[[phenylhydroxyphosphinyl]oxy]pentanedioic acid; 2-[[((4-pyridyl)methyl)hydroxyphosphinyl]oxy]pentanedioic acid; 2-[[((2-pyridyl)methyl)hydroxyphosphinyl]oxy]pentanedioic acid; 2-[[(phenylmethyl)hydroxyphosphinyl]oxy]pentanedioic acid; and 2[[((2-phenylethyl)methyl)hydroxyphosphinyl]oxy] pentanedioic acid.

Illustrative PSMA ligands (U.S. Pat. No. 5,962,521) include 2-[[(N-hydroxy)carbamoyl]methyl]pentanedioic acid; 2-[[(N-hydroxy-N-methyl)carbamoyl]methyl]pentanedioic acid; 2-[[(N-butyl-N-hydroxy) carbamoyl]methyl] pentanedioic acid; 2-[[(N-benzyl-N-hydroxy)carbamoyl] methyl]pentanedioic acid; 2-[[(N-hydroxy-N-phenyl) carbamoyl]methyl]pentanedioic acid; 2-[[(N-hydroxy-N-2-phenylethyl)carbamoyl]methyl]pentanedioic acid; 2-[[(N-ethyl-N-hydroxy) carbamoyl]methyl]pentanedioic acid; 2-[[(N-hydroxy-N-propyl)carbamoyl]methyl]pentanedioic acid; 2-[[(N-hydroxy-N-3-phenylpropyl)carbamoyl]methyl] pentanedioic acid; 2-[[(N-hydroxy-N-4-pyridyl) carbamoyl] methyl]pentanedioic acid; 2-[[(N-hydroxy)carboxamido] methyl]pentanedioic acid; 2-[[N-hydroxy (methyl) carboxamido]methyl]pentanedioic acid; 2-[[N-hydroxy (benzyl) carboxamido]methyl]pentanedioic acid; 2-[[N-hydroxy(phenyl)carboxamido]methyl]pentanedioic acid; 2-[[N-hydroxy(2-phenylethyl)carboxamido]methyl]pentanedioic acid; 2-[[N-hydroxy(ethyl)carboxamido]methyl] pentanedioic acid; 2-[[N-hydroxy(propyl) carboxamido]m- ethyl]pentanedioic acid; 2-[[N-hydroxy (3-phenylpropyl) carboxamido]methyl]pentanedioic acid; and 2-[[N-hydroxy (4-pyridyl)carboxamido]methyl]pentanedioic acid.

Illustrative PSMA ligands (U.S. Pat. No. 5,902,817) include 2-[(sulfinyl)methyl]pentanedioic acid; 2-[(methylsulfinyl)methyl]pentanedioic acid; 2-[(ethylsulfinyl)methyl]pentanedioic acid; 2-[(propylsulfinyl)methyl]pentanedioic acid; 2-[(butylsulfinyl)methyl]pentanedioic acid; 2-[(phenylsulfinyl)methyl]pentanedioic acid; 2-[[(2-phenylethyl) sulfinyl]methyl]pentanedioic acid; 2-[[(3-phenylpropyl) sulfinyl]methyl]pentanedioic acid; 2-[[(4-pyridyl)sulfinyl] methyl]pentanedioic acid; 2-[(benzylsulfinyl)methyl] pentanedioic acid; 2-[(sulfonyl)methyl]pentanedioic acid; 2-[(methylsulfonyl)methyl]pentanedioic acid; 2-[(ethylsulfonyl)methyl]pentanedioic acid; 2-[(propylsulfonyl) methyl]pentanedioic acid; 2-[(butylsulfonyl)methyl]pentanedioic acid; 2-[(phenylsulfonyl]methyl]pentanedioic acid; 2-[[(2-phenylethyl)sulfonyl]methyl]pentanedioic acid; 2-[[(3-phenylpropyl)sulfonyl]methyl]pentanedioic acid; 2-[[(4-pyridyl) sulfonyl]methyl]pentanedioic acid; 2-[(benzylsulfonyl)methyl]pentanedioic acid; 2-[(sulfoximinyl) methyl]pentanedioic acid; 2-[(methylsulfoximinyl)methyl] pentanedioic acid; 2-[(ethylsulfoximinyl)methyl] pentanedioic acid; 2-[(propylsulfoximinyl)methyl] pentanedioic acid; 2-[(butylsulfoximinyl)methyl] pentanedioic acid; 2-[(phenylsulfoximinyl]methyl] pentanedioic acid; 2-[[(2-phenylethyl)sulfoximinyl]methyl] pentanedioic acid; 2-[[(3-phenylpropyl) sulfoximinyl] methyl]pentanedioic acid; 2-[[(4-pyridyl)sulfoximinyl] methyl]pentanedioic acid; and 2-[(benzylsulfoximinyl) methyl]pentanedioic acid.

Illustrative PSMA ligands include

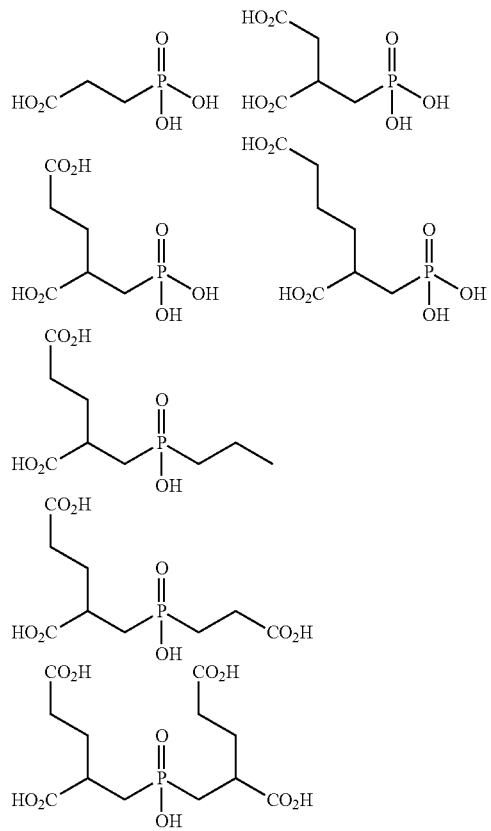

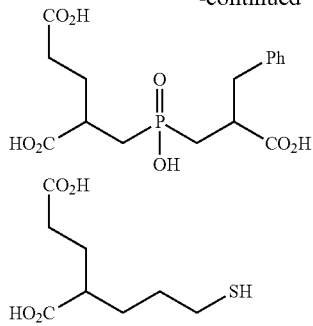

In another embodiment, the PSMA ligand is a urea of two amino acids. In one aspect, the amino acids include one or more additional carboxylic acids. In another embodiment, the amino acids include one or more additional phosphoric, phosphonic, phosphinic, sulfinic, sulfonic, or boronic acids. In another aspect, the amino acids include one or more thiol groups or derivatives thereof. In another aspect, the amino acids include one or more carboxylic acid bioisosteres, such as tetrazoles and the like.

In another embodiment, the PSMA ligand is a compound of the formula:

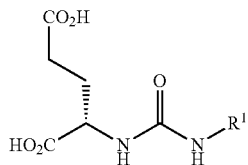

where $R^1$ is

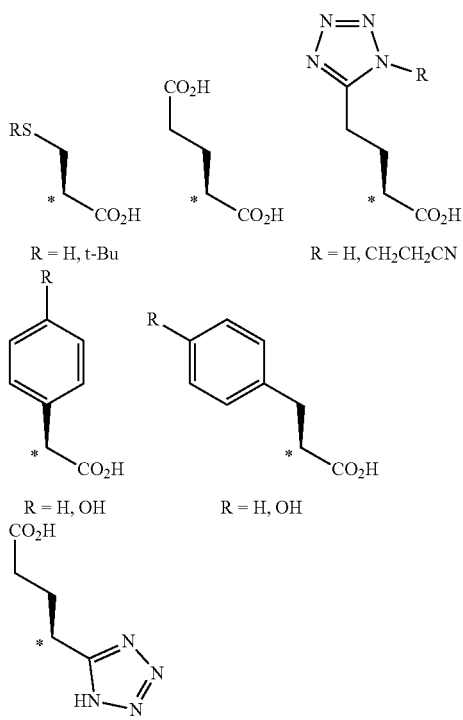

In another illustrative embodiment, the binding agent is a urea of an amino dicarboxylic acid, such as aspartic acid, glutamic acid, and the like, and another amino dicarboxylic acid, or an analog thereof, such as a binding agent of the formulae

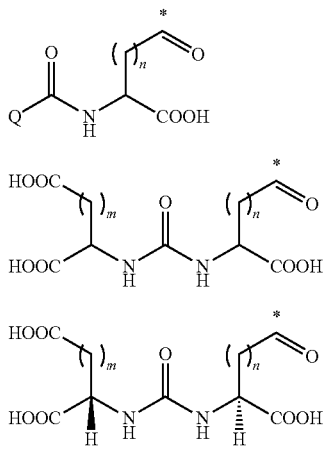

wherein Q is a an amino dicarboxylic acid, such as aspartic acid, glutamic acid, or an analog thereof, n and m are each independently selected from an integer between 1 and about 6, and (*) represents the point of attachment for the linker L.

Illustratively, the PSMA ligand is a compound of the formulae:

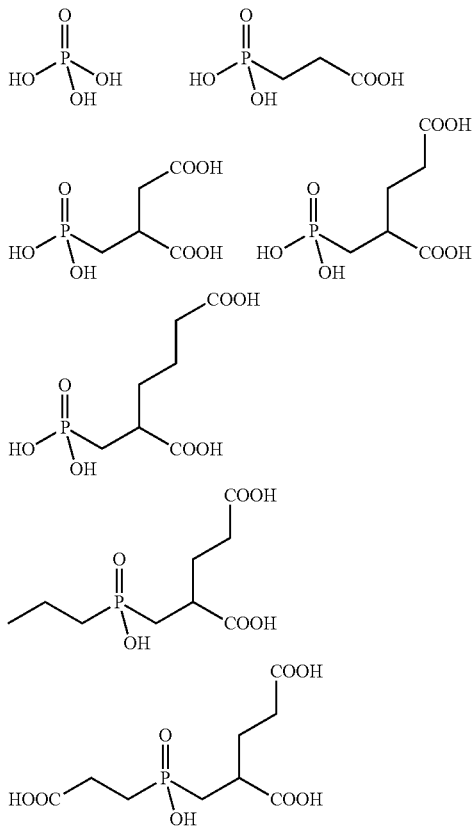

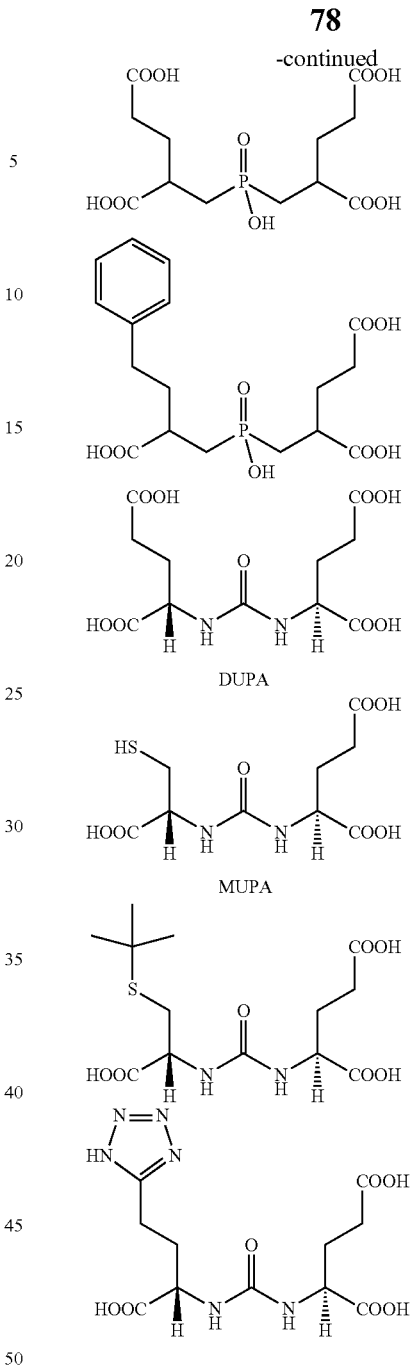

In another embodiment, the PSMA ligand is 2-[3-(1-Carboxy-2-mercapto-ethyl)-ureido]-pentanedioic acid (MUPA) or 2-[3-(1,3-Dicarboxy-propyl)-ureido]-pentanedioic acid (DUPA).

Other illustrative examples of PSMA ligands include peptide analogs such as quisqualic acid, aspartate glutamate (Asp-Glu), Glu-Glu, Gly-Glu, 7-Glu-Glu, beta-N-acetyl-L-aspartate-L-glutamate (3-NAAG), and the like.

In another embodiment, the PSMA ligand comprises a urea or thiourea of lysine and an amino acid, or one or more carboxylic acid derivatives thereof, including, but not limited to ureas or thioureas of lysine and aspartic acid, or glutamic acid, or homoglutamic acid.

In another embodiment, the PSMA ligand comprises a urea or thiourea of L-lysine and L-glutamate.

In another embodiment, the PSMA ligand comprises a compound selected from the following

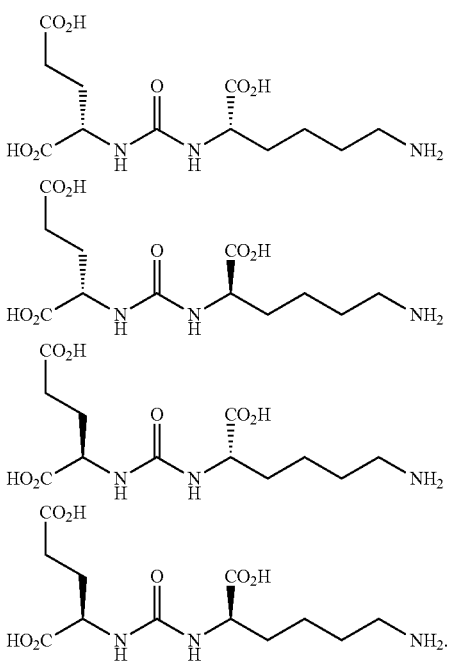

In another embodiment, the PSMA ligand comprises the following

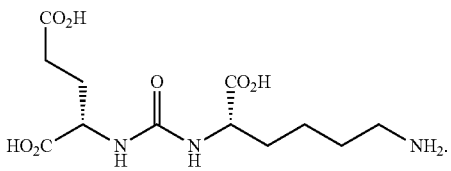 [SMILES: NCCCC[C@H](NC(=O)N[C@@H](CCC(=O)O)C(=O)O)C(=O)O]

The compounds, linkers, intermediates, and conjugates described herein may be prepared using conventional processes, including the described in International Patent Publication Nos. WO 2009/002993, WO 2004/069159, WO 2007/022494, and WO 2006/012527, and U.S. patent application Ser. No. 13/837,539 (filed Mar. 15, 2013). The disclosures of each of the foregoing are herein incorporated by reference in their entirety.

Each publication cited herein is incorporated herein by reference.

In another embodiment, a method is described for diagnosing and/or monitoring a disease or disease state where the method comprises the steps of administering to a patient being evaluated for the disease state an effective amount of a conjugate of the general formula B-L-P. The method includes allowing sufficient time for the conjugate to bind to the target tissue, and diagnosing and/or monitoring the disease or disease state extra-corporeally, such as by using positron emission tomography.

The radionuclide may include a positron-emitting isotope having a suitable half-life and toxicity profile. In various embodiments, the radioisotope has a half-life of more than 30 minutes, more than 70 minutes, more than 80 minutes, more than 90 minutes, more than 100 minutes, less than 8 hours, less than 6 hours, less than 4 hours, or less than 3 hours. In other embodiments, the radioisotope has a half-life of about 30 minutes to about 4 hours, about 70 minutes to about 4 hours, about 80 minutes to about 4 hours, about 90 minutes to about 4 hours, about 100 minutes to about 4 hours, about 30 minutes to about 6 hours, about 70 minutes to about 6 hours, about 80 minutes to about 6 hours, about 90 minutes to about 6 hours, about 100 minutes to about 6 hours, about 30 minutes to about 8 hours, about 70 minutes to about 8 hours, about 80 minutes to about 8 hours, about 90 minutes to about 8 hours, or about 100 minutes to about 8 hours.

The radionuclide may include one or more positron-emitting isotopes, such as but not limited to isotopes selected from $^{89}$Zr, $^{45}$Ti, $^{51}$Mn, $^{64}$Cu, $^{61}$Cu, $^{63}$Zn, $^{82}$Rb, $^{68}$Ga, $^{66}$Ga, $^{11}$C, $^{13}$N, $^{15}$O, $^{124}$I, $^{34}$Cl, and $^{18}$F. In another embodiment, the radionuclide is a halide, such as a positron-emitting halide. In another embodiment, the radionuclide is a metal ion, such as a positron-emitting metal ion. In another embodiment, the radionuclide is a gallium ion, such as a positron-emitting gallium ion. In another embodiment, the radionuclide is selected from $^{89}$Zr, $^{64}$Cu, $^{68}$Ga, $^{66}$Ga, $^{124}$I, and $^{18}$F. In another illustrative embodiment, the radioisotope is selected from $^{89}$Zr, $^{64}$Cu, $^{68}$Ga, $^{124}$I, and $^{18}$F. In another embodiment, the radioisotope is $^{68}$Ga, or $^{89}$Zr, or $^{18}$F. In another embodiment in each of the foregoing and following embodiments described herein, the radioisotope is $^{68}$Ga. In another embodiment in each of the foregoing and following embodiments described herein, the radioisotope is $^{18}$F. In another embodiment in each of the foregoing and following embodiments described herein, the radioisotope is $^{89}$Zr. In another embodiment in each of the foregoing and following embodiments described herein, the radioisotope is $^{64}$Cu. It is also to be understood that the fluorine isotopes described herein may be selected from various isotopic combinations of $^{18}$F and $^{19}$F. It is understood that factors that may be included during selection of a suitable isotope include sufficient half-life of the positron-emitting isotope to permit preparation of a diagnostic composition in a pharmaceutically acceptable carrier prior to administration to the patient, and sufficient remaining half-life to yield sufficient activity to permit extra-corporeal measurement by a PET scan. Further, a suitable isotope should have a sufficiently short half-life to limit patient exposure to unnecessary radiation. In an illustrative embodiment, $^{18}$F, having a half-life of 110 minutes, provides adequate time for preparation of the diagnostic composition, as well as an acceptable deterioration rate. Further, on decay $^{18}$F is converted to 18O.

Illustrative positron-decaying isotopes having suitable half-lives include $^{34}$Cl, half-life about 32 minutes; $^{45}$Ti, half-life about 3 hours; $^{51}$Mn, half-life about 45 minutes; $^{61}$Cu, half-life about 3.4 hours; $^{63}$Zn, half-life about 38 minutes; $^{82}$Rb, half-life about 2 minutes; $^{68}$Ga, half-life about 68 minutes, $^{66}$Ga, half-life about 9.5 hours, $^{11}$C, half-life about 20 minutes, $^{15}$O, half-life about 2 minutes, $^{13}$N, half-life about 10 minutes, or $^{18}$F, half-life about 110 minutes.

In another embodiment, the radionuclide is a radiotherapy agent. Illustrative radionuclides for radiotherapy include isotopes of lutetium such as $^{177}$Lu, isotopes of yttrium, such as $^{90}$Y, isotopes of copper, such as $^{67}$Cu and $^{64}$Cu, and the like.

The radionuclide may be covalently attached to the conjugate, such as to an aryl or heteroaryl aromatic group, including benzamidyl, benzylic, phenyl, pyridinyl, pyrimidinyl, pyridazinyl, naphthyl, benzothiazolyl, benzimizolyl, benzoxazolyl, and like groups. In one illustrative embodiment, the radioisotope is $^{18}$F and the radionuclide includes an aryl group to which the radioisotope is covalently attached.

The radionuclide may be non-covalently attached to the conjugate, such as within a chelate.

The methods may also be used in combination with any other methods of cancer diagnosis already developed and known in the art, including methods using other already developed diagnostic agents and utilizing x-ray computed tomography (CT), magnetic resonance imaging (MRI), functional magnetic resonance imaging (fMRI), ultrasound, and single photon emission computed tomography (SPECT).

It is understood that in certain applications of the methods described herein, each of the processes and synthetic methods described herein either substantially complete fluorination, or alternatively only partial fluorination may be desired. Accordingly, the processes and synthetic methods described herein may be performed in various alternative embodiments. It is therefore understood that in those aspects where only partial fluorination is desired, the processes and syntheses described herein may be performed with less than stoichiometric amounts of fluorinating agent. Similarly, it is understood that in certain applications of the methods described herein, each of the processes and synthetic methods described herein either substantially complete radiofluorination, or alternatively only partial radiofluorination may be desired. Accordingly, the processes and synthetic methods described herein may be performed in various alternative embodiments. It is therefore understood that in those aspects where only partial radiofluorination is desired, the processes and syntheses described herein may be performed with less than stoichiometric amounts of radiofluorination agent, where the balance is optionally $^{19}$F.

The following examples further illustrate specific embodiments of the invention; however, the following illustrative examples should not be interpreted in any way to limit the invention.

EXAMPLES

General. Water was distilled and then deionized (18 MΩ/cm2) by passing through a Milli-Q water filtration system (Millipore Corp., Milford, MA). All chemicals and solvents, unless specified, were purchased from Sigma (St. Louis, MO) and were used without further purification. Amino acids were purchased from Chem-Impex Int (Chicago, IL). 2,2'-(7-(2-((2,5-dioxopyrrolidin-1-yl)oxy)-2-oxoethyl)-1,4,7-triazonane-1,4-diyl)diacetic acid (NOTA-NHS) was purchased from CheMatech (France). N10-TFA-Pteroic Acid was provided by Endocyte, Inc. High-performance liquid chromatography (HPLC) analysis and purification of the DUPA-NOTA precursor were performed on an Agilent G6130B instrument. The radioactive HPLC was performed with a 7-counter using a Xselect CSH C18 (250×10 mm) column and MeCN and 0.1% Formic Acid as mobile phases.

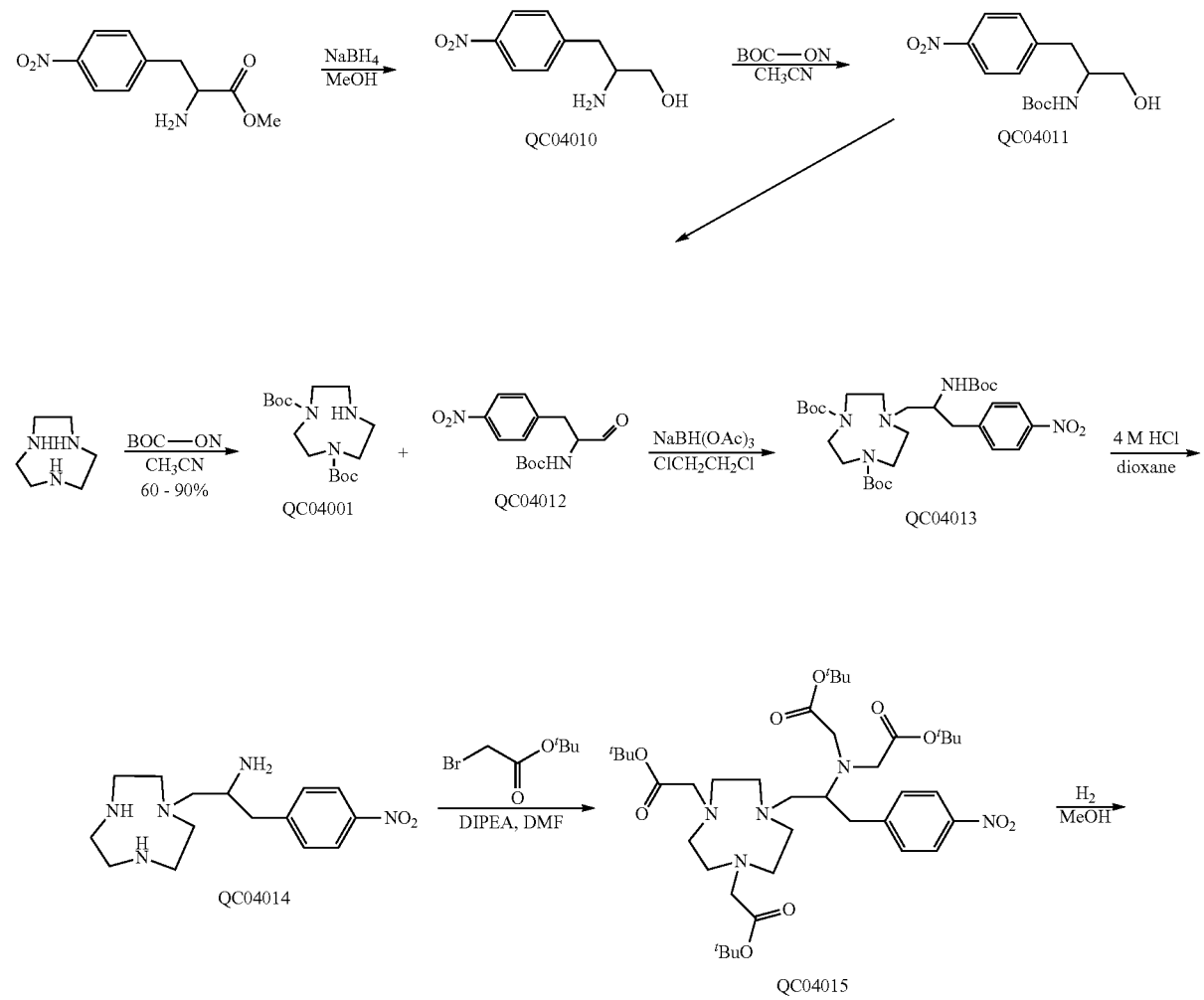

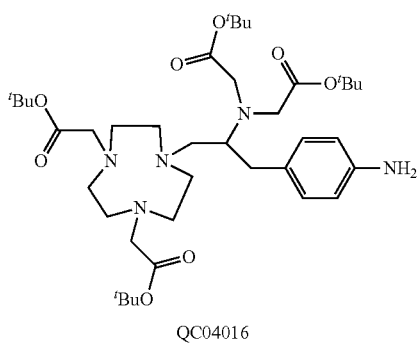 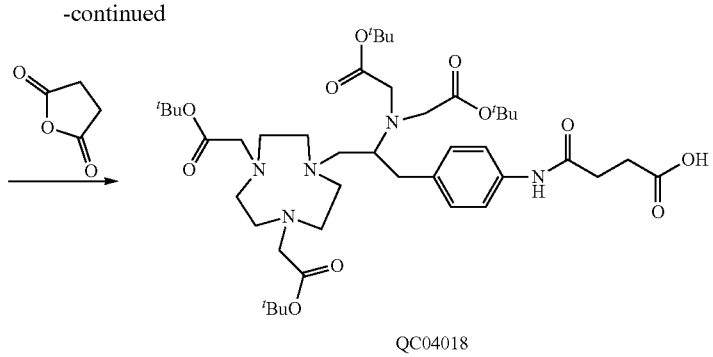

EXAMPLE. C-NETA. tert-Butyl [2-Hydroxy-1-(4-nitrobenzyl)ethyl]carbamate (QC04011) was prepared from the commercially available methyl 2-amino-3-(4-nitrophenyl)propanoate through NaBH4 reduction and Boc-protection. Successive Dess-Martin oxidation and reductive amination with QC04001 afforded tris-Boc protected compound QC04013, which was transformed to QC04014 after Boc-deprotection in 4M HCl in dioxane. Treatment of QC04014 with tert-butyl bromoacetate, followed by hydrogenolysis of the NO2 group provided QC04016. Further reaction of QC04016 with succinic anhydride provided the bifunctional C-NETA (QC04018) as the corresponding tert-butyl ester.

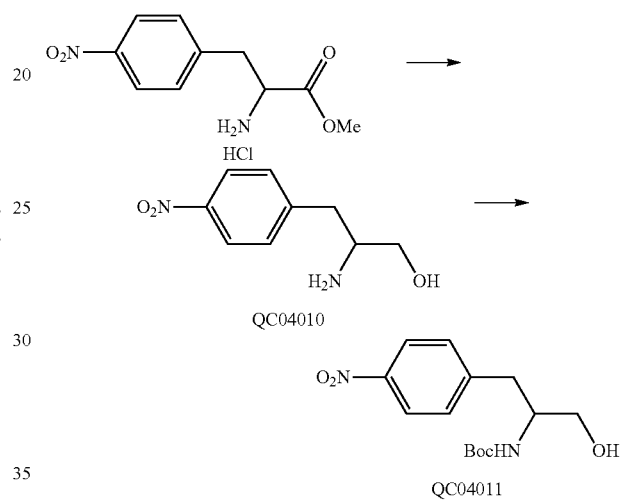

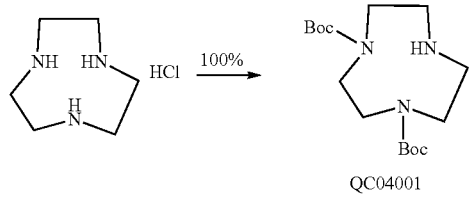 [SMILES: C1CNCCNCCN1 ; Cl ; CC(C)(C)OC(=O)N1CCNCCN(C(=O)OC(C)(C)C)CC1]

EXAMPLE. Di-tert-butyl [1,4,7]Triazanonane-1,4-dicarboxylate (QC04001). QC04001 was prepared according to a modification of a synthetic procedure reported previously. [19-21] To a solution of 1,4,7-triazonane trihydrogenchloride (TACN·3HCl, 1.85 g, 7.7 mmol, M.W.: 238.6) in CHCl3 (25 mL) was added DIPEA (4.0 mL, 3.0 g, 23.1 mmol, M.W.: 129.24, d: 0.742) and BOC—ON (3.77 g, 15.3 mmol, M.W.: 246.26) in portions. The resulting mixture was stirred for 5 days and the solvent evaporated under vacuum. The residue was partitioned between 10% NaOH solution (10 mL) and diethyl ether (30 mL). The ether layer was separated and washed with 10% NaOH solution (10 mL) and water (10 mL) several times. The ether layer was dried (MgSO4), filtered, and concentrated under vacuum to provide QC04001 (2.53 g, quantitative), which was used without further purification. $^1$H NMR (400 MHz, CDCl3) δ=3.47-3.50 (m, 2H), 3.42-3.45 (m, 2H), 3.38 (br, s, 1H), 3.28-3.34 (m, 2H), 3.16-3.28 (m, 2H), 2.86-2.99 (m, 4H), 1.48 (s, 18H); $^{13}$C NMR (101 MHz, CDCl3) δ=156.08, 155.85 (C=O), 79.80, 79.70 (t-Bu), 53.20, 52.62, 52.52, 51.78, 50.50, 49.91, 49.63, 48.39, 48.23, 47.83, 47.46 ACN ring from 53.20-47.46), 28.60 (t-Bu).

EXAMPLE. tert-Butyl [2-Hydroxy-1-(4-nitrobenzyl)ethyl]carbamate (QC04011)[19]. With minor revision to the reported procedure,[19] where the HCl salt of methyl 2-amino-3-(4-nitrophenyl)propanoate was used directly without neutralization with Et3N, to a solution of the methyl 2-amino-3-(4-nitrophenyl)propanoate hydrochloride salt (6.22 g, 23.9 mmol) in MeOH (70 mL) at 23° C. was added NaBH4 (2.86 g, 71.4 mmol) in multiple portions. The reaction was monitored by TLC and LC-MS. The mixture was heated to reflux (with water bath at ~70° C.), and NaBH4 was added portion-wise as needed until most of the starting material disappeared, requiring about 6 grams of NaBH4 in total. After evaporation of the solvent, the residue was treated with H2O (70 mL) and extracted with DCM/IPA (3/1). The combined organic layer was dried, filtered, and concentrated under vacuum to provide white solid QC04010 (4.4 g, 94), which was used without further purification.

EXAMPLE. QC04010 (4.4 g, 22.7 mmol) was dissolved in CH3CN (30 mL) at ambient temperature, to which was added BOC—ON (11.2 g, 27.2 mmol, 1.2 eq.) portionwise. To the above mixture was added DIPEA (5.24 mL, 3.76 g, 29.2 mmol, M.W.: 129.24, d: 0.742), the resulting mixture was stirred for 4 h and evaporated. The residue was partitioned between ether (50 mL) and 10% NaOH solution (20 mL). The ether layer was separated and washed with 10% NaOH solution (10 mL) and water (10 mL) sequentially. The ether layer was dried, filtered, and concentrated under vacuum. The residue was washed with ether (20 mL) to provide QC04011 (5.31 g, 75%), which was used without further purification. To prepare an analytical sample, the residue is purified via column chromatography on $SiO_2$ eluting with Hexane/Ethyl Acetate (3/1 to 1/1 with 1% of MeOH) to afford pure QC04011 as a white solid. $^1$H NMR (400 MHz, CDCl$_3$) δ=8.15 (d, J=8.8 MHz, 2H), 7.40 (d, J=8.8 MHz, 2H), 4.84 (d, J=6.8 MHz, 1H), 3.90 (s, 1H), 3.68 (dd, J=3.1 MHz, 1H), 3.57 (dd, J=3.1 MHz, 1H), 2.98 (d, J=6.0 MHz, 2H), 1.39 (s, 9H); $^{13}$C NMR (101 MHz, CDCl$_3$) δ=156.0, 146.4, 146.2, 130.1, 123.5, 79.8, 63.3, 53.1, 37.3, 28.0.

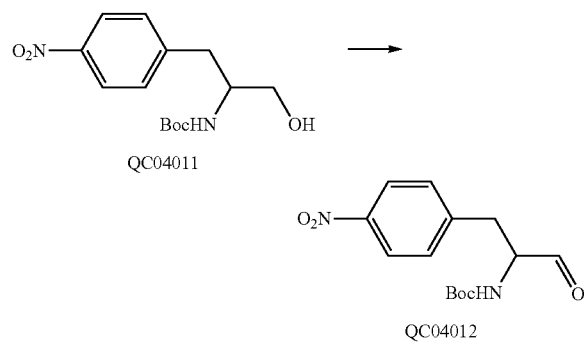

EXAMPLE. tert-Butyl (1-(4-nitrophenyl)-3-oxopropan-2-yl)carbamate. QC04011 (1.27 g, 4.3 mmol) was dissolved in CH$_2$Cl$_2$ (40 mL), and cooled to 0° C., to which Dess-Martin periodinane (1.70 g, 5.16 mmol, 1.2 equiv) was added in one portion. After stirring for 15 min at 0° C., the reaction was warmed to 23° C. and stirred for 45 min. The reaction was quenched by addition of a basic aq Na$_2$S$_2$O$_3$ solution (50/50, v/v of aq Na$_2$S$_2$O$_3$ and aq Na$_2$HCO$_3$), and the resulting mixture was vigorously stirred for 15 min. After extraction with CH$_2$Cl$_2$ (3×), the organic phases were washed successively with water and brine, dried over Na$_2$SO$_4$, filtered and concentrated in vacuo to provide QC04012, which was used without further purification.

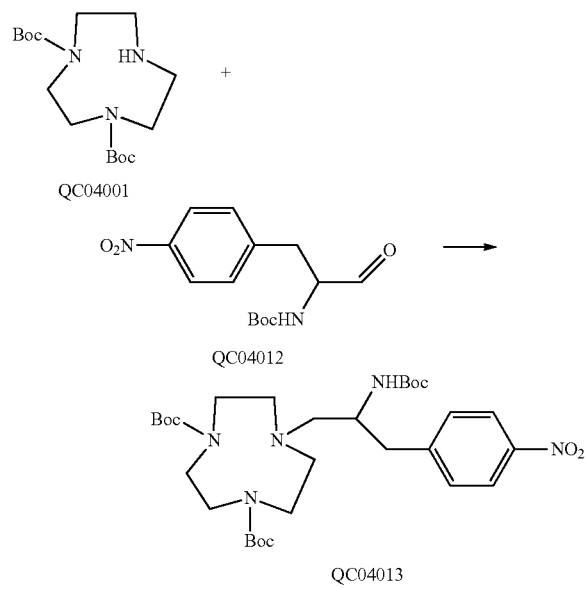

EXAMPLE. Reductive amination of QC04012 and QC04001 to prepare QC04013:$^4$. 1,4-Di-tert-butyl 7-(2-{[(tert-Butoxy)carbonyl]amino} 3-(4-nitrophenyl) propyl)-1,4,7-triazonane-1,4-dicarboxylate (QC04013): Compound QC04012 (4.3 mmol in theory) was added to a solution of QC04001 (1.40 g, 4.3 mmol) in DCE (100 mL) at 0° C. The resulting solution was stirred for 10 min and sodium triacetoxyborohydride (1.28 g, 6.02 mmol, 1.4 eq.) was added portionwise to the solution over 30 min. The mixture was stirred at ambient temperature overnight. The reaction mixture was concentrated, treated with a saturated aqueous solution of NaHCO$_3$ (50 mL), and extracted with ethyl acetate (3×50 mL). The combined organic layers were dried with Na$_2$SO$_4$, filtered, and concentrated in vacuo. The residue was purified via flash chromatography (SiO$_2$, Hex/EA=3/1) to provide QC04013 (2.31 g, 88.5% for 2 steps, based on 2.61 g in theory) as a pale yellow semi-solid. $^1$H NMR (400 MHz, CDCl$_3$) δ=8.11 (2H, d, J=7.6 Hz), 7.35 (2H, d, J=7.6 Hz), 5.28 (1H, s, br), 3.54-3.88 (2H, m), 3.39-3.54 (2H, m), 3.32-3.40 (1H, m), 3.15-3.32 (2H, m), 2.79-3.15 (4H, m), 2.37-2.73 (6H, m), 1.43 (9H, s), 1.42 (9H, s), 1.38 (9H, s); $^{13}$C NMR (101 MHz, CDCl$_3$) δ=156.15, 155.99, 155.70, 155.56, 147.00, 146.95, 146.81, 146.76, 130.36, 123.73, 123.65, 123.60, 80.07, 79.99, 79.92, 79.81, 79.57, 79.46, 60.79, 60.47, 55.52, 54.33, 54.06, 53.64, 53.15, 53.28, 51.54, 50.80, 50.71, 50.42, 49.87, 49.07, 48.12, 39.67, 39.45, 28.74, 28.61. MS m/z: MS-API: Calcd. for C$_{30}$H$_{50}$N$_5$O$_8$ ([M+H]$^+$): 608.4, Found: 608.3;

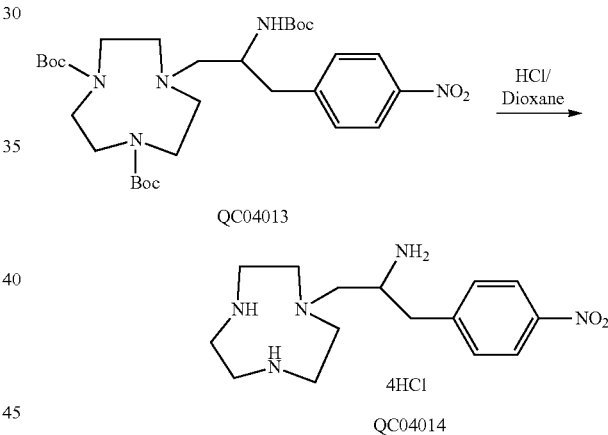

EXAMPLE. 1-(4-Nitrophenyl)-3-(1,4,7-triazonan-1-yl) propan-2-amine. QC04013 (2.31 g, 3.8 mmol) was dispersed in 30 mL of 4 M HCl/Dioxane, the resulting mixture was stirred at room temperature for 20 hours. The reaction mixture was rapidly added to cold Et$_2$O to precipitate a white solid. The solid was collected and dried in air to afford the pure product QC04014 (1.71 g, in quantitative yield) as a pale-white solid. MS m/z: MS-API: Calcd. for C$_{15}$H$_{26}$N$_5$O$_2$ ([M+H]$^+$): 308.2, Found: 308.2;

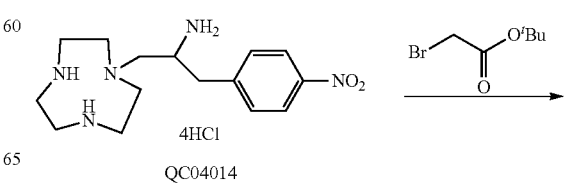

-continued

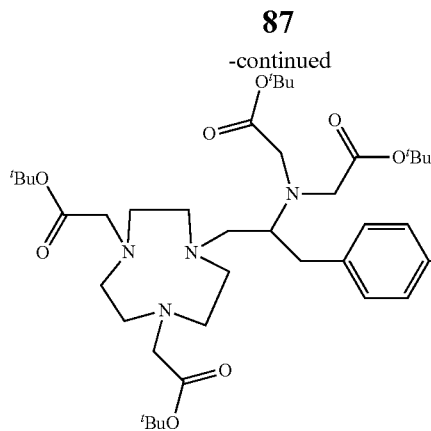

QC04015

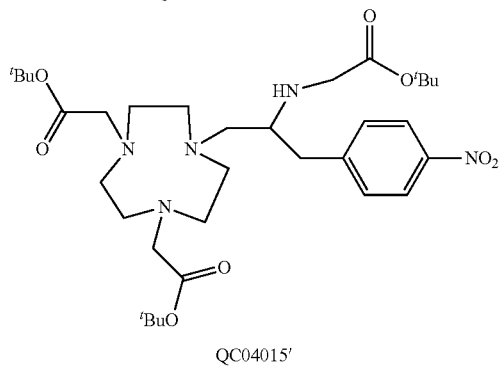

QC04015'

EXAMPLE. Introduction of the tri-tert-butyl ethylacetate[1b]. To a solution of QC04014 (78 mg, 0.19 mmol) and DIPEA (0.272 mL, 202 mg, 1.56 mmol, 8.2 eq. M.W.: 129.24, d: 0.742) in DMF (2 mL) was added NaI (233.8 mg, 1.56 mmol, 8.2 eq. M.W.: 149.89) and tert-Butyl bromoacetate (0.126 mL, 168 mg, 0.86 mmol, 4.5 eq. M.W.: 195.05, d: 1.321) slowly at room temperature. The resulting mixture was warmed to 60-70° C. and stirred for 20 hs. After completion, monitored by TLC and LC-MS, the reaction was quenched by water and extracted with $Et_2O$. The combined organic solvent was washed successively with water and brine, and dried over $Na_2SO_4$. After filtration, the solvent was evaporated under vacuum, and resulting deep-colored oil residue was purified by flash chromatography on $SiO_2$ (DCM/MeOH=100/1-100/4) to provide QC04015 (14 mg, 10%) as a yellow oil and QC04015' (61 mg, 49.4%). MS m/z: MS-API: Calcd. for $C_{39}H_{66}N_5O_{10}$ ([M+H]$^+$): 764.5, Found: 764.4;

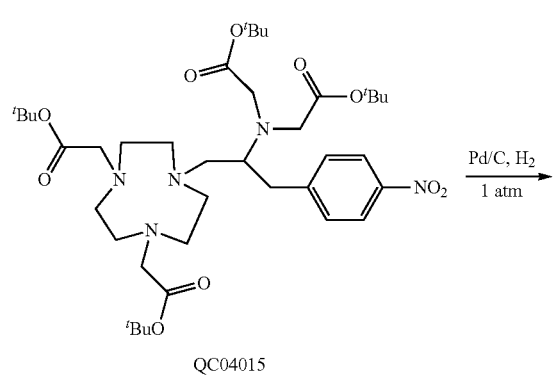

QC04015

-continued

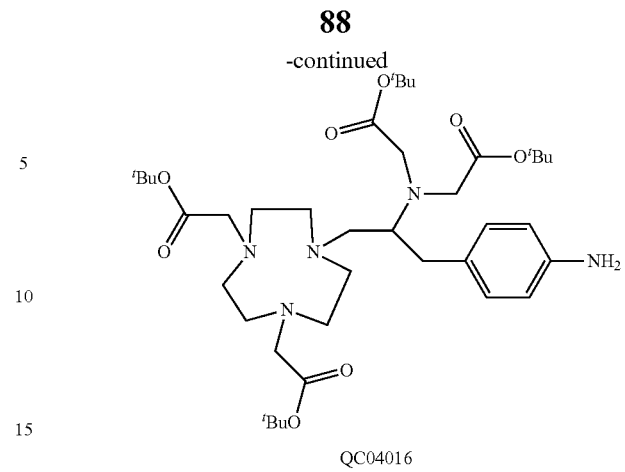

QC04016

EXAMPLE. To a solution of QC04015 (20 mg, 0.039 mmol) in MeOH (2 mL) was added 10% Pd/C catalyst (5 mg). The resulting mixture was subjected to hydrogenolysis by agitation with $H_2$ (g) at 1 atm (~15 psi) at ambient temperature for 14 h. The reaction mixture was diluted with excess DCM and filtered through celite, and the filtrate was concentrated in vacuo to provide QC04016 (13 mg, 67.5%). MS m/z: MS-API: Calcd. for $C_{39}H_{68}N_5O_8$ ([M+H]$^+$): 734.5, Found: 734.4.

Folate Targeted Examples

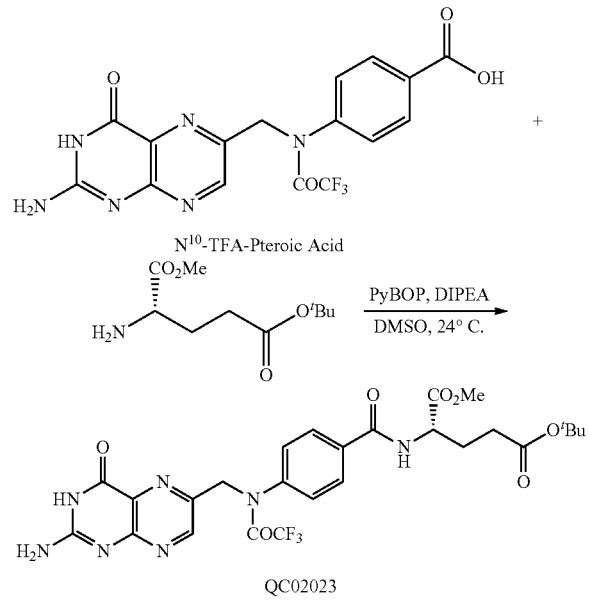

QC02023

EXAMPLE. (S)-5-tert-butyl 1-methyl 2-(4-(N-((2-amino-4-oxo-3,4-dihydropteridin-6-yl)methyl)-2,2,2-trifluoroacetamido)benzamido)pentanedioate (QC02023). HCl·$H_2$N-Glu(OtBu)-OMe (350 mg, 1.38 mmol) was added to a solution of $N^{10}$-TFA-Pteroic Acid (560 mg, 1.37 mmol) and DIPEA (1.2 mL, 6.85 mmol) in DMSO (6.0 mL) at 23° C. under $N_2$. After stirring for 15 min at 23° C., PyBOP (720 mg, 1.0 mmol) was added, and the reaction mixture was stirred for 24 h at 23° C. Volatile material was removed under reduced vacuum to afford the crude product as a semi-solid, which was further purified via solid extraction with Hex/EA (1/1) 3 times to provide QC02023 as a pale-yellow solid in quantitative yield, which was used without further purification. $\lambda_{max}$=280 nm; LC-MS (Agilent G6130B Quadrupole LC/MS): Mobile phase: Buffer (pH 7)—CH3CN; Column: Analytic C18 column; Method: 0-100 CH3CN-15 min, $t_R$=5.62 min. MS m/z: MS-API: Calcd. for $C_{26}H_{29}F_3N_7O_7$ ([M+H]$^+$): 608.2, Found: 608.1;

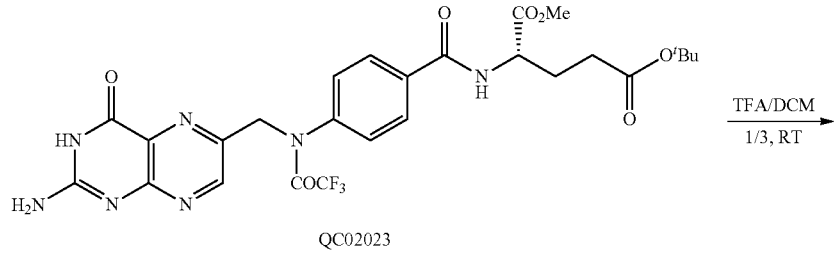

QC02023

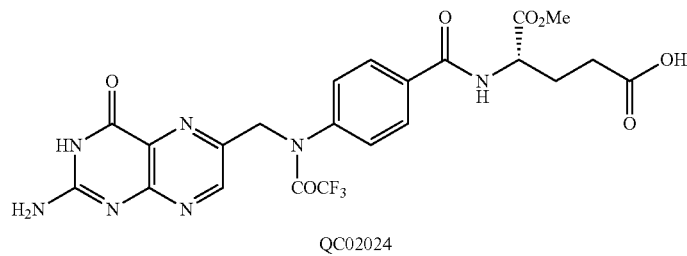

QC02024

EXAMPLE. (S)-4-(4-(N-((2-amino-4-oxo-3,4-dihydropteridin-6-yl)methyl)-2,2,2-trifluoroacetamido)benzamido)-5-methoxy-5-oxopentanoic acid (QC02024). 224 mg of QC02023 was treated with TFA/DCM (15 mL, 1/3) at 23° C. The reaction was stirred at 23° C. and monitored by TLC. After 1.5 hours, starting material was not observed by TLC. The volatile material was removed under reduced pressure resulting in a semi-solid residue, which was treated with cold $Et_2O$, to provide a pale white solid precipitate, which was collected by filtration and dried in air to provide (S)-4-(4-(N-((2-amino-4-oxo-3,4-dihydropteridin-6-yl) methyl)-2,2,2-trifluoroacetamido)benzamido)-5-methoxy-5-oxopentanoic acid QC02024 (169 mg, 83% for 2 steps). $\lambda_{max}$=280 nm; LC-MS (Agilent G6130B Quadrupole LC/MS): Mobile phase: Buffer (pH 7)—CH3CN; Column: Analytic C18 column; Method: 0-100 CH3CN-15 min, $t_R$=3.40 min. MS m/z: MS-API: Calcd. for $C_{22}H_{21}F_3N_7O_7$ ([M+H]$^+$): 552.1, Found: 552.1; $^1$H NMR (400 MHz, DMSO) δ=12.16 (s, br, 1H), 8.88 (d, J=7.2 Hz, 1H), 8.65 (s, 1H), 7.92 (d, J=8.0 Hz, 2H), 7.64 (d, J=8.0 Hz, 2H), 7.16 (s, br, 1H), 5.14 (s, 2H), 4.38-4.55 (m, 1H), 3.64 (s, 3H), 2.28-2.40 (m, 2H), 2.00-2.12 (m, 1H), 1.87-2.00 (m, 1H); $^{13}$C NMR (101 MHz, DMSO) δ=173.91, 172.36, 165.93, 161.03, 156.11, 155.76 (d, J=35.8 Hz), 154.19, 149.40, 144.45, 141.80, 134.30, 128.89, 128.62, 128.29, 117.91 (d, J=48.5 Hz), 53.90, 52.23, 52.06, 30.26, 25.81; $^{19}$F NMR (377 MHz, CDCl$_3$) δ=−62.87.

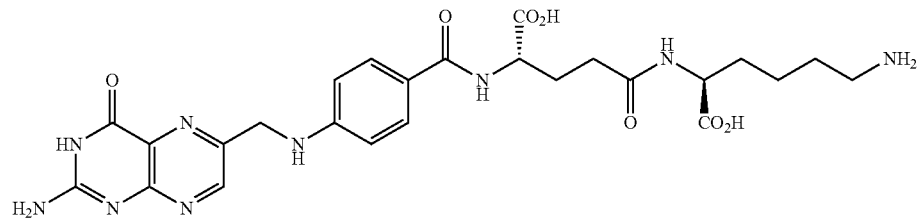

EC 1777

$C_{25}H_{31}N_9O_7$
Exact Mass: 569.23
Mol. Wt.: 569.57

EXAMPLE. Pte-γGlu-Lys-OH (EC1777). EC1777 was prepared using solid phase peptide synthesis as follows.

| Compound | mmol | Equivalent | Molecular Weight | Quantity (grams) |
|---|---|---|---|---|
| Fmoc-Lys-Resin (Loading~0.5 mmol/g) | 0.5 | 1 | | 1.00 |
| Fmoc-Glu-O$^t$Bu | 1.0 | 2 | 425.5 | 0.426 |
| N$^{10}$-TFA-Pteroic Acid | 0.65 | 1.3 | 408 | 0.265 |
| PyBOP | 1.3 | 2 | 520.31 | 0.52 |
| DIPEA | 1.5 | 3 | 129.24 (d = 0.742) | 0.168 |

In a peptide synthesis vessel, Fmoc-Lys-resin (1.0 g, 0.5 mmol) was placed and washed with DMF (3×10 ml). Initial Fmoc deprotection was performed using 20% piperidine in DMF (3×10 ml) solution for 10 mins per cycle. Subsequent washes of DMF (3×10 ml) and i-PrOH (3×10 ml), a Kaiser test was done to determine reaction completion. Following another DMF wash (3×10 ml); an amino acid solution (2.0 eq.) in DMF, PyBOP (2.0 eq.) and DIPEA (3.0 eq.) were added to the vessel and the solution bubbled with Argon for 1 hour. The coupling solution was filtered, the resin was washed with DMF (3×10 ml) and i-PrOH (3×10 ml) and a Kaiser test was done to assess reaction completion. The above process was performed successively for the additional coupling. Resin cleavage was performed with a cocktail consisting of 95% CF3CO2H, 2.5% H2O and 2.5% triisopropylsilane. The cleavage cocktail (10 ml) was poured onto the resin and bubbled with Argon for 30 mins, followed by filtration into a clean flask. Further cleavage was performed twice successively with fresh cleavage cocktail for 10 mins of bubbling. The combined filtrate was poured onto cold diethyl ether, the precipitate formed was collected by centrifugation at 4000 rpm for 5 mins (3×). The precipitate was obtained following decanting and drying of the solid under vacuum. Deprotection of the trifluoro-acetyl group was achieved by dissolving the crude precipitate in H2O (15 ml), which was basified with Na2CO3 to pH 9 with Argon bubbling. Upon completion of the reaction, confirmed by LCMS, the solution was acidified to pH 3 using 2 M HCl and the desired linker was purified by preparative HPLC (mobile phase A=10 mM Ammonium acetate, pH=5; Organic phase B=Acetonitrile; Method; 10% B to 100% B in 30 mins) to yield EC 1777 (112 mg, 39%); 1H NMR (500 MHz DMSO-d6) Pivotal signals: δ 8.60 (s, 1H), 7.58 (d, 2H), 6.60 (d, 2H), 4.45 (s, 2H). [M+H]+=Calculated 570.23, found 570.582.

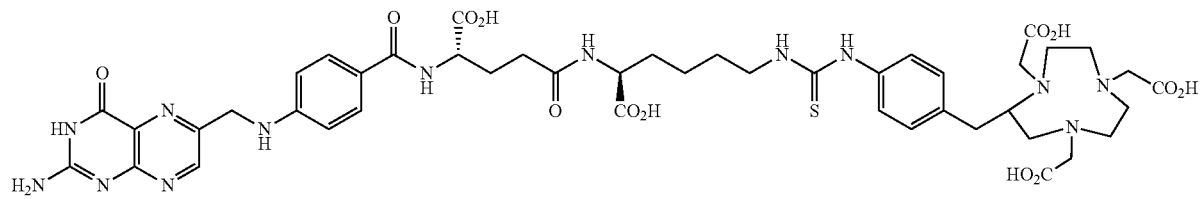

EC1778

$C_{45}H_{57}N_{13}O_{13}S$
Exact Mass: 1019.39
Mol. Wt.: 1020.08

EXAMPLE. Pte-γGlu-Lys-NOTA. In a dry flask, EC 1777 (30.5 mg, 0.054 mmol, 1.0 eq.), 1,1,3,3-tetramethylguanidine (13.45 μl, 0.107 mmol, 2.0 eq.) and DMSO (2.5 ml) under Argon were sonicated for 1 hour. DIPEA (0.19 ml, 1.07 mmol, 20 eq.) was added to the solution, followed by sonication for an addition hour. To the transparent solution was added p-SCN-Bn-NOTA.3HCl (33 mg, 0.059 mmol, 1.1 eq.) and the reaction was monitored until completion by LCMS and purified using preparative HPLC (mobile phase A=10 mM Ammonium acetate, pH=5; Organic phase B=Acetonitrile; Method; 10% B to 100% B in 30 mins) to yield EC 1778 (16 mg, 29%). 1H NMR (500 MHz DMSO-d6) Pivotal signals: δ 8.60 (s, 1H), 7.58 (d, 2H), 7.29 (d, 2H), 7.07 (d, 2H), 6.61 (d, 2H), 4.45 (s, 2H), 4.20 (t, 1H). [M+H]+=Calculated 1020.39, found 1020.63.

EXAMPLE. Pte-γGlu-Lys-NOTA-Al-18F is prepared by reaction of Pte-γGlu-Lys-NOTA with $Al^{18}F_3 \cdot 3H_2O$ (1 step method) or with $AlCl_3 \cdot H_2O$ followed by reaction with $Na^{18}F$ (2 step method) using published processes.

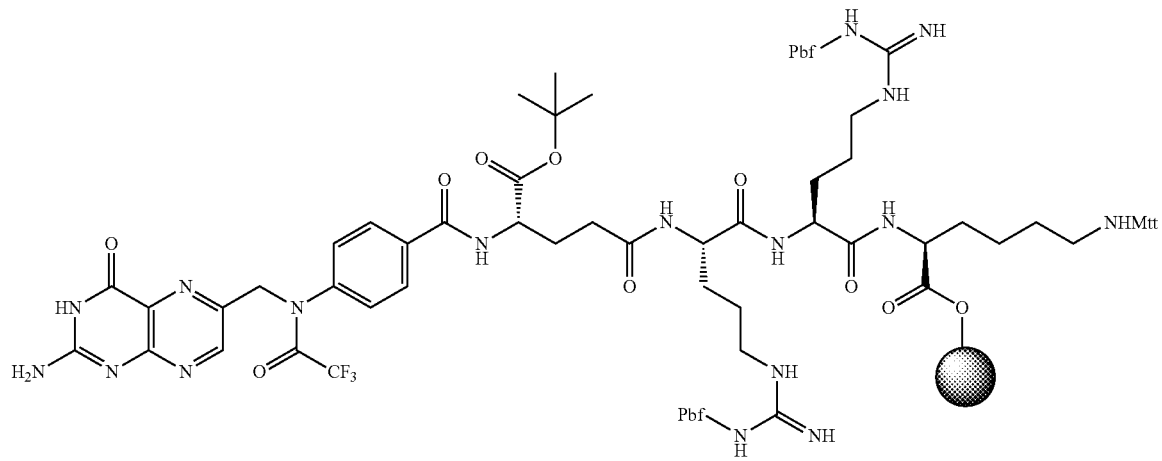

EXAMPLE. N10-TFA-Pte-γGlu-OtBu-Arg(Pbf)-Arg(Pbf)-Lys(Mtt)-resin 3. The general procedure described for the synthesis of resin bound folate-peptide resin 1 was followed for the coupling of 2×Fmoc-L-Arg(Pbf)-OH, Fmoc-Glu-OtBu, and N10-TFA-Pte-OH to Fmoc-L-Lys(Mtt)-Wang resin.

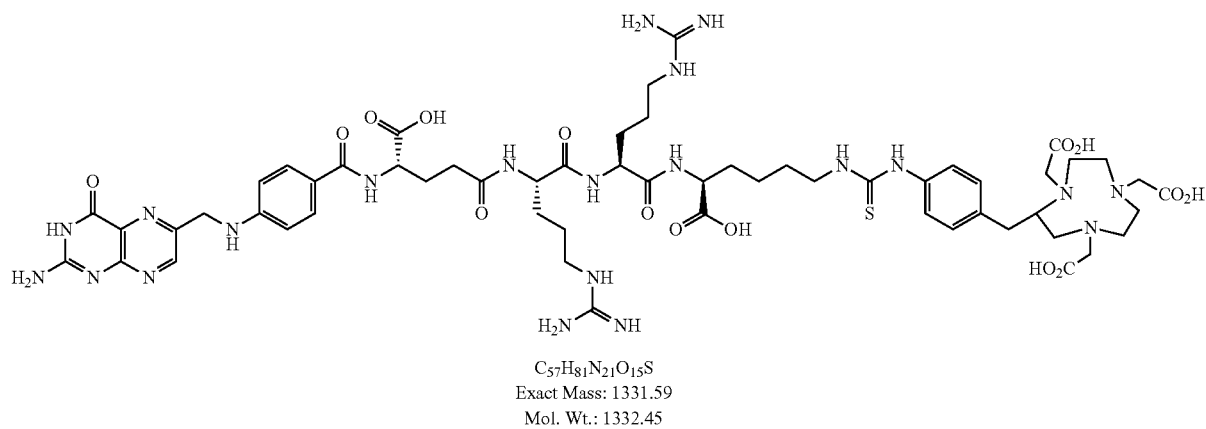

EC2217

$C_{57}H_{81}N_{21}O_{15}S$
Exact Mass: 1331.59
Mol. Wt.: 1332.45

EXAMPLE. Pte-γGlu-Arg-Arg-Lys-Bn-NOTA 4 (EC2217). In a peptide synthesis vessel, N10-TFA-Pte-γGlu-OtBu-Arg(Pbf)-Arg(Pbf)-Lys(Mtt)-resin (0.28 g, 0.07 mmol) was placed and washed with DCM (3×10 ml). Selective Mtt deprotection was performed by adding a 2% $CF_3CO_2H$/DCM solution to the vessel and bubbling with Argon for 10 min. After filtering, the resin was washed with dichloromethane followed by a fresh solution of 2% $CF_3CO_2H$/DCM. This process was repeated until there was no more yellow solution being yielded and a Kaiser test was done. Following a DMF wash (3×10 ml); p-SCN-Bn-NOTA·3HCl (50 mg, 0.09 mmol, 1.2 eq.) in DMF, and DIPEA (80 μl, 0.45 mmol, 6.0 eq.) were added to the vessel and the solution bubbled with Argon for 2 hour. The coupling solution was filtered, the resin was washed with DMF (3×10 ml) and i-PrOH (3×10 ml) and a Kaiser test was done to assess reaction completion. Resin cleavage/global tert-butyl ester deprotection was performed with a cocktail consisting of 95% $CF_3CO_2H$, 2.5% $H_2O$ and 2.5% triisopropylsilane. The cleavage cocktail (10 ml) was poured onto the resin and bubbled with Argon for 60 mins, followed by filtration into a clean flask. Further cleavage was performed twice successively with fresh cleavage cocktail for 20 mins of bubbling. The combined filtrate was poured onto cold diethyl ether, the precipitate formed was collected by centrifugation at 4000 rpm for 5 mins (3×). The precipitate was obtained following decanting and drying of the solid under vacuum. Deprotection of the trifluoro-acetyl group was achieved by dissolving the crude precipitate in H2O (15 ml), which was basified with $Na_2CO_3$ to pH 9 with Argon bubbling. Upon completion of the reaction, confirmed by LCMS, the solution was acidified to pH 5 using 2 M HCl and the desired linker was purified by preparative HPLC (mobile phase A=10 mM Ammonium acetate, pH=5; Organic phase B=Acetonitrile; Method; 10% B to 100% B in 30 mins) to yield EC2217 (35 mg, 35%). 1H NMR (500 MHz DMSO-d6) Pivotal signals: δ 8.61 (s, 1H), 7.54 (d, J=8.4 Hz, 2H), 7.17-7.03 (m, 2H), 6.99 (d, J=8.0 Hz, 2H), 6.66 (d, J=8.5 Hz, 2H), 4.52-4.45 (m, 1H), 4.17 (dt, J=8.9, 4.6 Hz, 2H), 4.12 (s, 1H), 4.07-3.97 (in, 1H). [M+H]+=Calculated 1332.59, found 1332.87

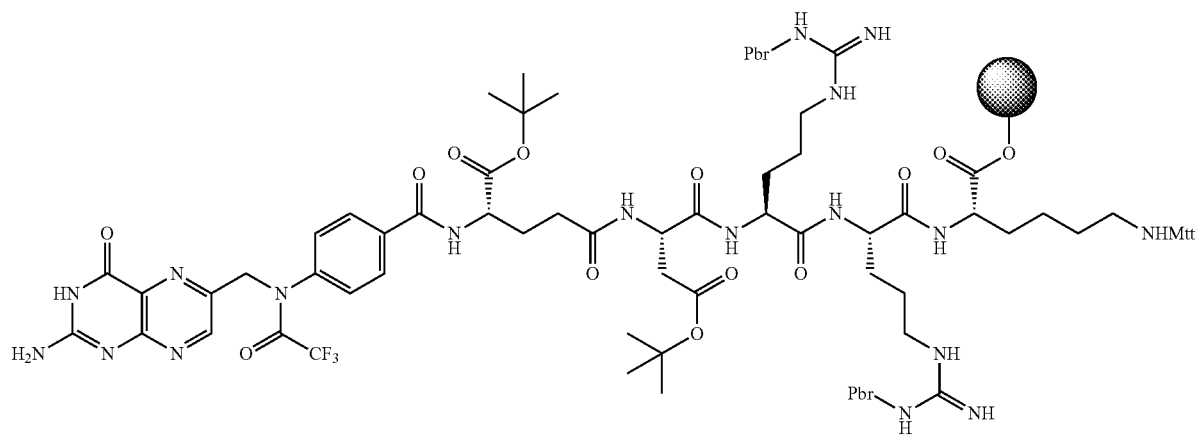

EXAMPLE. N10-TFA-Pte-γGlu-OtBu-Asp(OtBu)-Arg(Pbf)-Arg(Pbf)-Lys(Mtt)-resin 5. The general procedure described for the synthesis of resin bound folate-peptide resin 1 was followed for the coupling of 2×Fmoc-L-Arg(Pbf)-OH, Fmoc-L-Asp(OtBu)-OH, Fmoc-Glu-OtBu, and N10-TFA-Pte-OH to Fmoc-L-Lys(Mtt)-Wang resin.

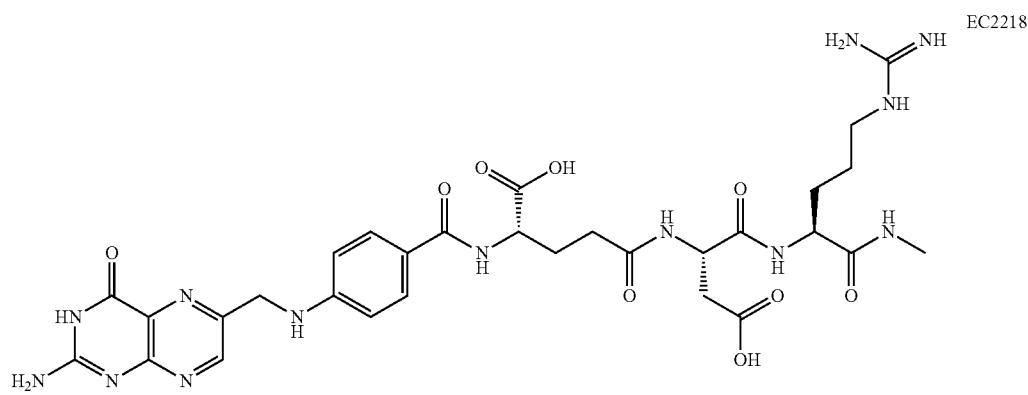

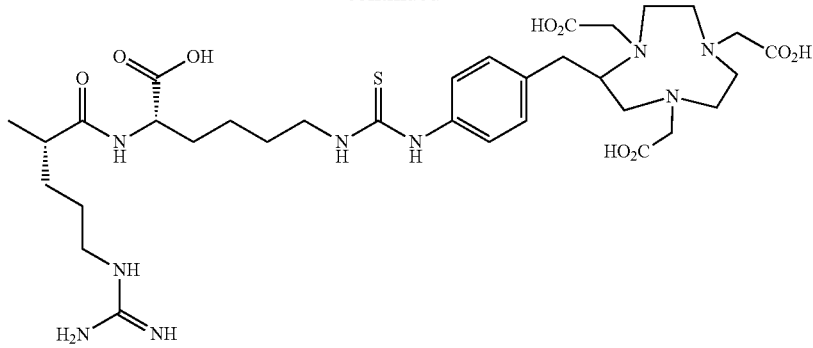

C₆₁H₈₆N₂₂O₁₈S
Exact Mass: 1446.62
Mol. Wt.: 1447.54

EXAMPLE. Pte-γGlu-Asp-Arg-Arg-Lys-Bn-NOTA 6 (EC2218). Pte-γGlu-Asp-Arg-Arg-Lys-Bn-NOTA, EC2218 was prepared in 18% yield according to the process described for folate-peptide-NOTA, 4. 1H NMR (500 MHz DMSO-d6) Pivotal signals: δ 8.58 (s, 1H), 7.52 (d, J=9.0 Hz, 2H), 7.14-7.08 (m, 4H), 6.61 (d, J=9.0 Hz, 2H), 4.16-4.09 (m, 2H), 4.06 (dd, J=10.0, 4.3 Hz, 1H), 3.90 (dd, J=7.8, 4.7 Hz, 1H). [M+H]+=Calculated 1449.64, found 1449.76

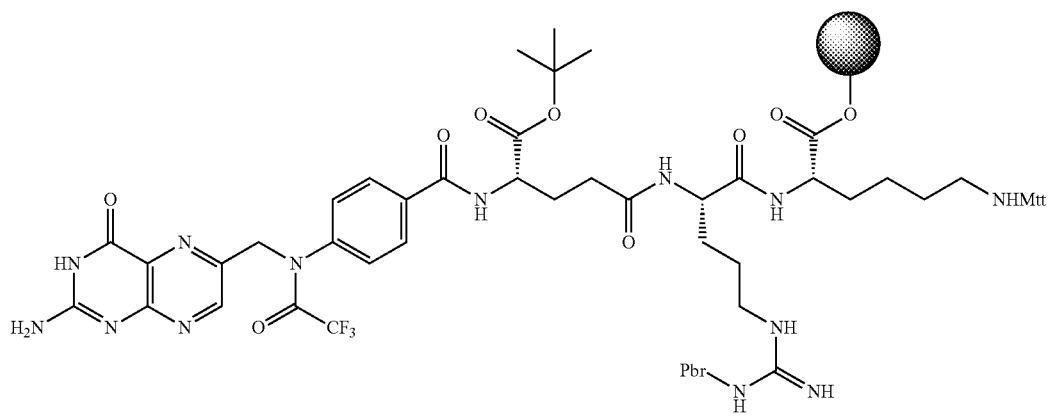

EXAMPLE. N10-TFA-Pte-γGlu-OtBu-Arg(Pbf)-Lys(Mtt)-resin 7. The general procedure described for the synthesis of resin bound folate-peptide resin 1 was followed for the coupling of Fmoc-L-Arg(Pbf)-OH, Fmoc-Glu-OtBu, and N10-TFA-Pte-OH to Fmoc-L-Lys(Mtt)-Wang resin.

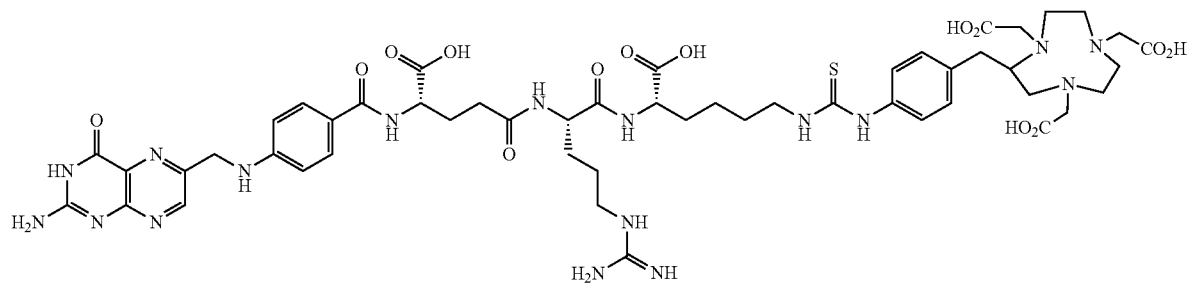

EC2219

C₅₁H₆₉N₁₇O₁₄S
Exact Mass: 1175.49
Mol. Wt.: 1176.27

EXAMPLE. Pte-γGlu-Arg-Lys-Bn-NOTA 8 (EC2219).
Pte-γGlu-Arg-Lys-Bn-NOTA, EC2219 was prepared in 20% yield according to the process described for folate-peptide-NOTA, 4. 1H NMR (500 MHz DMSO-d6) Pivotal signals: δ 8.68 (s, 1H), 7.60 (d, J=8.4 Hz, 3H), 7.27-6.97 (m, 4H), 6.77-6.69 (m, 2H), 4.28-f 4.19 (m, 2H), 4.08 (dd, J=9.0, 5.4 Hz, 1H), 4.01 (dd, J=8.5, 5.4 Hz, 1H). [M+H]+=Calculated 1178.51, found 1178.7

EC2222

C₄₉H₇₄N₂₀O₁₄
Exact Mass: 1166.57
Mol. Wt.: 1167.24

EXAMPLE. Pte-γGlu-Arg-Arg-Lys-NOTA 9 (EC2222). In a peptide synthesis vessel, N10-TFA-Pte-γGlu-OtBu-Arg(Pbf)-Arg(Pbf)-Lys(Mtt)-resin (0.5 g, 0.12 mmol) was placed and washed with DCM (3×10 ml). Selective Mtt deprotection was performed by adding a 2% CF₃CO₂H/DCM solution to the vessel and bubbling with Argon for 10 min. After filtering, the resin was washed with dichloromethane followed by a fresh solution of 2% CF₃CO₂H/DCM. This process was repeated until there was no more yellow solution being yielded and a Kaiser test was done. Following a DMF wash (3×10 ml); NOTA-Bis(tBu)ester (0.10 g, 0.24 mmol, 2.0 eq.) in DMF, PyBOP (0.14 g, 0.26 mmol, 2.2 eq) and DIPEA (64 μl, 0.36 mmol, 3.0 eq.) were added to the vessel and the solution bubbled with Argon for 2 hour. The coupling solution was filtered, the resin was washed with DMF (3×10 ml) and i-PrOH (3×10 ml) and a Kaiser test was done to assess reaction completion. Resin cleavage/global tert-butyl ester deprotection was performed with a cocktail consisting of 95% CF₃CO₂H, 2.5% H₂O and 2.5% triisopropylsilane. The cleavage cocktail (10 ml) was poured onto the resin and bubbled with Argon for 1 hr, followed by filtration into a clean flask. Further cleavage was performed twice successively with fresh cleavage cocktail for 10 mins of bubbling. The combined filtrate was poured onto cold diethyl ether, the precipitate formed was collected by centrifugation at 4000 rpm for 5 mins (3×). The precipitate was obtained following decanting and drying of the solid under vacuum. Deprotection of the trifluoro-acetyl group was achieved by dissolving the crude precipitate in H₂O (15 ml), which was basified with Na₂CO₃ to pH 9 with Argon bubbling. Upon completion of the reaction, confirmed by LCMS, the solution was acidified to pH 5 using 2 M HCl and the desired linker was purified by preparative HPLC (mobile phase A=10 mM Ammonium acetate, pH=5; Organic phase B=Acetonitrile; Method; 10% B to 100% B in 30 mins) to yield EC2222 (28 mg, 20%). 1H NMR (500 MHz DMSO-d6) Pivotal signals: δ 8.60 (s, 1H), 7.51 (d, J=8.1 Hz, 2H), 6.64 (d, J=8.4 Hz, 2H), 4.21-4.09 (m, 2H), 4.09-4.03 (m, 1H), 3.98-3.88 (m, 1H), 3.50 (s, 1H). [M+H]+= Calculated 1167.57, found 1167.8

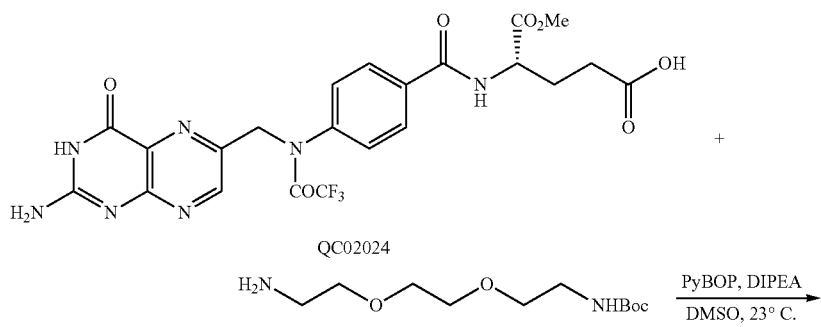

-continued

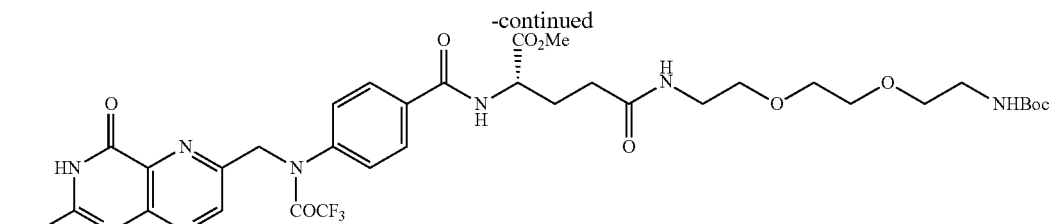

QC07010

EXAMPLE. (S)-Methyl 18-(4-(N-((2-amino-4-oxo-3,4-dihydropteridin-6-yl)methyl)-2,2,2-trifluoroacetamido)benzamido)-2,2-dimethyl-4,15-dioxo-3,8,11-trioxa-5,14-diazanonadecan-19-oate (QC07010). QC02024 (100 mg, 0.181 mmol) is added to a solution of Mono-Boc-PEG-NH$_2$ (45 mg, 0.181 mmol) and DIPEA (0.158 mL, 0.905 mmol) in DMSO (2 mL) at 23° C. under N$_2$. After being stirred for 15 min at 23° C., PyBOP (94.2 mg, 0.181 mmol) was added, and the reaction mixture was stirred for 24 h at 23° C. Volatile material was removed under reduced vacuum, the crude material was further purified by SPE purification: extract successively with ACN (2×), EA (1×) and Et$_2$O (1×) to afford pure product QC07010 (127 mg, 90%). λmax=280 nm; LC-MS (Agilent G6130B Quadrupole LC/MS): Mobile phase: Buffer (pH 7)—CH3CN; Column: Analytic C18 column; Method: 0-100 CH3CN-15 min, tR=5.06 min. MS m/z: MS-API: Calcd. for C33H43F3N9O10 ([M+H]+): 782.3, Found: 782.2; 1H NMR (400 MHz, DMSO) δ=11.59 (s, br, 1H), 8.92 (d, J=7.2 Hz, 1H), 8.64 (s, 1H), 7.85-8.02 (m, 3H), 7.64 (d, J=8.0 Hz, 2H), 6.75 (t, J=5.2 Hz, 1H), 5.13 (s, 2H), 4.33-4.48 (m, 1H), 3.64 (s, 3H), 3.46 (s, 4H), 3.30-3.41 (s, 4H), 3.14-3.23 (m, 2H), 3.01-3.08 (m, 2H), 2.19-2.30 (m, 2H), 2.02-2.12 (m, 1H), 1.89-2.00 (m, 1H), 1.35 (s, 9H); 13C NMR (101 MHz, DMSO) δ=172.43, 171.46, 165.73, 160.87, 156.80, 155.70 (d, J=35.5 Hz), 155.67, 154.17, 149.49, 144.20, 141.73, 134.30, 128.82, 128.55, 128.23, 116.20 (d, J=290.0 Hz), 77.65, 69.58, 69.50, 69.193, 69.192, 53.88, 52.52, 51.96, 38.89, 38.62, 31.65, 28.23, 26.32; 19F NMR (377 MHz, CDCl3) δ=−62.87.

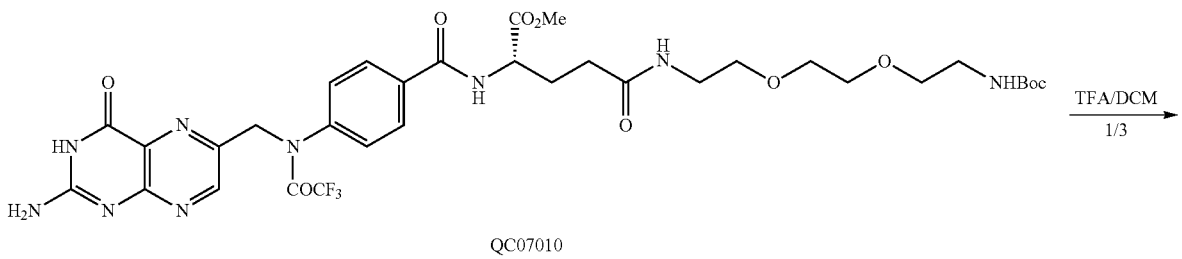

QC07010 →(TFA/DCM, 1/3)

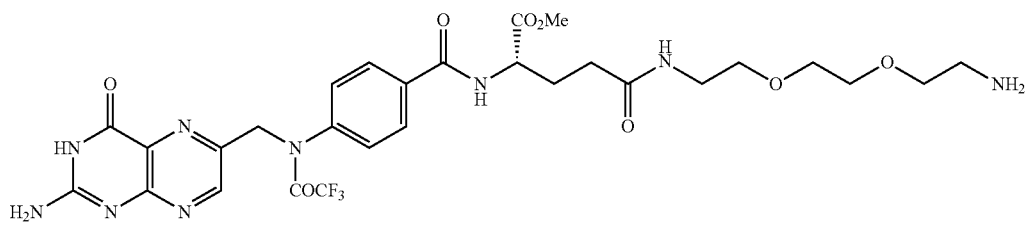

QC07011

EXAMPLE. (S)-methyl 2-(4-(N-((2-amino-4-oxo-3,4-dihydropteridin-6-yl)methyl)-2,2,2-trifluoroacetamido)benzamido)-5-((2-(2-(2-aminoethoxy)ethoxy)ethyl)amino)-5-oxopentanoate (QC07011). QC07010 (274 mg, 0.35 mmol) was treated with TFA/DCM (4 mL, 1/3) at 23° C. The reaction was stirred at 23° C. and monitored by LC-MS. After 1.5 h, TLC showed that all starting material disappeared. The mixture was diluted with CH3CN and evaporated to dry via rota-vap. Residue TFA (b.p. 72.4° C.) was removed through azeotropic distillation with ACN to afford the product QC07011 in quantitative yield, which was used without further purification. $\lambda_{max}$=280 nm; LC-MS (Agilent G6130B Quadrupole LC/MS): Mobile phase: Buffer (pH 7)-ACN; Column: Analytic C18 column; Method: 0-100 ACN 15 min, $t_R$=3.84 min. MS m/z: MS-API: Calcd. for $C_{28}H_{35}F_3N_9O_8$ ([M+H]$^+$): 682.2, Found: 682.2.

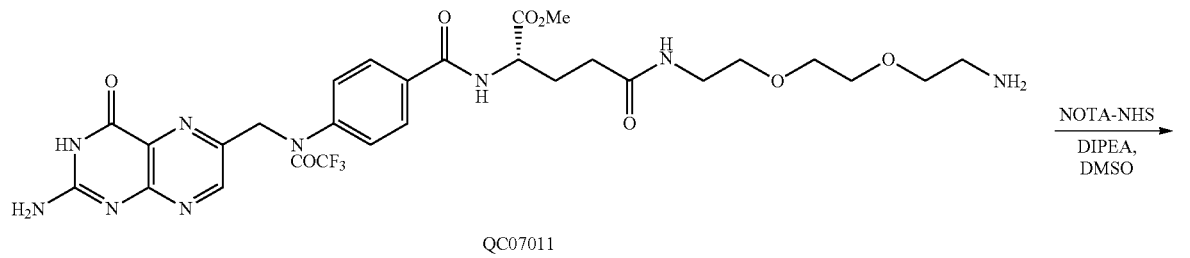

QC07011

EXAMPLE. (S)-2,2'-(7-(4-(4-(N-((2-amino-4-oxo-3,4-dihydropteridin-6-yl)methyl)-2,2,2-trifluoroacetamido)benzamido)-3,7,18-trioxo-2,11,14-trioxa-8,17-diazanonadecan-19-yl)-1,4,7-triazonane-1,4-diyl)diacetic acid (QC07013). QC07011 (15.7 mg, 0.023 mmol) in DMSO (0.5 ml) was added NOTA-NHS (18.2 mg, 0.028 mmol) followed by DIPEA (15 µL, 0.084 mmol). The reaction was stirred at 23° C., monitored by LC-MS, and most of the starting material was converted to QC07013 in 5 hours. The product was purified by RP-$C_{18}$ HPLC to afford the pure product QC07013 (13.0 mg, 58.5%). $\lambda_{max}$=280 nm; LC-MS (Agilent G6130B Quadrupole LC/MS): Mobile phase: Buffer (pH 7)—CH3CN; Method: 0-100 CH3CN-15 min, $t_R$=3.74 min. MS m/z: MS-API: Calcd. for $C_{40}H_{54}F_3N_{12}O_{13}$ ([M+H]$^+$): 967.4, Found: 967.2; HPLC (Agilent Preparative C18 Column): Mobile phase: Buffer (pH 7)—CH3CN; Method: 0-100 CH3CN-30 min, $t_R$=10.75 min

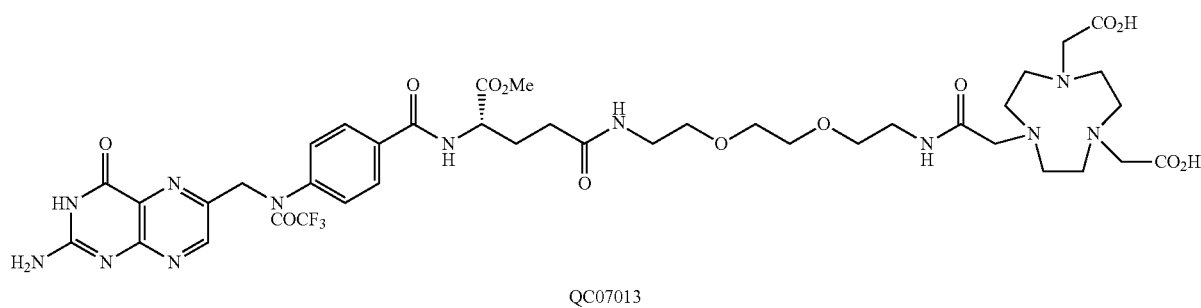

QC07013

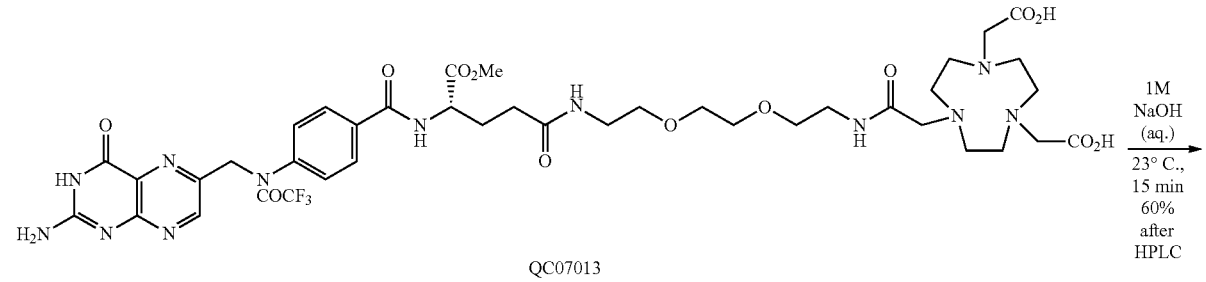

QC07013

-continued

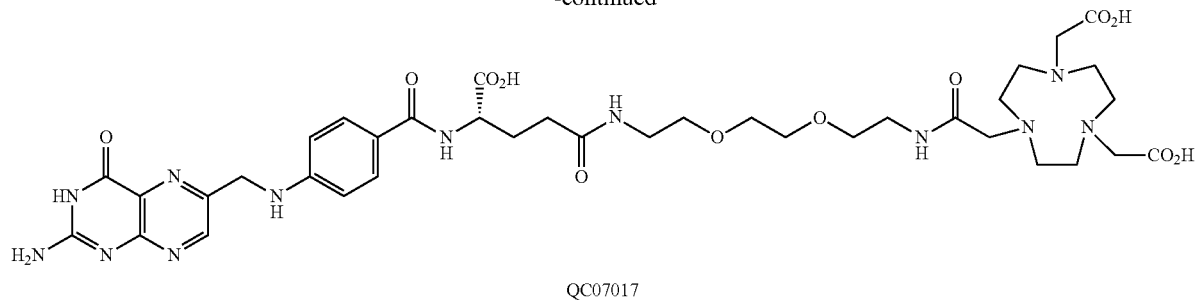

QC07017

EXAMPLE. (S)-2,2'-(7-(1-(4-(((2-amino-4-oxo-3,4-dihydropteridin-6-yl)methyl)amino)phenyl)-3-carboxy-1,6,17-trioxo-10,13-dioxa-2,7,16-triazaoctadecan-18-yl)-1,4,7-triazonane-1,4-diyl)diacetic acid (FA-PEG1-NOTA, QC07017). QC07013 (20.8 mg, 0.022 mmol) was stirred in 1.2 mL of 1 M NaOH (aq.) at 23° C. and the reaction was monitored by LC-MS. After 15 min, all starting material was transformed to product, the crude material was purified by RP-C18 HPLC to afford QC07017 (11.3 mg, 60%). λmax=280 nm; HPLC (Agilent Preparative C18 Column): Mobile phase: Buffer (pH 7)—CH3CN; Method: 0-30 CH3CN-30 min, tR=11.49 min. LC-MS (Agilent G6130B Quadrupole LC/MS): Mobile phase: Buffer (pH 7)—CH3CN; Method: 0-100 CH3CN 15 min, tR=2.72 min.

MS m/z: MS-API: Calcd. for C37H53N12O12 ([M+H]+): 857.4, Found: 857.2. 1H NMR (400 MHz, DMSO) δ=8.62 (s, 1H), 8.28 (t, J=5.6 Hz, 1H), 7.99 (t, J=5.6 Hz, 1H), 7.85 (d, J=7.2 Hz, 1H), 7.76-7.80 (s, br, 2H), 7.58 (d, J=8.8 Hz, 2H), 7.00 (t, J=6.0 Hz, 1H), 6.62 (d, J=8.8 Hz, 2H), 4.47 (d, J=5.2 Hz, 2H), 4.13-4.18 (m, 1H), 3.43 (s, 4H), 3.31-3.41 (m, 4H), 3.29-3.32 (m, 2H), 3.10-3.24 (m, 4H), 3.03-3.10 (s, br, 2H), 2.90-3.03 (s, br, 2H), 2.10-2.14 (m, 2H), 1.97-2.05 (m, 1H), 1.84-1.91 (m, 1H); 13C NMR (101 MHz, DMSO) δ=174.33, 172.21, 171.17, 170.35, 165.70, 161.85, 156.19, 154.95, 150.56, 148.45, 148.32, 128.62, 127.87, 121.84, 111.38, 69.44, 69.30, 69.08, 68.70, 60.95, 57.48, 53.11, 50.85, 49.41, 48.91, 45.88, 38.60, 38.18, 32.04, 27.52.

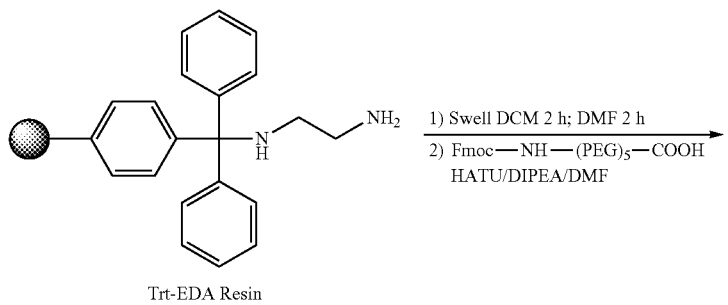

Trt-EDA Resin

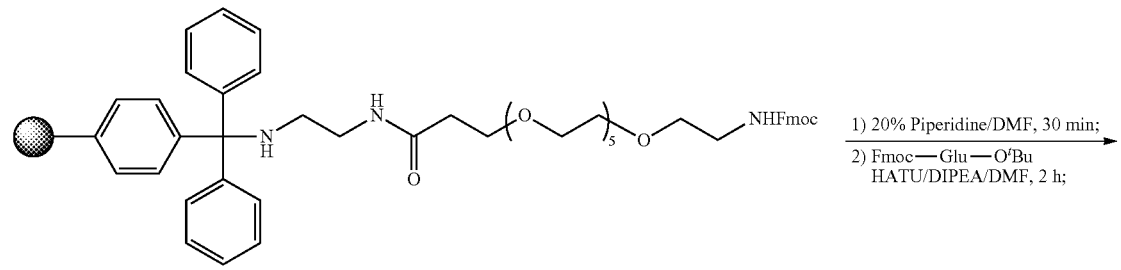

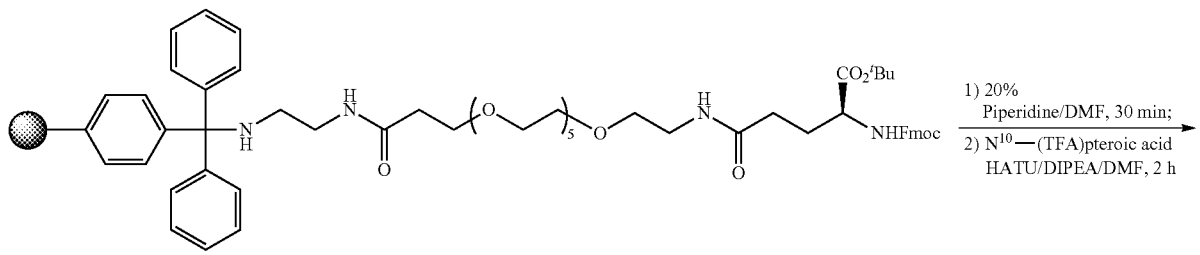

-continued

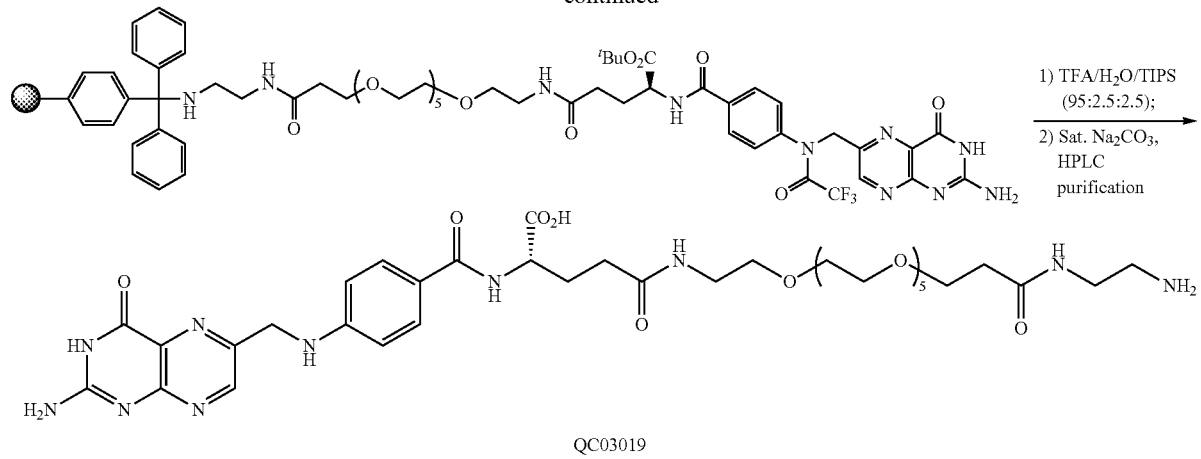

QC03019

EXAMPLE. Solid Phase Synthesis (SPS) of FA-PEG$_6$-EDA-NH$_2$ Precursor (QC03019). 1,2-Diaminoethane trityl resin (1.2 mmol/g, 100 mg, 0.12 mmol) was swollen with dichloromethane (DCM, 3 mL) followed by dimethyl formamide (DMF, 3 mL). After swelling the resin in DMF, a solution of fluorenylmethoxycarbonyl (Fmoc)-PEG$_6$-OH (1.5 equiv), HATU (1.5 equiv), and DIPEA (2.0 equiv) in DMF was added. Argon was bubbled for 2 h, and resin was washed with DMF (3×3 mL) and i-PrOH (3×3 mL). The above sequence was repeated for two more coupling steps for conjugation of Fmoc-Glu-(OtBu)-OH and N$^{10}$-TFA-Ptc-OH. The final product was cleaved from the resin using a trifluoroacetic acid (TFA):H$_2$O:triisopropylsilane cocktail (95:2.5:2.5) and concentrated under vacuum. The concentrated product was precipitated in diethyl ether and dried under vacuum, which was then incubated in Sat. Na$_2$CO$_3$ and monitored by LC-MS. 1 hour later, the mixture was neutralized to pH=7 with 2 M HCl (aq.) which was purified by preparative with preparative RP-C$_{18}$ HPLC [solvent gradient: 0% B to 50% B in 30 min; A=10 mM NH$_4$OAc, pH=7; B=CH$_3$CN]. Acetonitrile was removed under vacuum, and the residue was freeze-dried to yield QC03019 as a yellow solid (59 mg, 60%). Analytical RP-C$_{18}$ HPLC: t$_R$=4.22 min (A=10 mM NH$_4$OAc, pH=7.0; B=CH$_3$CN, solvent gradient: 0% B to 50% B in 15 min); Preparative RP-C$_{18}$ HPLC: t$_R$=11.7 min (A=10 mM NH$_4$OAc, pH=7.0; B=CH$_3$CN, solvent gradient: 0% B to 50% B in 30 min); $\lambda_{max}$=280 nm; HPLC (Agilent Preparative C18 Column): Mobile phase: Buffer (pH 7)—CH$_3$CN; Method: 0-30 CH$_3$CN-30 min, t$_R$=11.7 min. LC-MS (Agilent G6130B Quadrupole LC/MS): Mobile phase: Buffer (pH 7)—CH$_3$CN; Method: 0-50 CH$_3$CN-15 min, t$_R$=4.22 min. MS m/z: MS-API: Calcd. for C$_{36}$H$_{55}$N$_{10}$O$_{12}$ ([M+H]$^+$): 819.4, found, 819.2. $^1$H NMR (DMSO-d$_6$/D$_2$O) δ=8.63 (s, 1H), 7.64 (d, J=8.8 Hz, 2H), 6.64 (d, J=8.8 Hz, 2H), 4.48 (s, 2H), 4.12-4.21 (m, 1H), 3.58 (t, J=6.4 Hz, 2H), 3.41-3.53 (m, 24H), 3.18-3.25 (m, 2H), 3.11-3.18 (m, 2H), 2.28 (t, J=6.4 Hz, 2H), 2.15 (t, J=7.4 Hz, 2H), 2.03 (m, 1H), 1.88 (m, 1H) ppm.

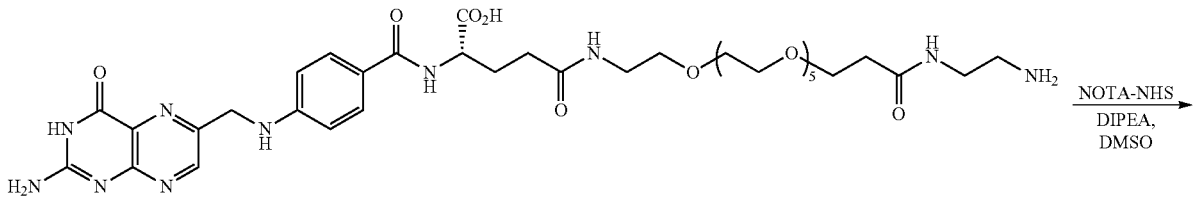

QC03019

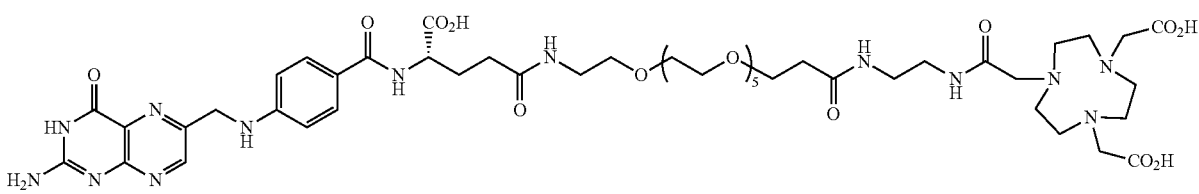

QC07029

EXAMPLE. FA-PEG$_6$-NOTA. To QC03019 (9.5 mg, 0.011 mmol) in DMSO (0.40 ml, with a concentration at 0.029 M) was added NOTA-NHS (8.6 mg, 0.013 mmol) followed by DIPEA (7.0 µL, 0.039 mmol). The reaction was stirred at 23° C., monitored by LC-MS, and most of the starting material was transformed to the corresponding product in 5 hours. The crude material was purified by RP-C$_{18}$ HPLC to afford the pure product QC07029 (5.5 mg, 45%). Analytical RP-C$_{18}$ HPLC: $t_R$=3.91 min (A=10 mM NH$_4$OAc, pH=7.0; B=CH$_3$CN, solvent gradient: 0% B to 50% B in 15 min); Preparative RP-C$_{18}$ HPLC: $t_R$=10.51 min (A=10 mM NH$_4$OAc, pH=7.0; B=CH$_3$CN, solvent gradient: 0% B to 50% B in 30 min); $\lambda_{max}$=280 nm; HPLC (Agilent Preparative C18 Column): Mobile phase: Buffer (pH 7)—CH$_3$CN; Method: 0-30 CH$_3$CN-30 min, $t_R$=10.51 min. LC-MS (Agilent G6130B Quadrupole LC/MS): Mobile phase: Buffer (pH 7)-ACN; Method: 0-50 ACN-15 min, $t_R$=3.91 min MS m/z: MS-API: Calcd. for C$_{48}$H$_{74}$N$_{13}$O$_{17}$ ([M+H]$^+$): 1104.5, Found: 1104.4.

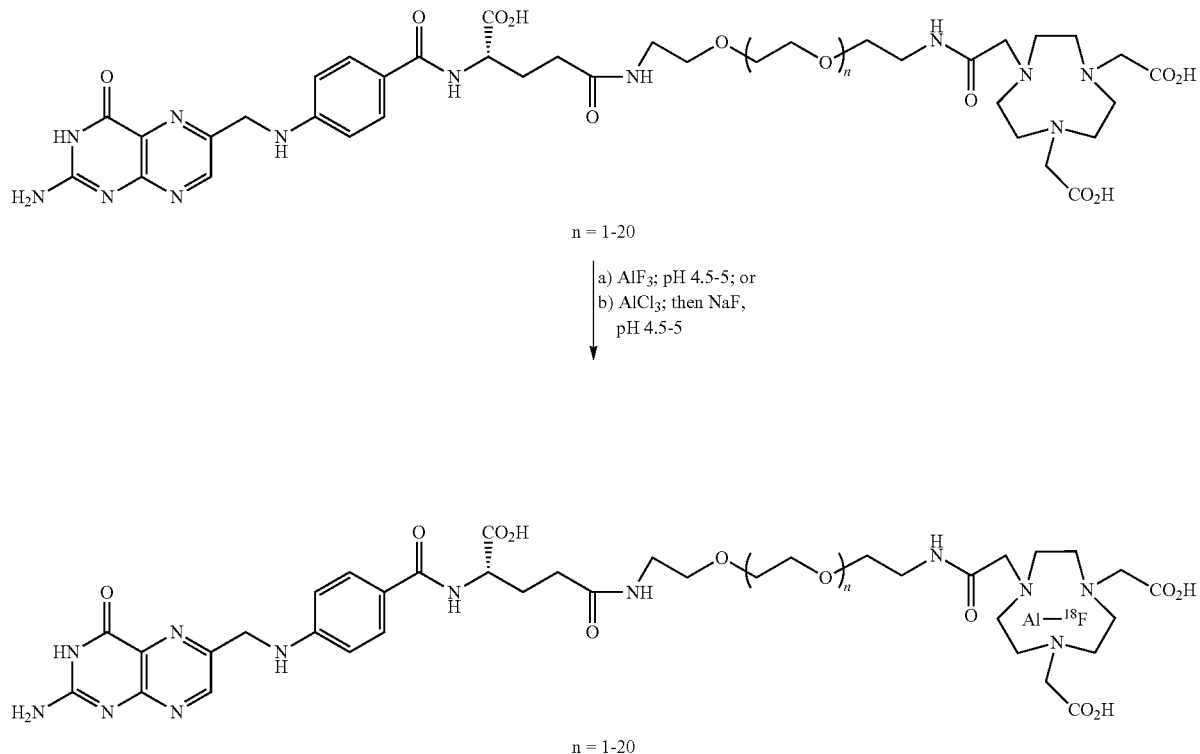

EXAMPLE. FA-NOTA-Al-$^{18}$F Radiotracer[2]. Two methods for the formation of FANOTA-Al-$^{18}$F are described herein. Conditions including the pH value, concentration of the substrates and temperature for the chelating reaction with $^{18}$F—Al can be varied. The general methods for FA-NOTA-Al-$^{18}$F are described as followed:

Method a). FA-NOTA Precursor was dissolved in 2 mM NaOAc (pH 4.5) and 0.5 mL of ethanol, which was treated with Al$^{18}$F$_3$·3H$_2$O (1.5 eq.) which was freshly prepared before application. The pH was adjusted to 4.5-5.0, and the reaction mixture was refluxed for 15-30 min with pH kept at 4.5-5.0. After being cooled down to room temperature, the crude material was loaded to a cartridge, and the radiotracer was eluted into vial. After sterile filtration and being diluted to appropriate radioactivity (5-10 mCi) and specific activity (>1 Ci/µmol), the radiotracer was ready for in vivo PET imaging study.

Method b). FA-NOTA Precursor was dissolved in 2 mM NaOAc (pH 4.5), and treated with AlCl$_3$·3H$_2$O (1.5 eq.). The pH was adjusted to 4.5-5.0, and the reaction mixture was refluxed for 15-30 min with pH kept at 4.5-5.0. The crude material was purified by RP-HPLC to afford the FA-NOTA-Al—OH intermediate ready for $^{18}$F-labeling. Appropriate amount of FA-NOTA-Al—OH was treated with Na$^{18}$F saline solution and ethanol (1/1, v/v), and the whole mixture was heated at 100-110° C. for 15 min. After being cooled down to room temperature, the crude material was loaded to a cartridge, and the radiotracer was eluted into vial. After sterile filtration and being diluted to appropriate radioactivity (5-10 mCi) and specific activity (>1 Ci/µmol), the radiotracer was ready for in vivo PET imaging study.

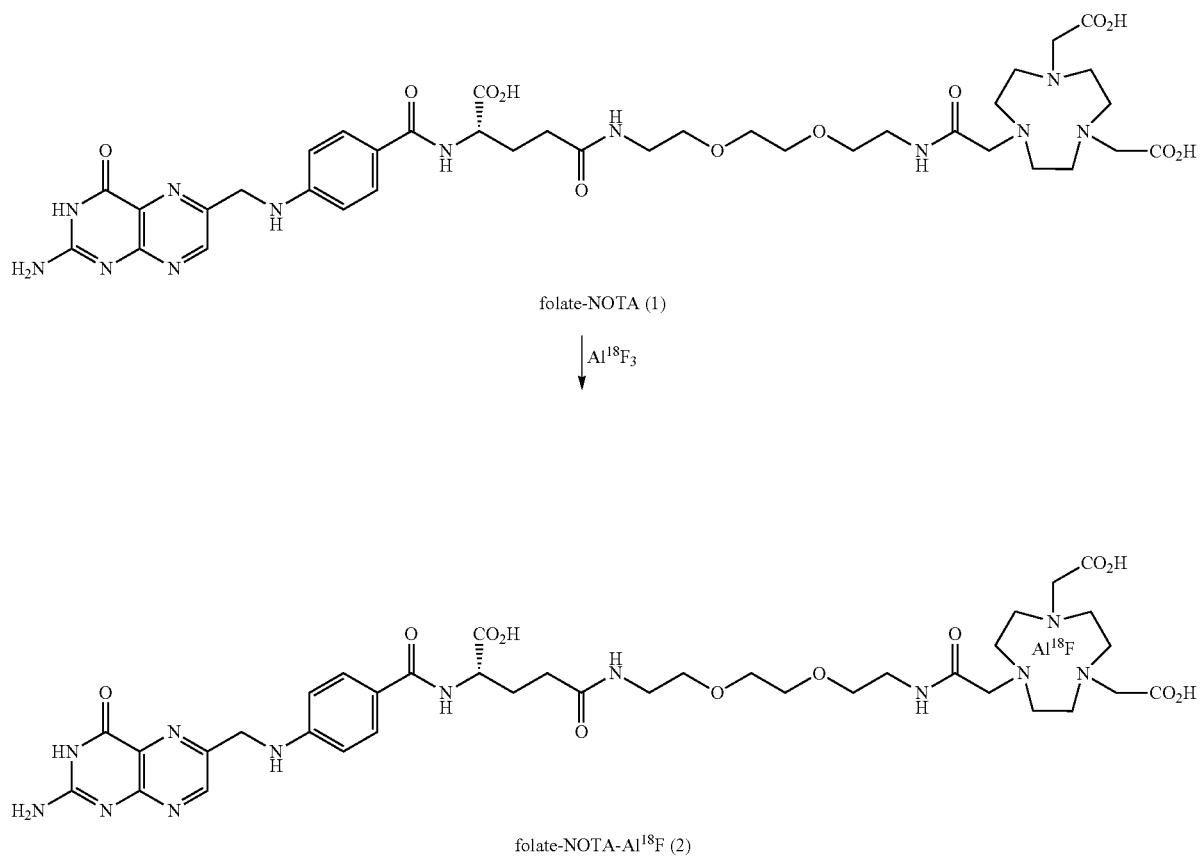

folate-NOTA (1)

folate-NOTA-Al¹⁸F (2)

EXAMPLE. Standard Protocol for the Formulation of Folate-NOTA-Al$^{18}$F Radiotracer. The resin containing $^{18}$F was first washed with 1.5 mL of ultrapure water, and then $^{18}$F was eluted out from resin by using 1.0 mL of 0.4 M KHCO$_3$ solution. 100 μL of the eluting solution containing $^{18}$F was added to a stem vial charged with 10 μL acetic acid, 25 μL AlCl$_3$ (2 mM in 0.1 M NaOAc pH 4 buffer) and 125 μL 0.1 M NaOAc pH 4 buffer. The whole mixture was incubated for 2 min before 0.25 mg folate-NOTA precursor (1) in 125 μL of 0.1 M NaOAc pH 4 buffer was transferred to the same stem vial. The reaction was immediately heated to 100° C. for 15 min.

After cooling to room temperature, the crude material was mixed with 0.7 mL 0.1% formic acid and purified by radioactive HPLC on a Xselect CSH C18 (250×10 mm) column using MeCN and 0.1% formic acid as the mobile phase. The fraction at 11.5 min was collected to afford pure radiotracer in ~40-50% radiochemical yield (RCY) with ~98% radiochemical purity (RCP). The total radiochemical synthesis of folate-NOTA-Al$^{18}$F (2, Al$^{18}$F-QC07017) was accomplished in ~37 min with a specific activity (SA) of 70±18.4 GBq/μmol. After sterile filtration and appropriate dilution in isotonic saline to the desired radioactivity, the folate-NOTA-Al$^{18}$F (2) radiotracer was ready for PET imaging study.

Using same strategy, radiochemcial synthesis of FA-PEG$_{12}$-NOTA-Al-$^{18}$F radiotracer (QC07043) was accomplished in ~35 min with a specific activity (SA) of 49±17.1 GBq/μmol. Although the radiochemical purity is excellent, 100% after radioactive HPLC purification, the total radiochemical yield (RCY) is relatively low, ~25-30%. After sterile filtration and appropriate dilution in isotonic saline to the desired radioactivity, the FA-PEG$_{12}$-NOTA-Al-$^{18}$F radiotracer was ready for PET imaging study.

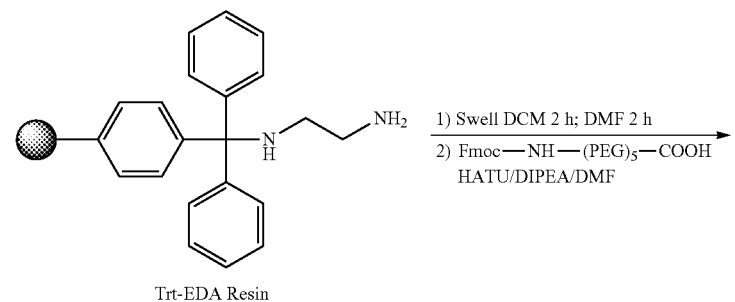

Trt-EDA Resin

1) Swell DCM 2 h; DMF 2 h
2) Fmoc—NH—(PEG)$_5$—COOH
HATU/DIPEA/DMF

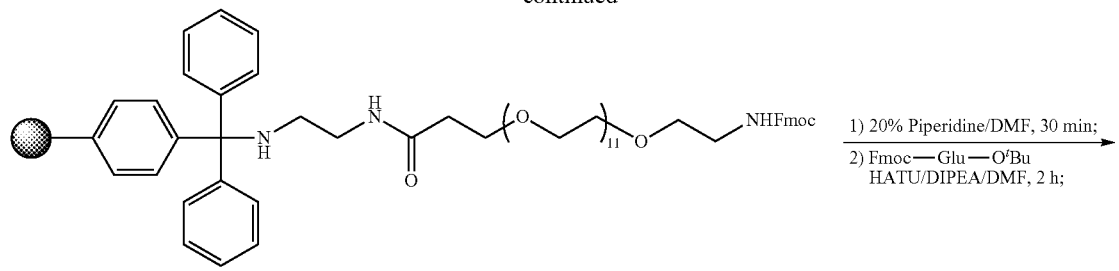

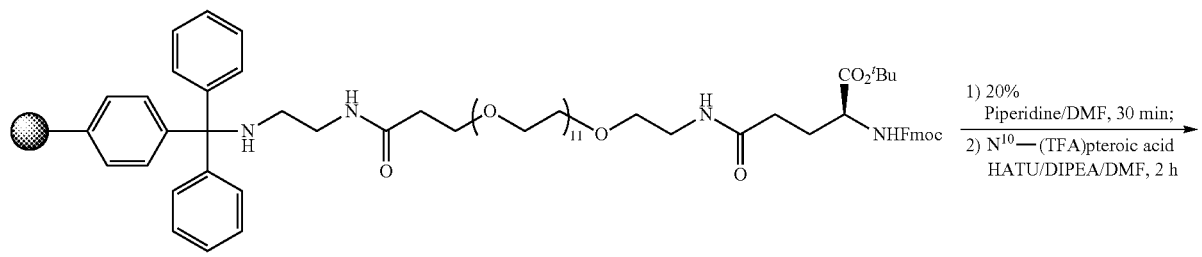

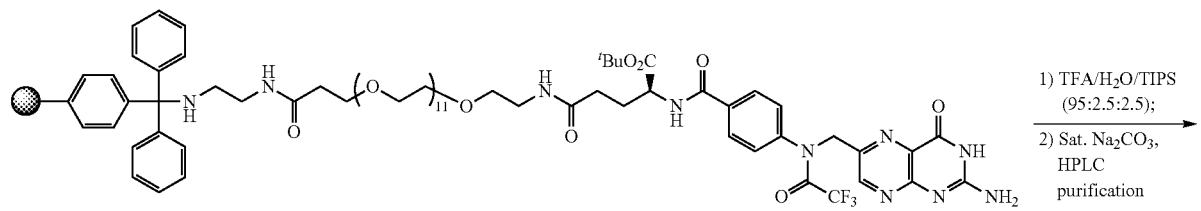

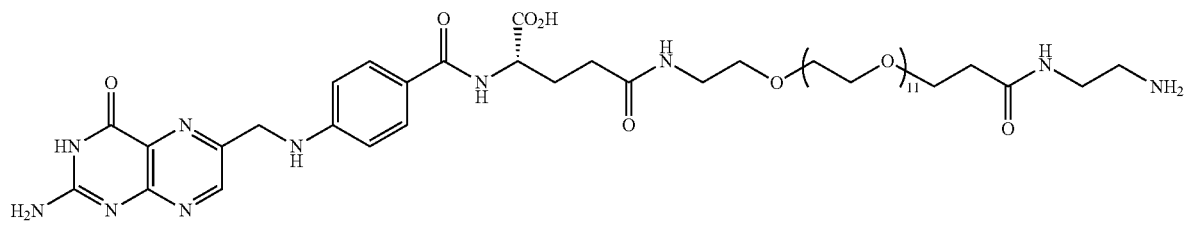

QC07041

EXAMPLE. Solid Phase Synthesis (SPS) of FA-PEG$_{12}$-EDA-NH$_2$ (QC07042)[11]. 1,2-Diaminoethane trityl resin (1.2 mmol/g, 50 mg, 0.06 mmol) was swollen with dichloromethane (DCM, 3 mL) followed by dimethyl formamide (DMF, 3 mL). After swelling the resin in DMF, a solution of fluorenylmethoxycarbonyl (Fmoc)-PEG$_{12}$-OH (1.5 equiv), HATU (1.5 equiv), and DIPEA (2.0 equiv) in DMF was added. Argon was bubbled for 2 h, and resin was washed with DMF (3×3 mL) and i-PrOH (3×3 mL). The above sequence was repeated for two more coupling steps for conjugation of Fmoc-Glu-(OtBu)-OH and N$^{10}$-TFA-Ptc-OH. The final product was cleaved from the resin using a trifluoroacetic acid (TFA):H$_2$O:triisopropylsilane cocktail (95:2.5:2.5) and concentrated under vacuum. The concentrated product was precipitated in diethyl ether and dried under vacuum, which was then incubated in Sat. Na$_2$CO$_3$ and monitored by LC-MS. 1 hour later, the mixture was neutralized to pH=7 with 2 M HCl (aq.) which was purified by preparative with preparative RP-C$_{18}$ HPLC [solvent gradient: 0% B to 50% B in 30 min; A=10 mM NH$_4$OAc, pH=7; B=CH$_3$CN]. Acetonitrile was removed under vacuum, and the residue was freeze-dried to yield pure QC07042 as a yellow solid (32.5 mg, 50%). Analytical RP-C$_{18}$ HPLC: t$_R$=4.76 min (A=10 mM NH$_4$OAc, pH=7.0; B=CH$_3$CN, solvent gradient: 0% B to 50% B in 15 min); Preparative RP-C$_{18}$ HPLC: t$_R$=13.75 min (A=10 mM NH$_4$OAc, pH=7.0; B=CH$_3$CN, solvent gradient: 0% B to 50% B in 30 min); UV-Vis: $\lambda_{max}$=280 nm; Preparative RP-C$_{18}$ HPLC: HPLC (Agilent Preparative C18 Column): Mobile phase: Buffer (pH 7)—CH$_3$CN; Method: 0-50 CH$_3$CN, 30 min, t$_R$=13.75 min. LC-MS: LC-MS (Agilent G6130B Quadrupole LC/MS) of Product Mobile phase: Buffer (pH 7)—CH$_3$CN; Method: 0-50 CH$_3$CN, 15 min, t$_R$=4.76 min. MS m/z: MS-API: Calcd. for C$_{48}$H$_{79}$N$_{10}$O$_{18}$ ([M+H]$^+$): 1083.6, Found: 1083.4;

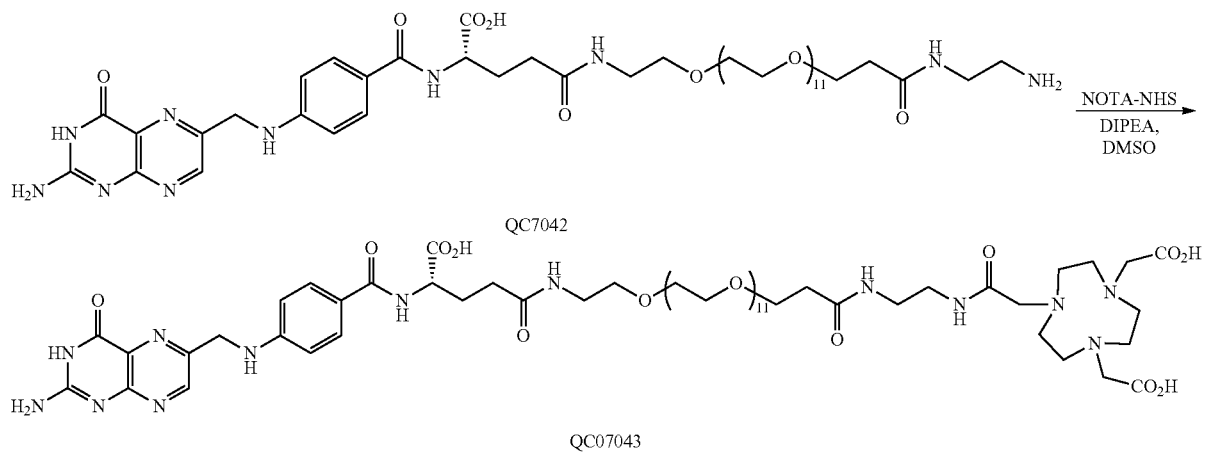

QC7042

QC07043

EXAMPLE. FA-PEG12-EDA-NH$_2$—NOTA (QC07043). To FA-PEG12-EDA-NH$_2$ (QC07042, 4.78 mg, 0.004 mmol, M.W.: 1082.5) in DMSO (0.25 ml, with a concentration at 0.025 M) was added NOTA-NHS (3.5 mg, 0.005 mmol, 1.2 eq.) followed by DIPEA (2.7 μL, 0.039 mmol). The whole mixture was stirred at 23° C. and monitored by LC-MS. 4 hours later, LC-MS showed that almost all of the starting material was transformed to the product. The crude material was then purified by preparative RP-HPLC to afford the pure FA-PEG12-EDA-NH$_2$—NOTA (QC07043, 4.09 mg, 68%). Analytical RP-C$_{18}$ HPLC: t$_R$=6.21 min (A=10 mM NH$_4$OAc, pH=7.0; B=CH$_3$CN, solvent gradient: 0% B to 30% B in 15 min); Preparative RP-C$_{18}$ HPLC: t$_R$=15.60 min (A=10 mM NH$_4$OAc, pH=7.0; B=CH$_3$CN, solvent gradient: 0% B to 30% B in 30 min); UV-Vis: λ$_{max}$=280 nm; LC-MS: LC-MS (Agilent G6130B Quadrupole LC/MS) of Product Mobile phase: Buffer (pH 7)—CH$_3$CN; Method: 0-8.00 (m, 1H), 7.55 (d, J=6.4 Hz, 1H), 7.54 (s, br, 2H), 6.81-6.93 (m, 1H), 6.62 (d, J=8.0 Hz, 2H), 4.45 (d, J=4.4 Hz, 2H), 3.95-4.03 (m, 1H), 3.64-3.70 (m, 2H), 3.56-3.63 (m, 6H), 3.38-3.50 (m, 28H), 3.33-3.36 (m, 6H), 3.20-3.24 (m, 4H), 3.09-3.18 (m, 10H), 3.04-3.09 (m, 4H), 2.50 (s, 12H, overlapping with the residue peak of DMSO), 2.27-2.34 (m, 2H), 2.02-2.12 (m, 2H), 1.99-2.01 (m, 2H).

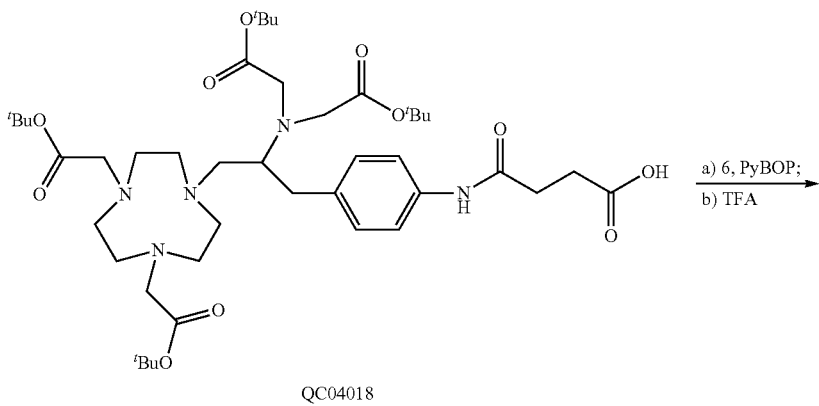

QC04018

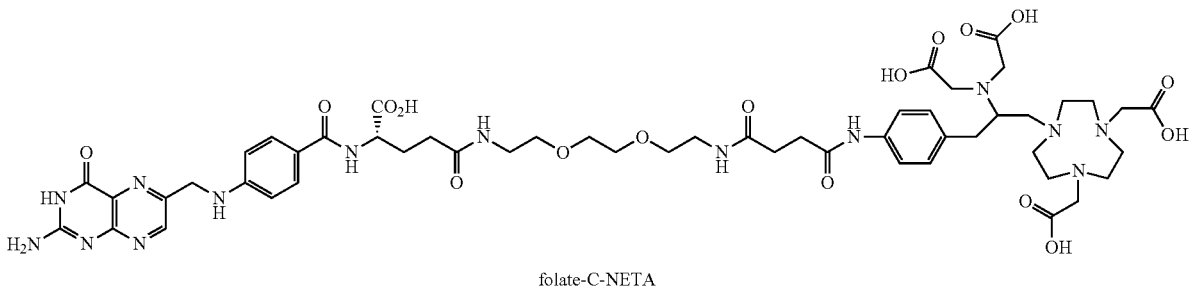

folate-C-NETA

EXAMPLE. C-NETA and folate-C-NETA. A PyBOP promoted coupling between QC04018 and compound 6, followed by deprotection of tert-butyl ester with TFA, provided folate-C-NETA. The folate-C-NETA is used to evaluate the labeling efficiency with Al[18]F and $^{68}$Ga and evaluate the in vivo PET imaging.

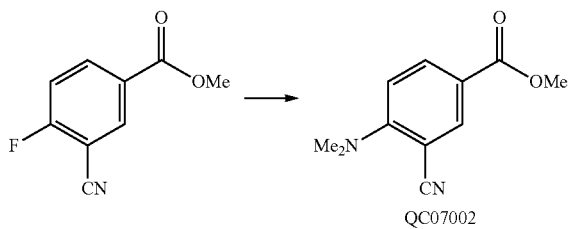 [SMILES: COC(=O)c1ccc(F)c(C#N)c1 ; COC(=O)c1ccc(N(C)C)c(C#N)c1]

EXAMPLE. Methyl 3-cyano-4-(dimethylamino)benzoate (QC07002)[1]. To a stirred solution of methyl 3-cyano-4-fluorobenzoate (5 g, 27.9 mmol) in DMSO (6 ml) was added dimethylamine hydrochloride (2.75 g, 33.7 mmol) followed by potassium carbonate (8.1 g, 58.6 mmol). The reaction mixture was stirred at room temperature overnight and concentrated. The residue was dissolved in dichloromethane (50 ml) and washed with water (2×25 ml), brine, dried over $Na_2SO_4$ and concentrated in vacuo to give the methyl 3-cyano-4-(dimethylamino)benzoate (QC07002) in quantitative yield and was used without further purification.

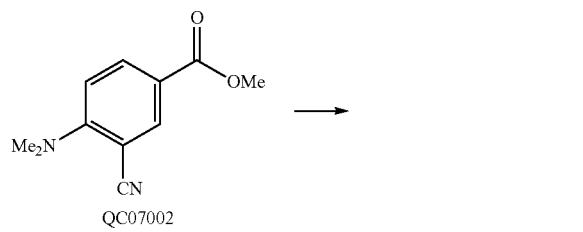

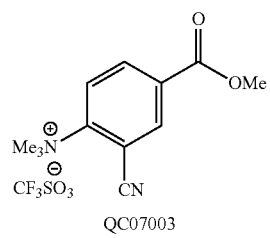

EXAMPLE. 2-Cyano-4-(methoxycarbonyl)-N,N,N-trimethylbenzenaminium trifluoromethanesulfonate (QC07003). To a stirred solution of methyl 3-cyano-4-(dimethylamino) benzoate (3.4 g, 16.7 mmol) in anhydrous dichloromethane (17 ml) was added methyl trifluoromethanesulfonate (10 g, 60.9 mmol, M.W. 164.1) dropwise. The reaction was stirred at RT for 16 h and another portion of methyl trifluoromethanesulfonate (10 g, 60.9 mmol, M.W.: 164.1) was added. The reaction was stirred for another 16 hours and tert-butylmethylether (20 ml) was added slowly. The suspension was filtered and the collected solid was washed with tert-butylmethylether. The crude product was purified by RP-$C_{18}$ HPLC: (acetonitrile/water-gradient 1:99 to 80:20) to afford product QC07003 (3.69 g) in 60% yield. Analytical RP-$C_{18}$ HPLC: $t_R$=0.49 min (A=10 mM $NH_4OAc$, pH=7.0; B=$CH_3CN$, solvent gradient: 0% B to 100% B in 15 min); $\lambda_{max}$=275 nm; LC-MS (Agilent G6130B Quadrupole LC/MS): Mobile phase: Buffer (pH 7)—$CH_3CN$; Column: Analytic $C_{18}$ column; Method: 0-100 $CH_3CN$-15 min, $t_R$=0.49 min. MS m/z: MS-API: Calcd. for $C_{12}H_{15}N_2O_2$ ([M]$^+$): 219.1, Found: 219.0; 1H NMR (400 MHz, $D_2O$) δ=8.67 (d, J=2.1 Hz, 1H), 8.44 (dd, J=9.1, 2.1 Hz, 1H), 8.15 (d, J=9.1 Hz, 1H), 3.93 (s, 3H), 3.87 (s, 9H) ppm.

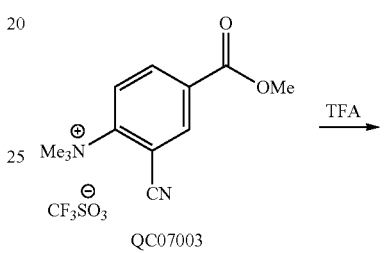

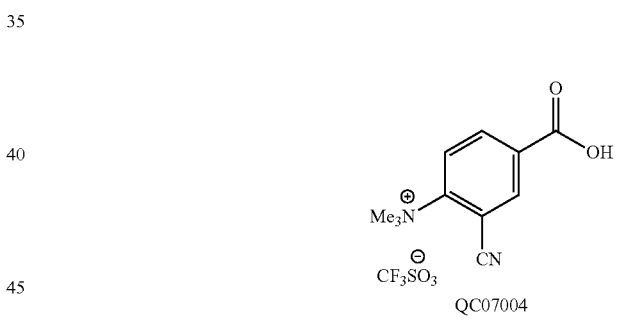

EXAMPLE. 4-Carboxy-2-cyano-N,N,N-trimethylbenzenaminium trifluoromethanesulfonate (QC07004). A solution of QC07003 (3.6 g, 9.8 mmol) in water (83 ml) and TFA (83 ml) was heated at 120° C. for 48 h. The reaction mixture was concentrated in vacuo, the light green oil was treated with diethylether to result a suspension. This solid was collected by filtration, washed with diethylether and dried in vacuo to give 4-carboxy-2-cyano-N,N,Ntrimethylbenzenaminium trifluoromethanesulfonate QC07004 (2.8 g, 82%). Analytical RP-$C_{18}$ HPLC: $t_R$=0.61 min (A=10 mM $NH_4OAc$, pH=7.0; B=$CH_3CN$, solvent gradient: 0% B to 100% B in 15 min); $\lambda_{max}$=240 nm. LC-MS (Agilent G6130B Quadrupole LC/MS): Mobile phase: Buffer (pH 7)—$CH_3CN$; Column: Analytic $C_{18}$ column; Method: 0-100 $CH_3CN$ 15 min, $t_R$=0.61 min. MS m/z: MS-API: Calcd. for $C_{11}H_{13}N_2O_2$ ([M]$^+$): 205.1, Found: 205.1; 1H NMR (400 MHz, DMSO) δ=8.58 (d, J=2.07 Hz, 1H), 8.39-8.49 (m, 1H), 8.23-8.35 (m, 1H), 3.85 (s, 9H).

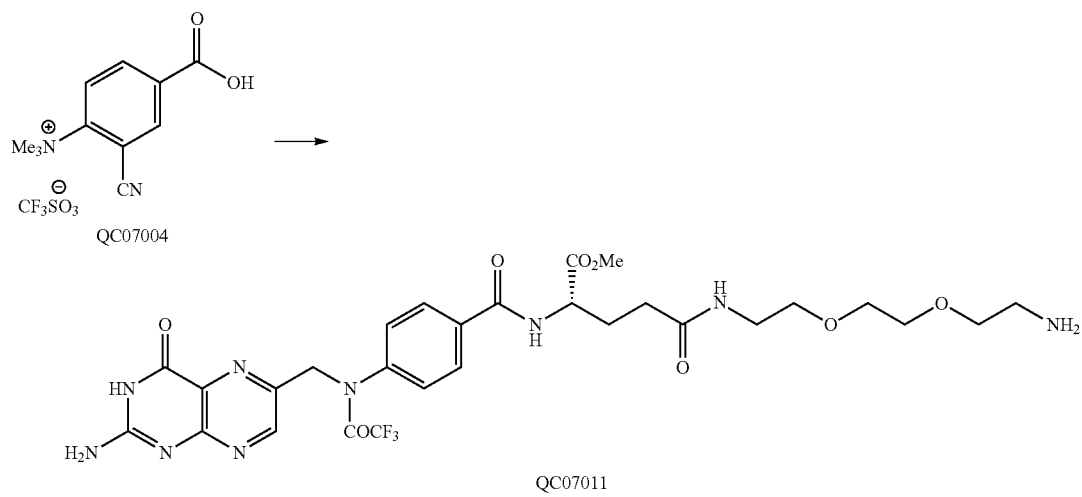

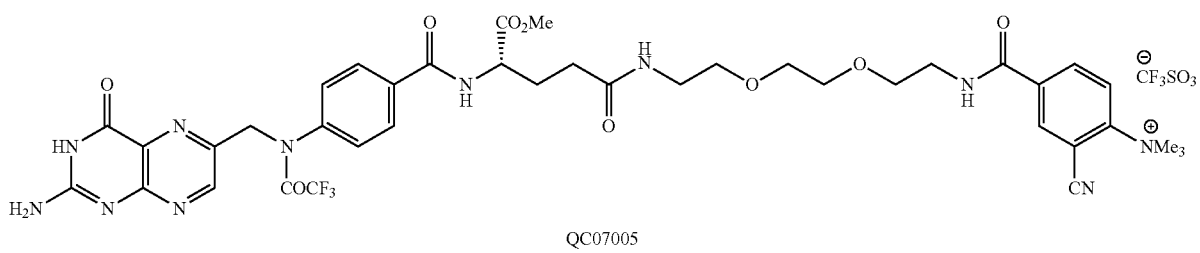

EXAMPLE. FA-PEG$_1$-TMA Precursor (QC07005). QC07004 (62 mg, 0.17 mmol) was added to the solution of QC07011 (0.14 mmol) and DIPEA (87 μL, 1.75 mmol) in DMSO (2.0 mL) at 23° C. under N$_2$. After being stirred for 15 min at 23° C., PyBOP (91 mg, 0.17 mmol) was added, and the reaction mixture was stirred for 24 h at 23° C. Volatile material was removed under reduced vacuum to afford the crude product which was further purified by RP-HPLC (C$_{18}$) to afford the pure compound QC07005 as pale yellow colored solid (125.1 mg, 72%). Analytical RP-C$_{18}$ HPLC: t$_R$=4.17 min (A=10 mM NH$_4$OAc, pH=7.0; B=CH$_3$CN, solvent gradient: 0% B to 100% B in 15 min); λ$_{max}$=280 nm; LC-MS (Agilent G6130B Quadrupole LC/MS): Mobile phase: Buffer (pH 7)—CH$_3$CN; Column: Analytic C$_{18}$ column; Method: 0-100 CH$_3$CN-15 min, t$_R$=4.17 min. MS m/z: MS-API: Calcd. for C$_{28}$H$_{35}$F$_3$N$_9$O$_8$ ([M]$^+$): 868.3, Found: 868.2.

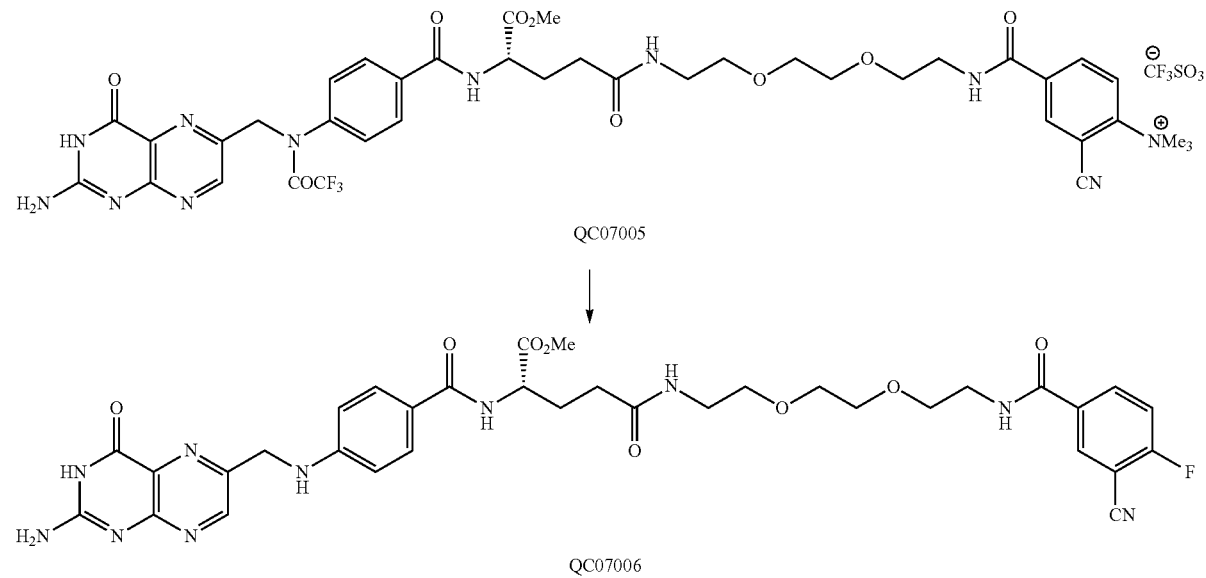

EXAMPLE. General procedure for the one-pot $^{19}$F-introduction and deprotection. 8.3 µL of freshly prepared KF-Kryptofix (1/1.5) (0.0012 mmol, 0.144 M) solution was azeotropically dried with $CH_3CN$ at 90-100° C., to which 1.2 mg (0.0012 mmol, 1.0 equiv.) QC07005 in 50 ul of anhydrous DMSO was added with a concentration of precursor at 0.024 M. The resulting mixture was immediately immersed into an oil bath preheated to 70-75° C. and kept at 70-75° C. for 10 min. After being cooled down to room temperature, 200 ul of 1M NaOH (aq.) was added with a concentration of NaOH (aq.) at 0.8 M. The reaction was monitored by LC-MS and found complete after 5 min, which was neutralized with 1 M HCl (aq.) and analyzed by LC-MS (QC07006). And the total labeling efficiency was about 30% based on the analysis of LC-MS. Analytical RP-$C_{18}$ HPLC: A=10 mM $NH_4OAc$, pH=7.0; B=$CH_3CN$, solvent gradient: 0% B to 100% B in 15 min; $\lambda_{max}$=280 nm; LC-MS: Method: 0-100 $CH_3CN$-15 min, $t_R$=5.13 min. MS m/z: MS-API: Calcd. for $C_{36}H_{37}F_4N_{10}O_9$ ([M+H]$^+$): 829.3, Found: 829.1.

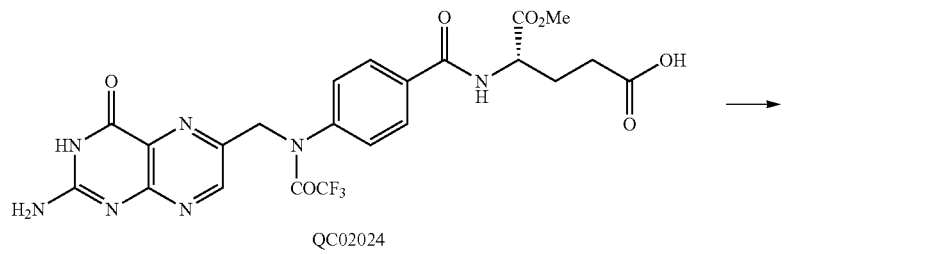

QC02024

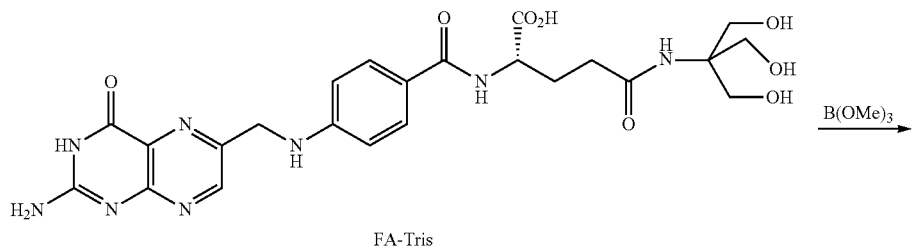

FA-Tris

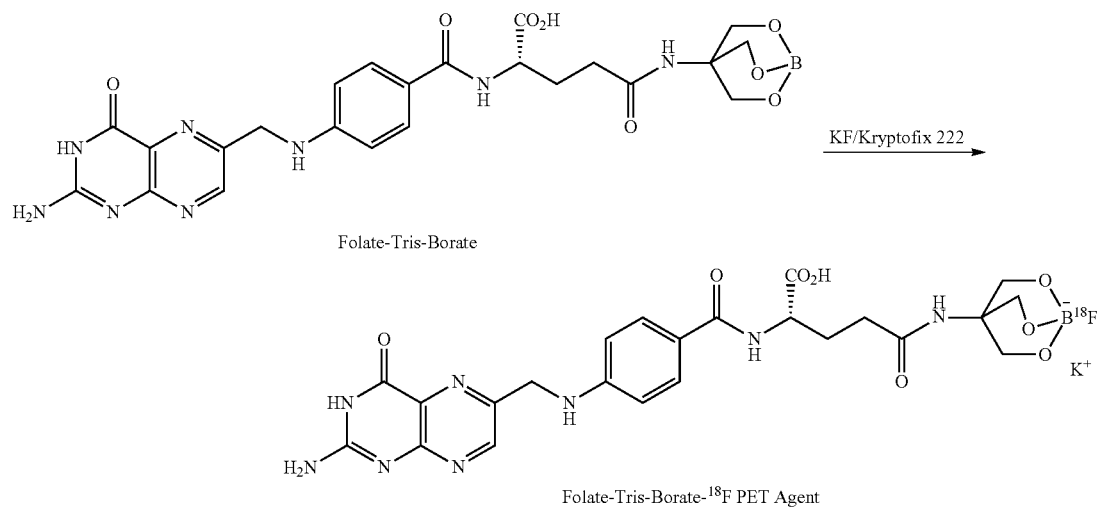

Folate-Tris-Borate

Folate-Tris-Borate-$^{18}$F PET Agent

Example. Folate-[18]F-Boronate PET Imaging Agent

PSMA Targeted Examples

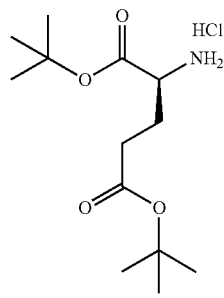

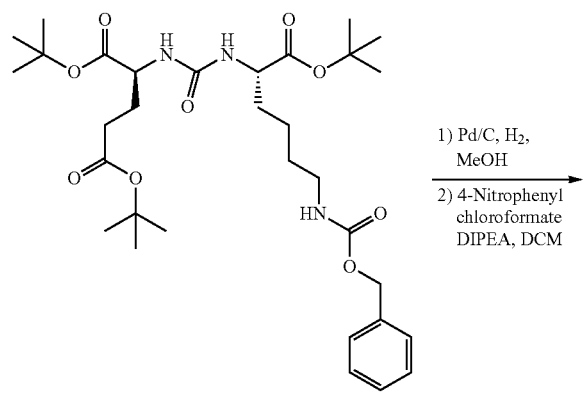

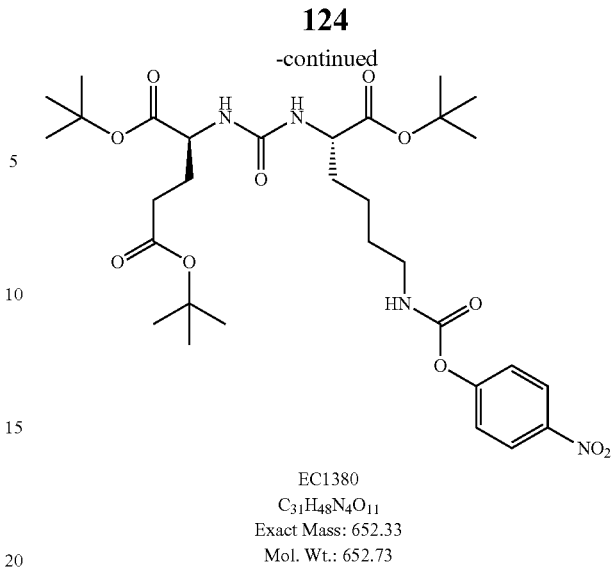

EC1380
$C_{31}H_{48}N_4O_{11}$
Exact Mass: 652.33
Mol. Wt.: 652.73

EXAMPLE. EC1380, 10. In a dry flask, H-Glu(O$^t$Bu)-O$^t$Bu·HCl (2.48 g, 8.41 mmol) and 4-nitrophenyl chloroformate (1.86 g, 9.25 mmol, 1.1 eq) were added, dissolved in CH$_2$Cl$_2$ (30 ml) under Argon atmosphere. The stirring solution was chilled to 0° C., followed by the dropwise addition of DIPEA (4.50 ml, 25.2 mmol, 3 eq). The reaction mixture was allowed to warm to room temperature and stirred for 1 hr. To the stirring solution was added H-Lys-(Z)—O$^t$Bu (4.39 g, 11.8 mmol, 1.4 eq), DIPEA (4.50 ml, 25.2 mmol, 3 eq) and stirred for 1 hr. Upon completion, the reaction was quenched with saturated NaHCO$_3$ and extracted with CH$_2$Cl$_2$ three times. The organic extracts were combined, dried over Na$_2$SO$_4$, filtered and the solvent was removed via reduced pressure. The product was purified using silica gel chromatography with petroleum ether and ethyl acetate. The Cbz protected amine was transferred to a round bottom flask with 10% Pd/C (10% wt eq), dissolved in MeOH (30 ml) under Hydrogen atmosphere (1 atm) and stirred for 3 hr. Upon completion, the reaction mixture was filtered through celite and the solvent was removed via reduced pressure to yield the crude amine. The amine was taken up in CH$_2$Cl$_2$ (30 ml) under Argon atmosphere and chilled to 0° C. To the chilled solution was added 4-nitrophenyl chloroformate (2.2 g, 10.9 mmol, 1.3 eq) and DIPEA (6.0 ml, 33.6 mmol, 4 eq) subsequently and stirred for 2 hr at room temperature. The reaction mixture was quenched with saturated NH$_4$Cl and extract three times with ethyl acetate. The organic extracts were combined, dried over Na$_2$SO$_4$, filtered, and solvent was removed under vacuum and purified using silica gel chromatography to yield the desired activated amine, EC1380 (2.54 g, 46%).

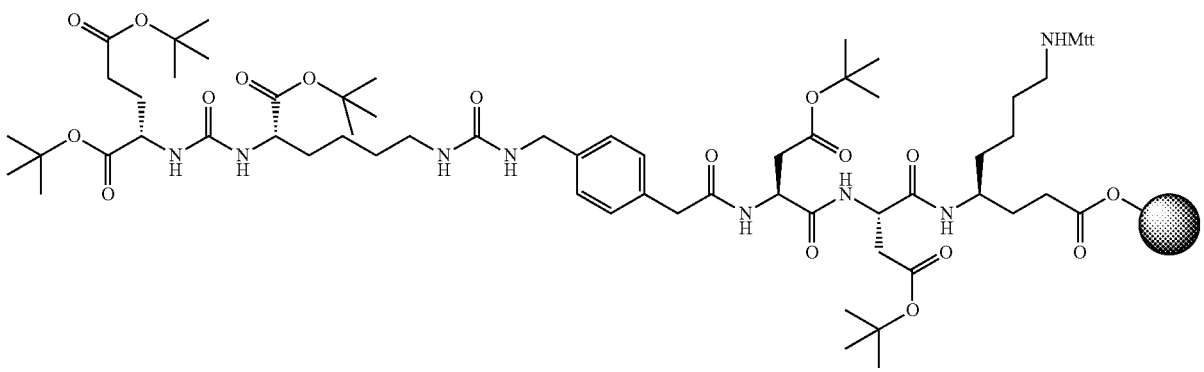

EXAMPLE. Glu(O^tBu)-O^tBu-Lys-O^tBu-AMPAA-Asp(O^tBu)-Asp(O^tBu)-Lys(Mtt)-resin 11. The general procedure described for the synthesis of resin bound folate-peptide resin 1 was followed for the coupling of 2×Fmoc-L-Asp(O^tBu)-OH, Fmoc-AMPAA-OH, Fmoc-L-Lys(Z)—O^tBu, and Fmoc-(L)-Glu(O^tBu) to Fmoc-L-Lys(Mtt)-Wang resin. The resin bound penta-peptide was subjected to standard Fmoc deprotection, washings and Kaiser test. Following another DMF wash (3×10 ml); an EC1380 solution (2.0 eq.) in DMF, and DIPEA (3.0 eq.) were added to the vessel and the solution bubbled with Argon for 2 hour. The coupling solution was filtered, the resin was washed with DMF (3×10 ml) and i-PrOH (3×10 ml) and a Kaiser test was done to assess reaction completion.

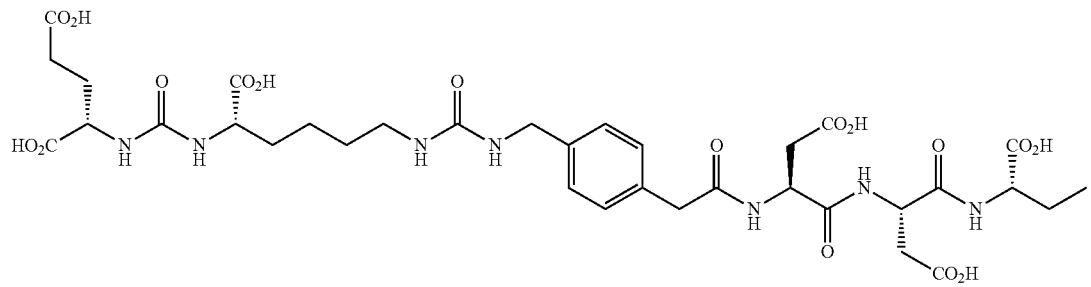

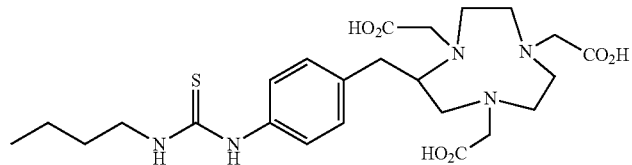

EC2209

$C_{56}H_{78}N_{12}O_{23}S$
Exact Mass: 1318.50
Mol. Wt.: 1319.35

EXAMPLE. Glu-Lys-AMPAA-Asp-Asp-Lys-Bn-NOTA 12. Glu-Lys-AMPAA-Asp-Asp-Lys-Bn-NOTA, EC2209 was prepared in 47% yield according to the process described for folate-peptide-NOTA, 4. $^1$H NMR (500 MHz DMSO-d$_6$) Pivotal signals: δ 7.25-7.18 (m, 2H), 7.14 (d, J=8.1 Hz, 1H), 7.12-7.06 (m, 5H), 4.47 (ddd, J=17.8, 7.5, 5.6 Hz, 2H), 4.11-4.08 (m, 3H), 4.08-4.02 (m, 2H), 3.98 (dd, J=8.2, 5.1 Hz, 1H). [M+H]$^+$=Calculated 1319.50, found 1319.70

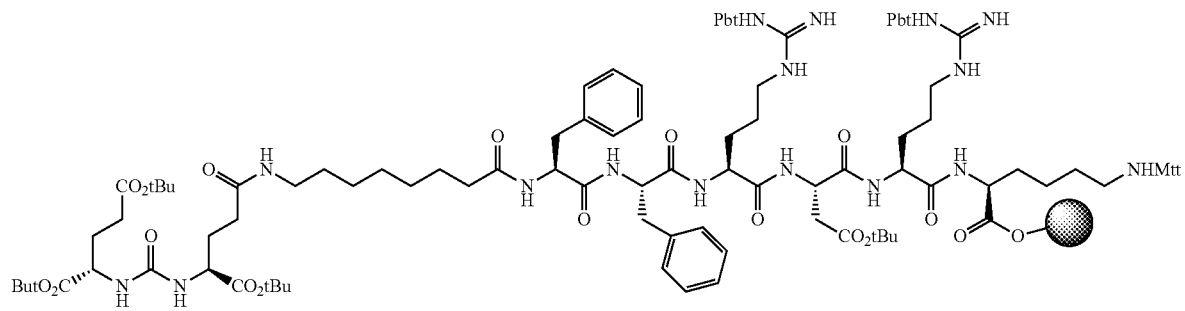

EXAMPLE. Glu(O$^t$Bu)-O$^t$Bu-Lys-O$^t$Bu-Aoc-Phe-Phe-Arg(Pbf)-Asp(O$^t$Bu)-Arg(Pbf)-Lys(Mtt)-resin 13. The general procedure described for the synthesis of resin bound folate-peptide resin 1 was followed for the coupling of Fmoc-L-Arg(Pbf)-OH, Fmoc-L-Asp(O$^t$Bu)-OH, Fmoc-L-Arg(Pbf)-OH, 2×Fmoc-Phe-OH, Fmoc-Aoc-OH, Fmoc-L-Lys(Z)—O$^t$Bu, Fmoc-(L)-Glu(O$^t$Bu) and EC1380 to Fmoc-L-Lys(Mtt)-Wan resin.

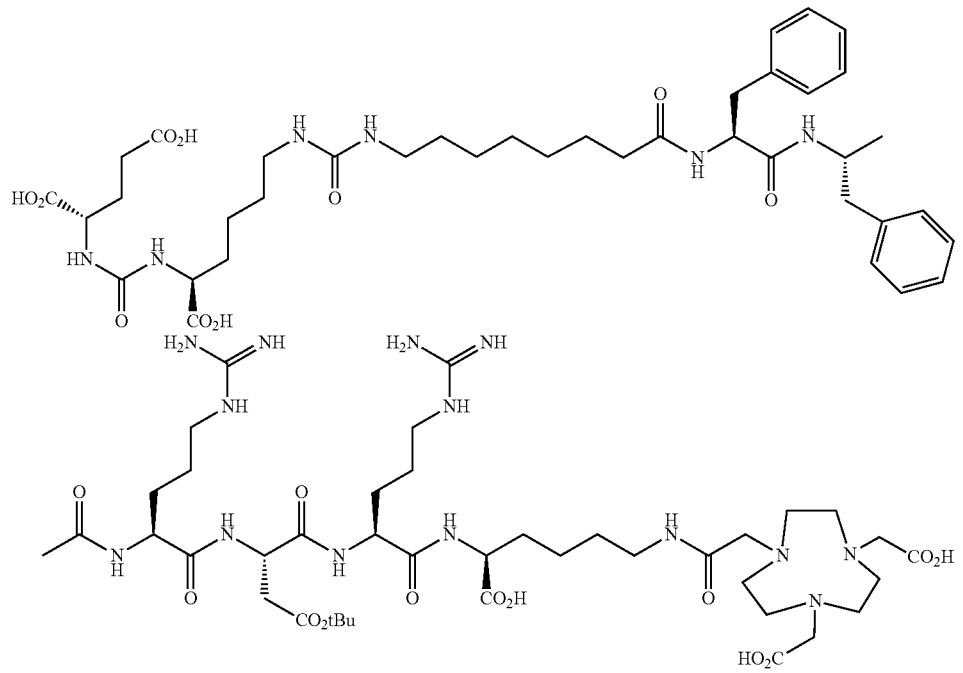

EC2390

C$_{73}$H$_{114}$N$_{20}$O$_{23}$
Exact Mass: 1638.84
Mol. Wt.: 1639.81

EXAMPLE. Glu-Lys-Aoc-Phe-Phe-Arg-Asp-Arg-Lys-NOTA 14. Glu-Lys-Aoc-Phe-Phe-Arg-Asp-Arg-Lys-NOTA, EC2390 was prepared in 37% yield according to the process described for folate-peptide-NOTA, 4. $^1$H NMR (500 MHz DMSO-d$_6$) Pivotal signals: δ 7.25-7.14 (m, 6H), 7.16-7.08 (m, 3H), 4.47 (dd, J=9.0, 4.7 Hz, 1H), 4.42 (t, J=5.9 Hz, 1H), 4.36 (dd, J=10.4, 4.4 Hz, 1H), 4.27 (t, J=6.9 Hz, 1H), 4.16 (t, J=5.6 Hz, 1H), 3.97-3.88 (m, 2H). [M+H]$^+$=Calculated 1639.84, found 1640.22

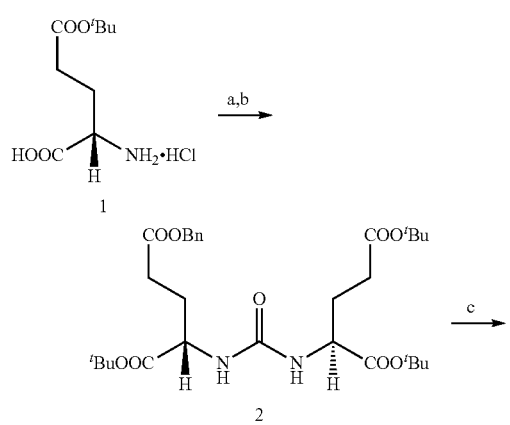

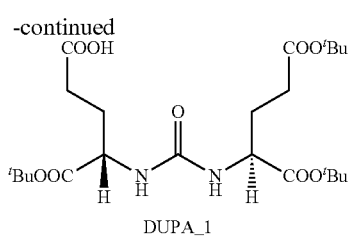

DUPA_1

Reagents and conditions:
(a) triphosgene, TEA/DCM, -78° C.; (b) H—L-Glu(OBn)-OtBu•HCl; (c) H$_2$; Pd—C/DCM.

EXAMPLE. DUPA-EAOA-Phe-Arg-Lys-NH$_2$. 2-[3-(3-Benzyloxycarbonyl-1-tert-butoxycarbonyl-propyl)-ureido]pentanedioic acid di-tert-butyl ester (2). [1, 2] To a solution of L-glutamate di-tert-butyl ester hydrochloride 1 (1.0 g, 3.39 mmol) and triphosgene (329.8 mg, 1.12 mmol) in DCM (25.0 mL) at -78° C., triethylamine (TEA, 1.0 mL, 8.19 mmol) was added. After stirring for 2 h at -78° C. under argon, a solution of L-Glu(OBn)-OtBu (1.2 g, 3.72 mmol) and TEA (600 μL, 4.91 mmol) in DCM (5.0 mL) was added. The reaction mixture was allowed to come to room temperature (rt) over a period of 1 h and stirred at ambient temperature overnight. The reaction was quenched with 1 M HCl, and the organic layer was washed with brine and dried over Na$_2$SO$_4$. The crude product was purified using flash chromatography (hexane:EtOAc) 1:1) to yield the intermediate 2 (1.76 g, 90.2%) as a colorless oil and crystallized using hexane:DCM. Rf) 0.67 (hexane:EtOAc) 1:1). $^1$H NMR (CDCl$_3$): δ 1.43 (s, 9H, CH3-tBu); 1.44 (s, 9H, CH3-tBu); 1.46 (s, 9H, CH3-tBu); 1.85 (m, 1H, Glu-H); 1.87 (m, 1H, Glu-H); 2.06 (m, 1H, Glu-H); 2.07 (m, 1H, Glu-H); 2.30 (m, 2H, Glu-H); 2.44 (m, 2H, Glu-H); 4.34 [s (broad), 1H, RH]; 4.38 [s (broad), 1H, R—H]; 5.10 (s, 2H, CH2-Ar); 5.22 [s (broad), 2H, Urea-H]; 7.34 (m, 5H, Ar—H). EI-HRMS (m/z): (M+H)+ calcd for C$_{30}$H$_{47}$N$_2$O$_9$, 579.3282; found, 579.3289.

EXAMPLE. 2-[3-(1,3-Bis-tert-butoxycarbonyl-propyl)-ureido]pentanedioic Acid 1-tert-Butyl Ester, DUPA_1. To a solution of 2 (250 mg, 432 mmol) in DCM, 10% Pd/C was added. The reaction mixture was hydrogenated at 1 atm for 24 h at rt. Pd/C was filtered through a Celite pad and washed with DCM. The crude product was purified using flash chromatography (hexane:EtOAc) 40:60) to yield DUPA_1 (169 mg, 80.2%) as a colorless oil, and crystallized using hexane:DCM. R$_f$=0.58 (hexane:EtOAc=40:60). $^1$H NMR (CDCl$_3$): δ 1.46 (m, 27H, CH3-tBu); 1.91 (m, 2H, Glu-H); 2.07 (m, 1H, Glu-H); 2.18 (m, 1H, Glu-H); 2.33 (m, 2H, Glu-H); 2.46 (m, 2H, Glu-H); 4.31 (s (broad), 1H, RH); 4.35 (s (broad), 1H, R—H); 5.05 (t, 2H, Urea-H); EI-HRMS (m/z): (M+H)$^+$ calcd for C$_{23}$H$_{41}$N$_2$O$_9$, 489.2812; found, 489.2808.

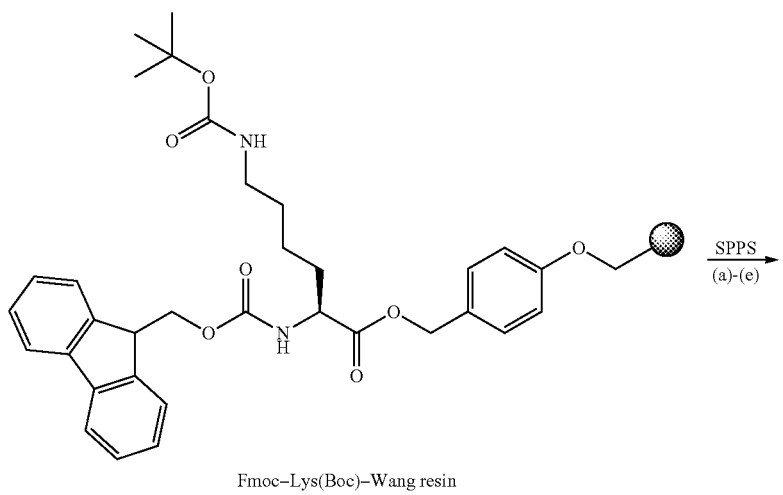

Fmoc–Lys(Boc)–Wang resin

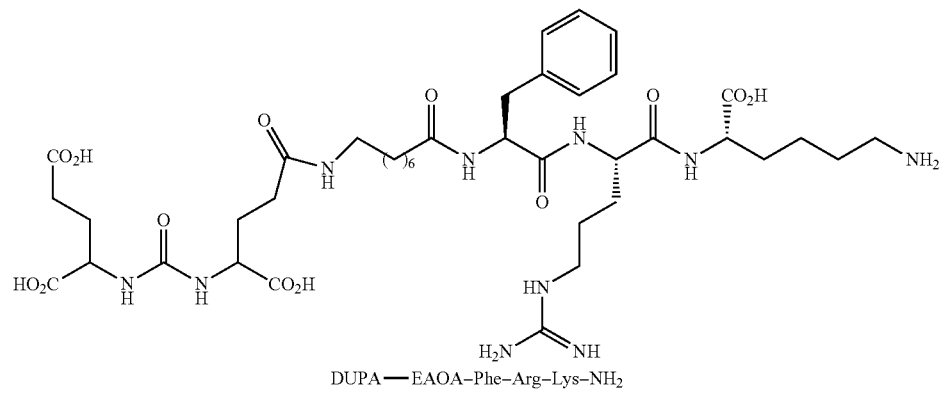

DUPA—EAOA–Phe–Arg–Lys–NH$_2$

Reagents and conditions: (a) (i) 20% piperidine/DMF, room temperature, 10 min; (ii) Fmoc-Arg(Boc)2-OH, HBTU, HOBt, DMF-DIPEA, 2 h. (b) (i) 20% piperidine/DMF, room temperature, 10 min; (ii) Fmoc-Phe-OH, HBTU, HOBt, DMF-DIPEA, 2 h. (c) (i) 20% piperidine/DMF, room temperature, 10 min; (ii) Fmoc-8-amino-octanoic(EAO)acid, HBTU, HOBt, DMF/DIPEA, 2 h. (d) (i) 20% piperidine/DMF, room temperature, 10 min; (ii) (tBuO)3-DUPA-OH, HBTU, HOBt, DIPEA, 2 h. (e) TFA/H2O/TIPS (95:2.5:2.5), 1 h EXAMPLE. DUPA-EAOA-Phe-Arg-Lys-NH$_2$. Fmoc-Lys(Boc)-Wang resin (0.43 mM) was swollen with DCM (3 mL) followed by dimethyl formamide (DMF, 3 mL). A solution of 20% piperidine in DMF (3×3 mL) was added to the resin, and argon was bubbled for 5 min. The resin was washed with DMF (3×3 mL) and isopropyl alcohol (i-PrOH, 3×3 mL). Formation of free amine was assessed by the Kaiser test. After swelling the resin in DMF, a solution of Fmoc-Arg(Boc)$_2$-OH (2.5 equiv), HBTU (2.5 equiv), HOBt (2.5 equiv), and DIPEA (4.0 equiv) in DMF was added. Argon was bubbled for 2 h, and resin was washed with DMF (3×3 mL) and i-PrOH (3×3 mL). The coupling efficiency was assessed by the Kaiser Test. The above sequence was repeated for 3 more coupling steps to introduce the phenylanaline (Phe), 8-amino-octanoic acid (EAO), and DUPA successively. Final compound was cleaved from the resin using a trifluoroacetic acid (TFA):H$_2$O:triisopropylsilane cocktail (95:2.5:2.5) and concentrated under vacuum. The concentrated product was precipitated in cold diethyl ether and dried under vacuum. The crude product was purified using preparative RP-HPLC [(A) 210 nm; solvent gradient: 0% B to 50% B in 30 min run; mobile phase: A) 0.1% TFA, pH=2; B) acetonitrile (ACN)]. ACN was removed under vacuum, and pure fractions were freeze-dried to yield DUPA-EAOA-Phe-Arg-Lys-NH$_2$ as a white solid. UV/vis: $\lambda_{max}$=205 nm. Analytical RP-HPLC: $t_R$=6.2 min (A=0.1% TFA; B=CH$_3$CN, solvent gradient: 0% B to 50% B in 15 min); ESI-MS (m/z): (M+H)$^+$ calcd for C$_{40}$H$_{64}$N$_{10}$O$_{13}$, 893.5; found, 893.4.

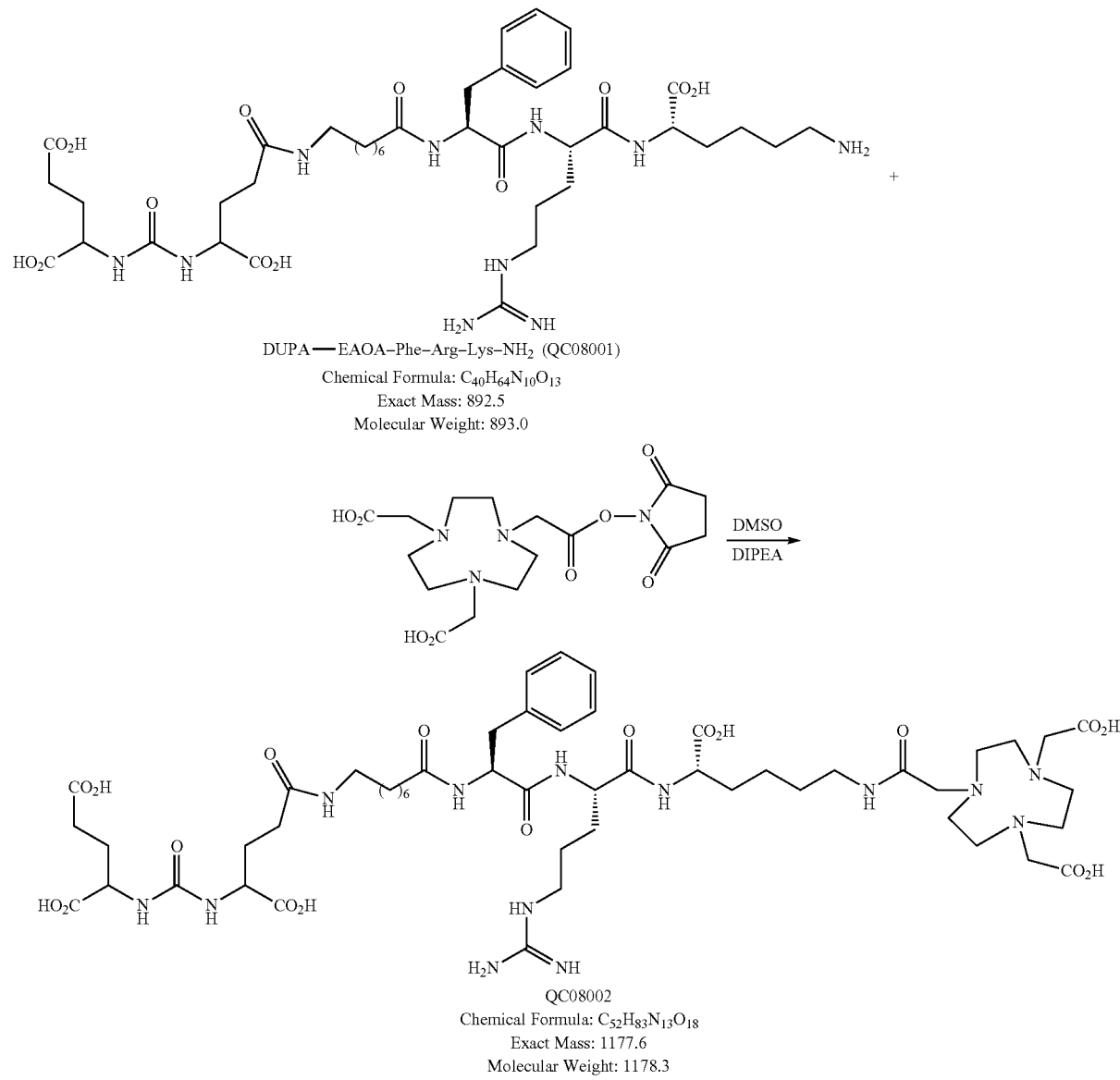

DUPA—EAOA–Phe–Arg–Lys–NH$_2$ (QC08001)
Chemical Formula: C$_{40}$H$_{64}$N$_{10}$O$_{13}$
Exact Mass: 892.5
Molecular Weight: 893.0

QC08002
Chemical Formula: C$_{52}$H$_{83}$N$_{13}$O$_{18}$
Exact Mass: 1177.6
Molecular Weight: 1178.3

EXAMPLE. DUPA-EAOA-Phe-Arg-Lys-NH$_2$-NOTA. To DUPA-EAOA-Phe-Arg-Lys-NH$_2$ (QC08001, 5.0 mg, 0.0056 mmol, M.W.: 893.0) in DMSO (0.20 ml, with a concentration at 0.028 M) was added NOTA-NHS (5.5 mg, 0.0084 mmol, 1.5 eq.) followed by DIPEA (2.9 μL, 0.017 mmol). The reaction was stirred at 23° C., monitored by LC-MS, and most of the starting material was transformed to the corresponding product in 5 hours. The crude material was purified by RP-C$_{18}$ HPLC. ACN was removed under vacuum, and pure fractions were freeze-dried to yield the pure DUPA-EAOA-Phe-Arg-Lys-NH$_2$-NOTA (QC08002, 3.3 mg, 50%). Analytical RP-C$_{18}$ HPLC: $t_R$=5.98 min (A=0.1% TFA; B=CH$_3$CN, solvent gradient: 0% B to 50% B in 15 min); Preparative RP-C$_{18}$ HPLC: $t_R$=16.16 min (A=0.1% TFA; B=CH$_3$CN, solvent gradient: 0% B to 50% B in 30 min); UV-Vis: $\lambda_{max}$=201 nm; HPLC (Agilent Preparative C18 Column): Mobile phase: A=0.1% TFA; B=CH$_3$CN; Method: 0-50 CH$_3$CN-30 min, $t_R$=16.16 min LC-MS (Agilent G6130B Quadrupole LC/MS): Mobile phase: A=0.1% TFA; B=CH$_3$CN; Method: 0-50 CH$_3$CN-30 min, $t_R$=5.98 min; MS m/z: MS-API: Calcd. for C$_{52}$H$_{84}$N$_{13}$O$_{18}$ ([M+H]$^+$): 1178.6, Found: 1178.4.

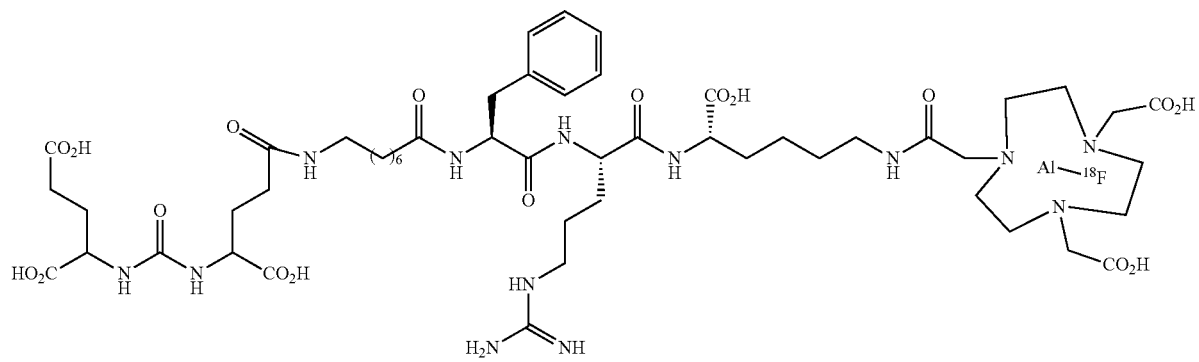

EXAMPLE. DUPA-EAOA-Phe-Arg-Lys-NH$_2$-NOTA-Al$^{18}$F. Method a): DUPA-EAOA-Phe-Arg-Lys-NH2-NOTA is dissolved in 2 mM NaOAc (pH 4.5) and 0.5 mL of ethanol, and treated with Al$^{18}$F$_3$·3H$_2$O (1.5 eq.) which is freshly prepared before application. The pH is adjusted to 4.5-5.0, and the reaction mixture is refluxed for 15-30 min with pH kept at 4.5-5.0. After cooling to room temperature, the crude material is loaded to a cartridge, and the radiotracer eluted into vial. After sterile filtration and being diluted to appropriate radioactivity (5-10 mCi) and specific activity (>1 Ci/μmol), the radiotracer is used in in vivo PET imaging.

Method b). DUPA-EAOA-Phe-Arg-Lys-NH$_2$—NOTA is dissolved in 2 mM NaOAc (pH 4.5), and treated with AlCl$_3$·3H$_2$O (1.5 eq.). The pH is adjusted to 4.5-5.0, and the reaction mixture is refluxed for 15-30 min with the pH kept at 4.5-5.0. The crude material is purified by RP-HPLC to afford the DUPA-EAOA-Phe-Arg-Lys-NH$_2$—NOTA-Al—OH intermediate ready for $^{18}$F-labeling. Appropriate amount of DUPA-EAOA-Phe-Arg-Lys-NH$_2$—NOTA-Al—OH is treated with Na$^{18}$F saline solution and ethanol (1/1, v/v), and the whole mixture is heated at 100-110° C. for 15 min. After cooling to room temperature, the crude material is loaded to a cartridge, and the radiotracer eluted into vial. After sterile filtration and being diluted to appropriate radioactivity (5-10 mCi) and specific activity (>1 Ci/μmol), the radiotracer is ready for use in in vivo PET imaging.

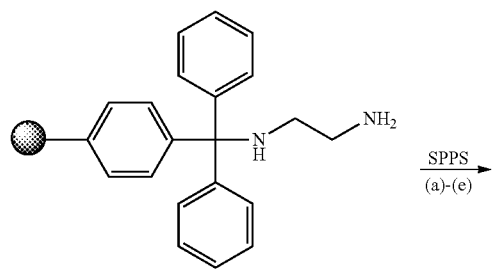

Trt-EDA Resin

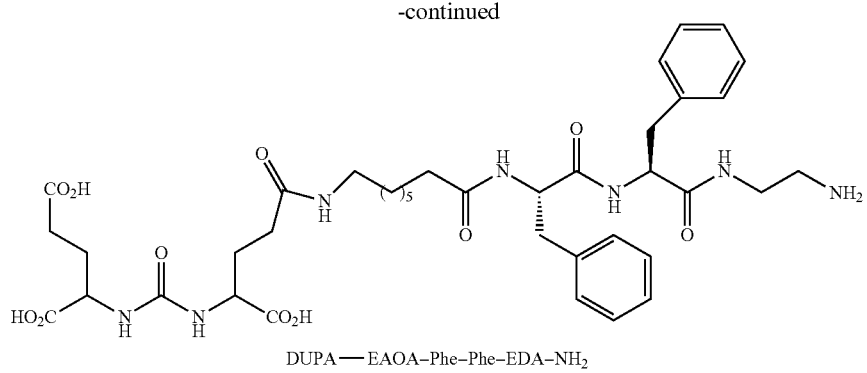

DUPA—EAOA-Phe-Phe-EDA-NH$_2$

Reagents and conditions: (a) Fmoc-Phe-OH, HBTU, HOBt, DMF/DIPEA, 2 h. (b) (i) 20% piperidine/DMF, room temperature, 10 min; (ii) Fmoc-Phe-OH, HBTU, HOBt, DMF/DIPEA, 2 h. (c) (i) 20% piperidine/DMF, room temperature, 10 min; (ii) Fmoc-8-amino-octanoic (EAO) acid, HBTU, HOBt, DMF/DIPEA, 2 h. (d) (i) 20% piperidine/DMF, room temperature, 10 min; (ii) (tBuO)3-DUPA-OH, HBTU, HOBt, DIPEA, 2 h. (e) TFA/H$_2$O/TIPS (95:2.5:2.5), 1 h.

EXAMPLE. Solid Phase Peptide Synthesis (SPPS) of DUPA-EAOA-Phe-Phe-EDA-NH$_2$.[2, 3]. As described herein for DUPA-EAOA-Phe-Arg-Lys-NH$_2$(QC08001), DUPA-EAOA-Phe-Phe-EDA-NH$_2$ is prepared. The commercially available Trt-EDA resin was swollen with DCM (3 mL) followed by dimethyl formamide (DMF, 3 mL), to which a solution of Fmoc-Phe-OH (2.5 equiv), HBTU (2.5 equiv), HOBt (2.5 equiv), and DIPEA (4.0 equiv) in DMF was added. Argon was bubbled for 2 h, and resin was washed with DMF (3×3 mL) and i-PrOH (3×3 mL). The coupling efficiency was assessed by the Kaiser Test. A solution of 20% piperidine in DMF (3×3 mL) was added to the resin, and argon was bubbled for 5 min. The resin was washed with DMF (3×3 mL) and isopropyl alcohol (i-PrOH, 3×3 mL). Formation of free amine was assessed by the Kaiser test. The above sequence was repeated for 3 more coupling steps to introduce the second phenylanaline (Phe), 8-amino-octanoic acid (EAO), and DUPA successively. Final compound was cleaved from the resin using a trifluoroacetic acid (TFA): H$_2$O:triisopropylsilane cocktail (95:2.5:2.5) and concentrated under vacuum. The concentrated product was precipitated in cold diethyl ether and dried under vacuum. The crude product was purified using preparative RP-HPLC [λ] 210 nm; solvent gradient: 0% B to 100% B in 30 min run; mobile phase: A) 10 mM NH$_4$OAc (pH=7, buffer); B) acetonitrile (ACN)]. ACN was removed under vacuum, and pure fractions were freeze-dried to yield DUPA-EAOA-Phe-Phe-EDA-NH$_2$ as a white solid. Analytical RP-C$_{18}$ HPLC: t$_R$=3.99 min (A=10 mM NH$_4$OAc, pH=7.0; B=CH$_3$CN, solvent gradient: 0% B to 100% B in 15 min); Preparative RP-C$_{18}$ HPLC: t$_R$=16.05 min (A=10 mM NH$_4$OAc, pH=7.0; B=CH$_3$CN, solvent gradient: 0% B to 100% B in 30 min); UV-Vis: λ$_{max}$=209 nm; LC-MS: LC-MS (Agilent G6130B Quadrupole LC/MS) of Product Mobile phase: Buffer (pH 7)—CH$_3$CN; Method: 0-100 ACN-15 min, t$_R$=3.99 min. MS m/z: MS-API: Calcd. for C$_{39}$H$_{56}$N$_7$O$_{11}$ ([M+H]$^+$): 798.4, Found: 798.3; Calcd. for C$_{39}$H$_{55}$N$_7$O$_{11}$K ([M+K]$^+$): 836.4, Found: 836.3. HPLC (Agilent Preparative C18 Column): Mobile phase: Buffer (pH 7)—CH$_3$CN; Method: 0-100 ACN-30 min, t$_R$=16.05 min.

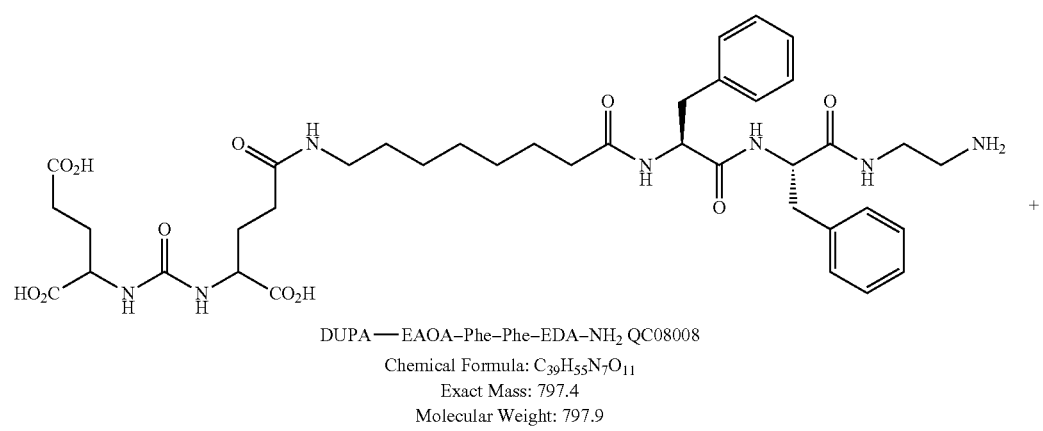

DUPA—EAOA-Phe-Phe-EDA-NH$_2$ QC08008

Chemical Formula: C$_{39}$H$_{55}$N$_7$O$_{11}$
Exact Mass: 797.4
Molecular Weight: 797.9

-continued

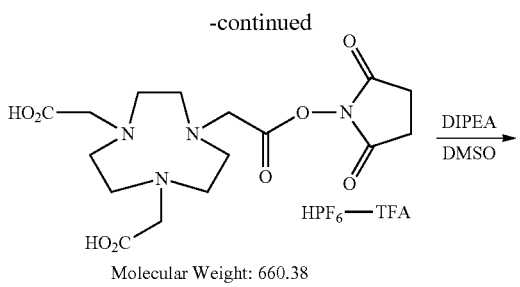

Molecular Weight: 660.38

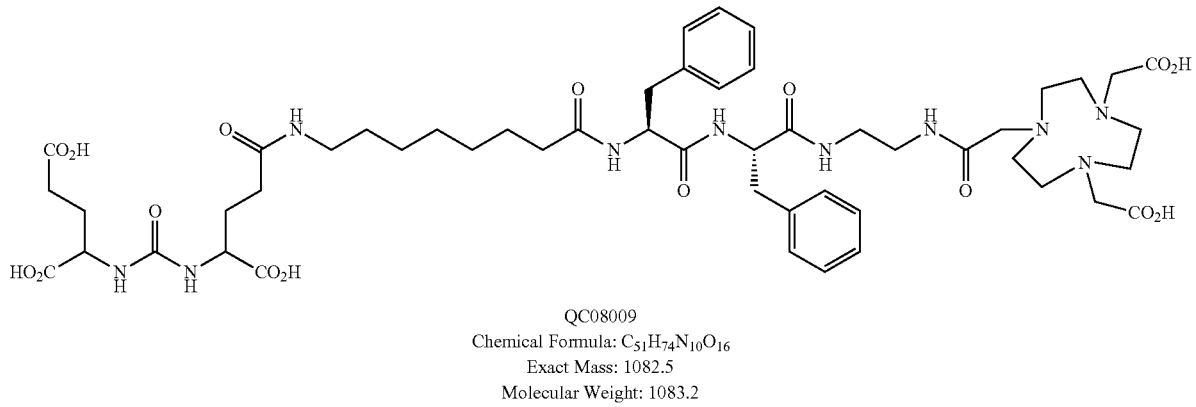

QC08009
Chemical Formula: $C_{51}H_{74}N_{10}O_{16}$
Exact Mass: 1082.5
Molecular Weight: 1083.2

EXAMPLE. To DUPA-EAOA-Phe-Phe-EDA-NH$_2$ (QC08008, 5.9 mg, 0.0074 mmol, M.W.: 797.4) in DMSO (0.25 ml, with a concentration at 0.025 M) was added NOTA-NHS (7.3 mg, 0.011 mmol, 1.5 eq.) followed by 4 drops of DIPEA. The mixture was stirred at 23° C. and monitored by LC-MS. 4 hours later, LC-MS showed that almost all of the starting material was transformed to the product. The crude material was then purified by preparative RP-HPLC to afford the pure DUPA-EAOA-Phe-Phe-NOTA (QC08009, 4.50 mg, 56%, based on 8.02 mg in theory, 97% purity by HPLC at 210 nm). Analytical RP-C$_{18}$ HPLC: $t_R$=3.45 min (A=10 mM NH$_4$OAc, pH=7.0; B=CH$_3$CN, solvent gradient: 0% B to 100% B in 15 min); Preparative RP-C$_{18}$ HPLC: $t_R$=10.09 min (A=10 mM NH$_4$OAc, pH=7.0; B=CH$_3$CN, solvent gradient: 0% B to 100% B in 30 min); UV-Vis: $\lambda_{max}$=211 nm; LC-MS: LC-MS (Agilent G6130B Quadrupole LC/MS) of Product Mobile phase: Buffer (pH 7)—CH$_3$CN; Method: 0-100 ACN-15 min, $t_R$=3.45 min. MS m/z: MS-API: Calcd. for $C_{51}H_{75}N_{10}O_{16}$ ([M+H]$^+$): 1083.5, Found: 1083.3; HPLC (Agilent Preparative C18 Column): Mobile phase: Buffer (pH 7)—CH$_3$CN; Method: 0-100 ACN-30 min, $t_R$=10.09 min. $^1$H NMR (400 MHz, DMSO-d$_6$) δ=10.13 (br, 1H), 8.98 (br, 1H), 8.43 (br, 1H), 7.90 (br, 3H), 7.30-7.10 (m, 10H), 6.37 (br, 1H), 6.28 (br, 1H), 4.60-4.52 (m, 1H), 4.32-4.44 (m, 1H), 4.24-4.31 (m, 2H), 3.95-4.03 (m, 2H), 3.85-3.92 (m, 2H), 3.28 (s, 4H), 3.25 (s, 2H), 3.09 (m, 1H), 3.05 (m, 1H), 2.92-3.02 (m, 4H), 2.54-2.67 (m, 12H), 2.31-2.38 (m, 2H), 2.19-2.31 (m, 3H), 2.11-2.18 (m, 2H), 2.02-2.10 (m, 3H), 1.52-1.72 (m, 4H), 1.25-1.37 (m, 4H), 1.05-1.13 (m, 2H),

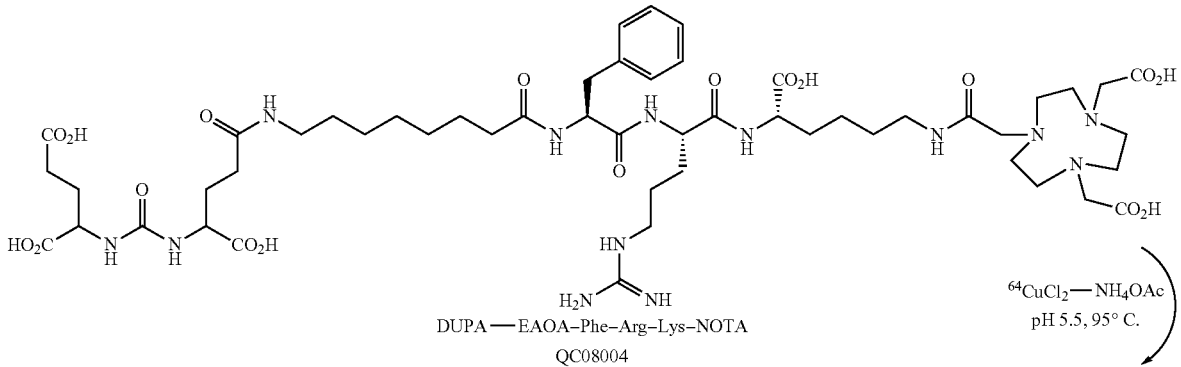

DUPA—EAOA-Phe-Arg-Lys-NOTA
QC08004

$^{64}$CuCl$_2$—NH$_4$OAc
pH 5.5, 95° C.

-continued

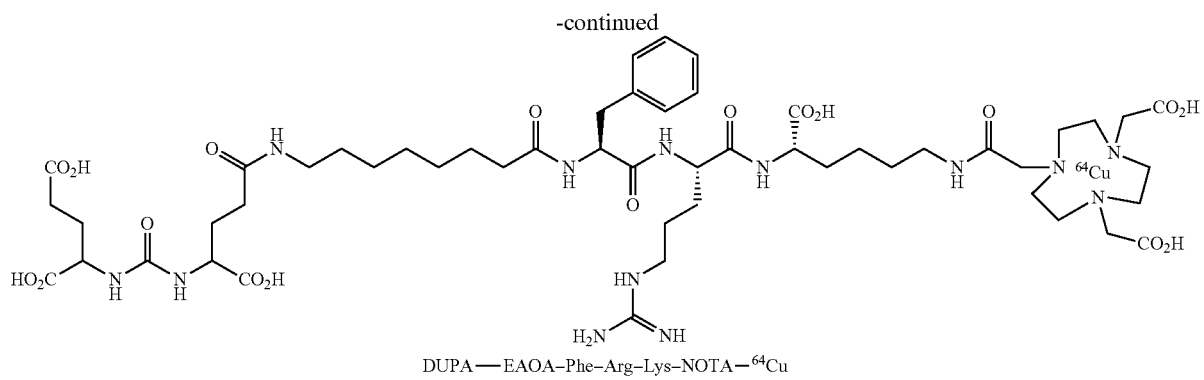

DUPA—EAOA-Phe-Arg-Lys-NOTA-⁶⁴Cu

EXAMPLE. Radiochemical Synthesis of DUPA-EAOA-Phe-Arg-Lys-NOTA-⁶⁴Cu Radiotracer. NOTA based chelators have also been reported and employed in the formulation of NOTA-⁶⁴/⁶⁷Cu for nuclear medicine/radiotherapy. [14-16] The corresponding DUPA-NOTA-⁶⁴Cu was prepare for the dual purpose of imaging and therapy, also referred to as theranostics. DUPA-EAOA-Phe-Arg-Lys-NOTA-⁶⁴Cu was prepared according a standard protocol with minor modifications. [4, 14-16] The ⁶⁴Cu(OAc)₂, in situ prepared from ⁶⁴CUCl₂ with 0.1 M ammonium acetate (pH 5.5), was added to the reaction tube containing the DUPA-NOTA precursor. The resulting mixture was then heated to 95° C. for 15 min. After cooling to room temperature, the crude material was purified by radioactive HPLC on a Cl18 column using MeCN and 0.1% TFA as the mobile phase to afford the target radiotracer with ~90% radiochemical purity (RCP). Sterile filtration and dilution in isotonic saline to the desired radioactivity provided the radiotracer ready for PET imaging.

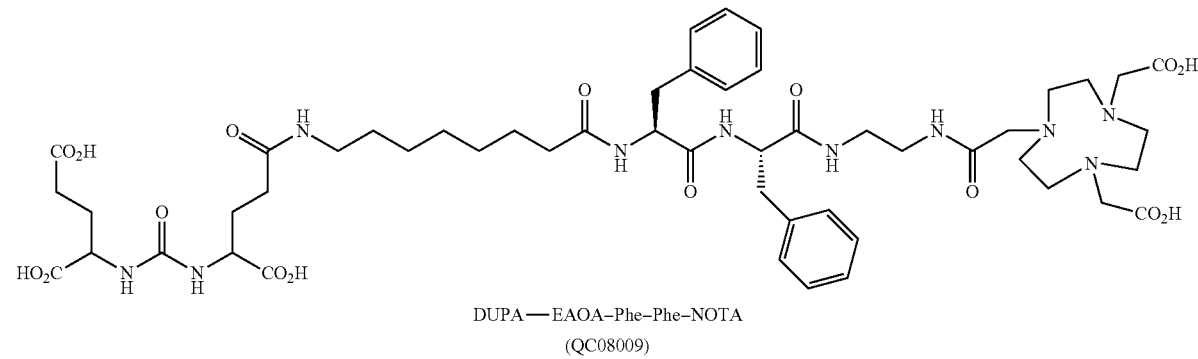

DUPA—EAOA-Phe-Phe-NOTA
(QC08009)

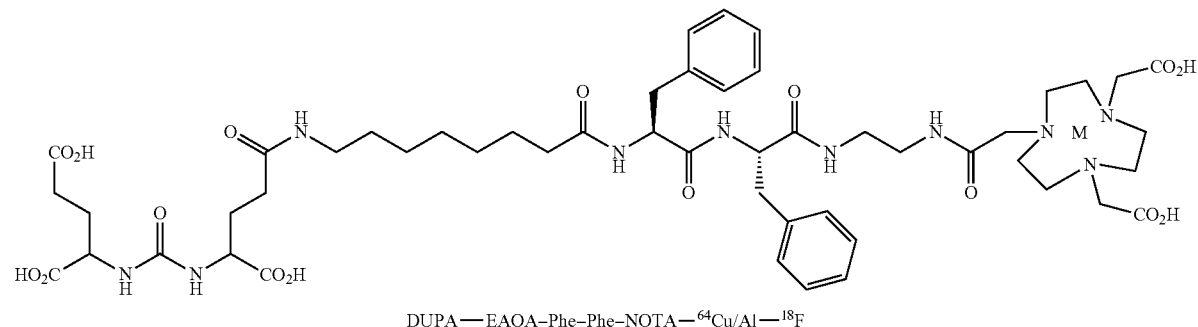

DUPA—EAOA-Phe-Phe-NOTA—⁶⁴Cu/Al—¹⁸F

M = ⁶⁸Ga, ⁶⁴Cu or Al—¹⁸F

Example. Radiochemical Synthesis of DUPA-EAOA-Phe-Phe-NOTA-$^{64}$Cu/Al-$^{18}$F

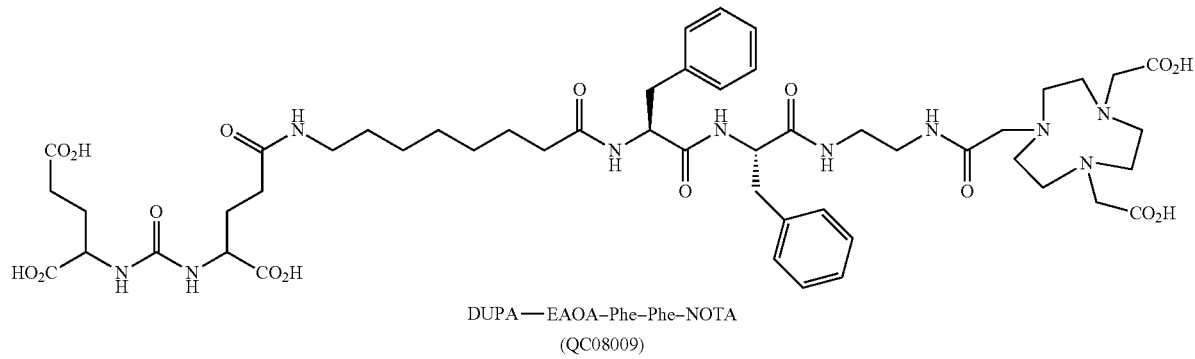

DUPA—EAOA-Phe-Phe-NOTA
(QC08009)

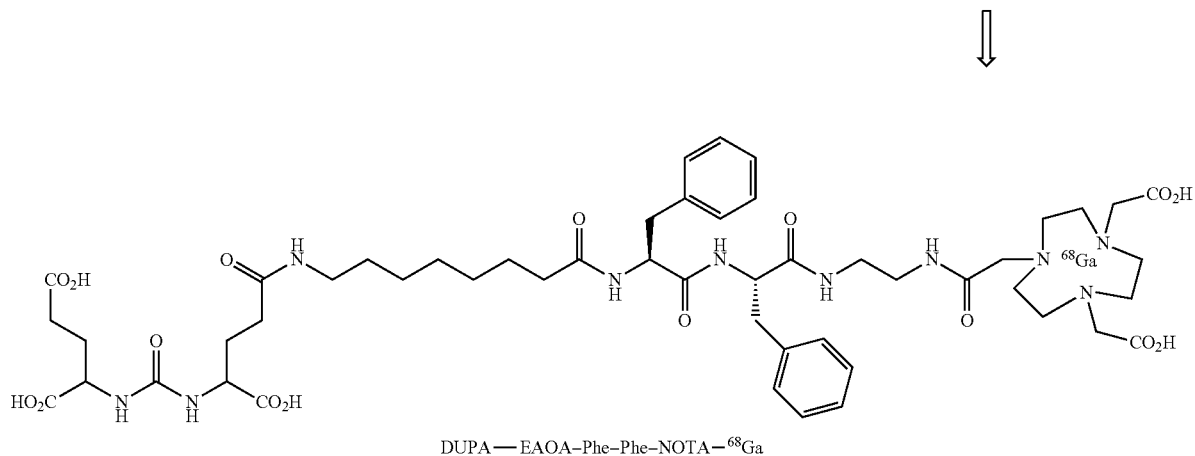

DUPA—EAOA-Phe-Phe-NOTA-$^{68}$Ga

Example. Radiochemical Synthesis of DUPA-EAOA-Phe-Phe-NOTA-$^{68}$Ga

EXAMPLE. General procedure for $^{68}$Ga labeling: $^{68}$Ga was eluted from the $^{68}$Ge/$^{68}$Ga generator with 0.1N HCl. A predetermined amount of $^{68}$Ga in 0.1N HCl was added to a DUPA-NOTA solution in acetate buffer (pH 4.8). The labeling mixture was incubated at room temperature, and labeling efficiencies were checked by radioactive HPLC. The radiolabeled product was purified by radioactive HPLC and the DUPA-NOTA-$^{68}$Ga peak sample was collected. After sterile filtration and being diluted to appropriate radioactivity (5-10 mCi) and specific activity (>1 Ci/μmol), the radiotracer was ready for in vivo PET imaging study.

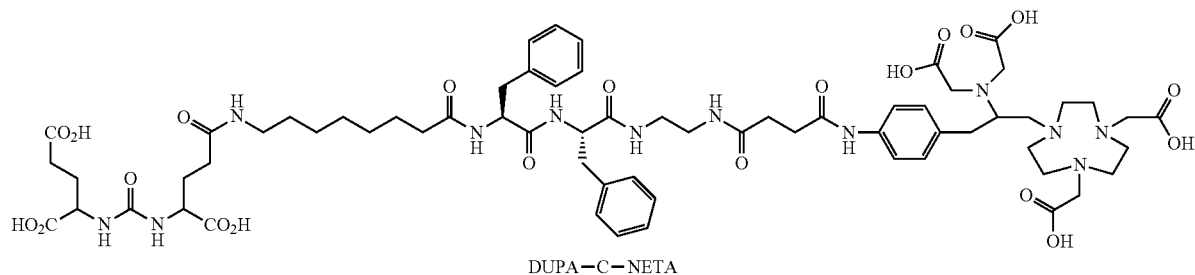

DUPA—C—NETA

-continued

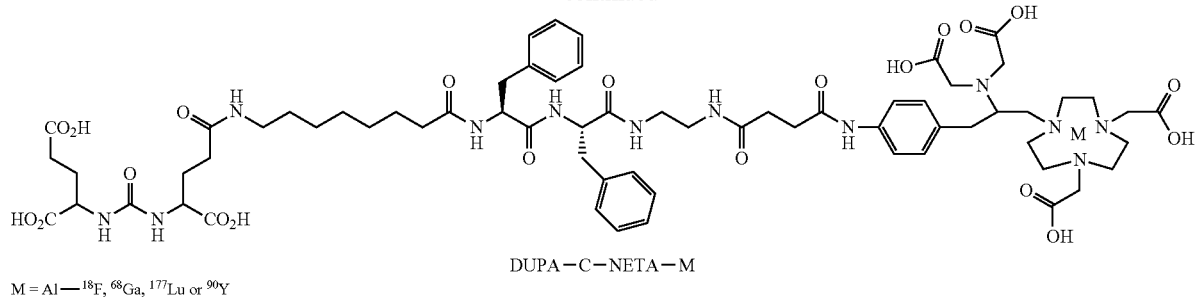

DUPA—C—NETA—M

M = Al—$^{18}$F, $^{68}$Ga, $^{177}$Lu or $^{90}$Y

Example. Radiochemical Synthesis of DUPA-C-NETA-Based Theranostics

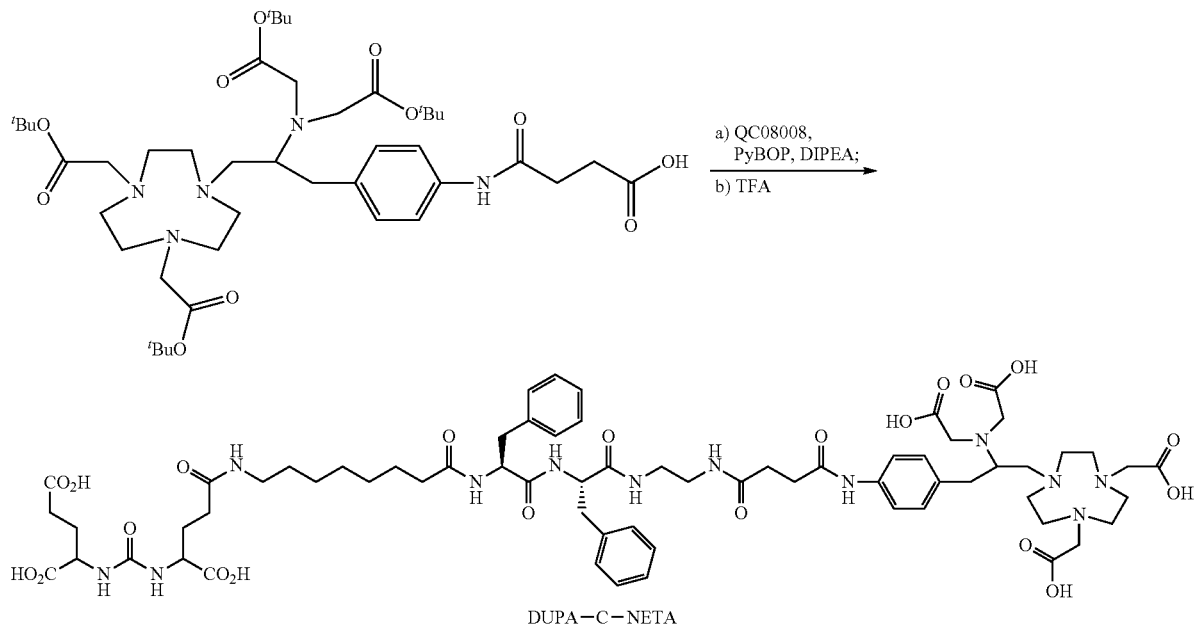

DUPA—C—NETA

EXAMPLE. Preparation of the NOTA Derivatives. Bifunctional conjugates, also referred to as theranostics, are described herein. Compounds described herein can tightly chelate both radionuclides such as $^{18}$F and $^{68}$Ga for PET imaging, and radionuclides $^{177}$Lu and $^{90}$Y for radiotherapy. C-NETA, a NOTA derivative, has been reported to chelate Al$^{18}$F with about twice the efficiency (87%) of NOTA.[17] Moreover, C-NETA also reportedly chelates the commonly used radiotherapeutic nuclides, such as $^{177}$Lu and $^{90}$Y, with high labeling efficiency.[18] Thus, it is appreciated herein, that C-NETA is useful as a bifunctional chelator that can be used for both PET imaging and radiotherapy, where the radionuclide is a metal or metal halide, such as Al$^{18}$F, $^{68}$Ga, $^{177}$Lu or $^{90}$Y.

EXAMPLE. A PyBOP promoted coupling between QC04018 and QC08008, followed by deprotection of tert-butyl ester with TFA provides DUPA-C-NETA. DUPA-C-NETA is used to evaluate the labeling efficiency to Al$^{18}$F, $^{68}$Ga, $^{177}$Lu and $^{90}$Y, and evaluate the in vivo PET imaging and radiotherapy.

Method Examples

EXAMPLE. The specificity of the radionuclide containing conjugates binding to FR is evaluated against KB xenografts homogenates and Cal51 xenografts homogenates. Concentration dependent binding was evaluated for $^{18}$F-AlF-QC07017 and $^{18}$F-AlF-QC07043, and separated into specific and non-specific binding. Significant non-specific binding was not observed in KB homogenates. Minor non-specific binding was observed in Cal51 homogenates, with a specific/non-specific binding ratio of >3:1 at all concentrations up to about 30 nM for $^{18}$F-AlF-QC07017, and a specific/non-specific binding ratio of >2:1 at all concentrations up to about 20 nM for $^{18}$F-AlF-QC07043. Minor non-specific binding was observed in A549 homogenates, with a specific/non-specific binding ratio of >2:1 at all concentrations up to about 10 nM for $^{18}$F-AlF-QC07043. Scatchard analyses were also performed. Displaceable and saturable binding of $^{18}$F-AlF-QC07017 in human tumor xenografts (KB and Cal51) by self competition was observed. Both $^{18}$F-AlF-QC07017 and $^{18}$F-AlF-QC07043 bound one site with high affinity in all cell xenografts. The high ratio of Bmax/Kd indicated a high specific binding affinity to KB xenografts. Moderate binding affinity was observed for Cal51 xenografts, and the lowest binding affinity was observed for A549 xenografts. Without being bound by theory, it is believed herein that the moderate expression of FR in Cal51 xenografts accounts for the lower binding affinity.

Binding affinities of $^{18}$F-AIF-QC07017 (2) to FR in KB and Cal51 tumor crude homogenate.

| Folate-NOTA-A118F (2) | Bmax, nM* | Kd, nM | Bmax/Kd |
|---|---|---|---|
| KB xenografts | 511 | 0.7 | >700 |
| Cal51 xenografts | 36 | 1.1 | >30 |

Binding affinities of $^{18}$F-AIF-QC07043 to FR in KB and Cal51 tumor crude homogenate.

| FA-PEG12-NOTA-Al18F | Bmax, nM* | Kd, nM | Bmax/Kd |
|---|---|---|---|
| KB xenografts | 241 | 0.4 | 603 |
| Cal51 xenografts | 13 | 1.2 | 11 |

EXAMPLE. μPET imaging was performed on nude mice bearing KB tumor xenografts under baseline and competed conditions to evaluate the in vivo binding specificity of $^{18}$F-AIF-QC07017 (2) to FR. Nude mice bearing KB tumor xenografts on their left shoulder were injected with 0.30-0.40 mCi (2). The competed group received 100 μg of folic acid 10 min before the i.v. injection of (2), and the treatment group was injected with a corresponding volume of phosphate buffer. Time course inspection of PET images obtained at various time points revealed that the data acquired in 60-90 min post tracer injection gave the best visual PET imaging. The KB tumors were clearly visualized in the treated group, whereas the uptake of (2) was completely inhibited by competing with folic acid, supporting a high specificity of (2) binding to FR in vivo. Without being bound by theory, it is believed herein that the high radioactivity found in kidneys was due to the uptake mediated by FR that is expressed in the proximal tubule cells in kidneys and the potential accumulation of radiotracer via renal excretion, which was further supported by the biodistribution studies described herein. With the exception of the liver, significant uptake in other organs was not observed. A significant blocking effect in liver uptake was observed in under competed conditions.

Figure 1B:
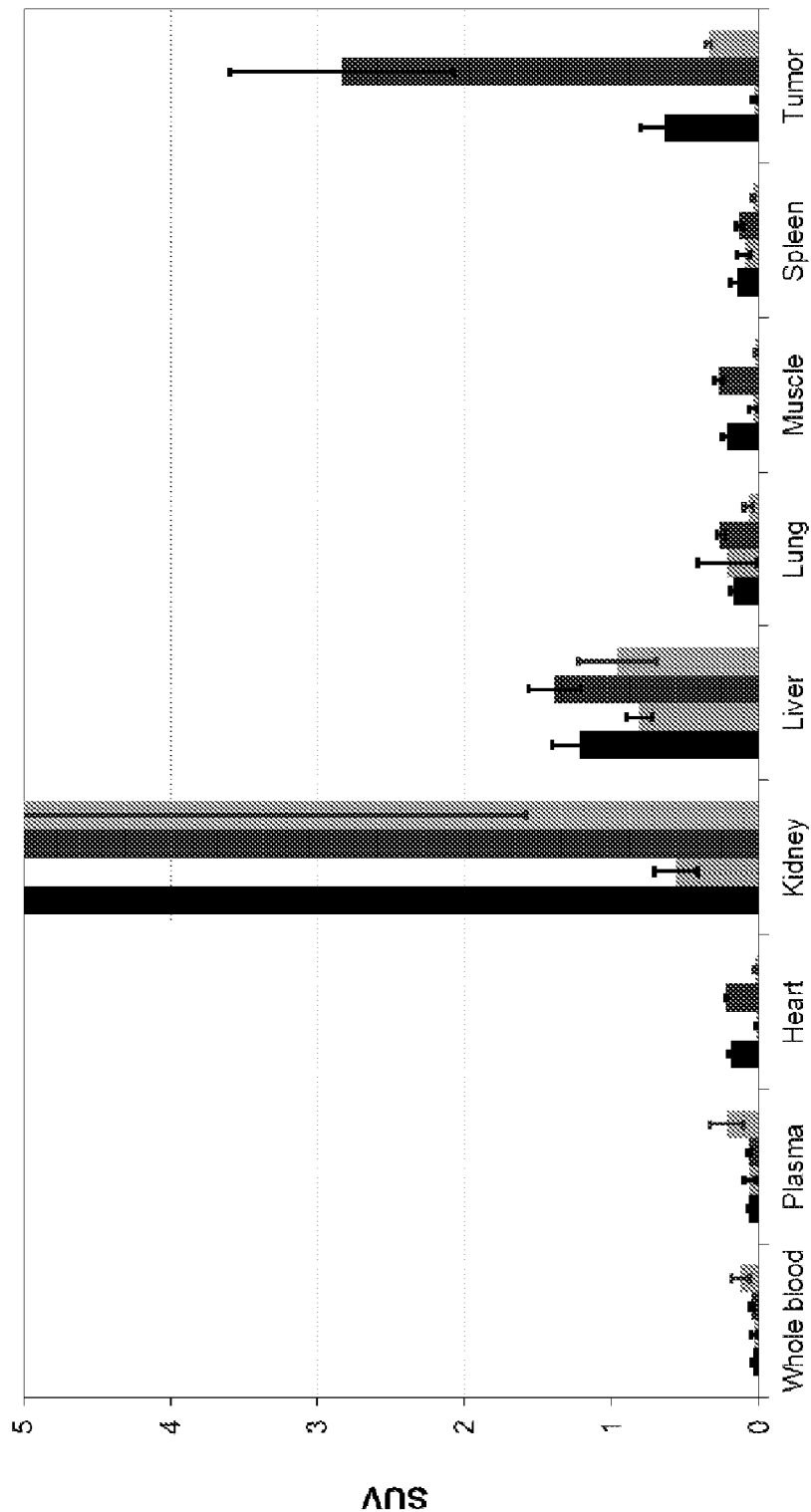
FIG. 1B shows a postmortem biodistribution study of $^{18}$F-AIF-QC07017 folate-NOTA-Al-$^{18}$F conjugate in various tissues at 90 minutes post injection in nude mice bearing KB tumor xenografts or A549 tumor xenografts. It is to be understood that the vertical axis has been expanded and that the kidney data is truncated. For each tissue, the histogram is in groups of 4 from left to right: $^{18}$F-AIF-QC07017 against A549 tumor xenografts, $^{18}$F-AIF-QC07017+excess folic acid against A549 tumor xenografts, $^{18}$F-AIF-QC07017 against KB tumor xenografts, $^{18}$F-AIF-QC07017+excess folic acid against KB tumor xenografts.
Figure 1C:
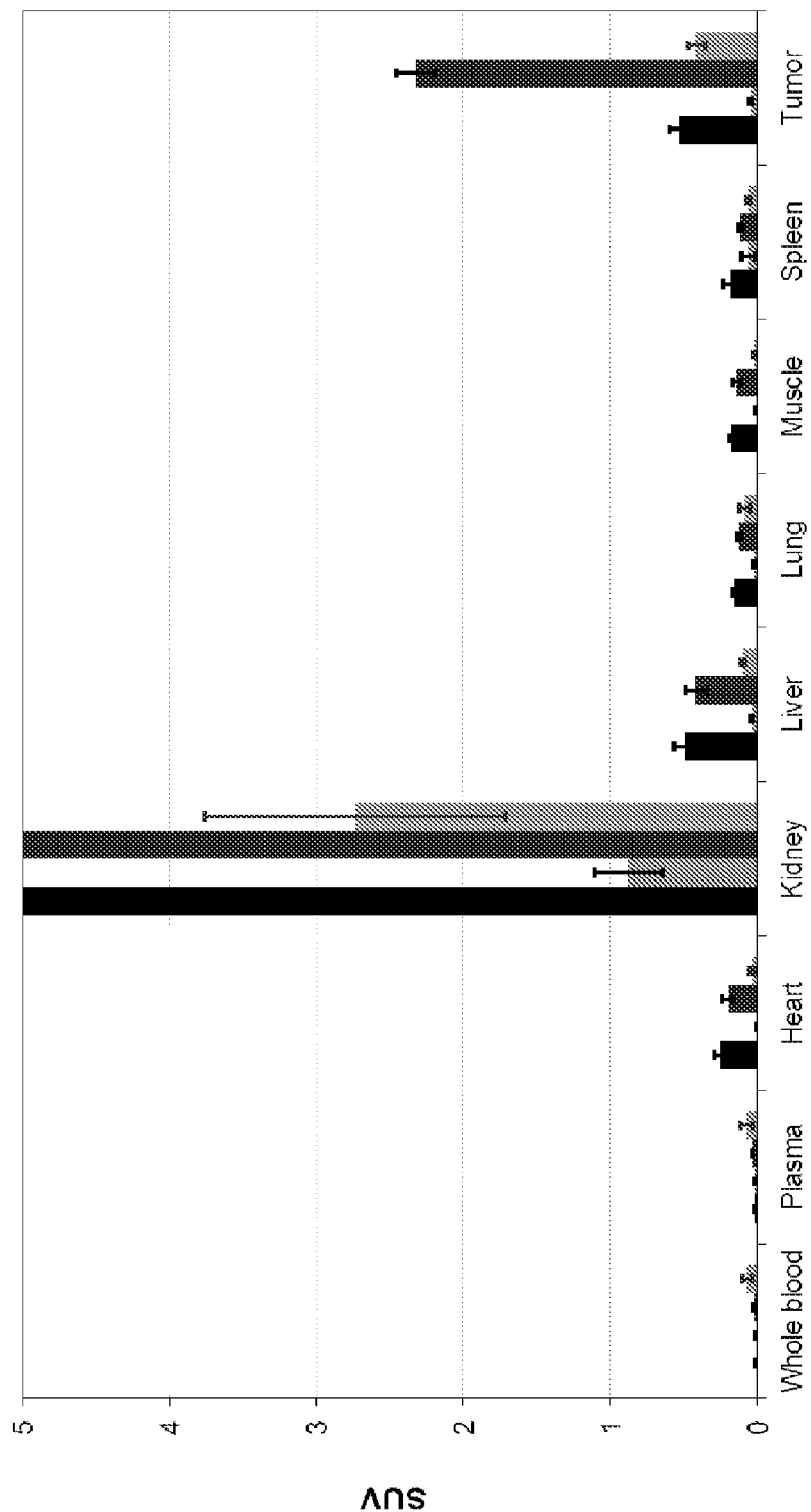
FIG. 1C shows a postmortem biodistribution study of $^{18}$F-AIF-QC07043 folate-NOTA-Al-$^{18}$F conjugate in various tissues at 90 minutes post injection in nude mice bearing KB tumor xenografts or A549 tumor xenografts. It is to be understood that the vertical axis has been expanded and that the kidney data is truncated. For each tissue, the histogram is in groups of 4 from left to right: $^{18}$F-AIF-QC07043 against A549 tumor xenografts, $^{18}$F-AIF-QC07043+excess folic acid against A549 tumor xenografts, $^{18}$F-AIF-QC07043 against KB tumor xenografts, $^{18}$F-AIF-QC07043+excess folic acid against KB tumor xenografts.
Figure 2A:
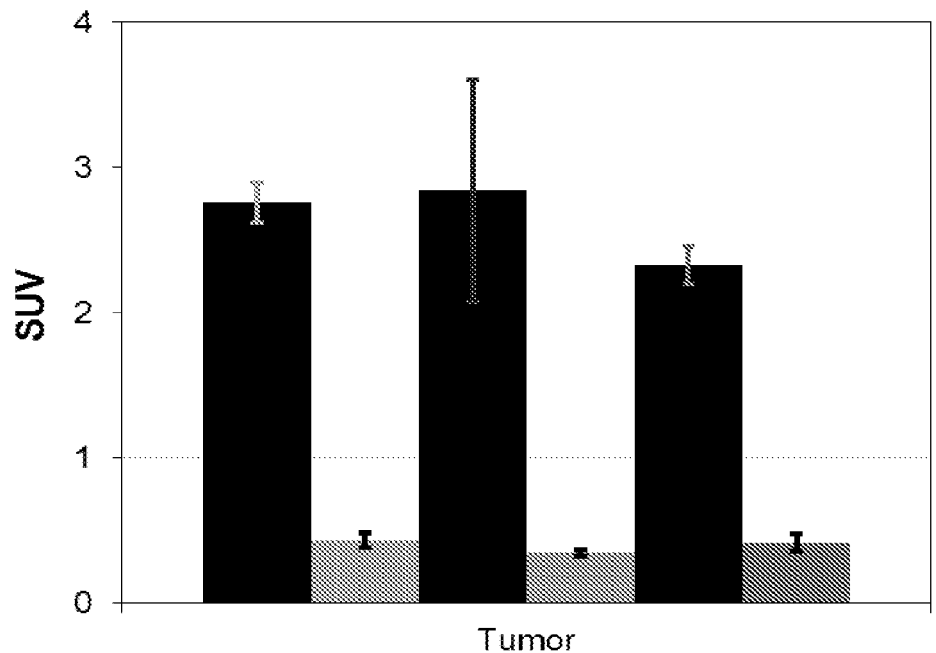
FIG. 2A shows a postmortem biodistribution study of $^{18}$F-AIF-QC07017 and $^{18}$F-AIF-QC07043 folate-NOTA-Al-$^{18}$F conjugates, compared to $^{99m}$Tc-EC20 in KB tumor xenograft tissues at 90 minutes post injection in nude mice. The histogram from left to right: $^{99m}$Tc-EC20 against KB tumor xenografts, $^{99m}$Tc-EC20+excess folic acid against KB tumor xenografts, $^{18}$F-AIF-QC07017 against KB tumor xenografts, $^{18}$F-AIF-QC07017+excess folic acid against KB tumor xenografts, $^{18}$F-AIF-QC07043 against KB tumor xenografts, $^{18}$F-AIF-QC07043+excess folic acid against KB tumor xenografts.
Figure 2B:
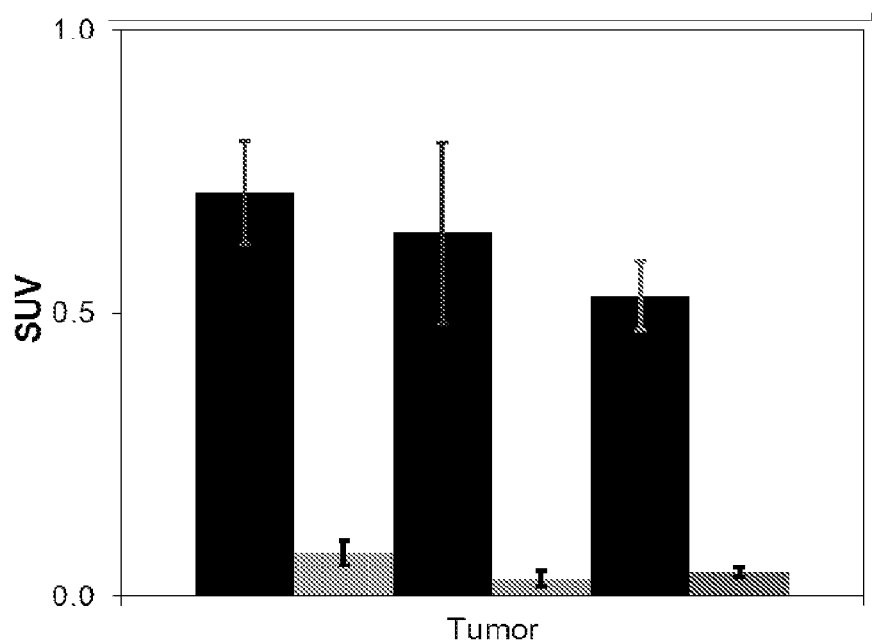
FIG. 2B shows a postmortem biodistribution study of $^{18}$F-AIF-QC07017 and $^{18}$F-AIF-QC07043 folate-NOTA-Al-$^{18}$F conjugates, compared to $^{99m}$Tc-EC20 in A549 tumor xenograft tissues at 90 minutes post injection in nude mice. The histogram from left to right: $^{99m}$Tc-EC20 against A549 tumor xenografts, $^{99m}$Tc-EC20+excess folic acid against A549 tumor xenografts, $^{18}$F-AIF-QC07017 against A549 tumor xenografts, $^{18}$F-AIF-QC07017+excess folic acid against A549 tumor xenografts, $^{18}$F-AIF-QC07043 against A549 tumor xenografts, $^{18}$F-AIF-QC07043+excess folic acid against A549 tumor xenografts.

EXAMPLE. Ex vivo biodistribution study of compounds described herein under both baseline and competed conditions in nude mice bearing KB tumor xenografts on their left shoulder demonstrates a high and specific uptake in FR(+) tumors. Radiotracer levels of $^{18}$F-AIF-QC07017 and $^{18}$F-AIF-QC07043 were determined in whole blood, plasma, heart, kidney, liver, lung, muscle, spleen, KB xenograft tumor tissues and A549 xenograft tumor tissues (FIG. 1A, FIG. 1B, and FIG. 1C). The highest signal was observed in the kidneys. Accumulation was observed to a substantially less extent in the liver. Without being bound by theory, it is believed herein that the highest accumulation of radioactivity in kidneys, along with the relative low uptake of radiotracer in the hepatobiliary system i.e. liver, bile and intestine/feces supports that renal elimination is the predominant excretion pathway. Except for the kidneys, accumulation in KB xenograft tumor tissues was greatest, and significantly greater than in the liver. Accumulation in A549 xenograft tumor tissues was comparable to the liver. Accumulation in both KB xenograft tumor tissues and A549 xenograft tumor tissues was blocked under competition conditions with folic acid (FIG. 2A and FIG. 2B). The FR specificity of $^{18}$F-AIF-QC07017 and $^{18}$F-AIF-QC07043 was comparable to etarfolatide (EC20), a compound in clinical trials, in both KB xenograft tumor tissues and A549 xenograft tumor tissues.

| Uptake in KB xenografts | | |
|---|---|---|
| Example | Uptake (SUV) (±SEM) | Uptake under competed conditions (SUV) (±SEM) |
| $^{18}$F-AIF-QC07017 | 2.84 ± 0.76 | 0.34 ± 0.02 |
| $^{18}$F-AIF-QC07043 | 2.33 ± 0.13 | 0.41 ± 0.06 |
| $^{99m}$Tc-EC20 | 2.75 ± 0.14 | 0.43 ± 0.05 |

P values: $^{99m}$Tc-EC20 vs $^{18}$F-AIF-QC07043, p = 0.15; $^{18}$F-AIF-QC07017 vs $^{18}$F-AIF-QC07043, p = 0.48; EC20 vs $^{18}$F-AIF-QC07017, p = 0.85.

| Uptake in A549 xenografts | | |
|---|---|---|
| Example | Uptake (SUV) (±SEM) | Uptake under competed conditions (SUV) (±SEM) |
| $^{18}$F-AIF-QC07017 | 0.64 ± 0.16 | 0.03 ± 0.01 |
| $^{18}$F-AIF-QC07043 | 0.53 ± 0.06 | 0.04 ± 0.01 |
| $^{99m}$Tc-EC20 | 0.71 ± 0.09 | 0.08 ± 0.02 |

P values: $^{99m}$Tc-EC20 vs $^{18}$F-AIF-QC07043, p = 0.13; $^{18}$F-AIF-QC07017 vs $^{18}$F-AIF-QC07043, p = 0.50; $^{99m}$Tc-EC20 vs $^{18}$F-AIF-QC07017, p = 0.74

EXAMPLE. In vitro evaluation of DUPA-EAOA-Phe-Phe-NOTA-$^{68}$Ga radiotracer ($^{68}$Ga-QC08009). $^{67}$Ga has a longer half life than $^{68}$Ga (about 3.3 days versus about 68 minutes, respectively). Thus, $^{67}$Ga is used as a surrogate of $^{68}$Ga for in vitro evaluation of Kd values and tissue imaging. It is to be understood that the in vitro evaluation of Kd values and tissue imaging observed for $^{67}$Ga is predictive of $^{68}$Ga. DUPA-EAOA-Phe-Phe-NOTA-$^{67}$Ga (67Ga-NOTA-LC-PSMA2) was prepared in nearly quantitative radiochemical yield. In vitro study in both the PSMA(−) cell line (PC3) and the PSMA(+) cell lines (LnCaP and PIP—PC3) revealed a PSMA mediated high and specific uptake with a Kd=8.45±2.16 nM. PC3 is a PSMA (−) cell line; LnCap is a PSMA (+) cell line; and PIP—PC3 is a transfect cell line with higher PSMA expression. Uptake of $^{68}$Ga-QC08009 by PC3 cells was minimal, and did not change when competed. Uptake of $^{68}$Ga-QC08009 by LnCaP and PIP—PC3 was substantial, with PIP—PC3 cells showing the highest uptake. In both cases, Uptake of $^{68}$Ga-QC08009 by LnCaP and PIP—PC3 is blocked by competing ligand. Compared to $^{67}$Ga-DKFZ-PSMA11, an imaging agent in clinical trials, $^{67}$Ga-NOTA-LC-PSMA2 demonstrated superior binding to PSMA(+) prostate cancer tissues.

EXAMPLE. In vivo PET imaging and BioD study of DUPA-EAOA-Phe-Phe-NOTA-$^{68}$Ga radiotracer ($^{68}$Ga-QC08009). In vivo micro-PET/CT scan with $^{68}$Ga-NOTA-LC-PSMA2 radiotracer in mice carrying PSMA (+) LnCaP xenografts showed 4.29% ID uptake in PSMA(+) tumor. At 1 hour post-injection, most of the radiotracer was found in bladder. Without being bound by theory, it is believed herein that the data support that the primary elimination pathway is in urine. In addition, compared to other tissues, minor accumulation of radiotracer was observed in the kidneys. Without being bound by theory, it is believed herein that the relatively high PSMA expression in mouse kidneys, compared to other tissues, accounts at least in part for the minor accumulation of $^{68}$Ga-NOTA-LC-PSMA2 radiotracer in kidneys.

What is claimed is:
1. A conjugate of formula

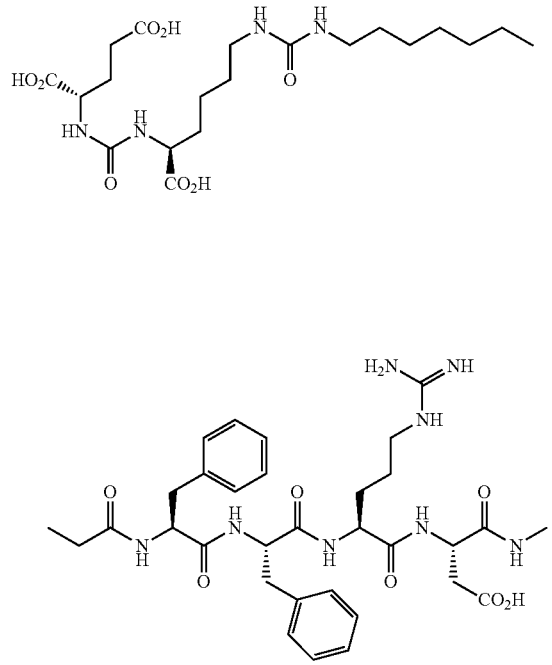

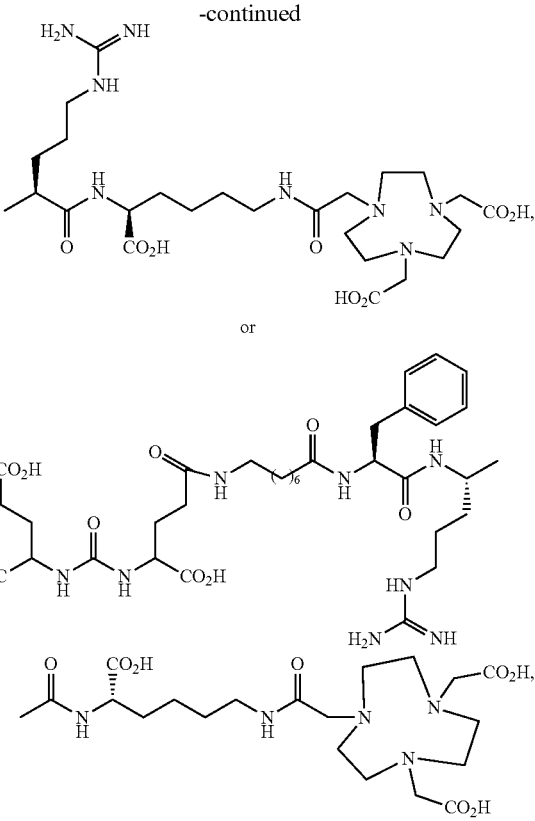

or a pharmaceutically acceptable salt thereof.

2. A pharmaceutical composition comprising a conjugate according to claim 1 and a pharmaceutically acceptable excipient.

* * * * *